US012774321B2

(12) United States Patent
Luk et al.

(10) Patent No.: US 12,774,321 B2
(45) Date of Patent: Oct. 27, 2026

(54) ANTI-α-SYNUCLEIN MONOCLONAL ANTIBODIES, AND METHODS USING SAME

(71) Applicant: THE TRUSTEES OF THE UNIVERSITY OF PENNSYLVANIA, Philadelphia, PA (US)

(72) Inventors: Kelvin C. Luk, Philadelphia, PA (US); Virginia M.Y. Lee, Philadelphia, PA (US); John Q. Trojanowski, Philadelphia, PA (US); Kurt R. Brunden, Media, PA (US); Dustin Covell, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1197 days.

(21) Appl. No.: 17/778,061

(22) PCT Filed: Nov. 19, 2020

(86) PCT No.: PCT/US2020/061376
§ 371 (c)(1),
(2) Date: May 19, 2022

(87) PCT Pub. No.: WO2021/102197
PCT Pub. Date: May 27, 2021

(65) Prior Publication Data

US 2023/0025707 A1 Jan. 26, 2023

Related U.S. Application Data

(60) Provisional application No. 62/937,636, filed on Nov. 19, 2019.

(51) Int. Cl.

*C07K 16/18* (2006.01)
*A61P 25/00* (2006.01)
*G01N 33/68* (2006.01)
*A61K 39/00* (2006.01)

(52) U.S. Cl.

CPC .............. *C07K 16/18* (2013.01); *A61P 25/00* (2018.01); *G01N 33/6896* (2013.01); *A61K 2039/505* (2013.01); *A61K 2039/54* (2013.01); *C07K 2317/24* (2013.01); *C07K 2317/33* (2013.01); *C07K 2317/565* (2013.01); *G01N 2800/2835* (2013.01)

(58) Field of Classification Search

CPC ........................... C07K 16/18; C07K 2317/24; C07K 2317/33; C07K 2317/565; C07K 2317/32; C07K 2317/30; C07K 2317/34; C07K 2317/76; C07K 2317/92; A61P 25/00; G01N 33/6896; G01N 2800/2835; A61K 2039/505; A61K 2039/54

See application file for complete search history.

(56) References Cited

U.S. PATENT DOCUMENTS

| | | | |
|---|---|---|---|
| 2003/0079253 | A1 | 4/2003 | Hiatt |
| 2008/0300204 | A1 | 12/2008 | Federoff |
| 2009/0252683 | A1 | 10/2009 | Kischel |
| 2010/0278814 | A1 | 11/2010 | Schenk |
| 2014/0241984 | A1 | 8/2014 | El-Agnaf |
| 2014/0241987 | A1 | 8/2014 | El-Agnaf |
| 2014/0275495 | A1 | 9/2014 | Saldanha |
| 2015/0139900 | A1 | 5/2015 | Nordström |
| 2015/0140003 | A1 | 5/2015 | Kaluza |
| 2015/0259404 | A1 | 9/2015 | Barbour |
| 2017/0015739 | A1 | 1/2017 | Kallunki |
| 2017/0114123 | A1 | 4/2017 | Kaluza |
| 2018/0079812 | A1 | 3/2018 | Lim |
| 2019/0070290 | A1 | 3/2019 | Kischel |

FOREIGN PATENT DOCUMENTS

| | | | |
|---|---|---|---|
| CN | 103627676 | | 3/2014 |
| CN | 110172098 | | 8/2019 |
| EP | 3067066 | A1 | 9/2016 |
| WO | 2005047860 | A2 | 5/2005 |
| WO | 2007062088 | A1 | 5/2007 |
| WO | 2011104696 | A1 | 9/2011 |
| WO | 2013059885 | A2 | 5/2013 |
| WO | 2015089117 | | 6/2015 |
| WO | 2016012623 | | 1/2016 |
| WO | 2017009312 | A1 | 1/2017 |
| WO | 2017158337 | | 9/2017 |
| WO | 2017180989 | | 10/2017 |
| WO | 2018115225 | | 6/2018 |
| WO | 2018204352 | | 11/2018 |

(Continued)

OTHER PUBLICATIONS

Partial Supplementary European Search Report issued Jan. 22, 2024 in European Patent Application No. 20889174.7.

(Continued)

*Primary Examiner* — Olga N Chernyshev

(74) *Attorney, Agent, or Firm* — Saul Ewing LLP; Kathryn Doyle; Domingos Silva

(57) ABSTRACT

The present disclosure provides in one aspect monoclonal antibodies that bind α-Synuclein. In certain aspects, the antibodies preferentially bind to α-Synuclein fibrils over α-Synuclein monomer. In other aspects, the disclosure provides a method of treating, ameliorating, and/or preventing α-Synucleopathic disease in a subject, comprising administering any one of the antibodies of the disclosure to the subject. In yet other aspects, the disclosure provides methods of detecting α-Synuclein fibrils using any one of the antibodies of the disclosure.

5 Claims, 25 Drawing Sheets

Specification includes a Sequence Listing.

(56) References Cited

FOREIGN PATENT DOCUMENTS

| | | |
|---|---|---|
| WO | 2019023809 | 2/2019 |
| WO | 2019040617 | 2/2019 |

OTHER PUBLICATIONS

Tran, H.T., et al., "α-Synuclein Immunotherapy Blocks Uptake and Templated Propogation of Misfolded α-Synuclein and Neurodegeneration", Cell Rep., 7(6):2054-2065, 2014.

Database Geneseq [Online] Dec. 9, 2010, "Mouse anti-amyloid beta monclonal antibody AL-204 VL DNA, SEQ ID 543.", XP002802557, retrieved from EBI accessioni No. GSN:AYL01844, Database accession No. AYL01844.

Notice of Allowance dated Apr. 22, 2024 for U.S. Appl. No. 17/572,309 (pp. 1-7).

Office Action (Notice of Allowance and Fees Due (PTOL-85)) dated May 3, 2024 for U.S. Appl. No. 17/572,309 (pp. 1-2).

Bae et al., J Neuroscience, Sep. 26, 2012; 32(39): 13454-69. (Year: 2012).

Klump et al, Retroviral vector-mediated expression of HoxB4 in hematopoietic cells using a novel coexpression strategy, Gene Therapy 8: 811-817, 2001.

Casset, F., et al., "A peptide mimetic of an anti-CD4 monoclonal antibody by rational design", BBRC, 307, pp. 198-205, 2003.

Covell, et al., "Novel conformation-selective alpha-synuclein antibodies raised against different in vitro fibril forms show distinct patterns of Lewy pathology in Parkinson's disease," Neuropathol Appl. Neurobiol., vol. 43, May 2017, pp. 604-620.

El-Agnaf, et al., "Differential effects of immunotherapy wit antibodies targeting a-synuclein oligomers and fibrils in a transgenic model of synucleinopathy," Neurobiol Dis., vol. 104, Aug. 2017, pp. 85-96.

Fodero-Tavoletti, et al. (2009) In vitro characterisation of BF227 binding to α-synuclein/Lewy bodies. Eur. J. Pharmacol. 617, 54-58. (Year: 2009).

Guo, et al., "Distinct a-Synuclein Strains Differentially Promote Tau Inclusions in Neurons," Cell, vol. 154, No. 1, Jul. 2013, 24 pages.

International Search Report and Written Opinion issued in App. No. PCT/US20/61376, mailing date Apr. 6, 2021, 13 pages.

International Search Report for International Application No. PCT/US2018/030436 dated Jul. 19, 2018. 9 pages.

Lashuel, et al., "The many faces of a-synuclein: from structure and toxicity to therapeutic target," Nat Rev Neurosci., vol. 14, No. 1, Jan. 2013, pp. 38-48.

Lindstrom, et al., "Immunotherapy targeting a-synuclein protofibrils reduced pathology in (Thy-1)-h[A30P] a-synuclein mice," Neurobiology of Disease, vol. 69, Sep. 2014, 134-143 (Abstract only).

Lindstrom, et al., "Immunotherapy targeting a-synuclein, with relevance for future treatment of Parkinson's disease and other Lewy body disorders," Immunotherapy, vol. 6, No. 2, Feb. 2014, 141-153 (Abstract only).

Luk, et al., "Exogenous a-synuclein fibrils seed the formation of Lewy body-like intracellular inclusions in cultured cells," PNAS, vol. 106, No. 6, Nov. 2009, pp. 20051-20056.

Morsut et al., "Engineering Customized Cell Sensing and Response Behaviors Using Synthetic Notch Receptors", Cell, (Feb. 11, 2016), vol. 164, No. 4, doi:10.1016/j.cell.2016.01.012, pp. 780-791, XP029416809.

Roberti, M.J., et al., "Fluorescence imaging of amyloid formation in living cells by a functional, tetracysteine-tagged a-synuclein", Nature Methods, vol. 4, pp. 345-351, 2007.

Rudikoff, S., et al., "Single amino acid substitution altering antigen-binding specificity", Proc Natl Acad Sci USA, vol. 79, pp. 1979-1983, 1982.

Sahin, et al., "Antibodies against the C-terminus of a-synuclein modulate its fibrillation," Biophysical Chemistry, vol. 220, Nov. 2017, pp. 34-41.

Supplementary Partial European Search Report for European Patent Application No. 18795033.2 issued Dec. 22, 2020.

Vaikath, et al., "Generation and characterization of novel conformation-specific monoclonal antibodies for a-synuclein pathology", Neurobiol Dis., vol. 79, Apr. 2015, pp. 81-99.

Schenk D.B., et al., "First-in-human assessment of PRX002, an anti-a-synuclein monoclonal antibody, in healthy volunteers", Movement Disorders, Feb. 2017;32(2):211-218, DOI:10.1002/mds.26878.

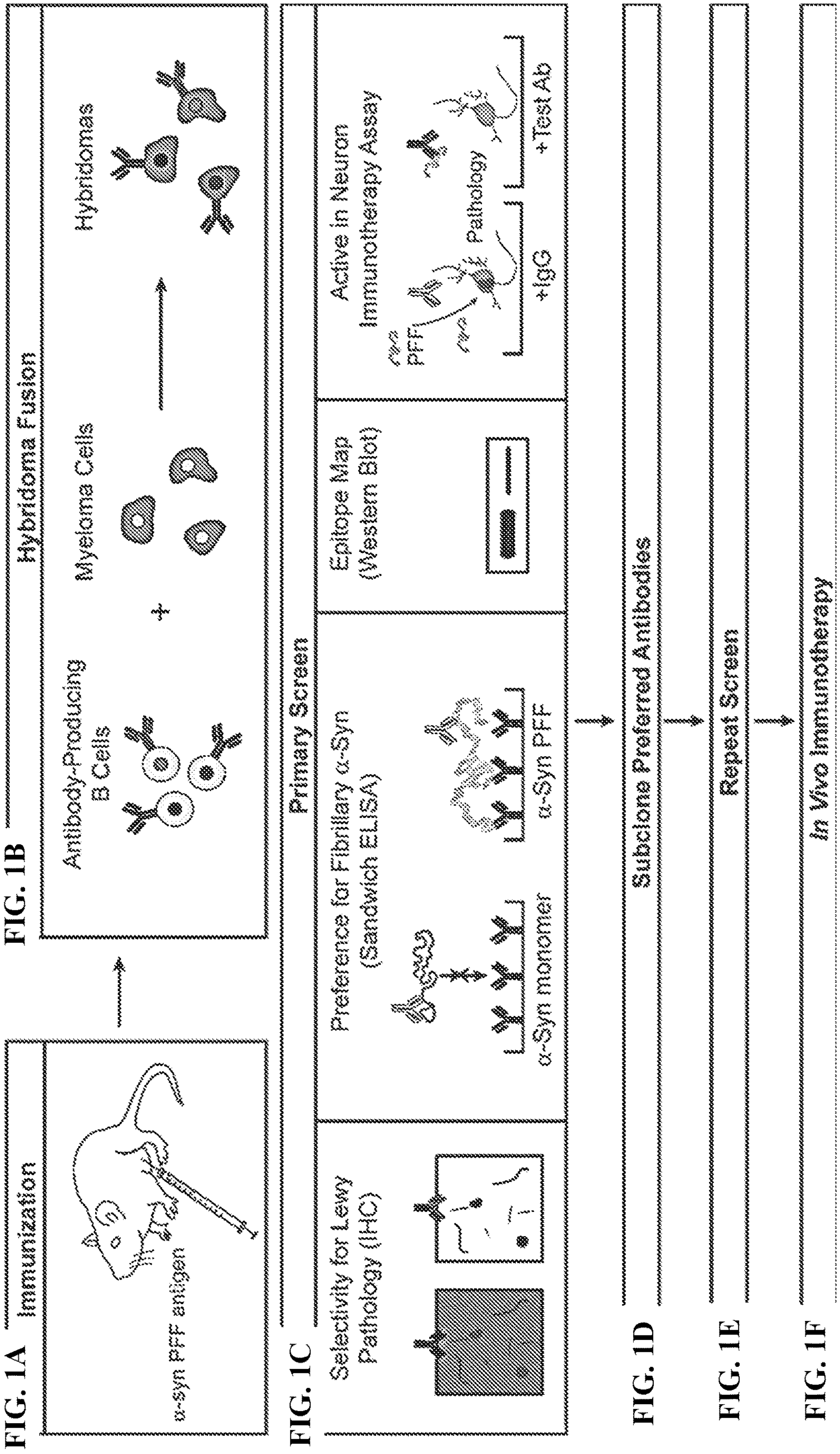
FIG. 1A
Immunization
α-syn PFF antigen
FIG. 1B
Hybridoma Fusion
Antibody-Producing B Cells
+
Myeloma Cells
Hybridomas
FIG. 1C
Primary Screen
Selectivity for Lewy Pathology (IHC)
Preference for Fibrillary α-Syn (Sandwich ELISA)
α-Syn monomer
α-Syn PFF
Epitope Map (Western Blot)
Active in Neuron Immunotherapy Assay
PFF
Pathology
+IgG
+Test Ab
FIG. 1D
Subclone Preferred Antibodies
FIG. 1E
Repeat Screen
FIG. 1F
In Vivo Immunotherapy 50 µm NB = Non Binding NB = Non Binding

SEQUENCE LISTING

```
<160> NUMBER OF SEQ ID NOS: 245

<210> SEQ ID NO 1
<211> LENGTH: 57
<212> TYPE: DNA
<213> ORGANISM: Artificial Sequence
<220> FEATURE:
<223> OTHER INFORMATION: Chemically synthesized

<400> SEQUENCE: 1

atgctgttgg ggctgaagtg ggttttcttt gttgtttttt atcaaggtgt gcattgt        57


<210> SEQ ID NO 2
<211> LENGTH: 90
<212> TYPE: DNA
<213> ORGANISM: Artificial Sequence
<220> FEATURE:
<223> OTHER INFORMATION: Chemically synthesized

<400> SEQUENCE: 2

gaggtgcagc ttgttgagtc tggtggagga ttggtgcaac ctaaagggtc attgaaactc     60
```

tcatgtgcag cctctggatt caccttcaat 90

<210> SEQ ID NO 3
<211> LENGTH: 15
<212> TYPE: DNA
<213> ORGANISM: Artificial Sequence
<220> FEATURE:
<223> OTHER INFORMATION: Chemically synthesized

<400> SEQUENCE: 3
acctacgcca tgcac 15

<210> SEQ ID NO 4
<211> LENGTH: 42
<212> TYPE: DNA
<213> ORGANISM: Artificial Sequence
<220> FEATURE:
<223> OTHER INFORMATION: Chemically synthesized

<400> SEQUENCE: 4
tgggtccgcc aggctccagg aaagggtttg gaatgggttg ct 42

<210> SEQ ID NO 5
<211> LENGTH: 57
<212> TYPE: DNA
<213> ORGANISM: Artificial Sequence
<220> FEATURE:
<223> OTHER INFORMATION: Chemically synthesized

<400> SEQUENCE: 5
cgcataagaa gtgaaagtaa taattttgca acatattatg ccgattcagt gaaagac 57

<210> SEQ ID NO 6
<211> LENGTH: 96
<212> TYPE: DNA
<213> ORGANISM: Artificial Sequence
<220> FEATURE:
<223> OTHER INFORMATION: Chemically synthesized

<400> SEQUENCE: 6
agtttcacca tctccagaga tgattcacaa agcatgctct atctgcaaat gaacaacttg 60
aaaactgagg acacagccgt atattactgt gtgaga 96

<210> SEQ ID NO 7
<211> LENGTH: 24
<212> TYPE: DNA
<213> ORGANISM: Artificial Sequence
<220> FEATURE:
<223> OTHER INFORMATION: Chemically synthesized

<400> SEQUENCE: 7
ggggggttat ctccctttga ctac 24

<210> SEQ ID NO 8
<211> LENGTH: 33
<212> TYPE: DNA
<213> ORGANISM: Artificial Sequence
<220> FEATURE:
<223> OTHER INFORMATION: Chemically synthesized

<400> SEQUENCE: 8
tggggccaag gcaccactct cacagtctcc tca 33

<210> SEQ ID NO 9
<211> LENGTH: 19

<212> TYPE: PRT
<213> ORGANISM: Artificial Sequence
<220> FEATURE:
<223> OTHER INFORMATION: Chemically synthesized

<400> SEQUENCE: 9

Met Leu Leu Gly Leu Lys Trp Val Phe Phe Val Val Phe Tyr Gln Gly
1 5 10 15

Val His Cys

<210> SEQ ID NO 10
<211> LENGTH: 30
<212> TYPE: PRT
<213> ORGANISM: Artificial Sequence
<220> FEATURE:
<223> OTHER INFORMATION: Chemically synthesized

<400> SEQUENCE: 10

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Asn
20 25 30

<210> SEQ ID NO 11
<211> LENGTH: 5
<212> TYPE: PRT
<213> ORGANISM: Artificial Sequence
<220> FEATURE:
<223> OTHER INFORMATION: Chemically synthesized

<400> SEQUENCE: 11

Thr Tyr Ala Met His
1 5

<210> SEQ ID NO 12
<211> LENGTH: 14
<212> TYPE: PRT
<213> ORGANISM: Artificial Sequence
<220> FEATURE:
<223> OTHER INFORMATION: Chemically synthesized

<400> SEQUENCE: 12

Trp Val Arg Gln Ala Pro Gly Lys Gly Leu Glu Trp Val Ala
1 5 10

<210> SEQ ID NO 13
<211> LENGTH: 19
<212> TYPE: PRT
<213> ORGANISM: Artificial Sequence
<220> FEATURE:
<223> OTHER INFORMATION: Chemically synthesized

<400> SEQUENCE: 13

Arg Ile Arg Ser Glu Ser Asn Asn Phe Ala Thr Tyr Tyr Ala Asp Ser
1 5 10 15

Val Lys Asp

<210> SEQ ID NO 14
<211> LENGTH: 32
<212> TYPE: PRT
<213> ORGANISM: Artificial Sequence
<220> FEATURE:
<223> OTHER INFORMATION: Chemically synthesized

<400> SEQUENCE: 14

Ser Phe Thr Ile Ser Arg Asp Asp Ser Gln Ser Met Leu Tyr Leu Gln
1               5                   10                  15

Met Asn Asn Leu Lys Thr Glu Asp Thr Ala Val Tyr Tyr Cys Val Arg
            20                  25                  30

<210> SEQ ID NO 15
<211> LENGTH: 8
<212> TYPE: PRT
<213> ORGANISM: Artificial Sequence
<220> FEATURE:
<223> OTHER INFORMATION: Chemically synthesized

<400> SEQUENCE: 15

Gly Gly Leu Ser Pro Phe Asp Tyr
1               5

<210> SEQ ID NO 16
<211> LENGTH: 11
<212> TYPE: PRT
<213> ORGANISM: Artificial Sequence
<220> FEATURE:
<223> OTHER INFORMATION: Chemically synthesized

<400> SEQUENCE: 16

Trp Gly Gln Gly Thr Thr Leu Thr Val Ser Ser
1               5                   10

<210> SEQ ID NO 17
<211> LENGTH: 66
<212> TYPE: DNA
<213> ORGANISM: Artificial Sequence
<220> FEATURE:
<223> OTHER INFORMATION: Chemically synthesized

<400> SEQUENCE: 17 atggatttc aagtgcagat tttcagcttc ctgctaatca gtgcctcagt cataatatcc     60
agagga                                                                66

<210> SEQ ID NO 18
<211> LENGTH: 69
<212> TYPE: DNA
<213> ORGANISM: Artificial Sequence
<220> FEATURE:
<223> OTHER INFORMATION: Chemically synthesized

<400> SEQUENCE: 18
caaattgttc tcacccagtc tccagcaatc atgtctgcat ctccagggga gaaggtcacc     60
atgacctgc                                                             69

<210> SEQ ID NO 19
<211> LENGTH: 30
<212> TYPE: DNA
<213> ORGANISM: Artificial Sequence
<220> FEATURE:
<223> OTHER INFORMATION: Chemically synthesized

<400> SEQUENCE: 19
agtgccagct caagtgtaag ttacatgcac                                      30

<210> SEQ ID NO 20
<211> LENGTH: 45
<212> TYPE: DNA
<213> ORGANISM: Artificial Sequence
<220> FEATURE:
<223> OTHER INFORMATION: Chemically synthesized

<400> SEQUENCE: 20
tggtaccaac agaagtcagg cacctccccc aaaagatgga tttat 45

<210> SEQ ID NO 21
<211> LENGTH: 21
<212> TYPE: DNA
<213> ORGANISM: Artificial Sequence
<220> FEATURE:
<223> OTHER INFORMATION: Chemically synthesized

<400> SEQUENCE: 21
gacacttcca aactggcttc t 21

<210> SEQ ID NO 22
<211> LENGTH: 96
<212> TYPE: DNA
<213> ORGANISM: Artificial Sequence
<220> FEATURE:
<223> OTHER INFORMATION: Chemically synthesized

<400> SEQUENCE: 22
ggagtccctg ctcgcttcag tggcagtggg tctgggacct cttactctct cacaatcaac 60
agcatggagg ctgaagatgc tgccacttat tactgc 96

<210> SEQ ID NO 23
<211> LENGTH: 27
<212> TYPE: DNA
<213> ORGANISM: Artificial Sequence
<220> FEATURE:
<223> OTHER INFORMATION: Chemically synthesized

<400> SEQUENCE: 23
cagcagtgga gtagaaatcc acccacg 27

<210> SEQ ID NO 24
<211> LENGTH: 30
<212> TYPE: DNA
<213> ORGANISM: Artificial Sequence
<220> FEATURE:
<223> OTHER INFORMATION: Chemically synthesized

<400> SEQUENCE: 24
ttcggagggg ggaccaagct ggaaataaaa 30

<210> SEQ ID NO 25
<211> LENGTH: 22
<212> TYPE: PRT
<213> ORGANISM: Artificial Sequence
<220> FEATURE:
<223> OTHER INFORMATION: Chemically synthesized

<400> SEQUENCE: 25

Met Asp Phe Gln Val Gln Ile Phe Ser Phe Leu Leu Ile Ser Ala Ser
1 5 10 15

Val Ile Ile Ser Arg Gly
20

<210> SEQ ID NO 26
<211> LENGTH: 23
<212> TYPE: PRT
<213> ORGANISM: Artificial Sequence
<220> FEATURE:
<223> OTHER INFORMATION: Chemically synthesized

<400> SEQUENCE: 26

```
Gln Ile Val Leu Thr Gln Ser Pro Ala Ile Met Ser Ala Ser Pro Gly
1               5                   10                  15

Glu Lys Val Thr Met Thr Cys
            20
```

<210> SEQ ID NO 27
<211> LENGTH: 10
<212> TYPE: PRT
<213> ORGANISM: Artificial Sequence
<220> FEATURE:
<223> OTHER INFORMATION: Chemically synthesized

<400> SEQUENCE: 27

```
Ser Ala Ser Ser Ser Val Ser Tyr Met His
1               5                   10
```

<210> SEQ ID NO 28
<211> LENGTH: 15
<212> TYPE: PRT
<213> ORGANISM: Artificial Sequence
<220> FEATURE:
<223> OTHER INFORMATION: Chemically synthesized

<400> SEQUENCE: 28

```
Trp Tyr Gln Gln Lys Ser Gly Thr Ser Pro Lys Arg Trp Ile Tyr
1               5                   10                  15
```

<210> SEQ ID NO 29
<211> LENGTH: 7
<212> TYPE: PRT
<213> ORGANISM: Artificial Sequence
<220> FEATURE:
<223> OTHER INFORMATION: Chemically synthesized

<400> SEQUENCE: 29

```
Asp Thr Ser Lys Leu Ala Ser
1               5
```

<210> SEQ ID NO 30
<211> LENGTH: 32
<212> TYPE: PRT
<213> ORGANISM: Artificial Sequence
<220> FEATURE:
<223> OTHER INFORMATION: Chemically synthesized

<400> SEQUENCE: 30

```
Gly Val Pro Ala Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30
```

<210> SEQ ID NO 31
<211> LENGTH: 9
<212> TYPE: PRT
<213> ORGANISM: Artificial Sequence
<220> FEATURE:
<223> OTHER INFORMATION: Chemically synthesized

<400> SEQUENCE: 31

```
Gln Gln Trp Ser Arg Asn Pro Pro Thr
1               5
```

<210> SEQ ID NO 32
<211> LENGTH: 10

<212> TYPE: PRT
<213> ORGANISM: Artificial Sequence
<220> FEATURE:
<223> OTHER INFORMATION: Chemically synthesized

<400> SEQUENCE: 32

Phe Gly Gly Gly Thr Lys Leu Glu Ile Lys
1               5                   10

<210> SEQ ID NO 33
<211> LENGTH: 69
<212> TYPE: DNA
<213> ORGANISM: Artificial Sequence
<220> FEATURE:
<223> OTHER INFORMATION: Chemically synthesized

<400> SEQUENCE: 33
atgacattga acgtgctgtt ggggctgaag tgggttttct ttgttgtttt ttatcaaggt     60
gtgcattgt     69

<210> SEQ ID NO 34
<211> LENGTH: 90
<212> TYPE: DNA
<213> ORGANISM: Artificial Sequence
<220> FEATURE:
<223> OTHER INFORMATION: Chemically synthesized

<400> SEQUENCE: 34
gaggtgcacc ttgttgagtc tggtggagga ttggtgcagc ctaaagggtc attgaaactc     60
tcatgtgcag cctctggatt caccttcaat     90

<210> SEQ ID NO 35
<211> LENGTH: 57
<212> TYPE: DNA
<213> ORGANISM: Artificial Sequence
<220> FEATURE:
<223> OTHER INFORMATION: Chemically synthesized

<400> SEQUENCE: 35
cgcataagaa gtaaaagtaa taattatgca acatattatg ccgattcagt gaaagac     57

<210> SEQ ID NO 36
<211> LENGTH: 96
<212> TYPE: DNA
<213> ORGANISM: Artificial Sequence
<220> FEATURE:
<223> OTHER INFORMATION: Chemically synthesized

<400> SEQUENCE: 36
aggttcacca tctccagaga tgattcacaa agcatgctct atctgcaaat gaacaacttg     60
aaaactgagg acacagccat gtattactgt gtgaga     96

<210> SEQ ID NO 37
<211> LENGTH: 33
<212> TYPE: DNA
<213> ORGANISM: Artificial Sequence
<220> FEATURE:
<223> OTHER INFORMATION: Chemically synthesized

<400> SEQUENCE: 37
tggggccaag gcaccacact cacagtctcc tca     33

<210> SEQ ID NO 38
<211> LENGTH: 23

<212> TYPE: PRT
<213> ORGANISM: Artificial Sequence
<220> FEATURE:
<223> OTHER INFORMATION: Chemically synthesized

<400> SEQUENCE: 38

Met Thr Leu Asn Val Leu Leu Gly Leu Lys Trp Val Phe Phe Val Val
1 5 10 15

Phe Tyr Gln Gly Val His Cys
20

<210> SEQ ID NO 39
<211> LENGTH: 30
<212> TYPE: PRT
<213> ORGANISM: Artificial Sequence
<220> FEATURE:
<223> OTHER INFORMATION: Chemically synthesized

<400> SEQUENCE: 39

Glu Val His Leu Val Glu Ser Gly Gly Gly Leu Val Gln Pro Lys Gly
1 5 10 15

Ser Leu Lys Leu Ser Cys Ala Ala Ser Gly Phe Thr Phe Asn
20 25 30

<210> SEQ ID NO 40
<211> LENGTH: 19
<212> TYPE: PRT
<213> ORGANISM: Artificial Sequence
<220> FEATURE:
<223> OTHER INFORMATION: Chemically synthesized

<400> SEQUENCE: 40

Arg Ile Arg Ser Lys Ser Asn Asn Tyr Ala Thr Tyr Tyr Ala Asp Ser
1 5 10 15

Val Lys Asp

<210> SEQ ID NO 41
<211> LENGTH: 32
<212> TYPE: PRT
<213> ORGANISM: Artificial Sequence
<220> FEATURE:
<223> OTHER INFORMATION: Chemically synthesized

<400> SEQUENCE: 41

Arg Phe Thr Ile Ser Arg Asp Asp Ser Gln Ser Met Leu Tyr Leu Gln
1 5 10 15

Met Asn Asn Leu Lys Thr Glu Asp Thr Ala Met Tyr Tyr Cys Val Arg
20 25 30

<210> SEQ ID NO 42
<211> LENGTH: 45
<212> TYPE: DNA
<213> ORGANISM: Artificial Sequence
<220> FEATURE:
<223> OTHER INFORMATION: Chemically synthesized

<400> SEQUENCE: 42
tggtaccagc agaagtcagg cacctccccc aaaagatgga tttat 45

<210> SEQ ID NO 43
<211> LENGTH: 21
<212> TYPE: DNA
<213> ORGANISM: Artificial Sequence
<220> FEATURE:
<223> OTHER INFORMATION: Chemically synthesized

<400> SEQUENCE: 43
gacacatcca aactggcttc t 21

<210> SEQ ID NO 44
<211> LENGTH: 27
<212> TYPE: DNA
<213> ORGANISM: Artificial Sequence
<220> FEATURE:
<223> OTHER INFORMATION: Chemically synthesized

<400> SEQUENCE: 44
cagcagtgga gtagtaaccc acccacg 27

<210> SEQ ID NO 45
<211> LENGTH: 30
<212> TYPE: DNA
<213> ORGANISM: Artificial Sequence
<220> FEATURE:
<223> OTHER INFORMATION: Chemically synthesized

<400> SEQUENCE: 45
ttcggagggg ggaccaagct ggaaataaga 30

<210> SEQ ID NO 46
<211> LENGTH: 10
<212> TYPE: PRT
<213> ORGANISM: Artificial Sequence
<220> FEATURE:
<223> OTHER INFORMATION: Chemically synthesized

<400> SEQUENCE: 46

Ser Ala Ser Ser Ser Val Thr Tyr Met His
1 5 10

<210> SEQ ID NO 47
<211> LENGTH: 10
<212> TYPE: PRT
<213> ORGANISM: Artificial Sequence
<220> FEATURE:
<223> OTHER INFORMATION: Chemically synthesized

<400> SEQUENCE: 47

Phe Gly Gly Gly Thr Lys Leu Glu Ile Arg
1 5 10

<210> SEQ ID NO 48
<211> LENGTH: 57
<212> TYPE: DNA
<213> ORGANISM: Artificial Sequence
<220> FEATURE:
<223> OTHER INFORMATION: Chemically synthesized

<400> SEQUENCE: 48
atgaacttcg ggctcagctt gattttcctt gtccttgttt taaaaggtgt ccagtgt 57

<210> SEQ ID NO 49
<211> LENGTH: 90
<212> TYPE: DNA
<213> ORGANISM: Artificial Sequence
<220> FEATURE:
<223> OTHER INFORMATION: Chemically synthesized

<400> SEQUENCE: 49
gaagtgatgc tggtggagtc tgggggaggc ttagtgaagt ctggagggtc cctaaaactc 60
tcctgtgcag cctctggatt cactttcagt 90

<210> SEQ ID NO 50
<211> LENGTH: 15
<212> TYPE: DNA
<213> ORGANISM: Artificial Sequence
<220> FEATURE:
<223> OTHER INFORMATION: Chemically synthesized

<400> SEQUENCE: 50
agctatgcca tgtct 15

<210> SEQ ID NO 51
<211> LENGTH: 42
<212> TYPE: DNA
<213> ORGANISM: Artificial Sequence
<220> FEATURE:
<223> OTHER INFORMATION: Chemically synthesized

<400> SEQUENCE: 51
tgggttcgcc agactccgga gaagaggctg gagtgggtcg ca 42

<210> SEQ ID NO 52
<211> LENGTH: 51
<212> TYPE: DNA
<213> ORGANISM: Artificial Sequence
<220> FEATURE:
<223> OTHER INFORMATION: Chemically synthesized

<400> SEQUENCE: 52
actattagta ctggtggtgg ttacacctac tatccagaca gtgtgaaggg g 51

<210> SEQ ID NO 53
<211> LENGTH: 96
<212> TYPE: DNA
<213> ORGANISM: Artificial Sequence
<220> FEATURE:
<223> OTHER INFORMATION: Chemically synthesized

<400> SEQUENCE: 53
cgattcacca tctccagaga caatgccaag aacaccctgt acctgcaaat gagcagtctg 60
aggtctgagg acacggccat gtattattgt gtaaga 96

<210> SEQ ID NO 54
<211> LENGTH: 30
<212> TYPE: DNA
<213> ORGANISM: Artificial Sequence
<220> FEATURE:
<223> OTHER INFORMATION: Chemically synthesized

<400> SEQUENCE: 54
agggggacgg ctagagggta cttcgatgtc 30

<210> SEQ ID NO 55
<211> LENGTH: 33
<212> TYPE: DNA
<213> ORGANISM: Artificial Sequence
<220> FEATURE:
<223> OTHER INFORMATION: Chemically synthesized

<400> SEQUENCE: 55
tggggcgcag ggaccacggt caccgtctcc tca 33

<210> SEQ ID NO 56
<211> LENGTH: 19

<212> TYPE: PRT
<213> ORGANISM: Artificial Sequence
<220> FEATURE:
<223> OTHER INFORMATION: Chemically synthesized

<400> SEQUENCE: 56

Met Asn Phe Gly Leu Ser Leu Ile Phe Leu Val Leu Val Leu Lys Gly
1               5                   10                  15

Val Gln Cys

<210> SEQ ID NO 57
<211> LENGTH: 30
<212> TYPE: PRT
<213> ORGANISM: Artificial Sequence
<220> FEATURE:
<223> OTHER INFORMATION: Chemically synthesized

<400> SEQUENCE: 57

Glu Val Met Leu Val Glu Ser Gly Gly Gly Leu Val Lys Ser Gly Gly
1               5                   10                  15

Ser Leu Lys Leu Ser Cys Ala Ala Ser Gly Phe Thr Phe Ser
            20                  25                  30

<210> SEQ ID NO 58
<211> LENGTH: 5
<212> TYPE: PRT
<213> ORGANISM: Artificial Sequence
<220> FEATURE:
<223> OTHER INFORMATION: Chemically synthesized

<400> SEQUENCE: 58

Ser Tyr Ala Met Ser
1               5

<210> SEQ ID NO 59
<211> LENGTH: 14
<212> TYPE: PRT
<213> ORGANISM: Artificial Sequence
<220> FEATURE:
<223> OTHER INFORMATION: Chemically synthesized

<400> SEQUENCE: 59

Trp Val Arg Gln Thr Pro Glu Lys Arg Leu Glu Trp Val Ala
1               5                   10

<210> SEQ ID NO 60
<211> LENGTH: 17
<212> TYPE: PRT
<213> ORGANISM: Artificial Sequence
<220> FEATURE:
<223> OTHER INFORMATION: Chemically synthesized

<400> SEQUENCE: 60

Thr Ile Ser Thr Gly Gly Gly Tyr Thr Tyr Tyr Pro Asp Ser Val Lys
1               5                   10                  15

Gly

<210> SEQ ID NO 61
<211> LENGTH: 32
<212> TYPE: PRT
<213> ORGANISM: Artificial Sequence
<220> FEATURE:
<223> OTHER INFORMATION: Chemically synthesized

<400> SEQUENCE: 61

Arg Phe Thr Ile Ser Arg Asp Asn Ala Lys Asn Thr Leu Tyr Leu Gln
1               5                   10                  15

Met Ser Ser Leu Arg Ser Glu Asp Thr Ala Met Tyr Tyr Cys Val Arg
            20                  25                  30

<210> SEQ ID NO 62
<211> LENGTH: 10
<212> TYPE: PRT
<213> ORGANISM: Artificial Sequence
<220> FEATURE:
<223> OTHER INFORMATION: Chemically synthesized

<400> SEQUENCE: 62

Arg Gly Thr Ala Arg Gly Tyr Phe Asp Val
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Chemically synthesized

<400> SEQUENCE: 63

Trp Gly Ala Gly Thr Thr Val Thr Val Ser Ser
1               5                   10

<210> SEQ ID NO 64
<211> LENGTH: 66
<212> TYPE: DNA
<213> ORGANISM: Artificial Sequence
<220> FEATURE:
<223> OTHER INFORMATION: Chemically synthesized

<400> SEQUENCE: 64 atggatttc aagtgcagat tttcagcttc ctgctaatca gtgcctcagt catactgtcc     60
agagga                                                                66

<210> SEQ ID NO 65
<211> LENGTH: 45
<212> TYPE: DNA
<213> ORGANISM: Artificial Sequence
<220> FEATURE:
<223> OTHER INFORMATION: Chemically synthesized

<400> SEQUENCE: 65
tggtaccagc agaagccaga atcctccccc agactcctga tttat                     45

<210> SEQ ID NO 66
<211> LENGTH: 21
<212> TYPE: DNA
<213> ORGANISM: Artificial Sequence
<220> FEATURE:
<223> OTHER INFORMATION: Chemically synthesized

<400> SEQUENCE: 66
gacacatcca acctggcttc t                                               21

<210> SEQ ID NO 67
<211> LENGTH: 96
<212> TYPE: DNA
<213> ORGANISM: Artificial Sequence
<220> FEATURE:
<223> OTHER INFORMATION: Chemically synthesized

<400> SEQUENCE: 67
ggagtccctg ttcgcttcag tggcagtggg tctgggacct cttattttct cacaatcagc 60
cgaatggagg ctgaagatgc tgccacttat tactgc 96

<210> SEQ ID NO 68
<211> LENGTH: 27
<212> TYPE: DNA
<213> ORGANISM: Artificial Sequence
<220> FEATURE:
<223> OTHER INFORMATION: Chemically synthesized

<400> SEQUENCE: 68
cagcagtgga agacttaccc acccacg 27

<210> SEQ ID NO 69
<211> LENGTH: 22
<212> TYPE: PRT
<213> ORGANISM: Artificial Sequence
<220> FEATURE:
<223> OTHER INFORMATION: Chemically synthesized

<400> SEQUENCE: 69

Met Asp Phe Gln Val Gln Ile Phe Ser Phe Leu Leu Ile Ser Ala Ser
1 5 10 15

Val Ile Leu Ser Arg Gly
20

<210> SEQ ID NO 70
<211> LENGTH: 10
<212> TYPE: PRT
<213> ORGANISM: Artificial Sequence
<220> FEATURE:
<223> OTHER INFORMATION: Chemically synthesized

<400> SEQUENCE: 70

Ser Ala Ser Ser Ser Val Ser Tyr Met Tyr
1 5 10

<210> SEQ ID NO 71
<211> LENGTH: 15
<212> TYPE: PRT
<213> ORGANISM: Artificial Sequence
<220> FEATURE:
<223> OTHER INFORMATION: Chemically synthesized

<400> SEQUENCE: 71

Trp Tyr Gln Gln Lys Pro Glu Ser Ser Pro Arg Leu Leu Ile Tyr
1 5 10 15

<210> SEQ ID NO 72
<211> LENGTH: 7
<212> TYPE: PRT
<213> ORGANISM: Artificial Sequence
<220> FEATURE:
<223> OTHER INFORMATION: Chemically synthesized

<400> SEQUENCE: 72

Asp Thr Ser Asn Leu Ala Ser
1 5

<210> SEQ ID NO 73
<211> LENGTH: 32
<212> TYPE: PRT
<213> ORGANISM: Artificial Sequence
<220> FEATURE:
<223> OTHER INFORMATION: Chemically synthesized

<400> SEQUENCE: 73

Gly Val Pro Val Arg Phe Ser Gly Ser Gly Ser Gly Thr Ser Tyr Phe
1               5                   10                  15

Leu Thr Ile Ser Arg Met Glu Ala Glu Asp Ala Ala Thr Tyr Tyr Cys
            20                  25                  30

<210> SEQ ID NO 74
<211> LENGTH: 90
<212> TYPE: DNA
<213> ORGANISM: Artificial Sequence
<220> FEATURE:
<223> OTHER INFORMATION: Chemically synthesized

<400> SEQUENCE: 74
gaagtgatgc tggtggagtc tgggggaggc ttagtgaagc ctggagggtc cctgaaactc     60
tcctgtgcag cctctggatt cactttcagt                                      90

<210> SEQ ID NO 75
<211> LENGTH: 51
<212> TYPE: DNA
<213> ORGANISM: Artificial Sequence
<220> FEATURE:
<223> OTHER INFORMATION: Chemically synthesized

<400> SEQUENCE: 75
accattagta ctggtggtgg ttacacctac tatccagaca gtgtgaaggg g              51

<210> SEQ ID NO 76
<211> LENGTH: 96
<212> TYPE: DNA
<213> ORGANISM: Artificial Sequence
<220> FEATURE:
<223> OTHER INFORMATION: Chemically synthesized

<400> SEQUENCE: 76
cgattcaccg tctccagaga caatgccaag aacaccctgt acctgcaaat gagcagtctg     60
aggtctgagg acacggccat gtattactgt gcaaga                               96

<210> SEQ ID NO 77
<211> LENGTH: 30
<212> TYPE: DNA
<213> ORGANISM: Artificial Sequence
<220> FEATURE:
<223> OTHER INFORMATION: Chemically synthesized

<400> SEQUENCE: 77 aggggacgt ctagagggta cttcgatgtc                                       30

<210> SEQ ID NO 78
<211> LENGTH: 33
<212> TYPE: DNA
<213> ORGANISM: Artificial Sequence
<220> FEATURE:
<223> OTHER INFORMATION: Chemically synthesized

<400> SEQUENCE: 78
tggggcgcag ggactacggt caccgtctcc tca                                  33

<210> SEQ ID NO 79
<211> LENGTH: 30
<212> TYPE: PRT
<213> ORGANISM: Artificial Sequence
<220> FEATURE:

<223> OTHER INFORMATION: Chemically synthesized

<400> SEQUENCE: 79

Glu Val Met Leu Val Glu Ser Gly Gly Gly Leu Val Lys Pro Gly Gly
1 5 10 15

Ser Leu Lys Leu Ser Cys Ala Ala Ser Gly Phe Thr Phe Ser
20 25 30

<210> SEQ ID NO 80
<211> LENGTH: 32
<212> TYPE: PRT
<213> ORGANISM: Artificial Sequence
<220> FEATURE:
<223> OTHER INFORMATION: Chemically synthesized

<400> SEQUENCE: 80

Arg Phe Thr Val Ser Arg Asp Asn Ala Lys Asn Thr Leu Tyr Leu Gln
1 5 10 15

Met Ser Ser Leu Arg Ser Glu Asp Thr Ala Met Tyr Tyr Cys Ala Arg
20 25 30

<210> SEQ ID NO 81
<211> LENGTH: 10
<212> TYPE: PRT
<213> ORGANISM: Artificial Sequence
<220> FEATURE:
<223> OTHER INFORMATION: Chemically synthesized

<400> SEQUENCE: 81

Arg Gly Thr Ser Arg Gly Tyr Phe Asp Val
1 5 10

<210> SEQ ID NO 82
<211> LENGTH: 69
<212> TYPE: DNA
<213> ORGANISM: Artificial Sequence
<220> FEATURE:
<223> OTHER INFORMATION: Chemically synthesized

<400> SEQUENCE: 82
caaattattc tcacccagtc tccagcaatc atgtctgcat ctccagggga gaaggtcacc 60
atgacctgc 69

<210> SEQ ID NO 83
<211> LENGTH: 30
<212> TYPE: DNA
<213> ORGANISM: Artificial Sequence
<220> FEATURE:
<223> OTHER INFORMATION: Chemically synthesized

<400> SEQUENCE: 83
ttcggagggg ggaccaggct ggaaataaaa 30

<210> SEQ ID NO 84
<211> LENGTH: 23
<212> TYPE: PRT
<213> ORGANISM: Artificial Sequence
<220> FEATURE:
<223> OTHER INFORMATION: Chemically synthesized

<400> SEQUENCE: 84

Gln Ile Ile Leu Thr Gln Ser Pro Ala Ile Met Ser Ala Ser Pro Gly
1 5 10 15

Glu Lys Val Thr Met Thr Cys

20

<210> SEQ ID NO 85
<211> LENGTH: 9
<212> TYPE: PRT
<213> ORGANISM: Artificial Sequence
<220> FEATURE:
<223> OTHER INFORMATION: Chemically synthesized

<400> SEQUENCE: 85

Gln Gln Trp Lys Thr Tyr Pro Pro Thr
1 5

<210> SEQ ID NO 86
<211> LENGTH: 10
<212> TYPE: PRT
<213> ORGANISM: Artificial Sequence
<220> FEATURE:
<223> OTHER INFORMATION: Chemically synthesized

<400> SEQUENCE: 86

Phe Gly Gly Gly Thr Arg Leu Glu Ile Lys
1 5 10

<210> SEQ ID NO 87
<211> LENGTH: 90
<212> TYPE: DNA
<213> ORGANISM: Artificial Sequence
<220> FEATURE:
<223> OTHER INFORMATION: Chemically synthesized

<400> SEQUENCE: 87
gaagtgatga tggtggagtc tgggggaggc ttagtgaagc ctggagggtc cctgaaactc 60
tcctgtgcag cctctggatt cactttcagt 90

<210> SEQ ID NO 88
<211> LENGTH: 15
<212> TYPE: DNA
<213> ORGANISM: Artificial Sequence
<220> FEATURE:
<223> OTHER INFORMATION: Chemically synthesized

<400> SEQUENCE: 88
aactatgcca tgtct 15

<210> SEQ ID NO 89
<211> LENGTH: 51
<212> TYPE: DNA
<213> ORGANISM: Artificial Sequence
<220> FEATURE:
<223> OTHER INFORMATION: Chemically synthesized

<400> SEQUENCE: 89
acgattagta ctggtggtgg ttacacctac tatccagaca gtatgaaggg g 51

<210> SEQ ID NO 90
<211> LENGTH: 96
<212> TYPE: DNA
<213> ORGANISM: Artificial Sequence
<220> FEATURE:
<223> OTHER INFORMATION: Chemically synthesized

<400> SEQUENCE: 90
cgattcacca tctccagaga caatgccaag aacaccctgt acctgcaaat gagcagtctg 60
aggtctgagg acacggccat gtattactgt gcaaga 96

<210> SEQ ID NO 91
<211> LENGTH: 30
<212> TYPE: PRT
<213> ORGANISM: Artificial Sequence
<220> FEATURE:
<223> OTHER INFORMATION: Chemically synthesized

<400> SEQUENCE: 91

Glu Val Met Met Val Glu Ser Gly Gly Gly Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 92
<211> LENGTH: 5
<212> TYPE: PRT
<213> ORGANISM: Artificial Sequence
<220> FEATURE:
<223> OTHER INFORMATION: Chemically synthesized

<400> SEQUENCE: 92

Asn Tyr Ala Met Ser
1               5

<210> SEQ ID NO 93
<211> LENGTH: 17
<212> TYPE: PRT
<213> ORGANISM: Artificial Sequence
<220> FEATURE:
<223> OTHER INFORMATION: Chemically synthesized

<400> SEQUENCE: 93

Thr Ile Ser Thr Gly Gly Gly Tyr Thr Tyr Tyr Pro Asp Ser Met Lys
1               5                   10                  15

Gly

<210> SEQ ID NO 94
<211> LENGTH: 32
<212> TYPE: PRT
<213> ORGANISM: Artificial Sequence
<220> FEATURE:
<223> OTHER INFORMATION: Chemically synthesized

<400> SEQUENCE: 94

Arg Phe Thr Ile Ser Arg Asp Asn Ala Lys Asn Thr Leu Tyr Leu Gln
1               5                   10                  15

Met Ser Ser Leu Arg Ser Glu Asp Thr Ala Met Tyr Tyr Cys Ala Arg
            20                  25                  30

<210> SEQ ID NO 95
<211> LENGTH: 96
<212> TYPE: DNA
<213> ORGANISM: Artificial Sequence
<220> FEATURE:
<223> OTHER INFORMATION: Chemically synthesized

<400> SEQUENCE: 95
ggagtccctg ttcgcttcag tggcagtggg tctgggacct cttattttct cacaatcagc     60
cgaatggagg ctgaagatgc tgccacttat tattgc                               96

<210> SEQ ID NO 96
<211> LENGTH: 27
<212> TYPE: DNA

<213> ORGANISM: Artificial Sequence
<220> FEATURE:
<223> OTHER INFORMATION: Chemically synthesized

<400> SEQUENCE: 96
caacagtgga agacttaccc acccacg 27

<210> SEQ ID NO 97
<211> LENGTH: 15
<212> TYPE: DNA
<213> ORGANISM: Artificial Sequence
<220> FEATURE:
<223> OTHER INFORMATION: Chemically synthesized

<400> SEQUENCE: 97
cgctatgcca tgtct 15

<210> SEQ ID NO 98
<211> LENGTH: 42
<212> TYPE: DNA
<213> ORGANISM: Artificial Sequence
<220> FEATURE:
<223> OTHER INFORMATION: Chemically synthesized

<400> SEQUENCE: 98
tgggttcgac agactccgga gaagaggctg gagtgggtcg ca 42

<210> SEQ ID NO 99
<211> LENGTH: 51
<212> TYPE: DNA
<213> ORGANISM: Artificial Sequence
<220> FEATURE:
<223> OTHER INFORMATION: Chemically synthesized

<400> SEQUENCE: 99
accactagta ttggtggtgg ttacacctac tatcttgaca gtgtgaaggg g 51

<210> SEQ ID NO 100
<211> LENGTH: 96
<212> TYPE: DNA
<213> ORGANISM: Artificial Sequence
<220> FEATURE:
<223> OTHER INFORMATION: Chemically synthesized

<400> SEQUENCE: 100
cgattcacca tctccagaga caatgtcgag aataccctat acctgcaaat gaccagtctg 60
aggtctgagg acacggccat gtatttctgt acaaga 96

<210> SEQ ID NO 101
<211> LENGTH: 5
<212> TYPE: PRT
<213> ORGANISM: Artificial Sequence
<220> FEATURE:
<223> OTHER INFORMATION: Chemically synthesized

<400> SEQUENCE: 101

Arg Tyr Ala Met Ser
1               5

<210> SEQ ID NO 102
<211> LENGTH: 17
<212> TYPE: PRT
<213> ORGANISM: Artificial Sequence
<220> FEATURE:
<223> OTHER INFORMATION: Chemically synthesized

<400> SEQUENCE: 102

Thr Thr Ser Ile Gly Gly Gly Tyr Thr Tyr Tyr Leu Asp Ser Val Lys
1               5                   10                  15

Gly

<210> SEQ ID NO 103
<211> LENGTH: 32
<212> TYPE: PRT
<213> ORGANISM: Artificial Sequence
<220> FEATURE:
<223> OTHER INFORMATION: Chemically synthesized

<400> SEQUENCE: 103

Arg Phe Thr Ile Ser Arg Asp Asn Val Glu Asn Thr Leu Tyr Leu Gln
1               5                   10                  15

Met Thr Ser Leu Arg Ser Glu Asp Thr Ala Met Tyr Phe Cys Thr Arg
            20                  25                  30

<210> SEQ ID NO 104
<211> LENGTH: 60
<212> TYPE: DNA
<213> ORGANISM: Artificial Sequence
<220> FEATURE:
<223> OTHER INFORMATION: Chemically synthesized

<400> SEQUENCE: 104
atggagacac attctcaggt ctttgtatac atgttgctgt ggttgtctgg tgttgaagga     60

<210> SEQ ID NO 105
<211> LENGTH: 69
<212> TYPE: DNA
<213> ORGANISM: Artificial Sequence
<220> FEATURE:
<223> OTHER INFORMATION: Chemically synthesized

<400> SEQUENCE: 105
gacattgtga tgacccagtc tcacaaattc atgtccacat cagtaggaga cagggtcagc     60
atcacctgc                                                             69

<210> SEQ ID NO 106
<211> LENGTH: 33
<212> TYPE: DNA
<213> ORGANISM: Artificial Sequence
<220> FEATURE:
<223> OTHER INFORMATION: Chemically synthesized

<400> SEQUENCE: 106
aaggccagtc aggatgtggg tactgctgta gcc                                  33

<210> SEQ ID NO 107
<211> LENGTH: 45
<212> TYPE: DNA
<213> ORGANISM: Artificial Sequence
<220> FEATURE:
<223> OTHER INFORMATION: Chemically synthesized

<400> SEQUENCE: 107
tggtatcaac agaaaccagg gcaatctcct aaactactga tttac                     45

<210> SEQ ID NO 108
<211> LENGTH: 21
<212> TYPE: DNA
<213> ORGANISM: Artificial Sequence
<220> FEATURE:

<223> OTHER INFORMATION: Chemically synthesized

<400> SEQUENCE: 108
tgggcatcca cccggcacac t 21

<210> SEQ ID NO 109
<211> LENGTH: 96
<212> TYPE: DNA
<213> ORGANISM: Artificial Sequence
<220> FEATURE:
<223> OTHER INFORMATION: Chemically synthesized

<400> SEQUENCE: 109
ggagtccctg atcgcttcac aggcagtgga tctgggacag atttcactct caccattagc 60
aatgtgcagt ctgaagactt ggcagattat ttctgt 96

<210> SEQ ID NO 110
<211> LENGTH: 27
<212> TYPE: DNA
<213> ORGANISM: Artificial Sequence
<220> FEATURE:
<223> OTHER INFORMATION: Chemically synthesized

<400> SEQUENCE: 110
cagcaatata gcagctatcc tctcacg 27

<210> SEQ ID NO 111
<211> LENGTH: 30
<212> TYPE: DNA
<213> ORGANISM: Artificial Sequence
<220> FEATURE:
<223> OTHER INFORMATION: Chemically synthesized

<400> SEQUENCE: 111
ttcggtgctg ggaccaagct ggagctgaaa 30

<210> SEQ ID NO 112
<211> LENGTH: 20
<212> TYPE: PRT
<213> ORGANISM: Artificial Sequence
<220> FEATURE:
<223> OTHER INFORMATION: Chemically synthesized

<400> SEQUENCE: 112

```
Met Glu Thr His Ser Gln Val Phe Val Tyr Met Leu Leu Trp Leu Ser
1               5                   10                  15

Gly Val Glu Gly
            20
```

<210> SEQ ID NO 113
<211> LENGTH: 23
<212> TYPE: PRT
<213> ORGANISM: Artificial Sequence
<220> FEATURE:
<223> OTHER INFORMATION: Chemically synthesized

<400> SEQUENCE: 113

```
Asp Ile Val Met Thr Gln Ser His Lys Phe Met Ser Thr Ser Val Gly
1               5                   10                  15

Asp Arg Val Ser Ile Thr Cys
            20
```

<210> SEQ ID NO 114
<211> LENGTH: 11

<212> TYPE: PRT
<213> ORGANISM: Artificial Sequence
<220> FEATURE:
<223> OTHER INFORMATION: Chemically synthesized

<400> SEQUENCE: 114

Lys Ala Ser Gln Asp Val Gly Thr Ala Val Ala
1 5 10

<210> SEQ ID NO 115
<211> LENGTH: 15
<212> TYPE: PRT
<213> ORGANISM: Artificial Sequence
<220> FEATURE:
<223> OTHER INFORMATION: Chemically synthesized

<400> SEQUENCE: 115

Trp Tyr Gln Gln Lys Pro Gly Gln Ser Pro Lys Leu Leu Ile Tyr
1 5 10 15

<210> SEQ ID NO 116
<211> LENGTH: 7
<212> TYPE: PRT
<213> ORGANISM: Artificial Sequence
<220> FEATURE:
<223> OTHER INFORMATION: Chemically synthesized

<400> SEQUENCE: 116

Trp Ala Ser Thr Arg His Thr
1 5

<210> SEQ ID NO 117
<211> LENGTH: 32
<212> TYPE: PRT
<213> ORGANISM: Artificial Sequence
<220> FEATURE:
<223> OTHER INFORMATION: Chemically synthesized

<400> SEQUENCE: 117

Gly Val Pro Asp Arg Phe Thr Gly Ser Gly Ser Gly Thr Asp Phe Thr
1 5 10 15

Leu Thr Ile Ser Asn Val Gln Ser Glu Asp Leu Ala Asp Tyr Phe Cys
20 25 30

<210> SEQ ID NO 118
<211> LENGTH: 9
<212> TYPE: PRT
<213> ORGANISM: Artificial Sequence
<220> FEATURE:
<223> OTHER INFORMATION: Chemically synthesized

<400> SEQUENCE: 118

Gln Gln Tyr Ser Ser Tyr Pro Leu Thr
1 5

<210> SEQ ID NO 119
<211> LENGTH: 10
<212> TYPE: PRT
<213> ORGANISM: Artificial Sequence
<220> FEATURE:
<223> OTHER INFORMATION: Chemically synthesized

<400> SEQUENCE: 119

Phe Gly Ala Gly Thr Lys Leu Glu Leu Lys
1 5 10

<210> SEQ ID NO 120
<211> LENGTH: 69
<212> TYPE: DNA
<213> ORGANISM: Artificial Sequence
<220> FEATURE:
<223> OTHER INFORMATION: Chemically synthesized

<400> SEQUENCE: 120
caaattgttc tcacccagtc tccagcaatc atgtctgcat ctccagggga caaggtcacc 60
atgacctgc 69

<210> SEQ ID NO 121
<211> LENGTH: 30
<212> TYPE: DNA
<213> ORGANISM: Artificial Sequence
<220> FEATURE:
<223> OTHER INFORMATION: Chemically synthesized

<400> SEQUENCE: 121
agtgccacct caagtgtaag ttacatgtac 30

<210> SEQ ID NO 122
<211> LENGTH: 45
<212> TYPE: DNA
<213> ORGANISM: Artificial Sequence
<220> FEATURE:
<223> OTHER INFORMATION: Chemically synthesized

<400> SEQUENCE: 122
tggtaccagc agaagccagg atcctccccc agactcctga tttat 45

<210> SEQ ID NO 123
<211> LENGTH: 96
<212> TYPE: DNA
<213> ORGANISM: Artificial Sequence
<220> FEATURE:
<223> OTHER INFORMATION: Chemically synthesized

<400> SEQUENCE: 123
ggagtccctg ttcgcttcag tggcagtggg tctgggacct cttactctct cacaatcagc 60
cgaatggagc ctgaagatgc tgcctcttat tactgc 96

<210> SEQ ID NO 124
<211> LENGTH: 30
<212> TYPE: DNA
<213> ORGANISM: Artificial Sequence
<220> FEATURE:
<223> OTHER INFORMATION: Chemically synthesized

<400> SEQUENCE: 124
ttcggctcgg ggacaaagtt ggaaataaaa 30

<210> SEQ ID NO 125
<211> LENGTH: 23
<212> TYPE: PRT
<213> ORGANISM: Artificial Sequence
<220> FEATURE:
<223> OTHER INFORMATION: Chemically synthesized

<400> SEQUENCE: 125

Gln Ile Val Leu Thr Gln Ser Pro Ala Ile Met Ser Ala Ser Pro Gly
1 5 10 15

Asp Lys Val Thr Met Thr Cys
20

<210> SEQ ID NO 126
<211> LENGTH: 10
<212> TYPE: PRT
<213> ORGANISM: Artificial Sequence
<220> FEATURE:
<223> OTHER INFORMATION: Chemically synthesized

<400> SEQUENCE: 126

```
Ser Ala Thr Ser Ser Val Ser Tyr Met Tyr
1               5                   10
```

<210> SEQ ID NO 127
<211> LENGTH: 15
<212> TYPE: PRT
<213> ORGANISM: Artificial Sequence
<220> FEATURE:
<223> OTHER INFORMATION: Chemically synthesized

<400> SEQUENCE: 127

```
Trp Tyr Gln Gln Lys Pro Gly Ser Ser Pro Arg Leu Leu Ile Tyr
1               5                   10                  15
```

<210> SEQ ID NO 128
<211> LENGTH: 32
<212> TYPE: PRT
<213> ORGANISM: Artificial Sequence
<220> FEATURE:
<223> OTHER INFORMATION: Chemically synthesized

<400> SEQUENCE: 128

```
Gly Val Pro Val Arg Phe Ser Gly Ser Gly Ser Gly Thr Ser Tyr Ser
1               5                   10                  15

Leu Thr Ile Ser Arg Met Glu Pro Glu Asp Ala Ala Ser Tyr Tyr Cys
            20                  25                  30
```

<210> SEQ ID NO 129
<211> LENGTH: 9
<212> TYPE: PRT
<213> ORGANISM: Artificial Sequence
<220> FEATURE:
<223> OTHER INFORMATION: Chemically synthesized

<400> SEQUENCE: 129

```
Gln Gln Trp Lys Ser Tyr Pro Pro Thr
1               5
```

<210> SEQ ID NO 130
<211> LENGTH: 10
<212> TYPE: PRT
<213> ORGANISM: Artificial Sequence
<220> FEATURE:
<223> OTHER INFORMATION: Chemically synthesized

<400> SEQUENCE: 130

```
Phe Gly Ser Gly Thr Lys Leu Glu Ile Lys
1               5                   10
```

<210> SEQ ID NO 131
<211> LENGTH: 90
<212> TYPE: DNA
<213> ORGANISM: Artificial Sequence
<220> FEATURE:
<223> OTHER INFORMATION: Chemically synthesized

<400> SEQUENCE: 131

```
gaggtacacc ttgttgagtc tggtggagga ttggtgcagc ctaaagggtc attgaaactc     60
```

tcatgtgcag cctctggatt caccttcaat 90

<210> SEQ ID NO 132
<211> LENGTH: 57
<212> TYPE: DNA
<213> ORGANISM: Artificial Sequence
<220> FEATURE:
<223> OTHER INFORMATION: Chemically synthesized

<400> SEQUENCE: 132
cgcataagaa ataaaagtaa taattatgca acatattatg ccgattcagt gaaagac 57

<210> SEQ ID NO 133
<211> LENGTH: 96
<212> TYPE: DNA
<213> ORGANISM: Artificial Sequence
<220> FEATURE:
<223> OTHER INFORMATION: Chemically synthesized

<400> SEQUENCE: 133
aggttcacca tctccagaga tgattcacaa agcatgctct ttctgcaaat ggacaacttg 60
aaaactgagg acacagccat atattactgt gtgaga 96

<210> SEQ ID NO 134
<211> LENGTH: 19
<212> TYPE: PRT
<213> ORGANISM: Artificial Sequence
<220> FEATURE:
<223> OTHER INFORMATION: Chemically synthesized

<400> SEQUENCE: 134

Arg Ile Arg Asn Lys Ser Asn Asn Tyr Ala Thr Tyr Tyr Ala Asp Ser
1 5 10 15

Val Lys Asp

<210> SEQ ID NO 135
<211> LENGTH: 32
<212> TYPE: PRT
<213> ORGANISM: Artificial Sequence
<220> FEATURE:
<223> OTHER INFORMATION: Chemically synthesized

<400> SEQUENCE: 135

Arg Phe Thr Ile Ser Arg Asp Asp Ser Gln Ser Met Leu Phe Leu Gln
1 5 10 15

Met Asp Asn Leu Lys Thr Glu Asp Thr Ala Ile Tyr Tyr Cys Val Arg
20 25 30

<210> SEQ ID NO 136
<211> LENGTH: 57
<212> TYPE: DNA
<213> ORGANISM: Artificial Sequence
<220> FEATURE:
<223> OTHER INFORMATION: Chemically synthesized

<400> SEQUENCE: 136
atgaactttg tgctcagctt gattttcctt gccctcattt taaaaggtgt ccagtgt 57

<210> SEQ ID NO 137
<211> LENGTH: 90
<212> TYPE: DNA
<213> ORGANISM: Artificial Sequence
<220> FEATURE:
<223> OTHER INFORMATION: Chemically synthesized

<400> SEQUENCE: 137
gaagtgcagc tggtggagtc tgggggaggc ttagtgaagc ctggagggtc cctgaaactc 60
tcctgtgcag cctctggatt cactttcagt 90

<210> SEQ ID NO 138
<211> LENGTH: 15
<212> TYPE: DNA
<213> ORGANISM: Artificial Sequence
<220> FEATURE:
<223> OTHER INFORMATION: Chemically synthesized

<400> SEQUENCE: 138
gggtatgcca tgtct 15

<210> SEQ ID NO 139
<211> LENGTH: 51
<212> TYPE: DNA
<213> ORGANISM: Artificial Sequence
<220> FEATURE:
<223> OTHER INFORMATION: Chemically synthesized

<400> SEQUENCE: 139
accattagta atggtggtag ttacacctac tatccagaca gtgtgaaggg t 51

<210> SEQ ID NO 140
<211> LENGTH: 96
<212> TYPE: DNA
<213> ORGANISM: Artificial Sequence
<220> FEATURE:
<223> OTHER INFORMATION: Chemically synthesized

<400> SEQUENCE: 140
cgattcacca tctccagaga caatgccaag aagaccctgt acctgcaaat gagcagtctg 60
aggtctgagg acacggccat gtattactgt acaaga 96

<210> SEQ ID NO 141
<211> LENGTH: 30
<212> TYPE: DNA
<213> ORGANISM: Artificial Sequence
<220> FEATURE:
<223> OTHER INFORMATION: Chemically synthesized

<400> SEQUENCE: 141
cgggctgcta cgaggggata ctttgactac 30

<210> SEQ ID NO 142
<211> LENGTH: 19
<212> TYPE: PRT
<213> ORGANISM: Artificial Sequence
<220> FEATURE:
<223> OTHER INFORMATION: Chemically synthesized

<400> SEQUENCE: 142

Met Asn Phe Val Leu Ser Leu Ile Phe Leu Ala Leu Ile Leu Lys Gly
1 5 10 15

Val Gln Cys

<210> SEQ ID NO 143
<211> LENGTH: 30
<212> TYPE: PRT
<213> ORGANISM: Artificial Sequence
<220> FEATURE:
<223> OTHER INFORMATION: Chemically synthesized

<400> SEQUENCE: 143

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 144
<211> LENGTH: 5
<212> TYPE: PRT
<213> ORGANISM: Artificial Sequence
<220> FEATURE:
<223> OTHER INFORMATION: Chemically synthesized

<400> SEQUENCE: 144

Gly Tyr Ala Met Ser
1               5

<210> SEQ ID NO 145
<211> LENGTH: 17
<212> TYPE: PRT
<213> ORGANISM: Artificial Sequence
<220> FEATURE:
<223> OTHER INFORMATION: Chemically synthesized

<400> SEQUENCE: 145

Thr Ile Ser Asn Gly Gly Ser Tyr Thr Tyr Tyr Pro Asp Ser Val Lys
1               5                   10                  15

Gly

<210> SEQ ID NO 146
<211> LENGTH: 32
<212> TYPE: PRT
<213> ORGANISM: Artificial Sequence
<220> FEATURE:
<223> OTHER INFORMATION: Chemically synthesized

<400> SEQUENCE: 146

Arg Phe Thr Ile Ser Arg Asp Asn Ala Lys Lys Thr Leu Tyr Leu Gln
1               5                   10                  15

Met Ser Ser Leu Arg Ser Glu Asp Thr Ala Met Tyr Tyr Cys Thr Arg
            20                  25                  30

<210> SEQ ID NO 147
<211> LENGTH: 10
<212> TYPE: PRT
<213> ORGANISM: Artificial Sequence
<220> FEATURE:
<223> OTHER INFORMATION: Chemically synthesized

<400> SEQUENCE: 147

Arg Ala Ala Thr Arg Gly Tyr Phe Asp Tyr
1               5                   10

<210> SEQ ID NO 148
<211> LENGTH: 21
<212> TYPE: DNA
<213> ORGANISM: Artificial Sequence
<220> FEATURE:
<223> OTHER INFORMATION: Chemically synthesized

<400> SEQUENCE: 148
gacacatcca agctggcttc t                                                  21

<210> SEQ ID NO 149
<211> LENGTH: 96
<212> TYPE: DNA
<213> ORGANISM: Artificial Sequence
<220> FEATURE:
<223> OTHER INFORMATION: Chemically synthesized

<400> SEQUENCE: 149
ggcgtccctg ttcgcttcag tggcagtggg tctgggacct cttactctct cacaatcagc 60
cgaatggagg ctgaagatgc tgccacttat tactgc 96

<210> SEQ ID NO 150
<211> LENGTH: 27
<212> TYPE: DNA
<213> ORGANISM: Artificial Sequence
<220> FEATURE:
<223> OTHER INFORMATION: Chemically synthesized

<400> SEQUENCE: 150
cagcagtgga gaagttaccc acccacg 27

<210> SEQ ID NO 151
<211> LENGTH: 32
<212> TYPE: PRT
<213> ORGANISM: Artificial Sequence
<220> FEATURE:
<223> OTHER INFORMATION: Chemically synthesized

<400> SEQUENCE: 151

Gly Val Pro Val Arg Phe Ser Gly Ser Gly Ser Gly Thr Ser Tyr Ser
1 5 10 15

Leu Thr Ile Ser Arg Met Glu Ala Glu Asp Ala Ala Thr Tyr Tyr Cys
20 25 30

<210> SEQ ID NO 152
<211> LENGTH: 9
<212> TYPE: PRT
<213> ORGANISM: Artificial Sequence
<220> FEATURE:
<223> OTHER INFORMATION: Chemically synthesized

<400> SEQUENCE: 152

Gln Gln Trp Arg Ser Tyr Pro Pro Thr
1 5

<210> SEQ ID NO 153
<211> LENGTH: 90
<212> TYPE: DNA
<213> ORGANISM: Artificial Sequence
<220> FEATURE:
<223> OTHER INFORMATION: Chemically synthesized

<400> SEQUENCE: 153
gaagtgcagc tggtggagtc tgggggaggc ttagtgaagc ctggagggtc cctgaaactc 60
tcctgtggag cctctggatt cactttcagt 90

<210> SEQ ID NO 154
<211> LENGTH: 42
<212> TYPE: DNA
<213> ORGANISM: Artificial Sequence
<220> FEATURE:
<223> OTHER INFORMATION: Chemically synthesized

<400> SEQUENCE: 154
tgggttcgcc agactccgga aaagaggctg gagtgggtcg ca 42

<210> SEQ ID NO 155
<211> LENGTH: 51
<212> TYPE: DNA
<213> ORGANISM: Artificial Sequence
<220> FEATURE:
<223> OTHER INFORMATION: Chemically synthesized

<400> SEQUENCE: 155
accattagta atggtggcag ttacacctac tatccagaca gtgtgcaggg t 51

<210> SEQ ID NO 156
<211> LENGTH: 96
<212> TYPE: DNA
<213> ORGANISM: Artificial Sequence
<220> FEATURE:
<223> OTHER INFORMATION: Chemically synthesized

<400> SEQUENCE: 156
cgattcacca tctccagaga caatgccaag aacaccctgt acctgcgcat gagcagtctg 60
cggtctgagg acacggccat gtattactgt gcaaga 96

<210> SEQ ID NO 157
<211> LENGTH: 30
<212> TYPE: DNA
<213> ORGANISM: Artificial Sequence
<220> FEATURE:
<223> OTHER INFORMATION: Chemically synthesized

<400> SEQUENCE: 157
cggagtagta cgaggggctt ctttgactac 30

<210> SEQ ID NO 158
<211> LENGTH: 33
<212> TYPE: DNA
<213> ORGANISM: Artificial Sequence
<220> FEATURE:
<223> OTHER INFORMATION: Chemically synthesized

<400> SEQUENCE: 158
tggggccacg gcaccactct cacagtctcc tca 33

<210> SEQ ID NO 159
<211> LENGTH: 30
<212> TYPE: PRT
<213> ORGANISM: Artificial Sequence
<220> FEATURE:
<223> OTHER INFORMATION: Chemically synthesized

<400> SEQUENCE: 159

Glu Val Gln Leu Val Glu Ser Gly Gly Gly Leu Val Lys Pro Gly Gly
1               5                   10                  15

Ser Leu Lys Leu Ser Cys Gly Ala Ser Gly Phe Thr Phe Ser
            20                  25                  30

<210> SEQ ID NO 160
<211> LENGTH: 5
<212> TYPE: PRT
<213> ORGANISM: Artificial Sequence
<220> FEATURE:
<223> OTHER INFORMATION: Chemically synthesized

<400> SEQUENCE: 160

Ser Phe Ala Met Ser
1               5

<210> SEQ ID NO 161
<211> LENGTH: 17
<212> TYPE: PRT
<213> ORGANISM: Artificial Sequence
<220> FEATURE:
<223> OTHER INFORMATION: Chemically synthesized

<400> SEQUENCE: 161

Thr Ile Ser Asn Gly Gly Ser Tyr Thr Tyr Tyr Pro Asp Ser Val Gln
1 5 10 15

Gly

<210> SEQ ID NO 162
<211> LENGTH: 32
<212> TYPE: PRT
<213> ORGANISM: Artificial Sequence
<220> FEATURE:
<223> OTHER INFORMATION: Chemically synthesized

<400> SEQUENCE: 162

Arg Phe Thr Ile Ser Arg Asp Asn Ala Lys Asn Thr Leu Tyr Leu Arg
1 5 10 15

Met Ser Ser Leu Arg Ser Glu Asp Thr Ala Met Tyr Tyr Cys Ala Arg
20 25 30

<210> SEQ ID NO 163
<211> LENGTH: 10
<212> TYPE: PRT
<213> ORGANISM: Artificial Sequence
<220> FEATURE:
<223> OTHER INFORMATION: Chemically synthesized

<400> SEQUENCE: 163

Arg Ser Ser Thr Arg Gly Phe Phe Asp Tyr
1 5 10

<210> SEQ ID NO 164
<211> LENGTH: 11
<212> TYPE: PRT
<213> ORGANISM: Artificial Sequence
<220> FEATURE:
<223> OTHER INFORMATION: Chemically synthesized

<400> SEQUENCE: 164

Trp Gly His Gly Thr Thr Leu Thr Val Ser Ser
1 5 10

<210> SEQ ID NO 165
<211> LENGTH: 66
<212> TYPE: DNA
<213> ORGANISM: Artificial Sequence
<220> FEATURE:
<223> OTHER INFORMATION: Chemically synthesized

<400> SEQUENCE: 165
atggattttc aagtgcagat tttcagcttc ctgctaatca gtgcctcagt catactgtcc 60
cgagga 66

<210> SEQ ID NO 166
<211> LENGTH: 69
<212> TYPE: DNA
<213> ORGANISM: Artificial Sequence
<220> FEATURE:
<223> OTHER INFORMATION: Chemically synthesized

<400> SEQUENCE: 166
caaatttttc tcacccagtc tccagcaatc atgtctgcat ctccagggga gaaggtcacc 60
atgacctgc 69

<210> SEQ ID NO 167
<211> LENGTH: 30
<212> TYPE: DNA
<213> ORGANISM: Artificial Sequence
<220> FEATURE:
<223> OTHER INFORMATION: Chemically synthesized

<400> SEQUENCE: 167
agtgccagct caagtgttag ttacatgtac 30

<210> SEQ ID NO 168
<211> LENGTH: 21
<212> TYPE: DNA
<213> ORGANISM: Artificial Sequence
<220> FEATURE:
<223> OTHER INFORMATION: Chemically synthesized

<400> SEQUENCE: 168
gactcatcca agctggcttc t 21

<210> SEQ ID NO 169
<211> LENGTH: 96
<212> TYPE: DNA
<213> ORGANISM: Artificial Sequence
<220> FEATURE:
<223> OTHER INFORMATION: Chemically synthesized

<400> SEQUENCE: 169
ggagtccctg ttcagttcag cggcagtggg tctgggacct cttactctct cacaatcagc 60
cgaatggagg ctgaagatgc tgccacttat tactgc 96

<210> SEQ ID NO 170
<211> LENGTH: 27
<212> TYPE: DNA
<213> ORGANISM: Artificial Sequence
<220> FEATURE:
<223> OTHER INFORMATION: Chemically synthesized

<400> SEQUENCE: 170
cagcagtgga ggagttaccc acccacg 27

<210> SEQ ID NO 171
<211> LENGTH: 23
<212> TYPE: PRT
<213> ORGANISM: Artificial Sequence
<220> FEATURE:
<223> OTHER INFORMATION: Chemically synthesized

<400> SEQUENCE: 171

Gln Ile Phe Leu Thr Gln Ser Pro Ala Ile Met Ser Ala Ser Pro Gly
1 5 10 15

Glu Lys Val Thr Met Thr Cys
20

<210> SEQ ID NO 172
<211> LENGTH: 32
<212> TYPE: PRT
<213> ORGANISM: Artificial Sequence
<220> FEATURE:

<223> OTHER INFORMATION: Chemically synthesized

<400> SEQUENCE: 172

Gly Val Pro Val Gln Phe Ser Gly Ser Gly Ser Gly Thr Ser Tyr Ser
1 5 10 15

Leu Thr Ile Ser Arg Met Glu Ala Glu Asp Ala Ala Thr Tyr Tyr Cys
20 25 30

<210> SEQ ID NO 173
<211> LENGTH: 57
<212> TYPE: DNA
<213> ORGANISM: Artificial Sequence
<220> FEATURE:
<223> OTHER INFORMATION: Chemically synthesized

<400> SEQUENCE: 173
atgaactttg tgctcagttt gattttcctt gccctcattt taaaaggtgt ccagtgt 57

<210> SEQ ID NO 174
<211> LENGTH: 96
<212> TYPE: DNA
<213> ORGANISM: Artificial Sequence
<220> FEATURE:
<223> OTHER INFORMATION: Chemically synthesized

<400> SEQUENCE: 174
cgattcacca tctccagaga caatgccaag aacaccctgt acctgcgcat gagcagtctg 60
cggtctgagg acacggccct gtattactgt acaaga 96

<210> SEQ ID NO 175
<211> LENGTH: 30
<212> TYPE: DNA
<213> ORGANISM: Artificial Sequence
<220> FEATURE:
<223> OTHER INFORMATION: Chemically synthesized

<400> SEQUENCE: 175
cggagttcta cgaggggctt ctttgactac 30

<210> SEQ ID NO 176
<211> LENGTH: 33
<212> TYPE: DNA
<213> ORGANISM: Artificial Sequence
<220> FEATURE:
<223> OTHER INFORMATION: Chemically synthesized

<400> SEQUENCE: 176
tggggccccg gcaccactct cacagtctcc tca 33

<210> SEQ ID NO 177
<211> LENGTH: 32
<212> TYPE: PRT
<213> ORGANISM: Artificial Sequence
<220> FEATURE:
<223> OTHER INFORMATION: Chemically synthesized

<400> SEQUENCE: 177

Arg Phe Thr Ile Ser Arg Asp Asn Ala Lys Asn Thr Leu Tyr Leu Arg
1 5 10 15

Met Ser Ser Leu Arg Ser Glu Asp Thr Ala Leu Tyr Tyr Cys Thr Arg
20 25 30

<210> SEQ ID NO 178
<211> LENGTH: 11

<212> TYPE: PRT
<213> ORGANISM: Artificial Sequence
<220> FEATURE:
<223> OTHER INFORMATION: Chemically synthesized

<400> SEQUENCE: 178

Trp Gly Pro Gly Thr Thr Leu Thr Val Ser Ser
1 5 10

<210> SEQ ID NO 179
<211> LENGTH: 66
<212> TYPE: DNA
<213> ORGANISM: Artificial Sequence
<220> FEATURE:
<223> OTHER INFORMATION: Chemically synthesized

<400> SEQUENCE: 179
atggattttc aagtgcagat tttcagcttc ctgctaatca gtgcctcagt cttactgtcc 60
cgagga 66

<210> SEQ ID NO 180
<211> LENGTH: 30
<212> TYPE: DNA
<213> ORGANISM: Artificial Sequence
<220> FEATURE:
<223> OTHER INFORMATION: Chemically synthesized

<400> SEQUENCE: 180
agtgccagct caagtgttac ttacatgtac 30

<210> SEQ ID NO 181
<211> LENGTH: 45
<212> TYPE: DNA
<213> ORGANISM: Artificial Sequence
<220> FEATURE:
<223> OTHER INFORMATION: Chemically synthesized

<400> SEQUENCE: 181
tggtaccagc agaatccagg atcctccccc agactcctga tttat 45

<210> SEQ ID NO 182
<211> LENGTH: 96
<212> TYPE: DNA
<213> ORGANISM: Artificial Sequence
<220> FEATURE:
<223> OTHER INFORMATION: Chemically synthesized

<400> SEQUENCE: 182
ggagtccctg ttcggttcag cggcagtggg tctgggacct cttactctct cacaatcagc 60
cgaatggagg ctgaagatgc taccacttat tactgc 96

<210> SEQ ID NO 183
<211> LENGTH: 30
<212> TYPE: DNA
<213> ORGANISM: Artificial Sequence
<220> FEATURE:
<223> OTHER INFORMATION: Chemically synthesized

<400> SEQUENCE: 183
ttcggtactg ggaccaagct ggacctgaaa 30

<210> SEQ ID NO 184
<211> LENGTH: 22
<212> TYPE: PRT
<213> ORGANISM: Artificial Sequence
<220> FEATURE:
<223> OTHER INFORMATION: Chemically synthesized

<400> SEQUENCE: 184

```
Met Asp Phe Gln Val Gln Ile Phe Ser Phe Leu Leu Ile Ser Ala Ser
1               5                   10                  15

Val Leu Leu Ser Arg Gly
            20
```

<210> SEQ ID NO 185
<211> LENGTH: 10
<212> TYPE: PRT
<213> ORGANISM: Artificial Sequence
<220> FEATURE:
<223> OTHER INFORMATION: Chemically synthesized

<400> SEQUENCE: 185

```
Ser Ala Ser Ser Ser Val Thr Tyr Met Tyr
1               5                   10
```

<210> SEQ ID NO 186
<211> LENGTH: 15
<212> TYPE: PRT
<213> ORGANISM: Artificial Sequence
<220> FEATURE:
<223> OTHER INFORMATION: Chemically synthesized

<400> SEQUENCE: 186

```
Trp Tyr Gln Gln Asn Pro Gly Ser Ser Pro Arg Leu Leu Ile Tyr
1               5                   10                  15
```

<210> SEQ ID NO 187
<211> LENGTH: 32
<212> TYPE: PRT
<213> ORGANISM: Artificial Sequence
<220> FEATURE:
<223> OTHER INFORMATION: Chemically synthesized

<400> SEQUENCE: 187

```
Gly Val Pro Val Arg Phe Ser Gly Ser Gly Ser Gly Thr Ser Tyr Ser
1               5                   10                  15

Leu Thr Ile Ser Arg Met Glu Ala Glu Asp Ala Thr Thr Tyr Tyr Cys
            20                  25                  30
```

<210> SEQ ID NO 188
<211> LENGTH: 10
<212> TYPE: PRT
<213> ORGANISM: Artificial Sequence
<220> FEATURE:
<223> OTHER INFORMATION: Chemically synthesized

<400> SEQUENCE: 188

```
Phe Gly Thr Gly Thr Lys Leu Asp Leu Lys
1               5                   10
```

<210> SEQ ID NO 189
<211> LENGTH: 90
<212> TYPE: DNA
<213> ORGANISM: Artificial Sequence
<220> FEATURE:
<223> OTHER INFORMATION: Chemically synthesized

<400> SEQUENCE: 189

```
gaagtgcagc tggtggagtc tgggggagtc ttagtgaagc ctggagggtc cctgaaactc     60

tcctgtgcag cctctggatt cactttcagt                                      90
```

<210> SEQ ID NO 190
<211> LENGTH: 96
<212> TYPE: DNA
<213> ORGANISM: Artificial Sequence
<220> FEATURE:
<223> OTHER INFORMATION: Chemically synthesized

<400> SEQUENCE: 190
cgattcacca tctccagaga caatgccaag aacaccctgt acctgcgaat gagcagtctg 60
cggtctgagg acacggccat gtattactgt gtaaga 96

<210> SEQ ID NO 191
<211> LENGTH: 30
<212> TYPE: DNA
<213> ORGANISM: Artificial Sequence
<220> FEATURE:
<223> OTHER INFORMATION: Chemically synthesized

<400> SEQUENCE: 191
cgggctacta cgaggggcta ctttgactac 30

<210> SEQ ID NO 192
<211> LENGTH: 30
<212> TYPE: PRT
<213> ORGANISM: Artificial Sequence
<220> FEATURE:
<223> OTHER INFORMATION: Chemically synthesized

<400> SEQUENCE: 192

Glu Val Gln Leu Val Glu Ser Gly Gly Val Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 193
<211> LENGTH: 32
<212> TYPE: PRT
<213> ORGANISM: Artificial Sequence
<220> FEATURE:
<223> OTHER INFORMATION: Chemically synthesized

<400> SEQUENCE: 193

Arg Phe Thr Ile Ser Arg Asp Asn Ala Lys Asn Thr Leu Tyr Leu Arg
1               5                   10                  15

Met Ser Ser Leu Arg Ser Glu Asp Thr Ala Met Tyr Tyr Cys Val Arg
            20                  25                  30

<210> SEQ ID NO 194
<211> LENGTH: 10
<212> TYPE: PRT
<213> ORGANISM: Artificial Sequence
<220> FEATURE:
<223> OTHER INFORMATION: Chemically synthesized

<400> SEQUENCE: 194

Arg Ala Thr Thr Arg Gly Tyr Phe Asp Tyr
1               5                   10

<210> SEQ ID NO 195
<211> LENGTH: 27
<212> TYPE: DNA
<213> ORGANISM: Artificial Sequence
<220> FEATURE:
<223> OTHER INFORMATION: Chemically synthesized

<400> SEQUENCE: 195
cagcagtgga ggagttatcc acccacg 27

<210> SEQ ID NO 196
<211> LENGTH: 90
<212> TYPE: DNA
<213> ORGANISM: Artificial Sequence
<220> FEATURE:
<223> OTHER INFORMATION: Chemically synthesized

<400> SEQUENCE: 196
gaagtgcagc tggtggagtc tgggagaggc ttagtgaagc ctggcgggtc cctgaaactc 60
tcctgtgcag cctctggatt cactttcagt 90

<210> SEQ ID NO 197
<211> LENGTH: 51
<212> TYPE: DNA
<213> ORGANISM: Artificial Sequence
<220> FEATURE:
<223> OTHER INFORMATION: Chemically synthesized

<400> SEQUENCE: 197
accattagta ctggtggtag ttacacctac tatccagaca gtgtgaaggg t 51

<210> SEQ ID NO 198
<211> LENGTH: 30
<212> TYPE: DNA
<213> ORGANISM: Artificial Sequence
<220> FEATURE:
<223> OTHER INFORMATION: Chemically synthesized

<400> SEQUENCE: 198
cggggtacta cgaggggata ctttgactac 30

<210> SEQ ID NO 199
<211> LENGTH: 30
<212> TYPE: PRT
<213> ORGANISM: Artificial Sequence
<220> FEATURE:
<223> OTHER INFORMATION: Chemically synthesized

<400> SEQUENCE: 199

Glu Val Gln Leu Val Glu Ser Gly Arg Gly Leu Val Lys Pro Gly Gly
1 5 10 15

Ser Leu Lys Leu Ser Cys Ala Ala Ser Gly Phe Thr Phe Ser
20 25 30

<210> SEQ ID NO 200
<211> LENGTH: 17
<212> TYPE: PRT
<213> ORGANISM: Artificial Sequence
<220> FEATURE:
<223> OTHER INFORMATION: Chemically synthesized

<400> SEQUENCE: 200

Thr Ile Ser Thr Gly Gly Ser Tyr Thr Tyr Tyr Pro Asp Ser Val Lys
1 5 10 15

Gly

<210> SEQ ID NO 201
<211> LENGTH: 10
<212> TYPE: PRT
<213> ORGANISM: Artificial Sequence
<220> FEATURE:
<223> OTHER INFORMATION: Chemically synthesized

<400> SEQUENCE: 201

Arg Gly Thr Thr Arg Gly Tyr Phe Asp Tyr
1 5 10

<210> SEQ ID NO 202
<211> LENGTH: 96
<212> TYPE: DNA
<213> ORGANISM: Artificial Sequence
<220> FEATURE:
<223> OTHER INFORMATION: Chemically synthesized

<400> SEQUENCE: 202
ggagtccctg ttcgcttcag tggcagtggg tctgggacct cttactctct cacaatcagc 60
cgaatggagg ctgaagatgc tgccacttat tcctgc 96

<210> SEQ ID NO 203
<211> LENGTH: 27
<212> TYPE: DNA
<213> ORGANISM: Artificial Sequence
<220> FEATURE:
<223> OTHER INFORMATION: Chemically synthesized

<400> SEQUENCE: 203
cagcagtgga gtagttaccc acccacg 27

<210> SEQ ID NO 204
<211> LENGTH: 32
<212> TYPE: PRT
<213> ORGANISM: Artificial Sequence
<220> FEATURE:
<223> OTHER INFORMATION: Chemically synthesized

<400> SEQUENCE: 204

Gly Val Pro Val Arg Phe Ser Gly Ser Gly Ser Gly Thr Ser Tyr Ser
1 5 10 15

Leu Thr Ile Ser Arg Met Glu Ala Glu Asp Ala Ala Thr Tyr Ser Cys
20 25 30

<210> SEQ ID NO 205
<211> LENGTH: 9
<212> TYPE: PRT
<213> ORGANISM: Artificial Sequence
<220> FEATURE:
<223> OTHER INFORMATION: Chemically synthesized

<400> SEQUENCE: 205

Gln Gln Trp Ser Ser Tyr Pro Pro Thr
1 5

<210> SEQ ID NO 206
<211> LENGTH: 60
<212> TYPE: DNA
<213> ORGANISM: Artificial Sequence
<220> FEATURE:
<223> OTHER INFORMATION: Chemically synthesized

<400> SEQUENCE: 206
atggagtcac agattcaggt ctttgtattc gtgtttctct ggttgtctgg tgttgacgga 60

<210> SEQ ID NO 207
<211> LENGTH: 33
<212> TYPE: DNA

<213> ORGANISM: Artificial Sequence
<220> FEATURE:
<223> OTHER INFORMATION: Chemically synthesized

<400> SEQUENCE: 207
aaggccagtc aggatgtgag tactgctgta gcc 33

<210> SEQ ID NO 208
<211> LENGTH: 45
<212> TYPE: DNA
<213> ORGANISM: Artificial Sequence
<220> FEATURE:
<223> OTHER INFORMATION: Chemically synthesized

<400> SEQUENCE: 208
tggtatcaac agaaaccagg acaatctcct aaactactga tttac 45

<210> SEQ ID NO 209
<211> LENGTH: 21
<212> TYPE: DNA
<213> ORGANISM: Artificial Sequence
<220> FEATURE:
<223> OTHER INFORMATION: Chemically synthesized

<400> SEQUENCE: 209
tcggcatcct accggtacac t 21

<210> SEQ ID NO 210
<211> LENGTH: 96
<212> TYPE: DNA
<213> ORGANISM: Artificial Sequence
<220> FEATURE:
<223> OTHER INFORMATION: Chemically synthesized

<400> SEQUENCE: 210
ggagtccctg atcgcttcac tggcagtgga tctgggacgg atttcacttt caccatcagc 60
agtgtgcagg ctgaagacct ggcagtttat tactgt 96

<210> SEQ ID NO 211
<211> LENGTH: 27
<212> TYPE: DNA
<213> ORGANISM: Artificial Sequence
<220> FEATURE:
<223> OTHER INFORMATION: Chemically synthesized

<400> SEQUENCE: 211
cagcaacatt atagtactcc gtacacg 27

<210> SEQ ID NO 212
<211> LENGTH: 20
<212> TYPE: PRT
<213> ORGANISM: Artificial Sequence
<220> FEATURE:
<223> OTHER INFORMATION: Chemically synthesized

<400> SEQUENCE: 212

Met Glu Ser Gln Ile Gln Val Phe Val Phe Val Phe Leu Trp Leu Ser
1 5 10 15

Gly Val Asp Gly
20

<210> SEQ ID NO 213
<211> LENGTH: 11
<212> TYPE: PRT
<213> ORGANISM: Artificial Sequence
<220> FEATURE:
<223> OTHER INFORMATION: Chemically synthesized

<400> SEQUENCE: 213

Lys Ala Ser Gln Asp Val Ser Thr Ala Val Ala
1 5 10

<210> SEQ ID NO 214
<211> LENGTH: 7
<212> TYPE: PRT
<213> ORGANISM: Artificial Sequence
<220> FEATURE:
<223> OTHER INFORMATION: Chemically synthesized

<400> SEQUENCE: 214

Ser Ala Ser Tyr Arg Tyr Thr
1 5

<210> SEQ ID NO 215
<211> LENGTH: 32
<212> TYPE: PRT
<213> ORGANISM: Artificial Sequence
<220> FEATURE:
<223> OTHER INFORMATION: Chemically synthesized

<400> SEQUENCE: 215

Gly Val Pro Asp Arg Phe Thr Gly Ser Gly Ser Gly Thr Asp Phe Thr
1 5 10 15

Phe Thr Ile Ser Ser Val Gln Ala Glu Asp Leu Ala Val Tyr Tyr Cys
20 25 30

<210> SEQ ID NO 216
<211> LENGTH: 9
<212> TYPE: PRT
<213> ORGANISM: Artificial Sequence
<220> FEATURE:
<223> OTHER INFORMATION: Chemically synthesized

<400> SEQUENCE: 216

Gln Gln His Tyr Ser Thr Pro Tyr Thr
1 5

<210> SEQ ID NO 217
<211> LENGTH: 57
<212> TYPE: DNA
<213> ORGANISM: Artificial Sequence
<220> FEATURE:
<223> OTHER INFORMATION: Chemically synthesized

<400> SEQUENCE: 217
atgggatgga gccggatctt tctcttcctc ctgtcaataa ttgcaggtgt ccattgc 57

<210> SEQ ID NO 218
<211> LENGTH: 90
<212> TYPE: DNA
<213> ORGANISM: Artificial Sequence
<220> FEATURE:
<223> OTHER INFORMATION: Chemically synthesized

<400> SEQUENCE: 218
caggtccagc tgcagcagtc tggacctgag ctggtgaagc ctggggcttc agtgcggata 60
tcctgcaagg cttctggcta caccttcaca 90

<210> SEQ ID NO 219
<211> LENGTH: 15

<212> TYPE: DNA
<213> ORGANISM: Artificial Sequence
<220> FEATURE:
<223> OTHER INFORMATION: Chemically synthesized

<400> SEQUENCE: 219 acttctatt tacac 15

<210> SEQ ID NO 220
<211> LENGTH: 42
<212> TYPE: DNA
<213> ORGANISM: Artificial Sequence
<220> FEATURE:
<223> OTHER INFORMATION: Chemically synthesized

<400> SEQUENCE: 220
tgggtgaagc agaggcctgg acagggactt gagtggattg ga 42

<210> SEQ ID NO 221
<211> LENGTH: 51
<212> TYPE: DNA
<213> ORGANISM: Artificial Sequence
<220> FEATURE:
<223> OTHER INFORMATION: Chemically synthesized

<400> SEQUENCE: 221
tggatttatc ctgtaaatgt taaaattaag tacagtgaga ggttcaaggg c 51

<210> SEQ ID NO 222
<211> LENGTH: 96
<212> TYPE: DNA
<213> ORGANISM: Artificial Sequence
<220> FEATURE:
<223> OTHER INFORMATION: Chemically synthesized

<400> SEQUENCE: 222
aaggccacac tgactgcaga caaatcctcc agcacagcct acatgcagct cggcagcctg 60
acctctgagg actctgcggt ctatttctgt gtaaga 96

<210> SEQ ID NO 223
<211> LENGTH: 21
<212> TYPE: DNA
<213> ORGANISM: Artificial Sequence
<220> FEATURE:
<223> OTHER INFORMATION: Chemically synthesized

<400> SEQUENCE: 223
ggggggaggg gacttgacta c 21

<210> SEQ ID NO 224
<211> LENGTH: 19
<212> TYPE: PRT
<213> ORGANISM: Artificial Sequence
<220> FEATURE:
<223> OTHER INFORMATION: Chemically synthesized

<400> SEQUENCE: 224

Met Gly Trp Ser Arg Ile Phe Leu Phe Leu Leu Ser Ile Ile Ala Gly
1 5 10 15

Val His Cys

<210> SEQ ID NO 225
<211> LENGTH: 30
<212> TYPE: PRT
<213> ORGANISM: Artificial Sequence
<220> FEATURE:
<223> OTHER INFORMATION: Chemically synthesized

<400> SEQUENCE: 225

Gln Val Gln Leu Gln Gln Ser Gly Pro Glu Leu Val Lys Pro Gly Ala
1 5 10 15

Ser Val Arg Ile Ser Cys Lys Ala Ser Gly Tyr Thr Phe Thr
20 25 30

<210> SEQ ID NO 226
<211> LENGTH: 5
<212> TYPE: PRT
<213> ORGANISM: Artificial Sequence
<220> FEATURE:
<223> OTHER INFORMATION: Chemically synthesized

<400> SEQUENCE: 226

Thr Phe Tyr Leu His
1 5

<210> SEQ ID NO 227
<211> LENGTH: 14
<212> TYPE: PRT
<213> ORGANISM: Artificial Sequence
<220> FEATURE:
<223> OTHER INFORMATION: Chemically synthesized

<400> SEQUENCE: 227

Trp Val Lys Gln Arg Pro Gly Gln Gly Leu Glu Trp Ile Gly
1 5 10

<210> SEQ ID NO 228
<211> LENGTH: 17
<212> TYPE: PRT
<213> ORGANISM: Artificial Sequence
<220> FEATURE:
<223> OTHER INFORMATION: Chemically synthesized

<400> SEQUENCE: 228

Trp Ile Tyr Pro Val Asn Val Lys Ile Lys Tyr Ser Glu Arg Phe Lys
1 5 10 15

Gly

<210> SEQ ID NO 229
<211> LENGTH: 32
<212> TYPE: PRT
<213> ORGANISM: Artificial Sequence
<220> FEATURE:
<223> OTHER INFORMATION: Chemically synthesized

<400> SEQUENCE: 229

Lys Ala Thr Leu Thr Ala Asp Lys Ser Ser Ser Thr Ala Tyr Met Gln
1 5 10 15

Leu Gly Ser Leu Thr Ser Glu Asp Ser Ala Val Tyr Phe Cys Val Arg
20 25 30

<210> SEQ ID NO 230
<211> LENGTH: 7
<212> TYPE: PRT
<213> ORGANISM: Artificial Sequence
<220> FEATURE:
<223> OTHER INFORMATION: Chemically synthesized

<400> SEQUENCE: 230

Gly Gly Arg Gly Leu Asp Tyr 1 5

<210> SEQ ID NO 231
<211> LENGTH: 60
<212> TYPE: DNA
<213> ORGANISM: Artificial Sequence
<220> FEATURE:
<223> OTHER INFORMATION: Chemically synthesized

<400> SEQUENCE: 231
atggaatcac agactcaggt cttcctctcc ctgctgctct gggtatctgg tacctgtggg 60

<210> SEQ ID NO 232
<211> LENGTH: 69
<212> TYPE: DNA
<213> ORGANISM: Artificial Sequence
<220> FEATURE:
<223> OTHER INFORMATION: Chemically synthesized

<400> SEQUENCE: 232
aacattatga tgacacagtc gccatcatct ctggctgtgt ctgcaggaga aaaggtcact 60
atgagctgt 69

<210> SEQ ID NO 233
<211> LENGTH: 51
<212> TYPE: DNA
<213> ORGANISM: Artificial Sequence
<220> FEATURE:
<223> OTHER INFORMATION: Chemically synthesized

<400> SEQUENCE: 233
aagtccagtc aaagtgtttt atacagttca aatcagaaga actacttggc c 51

<210> SEQ ID NO 234
<211> LENGTH: 45
<212> TYPE: DNA
<213> ORGANISM: Artificial Sequence
<220> FEATURE:
<223> OTHER INFORMATION: Chemically synthesized

<400> SEQUENCE: 234
tggtaccagc agaaaccagg gcagtctcct aaaatgctga tctac 45

<210> SEQ ID NO 235
<211> LENGTH: 21
<212> TYPE: DNA
<213> ORGANISM: Artificial Sequence
<220> FEATURE:
<223> OTHER INFORMATION: Chemically synthesized

<400> SEQUENCE: 235
tgggcatcct ttagggaatc t 21

<210> SEQ ID NO 236
<211> LENGTH: 96
<212> TYPE: DNA
<213> ORGANISM: Artificial Sequence
<220> FEATURE:
<223> OTHER INFORMATION: Chemically synthesized

<400> SEQUENCE: 236
ggtgtccctg atcgcttcac aggcagtgga tctgggacag attttactct taccatcagc 60
agtgtacaag ctgaagacct ggcagtttat tactgt 96

<210> SEQ ID NO 237
<211> LENGTH: 24
<212> TYPE: DNA
<213> ORGANISM: Artificial Sequence
<220> FEATURE:
<223> OTHER INFORMATION: Chemically synthesized

<400> SEQUENCE: 237
catcaatacc tctccttatt cacg 24

<210> SEQ ID NO 238
<211> LENGTH: 20
<212> TYPE: PRT
<213> ORGANISM: Artificial Sequence
<220> FEATURE:
<223> OTHER INFORMATION: Chemically synthesized

<400> SEQUENCE: 238

Met Glu Ser Gln Thr Gln Val Phe Leu Ser Leu Leu Leu Trp Val Ser
1 5 10 15

Gly Thr Cys Gly
20

<210> SEQ ID NO 239
<211> LENGTH: 23
<212> TYPE: PRT
<213> ORGANISM: Artificial Sequence
<220> FEATURE:
<223> OTHER INFORMATION: Chemically synthesized

<400> SEQUENCE: 239

Asn Ile Met Met Thr Gln Ser Pro Ser Ser Leu Ala Val Ser Ala Gly
1 5 10 15

Glu Lys Val Thr Met Ser Cys
20

<210> SEQ ID NO 240
<211> LENGTH: 17
<212> TYPE: PRT
<213> ORGANISM: Artificial Sequence
<220> FEATURE:
<223> OTHER INFORMATION: Chemically synthesized

<400> SEQUENCE: 240

Lys Ser Ser Gln Ser Val Leu Tyr Ser Ser Asn Gln Lys Asn Tyr Leu
1 5 10 15

Ala

<210> SEQ ID NO 241
<211> LENGTH: 15
<212> TYPE: PRT
<213> ORGANISM: Artificial Sequence
<220> FEATURE:
<223> OTHER INFORMATION: Chemically synthesized

<400> SEQUENCE: 241

Trp Tyr Gln Gln Lys Pro Gly Gln Ser Pro Lys Met Leu Ile Tyr
1 5 10 15

<210> SEQ ID NO 242
<211> LENGTH: 7
<212> TYPE: PRT
<213> ORGANISM: Artificial Sequence
<220> FEATURE:
<223> OTHER INFORMATION: Chemically synthesized

<400> SEQUENCE: 242

Trp Ala Ser Phe Arg Glu Ser
1 5

<210> SEQ ID NO 243
<211> LENGTH: 32
<212> TYPE: PRT
<213> ORGANISM: Artificial Sequence
<220> FEATURE:
<223> OTHER INFORMATION: Chemically synthesized

<400> SEQUENCE: 243

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 244
<211> LENGTH: 8
<212> TYPE: PRT
<213> ORGANISM: Artificial Sequence
<220> FEATURE:
<223> OTHER INFORMATION: Chemically synthesized

<400> SEQUENCE: 244

His Gln Tyr Leu Ser Leu Phe Thr
1 5

<210> SEQ ID NO 245
<211> LENGTH: 140
<212> TYPE: PRT
<213> ORGANISM: Artificial Sequence
<220> FEATURE:
<223> OTHER INFORMATION: Chemically synthesized

<400> SEQUENCE: 245

Met Asp Val Phe Met Lys Gly Leu Ser Lys Ala Lys Glu Gly Val Val
1 5 10 15

Ala Ala Ala Glu Lys Thr Lys Gln Gly Val Ala Glu Ala Ala Gly Lys
20 25 30

Thr Lys Glu Gly Val Leu Tyr Val Gly Ser Lys Thr Lys Glu Gly Val
35 40 45

Val His Gly Val Ala Thr Val Ala Glu Lys Thr Lys Glu Gln Val Thr
50 55 60

Asn Val Gly Gly Ala Val Val Thr Gly Val Thr Ala Val Ala Gln Lys
65 70 75 80

Thr Val Glu Gly Ala Gly Ser Ile Ala Ala Ala Thr Gly Phe Val Lys
85 90 95

Lys Asp Gln Leu Gly Lys Asn Glu Glu Gly Ala Pro Gln Glu Gly Ile
100 105 110

Leu Glu Asp Met Pro Val Asp Pro Asp Asn Glu Ala Tyr Glu Met Pro
115 120 125

Ser Glu Glu Gly Tyr Gln Asp Tyr Glu Pro Glu Ala
130 135 140

ANTI-α-SYNUCLEIN MONOCLONAL ANTIBODIES, AND METHODS USING SAME

CROSS-REFERENCE TO RELATED APPLICATIONS

This application is a 35 U.S.C. § 371 national phase application from, and claims priority to, International Application No. PCT/US2020/061376, filed Nov. 19, 2020, and published under PCT Article 21 (2) in English, and claims priority under 35 U.S.C. § 119 (e) to U.S. Provisional Patent Application No. 62/937,636 filed Nov. 19, 2019, all of which are incorporated herein by reference in their entireties.

STATEMENT REGARDING FEDERALLY SPONSORED RESEARCH OR DEVELOPMENT

This invention was made with government support under grant numbers T32-AG000255, P30-AG10124, P50-NS053488, and R01-NS088322 awarded by National Institutes of Health (NIH). The government has certain rights in the invention.

BACKGROUND OF THE DISCLOSURE

Parkinson's disease (PD) is a progressive neurodegenerative disease that affects 1% of the worldwide population but has no disease-modifying treatments. Even the most efficacious dopamine replacement therapy does not prevent disease progression, including the development of dementia which occurs in up to 80 percent of cases. Motor symptoms that are characteristic of the disease are often preceded by non-motor symptoms, including constipation, sleep disturbances, and olfactory dysfunction, and are often followed by cognitive decline, which can lead to a diagnosis of PD dementia (PDD). Dementia with Lewy bodies (DLB) bears symptom and pathology overlap with PD and PDD, suggesting that these three disorders lie along a spectrum of neurodegenerative diseases collectively known as α-synucleinopathies due to the abnormal accumulation of normally synaptic α-Synuclein protein into neuronal Lewy bodies (LBs) and axonal Lewy neurites (LNs). α-Synuclein is not merely a bystander in these diseases since rare mutations, duplications, and triplications of α-Synuclein lead to familial PD.

The progression of symptoms from manageable to debilitating corresponds with the burden of α-Synuclein pathology in higher cortical regions of the brain. Overexpression of α-Synuclein in mice with or without familial mutations is sufficient to drive the formation of LB-like inclusions and neurodegeneration. Further, reduction in α-Synuclein levels has a beneficial effect in neurotoxin-induced models of PD. Together, these studies suggest that a reduction of α-Synuclein, especially misfolded forms, may be a therapeutic strategy for treatment of PD and related α-synucleinopathies. Because α-Synuclein is primarily localized in the neuronal cytoplasm, it has been assumed that therapeutic molecules would need to cross not only the blood-brain-barrier (BBB), but also the neuronal plasma membrane, to interact with α-Synuclein. However, a number of recent in vitro and in vivo studies suggest that misfolded α-Synuclein species are released by neurons and can be taken up by nearby neurons, inducing the transcellular transmission of pathogenic α-Synuclein. Thus, minimizing the impact of this pool of extracellular, pathogenic α-Synuclein provides a unique and more easily accessed therapeutic opportunity for the treatment of PD, especially if pathological α-Synuclein is also present in the peripheral areas such as the enteric nervous system.

There are a number of potential approaches to inhibit the transmission of α-Synuclein pathology. For example, extracellular α-Synuclein could be targeted for vascular or glymphatic clearance, its uptake could be blocked, or glial cells could be modified to promote clearance of extracellular α-Synuclein. At least some of these possible mechanisms might be facilitated through antibody-mediated immunotherapy. For example, antibodies might block neuronal α-Synuclein uptake while also promoting glymphatic clearance to the periphery or glial clearance through binding to surface Fc receptors. Passive immunotherapy (treatment directly with antibodies, instead of injection of an immunogen) is a particularly attractive option because therapeutic antibodies have been demonstrated to be relatively safe and immunotherapy has been shown to promote clearance of extracellular targets. Sufficient brain levels of the administered antibody have to be achieved to affect disease biology, but antibodies are known to have poor BBB penetration.

There is a need for developing anti-α-Syn antibodies that can be used to investigate neuropathological features of PD and related disorders. In certain embodiments, these antibodies can be used in the treatment of these diseases. This disclosure addresses and meets those needs.

BRIEF SUMMARY OF THE DISCLOSURE

The present disclosure provides certain monoclonal antibodies comprising a light chain variable region (VL) and a heavy chain variable region (VH), as defined elsewhere herein. The present disclosure further provides pharmaceutical compositions comprising at least one monoclonal antibody contemplated herein and at least one pharmaceutical excipient. The present disclosure further provides certain isolated polynucleotides comprising at least one of the nucleic acid sequences contemplated herein.

The present disclosure further provides autonomously replicating or integrative mammalian cell vectors comprising at least one recombinant nucleic acid encoding at least one antibody comprising a light chain variable region (VL) and a heavy chain variable region (VH), as defined elsewhere herein. The present disclosure further provides isolated host cells comprising any of the vectors contemplated herein.

The present disclosure further provides methods of treating, ameliorating, and/or preventing a synucleopathic disease in a subject. In certain embodiments, the method comprises administering to the subject a therapeutically effective amount of at least one isolated monoclonal antibody contemplated herein.

The present disclosure further provides methods of detecting a synucleopathic disease in a subject. In certain embodiments, the method comprises administering to the subject at least one labeled isolated monoclonal antibody contemplated herein. In certain embodiments, the method comprises detecting presence or absence of a complex of the labeled isolated monoclonal antibody with any α-Syn fibrils, oligomers, and/or other misfolded α-Syn species present in the subject. In certain embodiments, if the complex is detected, the subject has a synucleopathic disease.

The present disclosure further provides methods of detecting total α-Syn, α-Syn fibrils, and/or α-Syn oligomeric species in a sample. In certain embodiments, the method comprises contacting the sample with at least one labeled isolated monoclonal antibody contemplated herein. In certain embodiments, the method comprises detecting presence or absence of a complex of the labeled isolated monoclonal antibody with total α-Syn, α-Syn monomer, α-Syn fibrils, and/or α-Syn oligomeric species present in the sample. In certain embodiments, if the complex is detected, total α-Syn, α-Syn monomers, α-Syn fibrils, and/or α-Syn oligomeric species are present in the sample.

BRIEF DESCRIPTION OF THE DRAWINGS

The following detailed description of specific embodiments of the disclosure will be better understood when read in conjunction with the appended drawings. For the purpose of illustrating the disclosure, the drawings show specific embodiments. It should be understood, however, that the disclosure is not limited to the precise arrangements and instrumentalities of the embodiments shown in the drawings.

FIGS. 1A-1F comprise a passive immunotherapy screen schematic. FIG. 1A: Mice were immunized with α-Synuclein pre-formed fibrils (PFFs) to induce an immune response and production of antibodies against pathogenic α-Synuclein. FIG. 1B: Antibody producing B cells were subsequently harvested from the spleen of immunized mice and fused with myeloma cells to produce hybridoma clonal cell lines expressing antibodies against α-Synuclein. FIG. 1C: Hybridomas were separated into individual clonal populations and the antibody-containing supernatant from each clone was passed through a primary screen to identify candidates with preferred properties. To confirm that antibodies would recognize pathogenic human α-Synuclein, antibodies were used in IHC of human tissue. In certain non-limiting embodiments, candidate antibodies also have a preference for fibrillar α-Synuclein, so they were screened in an indirect ELISA format for monomeric and fibrillar α-Synuclein. Each antibody was epitope mapped and tested for immunogenicity against mouse and human α-Synuclein so it could be utilized in a mouse disease model. Finally, antibodies were screened in a primary neuron immunotherapy assay for their ability to reduce α-Synuclein pathology in cultured neurons. FIG. 1D: Prioritized antibodies underwent a further two rounds of subcloning to ensure monoclonality. FIG. 1E: Final clones underwent confirmation screening to ensure they maintained optimal properties and to identify a final candidate for the in vivo experiment. FIG. 1F: A non-limiting candidate antibody was tested in a mouse model of PD for its ability to reduce α-Synuclein pathology and toxicity. The candidate was tested alongside and IgG control and an α-Synuclein antibody with proven therapeutic efficacy.

FIG. 2A: Sections of amygdala tissue containing abundant Lewy body pathology were stained using undiluted or 1:3 diluted hybridoma supernatant. Representative staining of Lewy bodies is shown for each of the screened antibody supernatants. Scale bar=50 μm. FIG. 2B: The optical density within Lewy bodies divided by the optical density of a 1 $mm^2$ tissue section containing those Lewy bodies was defined as the Lewy Body Discrimination Index. Antibodies preferentially recognizing Lewy bodies score high on this measure. Most antibodies showed some enhanced recognition of Lewy bodies, with the exception of those antibodies scoring below 1.5, which show little apparent preference for Lewy bodies above neuropil α-Synuclein staining.

FIG. 3A: Schematic of recombinant α-Synuclein fragments used to determine the epitope of the 9000 series antibodies. Full-length (FL) α-Synuclein is 140 amino acids with an internal non-amyloid component (NAC) domain. Constructs used for testing epitopes had truncated N- or C-terminal human α-Synuclein residues. FIG. 3B: Most antibodies recognized both human and mouse α-Synuclein to some extent. Further, all antibodies recognized α-Synuclein with truncated N-termini, suggesting that they all recognize the C-terminus of α-Synuclein. The most extreme of these did not recognize α-Synuclein if even the last 10 amino acids were not included, suggesting that the epitope is between aa 130-140. Many other antibodies recognized 1-130, but not 1-120, suggesting they have an epitope between 120-130. FIG. 3C: Another large batch of antibodies did not recognize 1-110, suggesting they recognize 110-120. Finally, there were several antibodies that recognized all constructs except 1-89, suggesting the epitope lies between amino acids 90-102. *Peptide 1-110 was loaded in the last lane of these gels, thereby shifting the lanes leftward.

(FIG. 4B) antibodies that are non-selective and have a similar binding to α-Synuclein monomer and PFF; and (FIG. 4C) antibodies that are PFF-selective, showing a markedly higher preference for α-Synuclein PFF than monomer. The histograms shown are representative of the three classes, but all antibodies tested can be classified in one of these categories. Plots represent the means from 3 technical replicates, and error bars represent standard error.

FIG. 5A: Examples of pS129 α-Synuclein pathology (green) and NeuN (magenta) immunostaining following treatment of primary neurons with α-Synuclein PFFs and the noted representative antibodies. Scale bar=50 μm. FIG. 5B: Quantification of pS129 α-Synuclein area/neuron number normalized to IgG-treated neurons. Antibodies had varying effects on α-Synuclein pathology and are ranked from least to most effective. Twenty-one of the antibodies showed statistically-significant reductions in pathology (Kruskal-Wallis test with Dunn's multiple comparisons test: *$p<0.05$; $p<0.01$; *$p<0.001$; ****$p<0.0001$). N=6-20/condition. Error bars represent standard error.

Finally, the % inhibition measure, derived from the primary neuron assay, indicates antibody ability to reduce pathology in a cellular system. In certain embodiments, an antibody of interest recognizes both mouse and human α-Synuclein, discriminate LBs from surrounding neuropil, have higher binding affinity for α-Synuclein PFFs than monomer, and inhibit nearly all in vitro neuronal α-Synuclein pathology. Based on these measures, Syn9048 and Syn9063 were chosen for further subcloning.

Figure 7A:
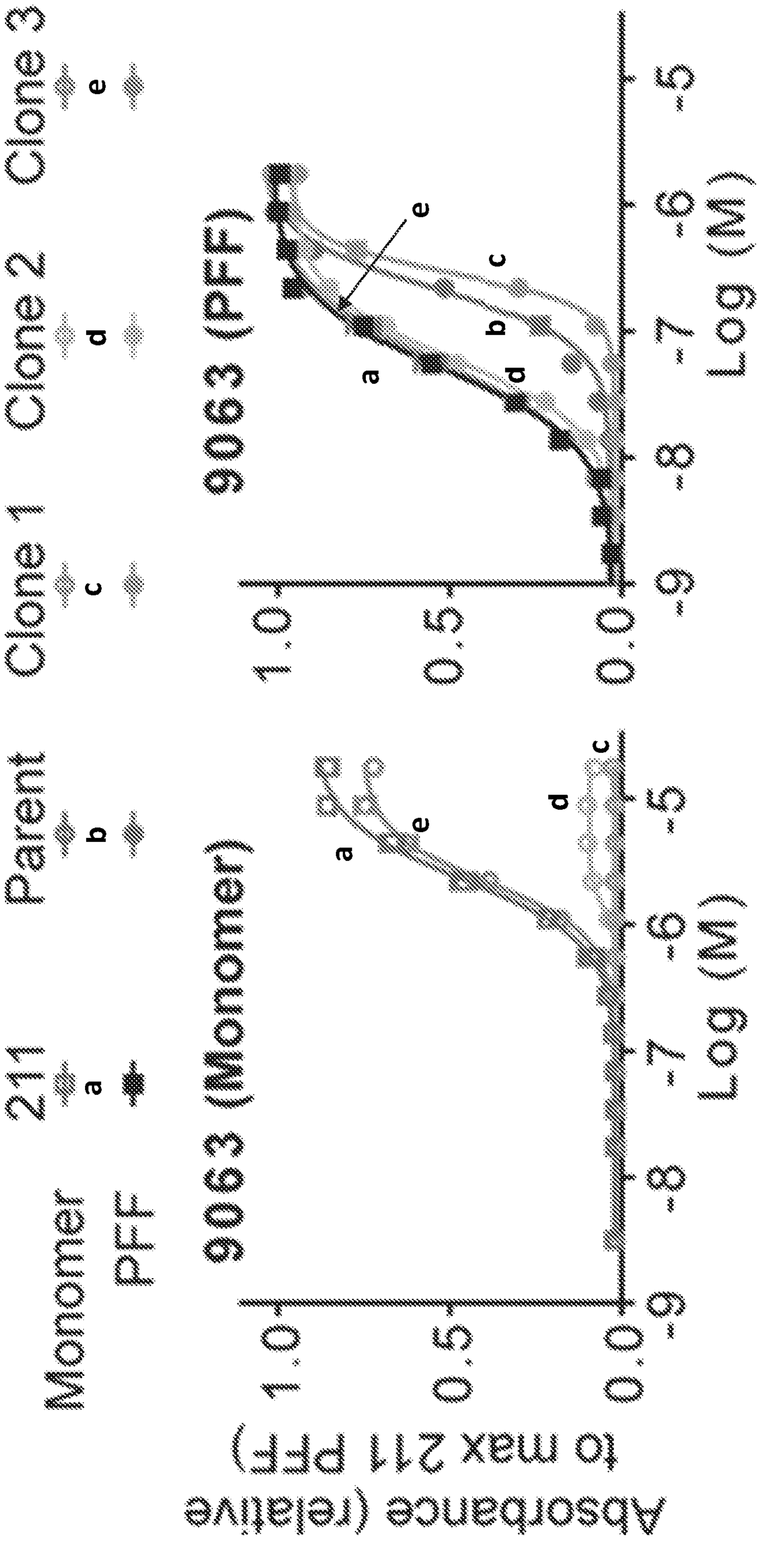
Figure 7B:
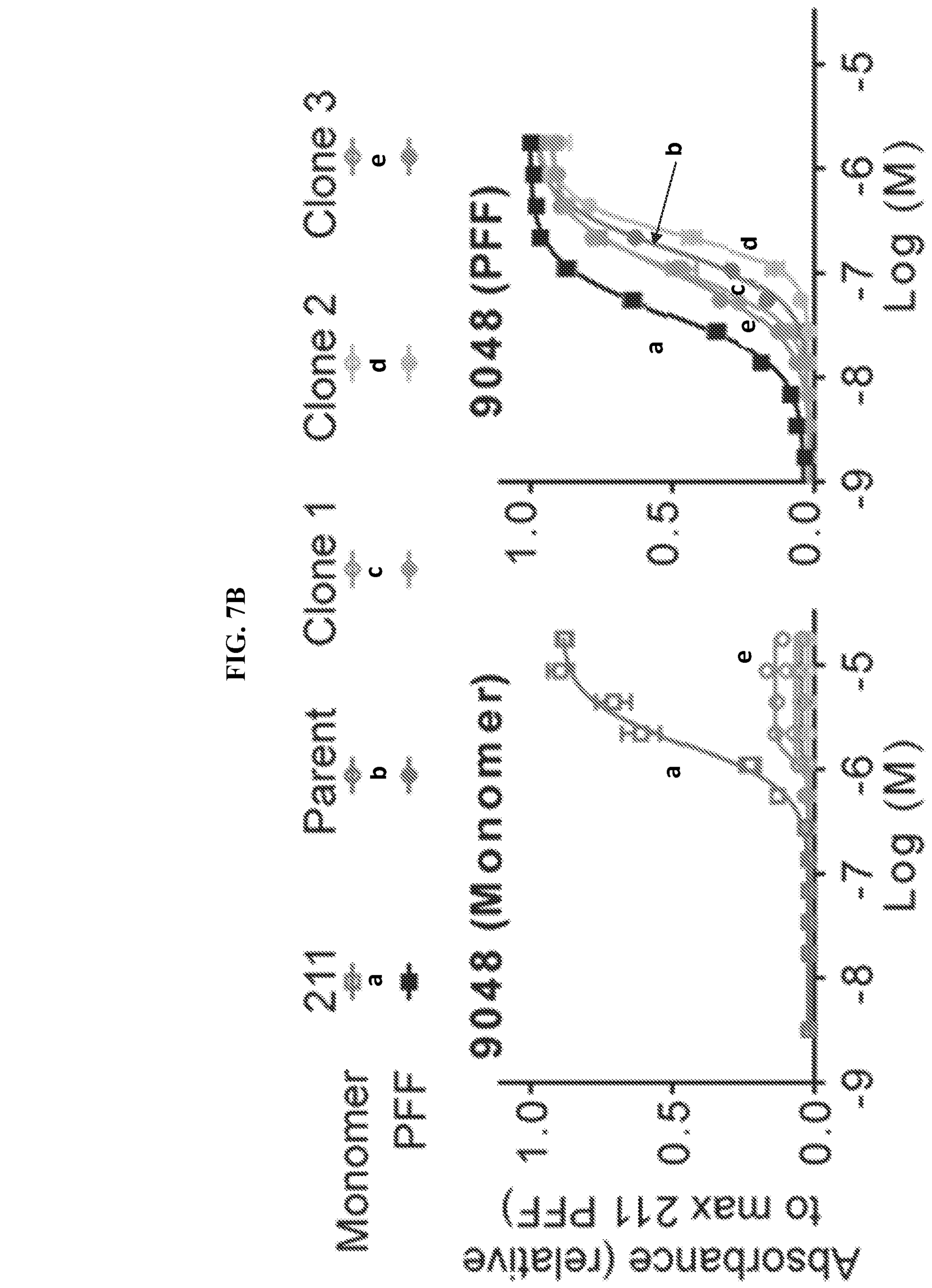
Figure 7C:
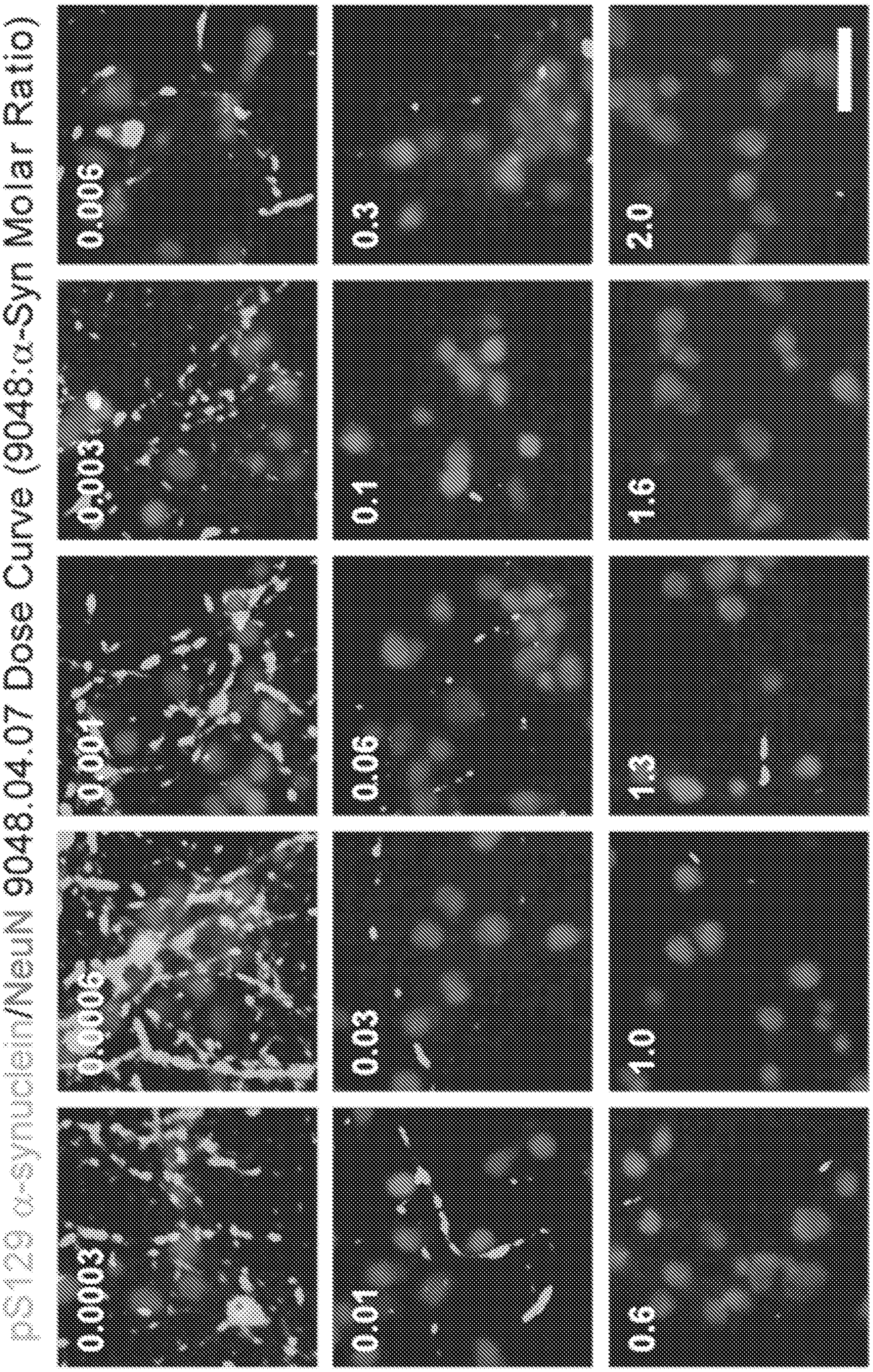
Figure 7D:
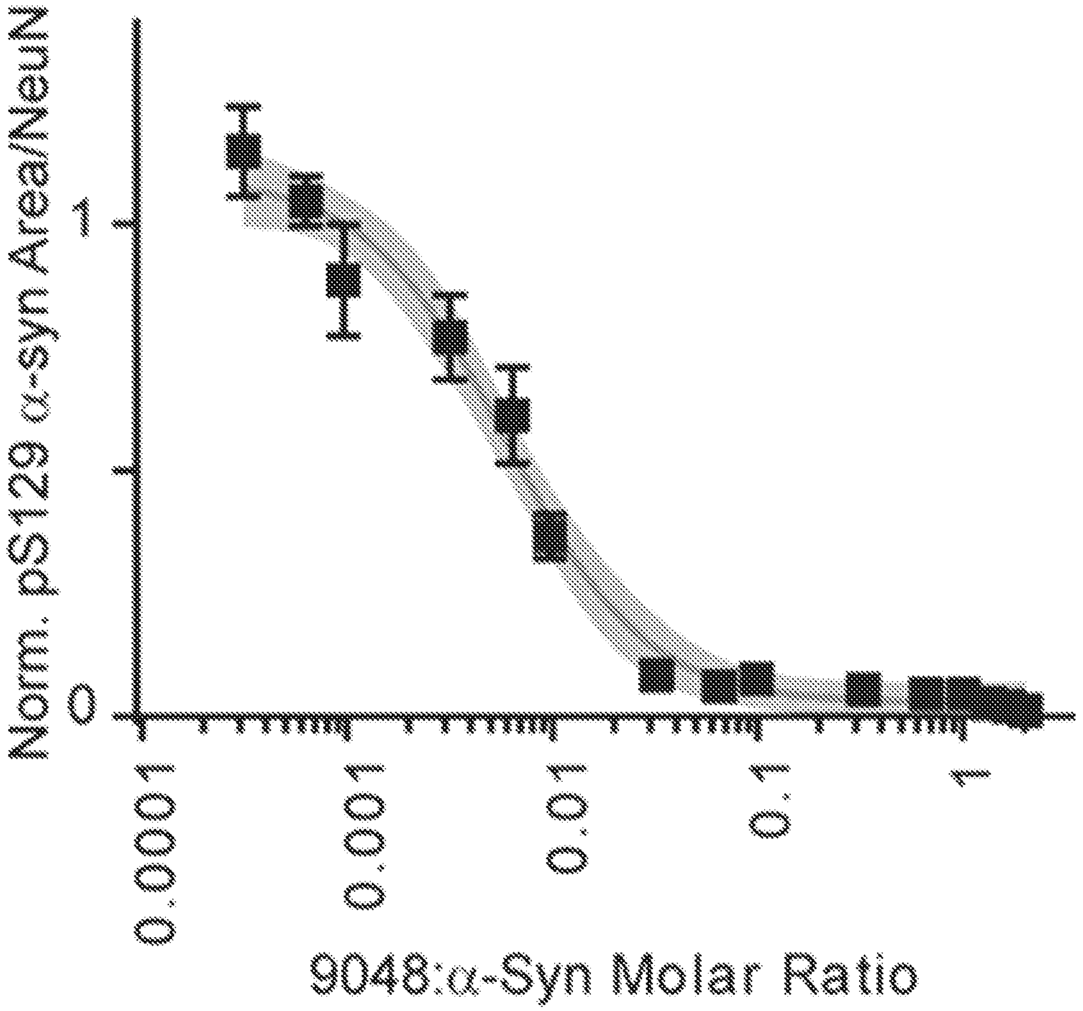

FIGS. 7A-7D illustrate non-limiting subclones, which retain properties of parent clones. FIG. 7A: Syn9063 subclones were assayed for PFF preference as previously described to ensure that all subclones showed the same selectivity as the parent clone. All but one of the subclones showed a high preference for α-Synuclein PFFs. FIG. 7B: All Syn9048 subclones showed similar selectivity for α-Synuclein PFFs. Plots in panels (FIG. 7A) and (FIG. 7B) represent the means from 3 technical replicates, and error bars represent standard error. FIG. 7C: Examples of pS129 α-Synuclein pathology (green) and NeuN (magenta) immunostaining following treatment of primary neurons with α-Synuclein PFFs and the noted molar ratios of purified Syn9048 clone #3 to α-Synuclein monomer. Scale bar=50 μm. FIG. 7D: Quantification of pS129 α-Synuclein area/neuron number normalized to control IgG-treated neurons. Increasing molar ratios of Syn9048 reduced pS129 α-Synuclein pathology in a dose-dependent manner and is fit by a sigmoidal dose curve with an $IC_{50}$ of 0.006 ($R^2$=0.9539). N=3/condition. Error bars represent standard error and the shaded area represents the 95% confidence interval of the sigmoidal fit.

Figures 8A, 8B, 8C, 8D, 8E, 8F, 8G:
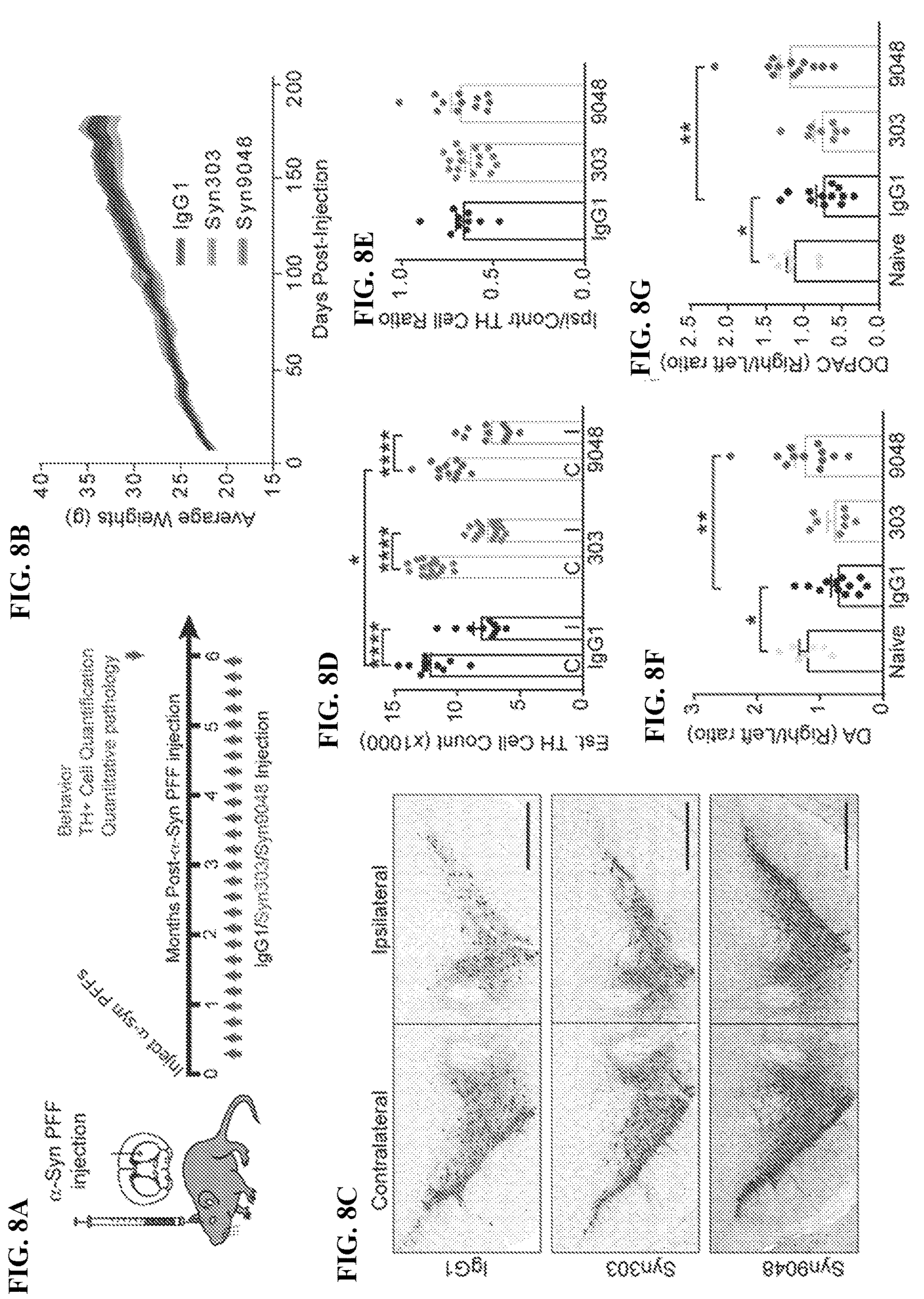

FIGS. 8A-8G illustrate that in vivo immunotherapy is well-tolerated and improves dopaminergic tone. FIG. 8A: Wild-type mice were injected with α-Synuclein PFFs in the dorsal striatum at 2-3 month of age. One week after α-Synuclein PFF injection, mice were injected with 30 mg/kg control IgG1, Syn303 or Syn9048. Mice were injected once weekly thereafter for 6 months, after which mice were sacrificed and assayed for pathology and motor behavior. FIG. 8B: Average weight for mice in each antibody treatment group with standard error represented in shaded bands. Weights increased over time, but were not different by group (Two-way ANOVA: Time p=0.0001; Treatment p=0.7209). N=16/group. Error bars represent standard error. FIG. 8C: Representative images of the SN stained with TH from mice treated with control IgG1, Syn303 or Syn9048. Scale bars=500 μm. FIG. 8D: Estimated TH+ neurons in the SN following manual quantification of neurons through the SN (C=contralateral; I=ipsilateral). Substantial neuron loss was observed ipsilateral to the injection site for all groups (Two-way ANOVA with Sidak's multiple comparisons test, contra vs. ipsi: IgG1 p<0.0001; Syn303 p<0.0001; Syn9048 p<0.0001), but was not different between groups (Two-way ANOVA with Sidak's multiple comparisons test Ipsi: IgG1 vs. Syn303 p=0.6266, IgG1 vs. Syn9048 p=0.3561). N=10-16/group. FIG. 8E: The ratio of neurons remaining on the ipsilateral SN to the contralateral SN similarly showed no difference between groups (One-way ANOVA with Dunnett's multiple comparison test: IgG1 vs. Syn303 p=0.6323, IgG1 vs. Syn9048 p=0.9084). FIG. 8F: Dopamine levels measured from the dorsal striatum of injected mice were reduced ipsilateral to the injection site in IgG1-treated animals, but were preserved in Syn9048-treated mice (One-way ANOVA with Dunnett's multiple comparison test: IgG1 vs. Naïve p=0.0283; IgG1 vs. Syn303 p=0.9791; IgG1 vs. Syn9048 p=0.0047). N=7-12/group. FIG. 8G: DOPAC levels were similarly preserved by Syn9048 treatment (One-way ANOVA with Dunnett's multiple comparison test: IgG1 vs. Naïve p=0.0469; IgG1 vs. Syn303 p=0.9969; IgG1 vs. Syn9048 p=0.0049). N=7-12/group. Error bars represent standard error.

Figure 9A:
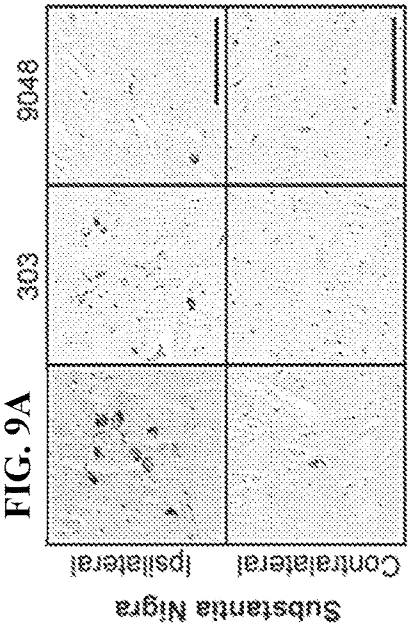
Figure 9B:
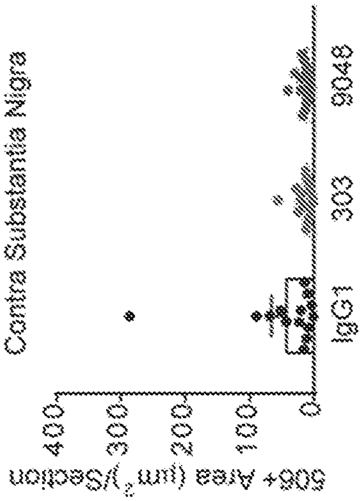
Figure 9C:
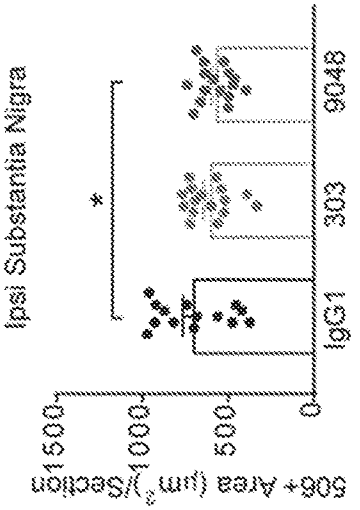
Figure 9D:
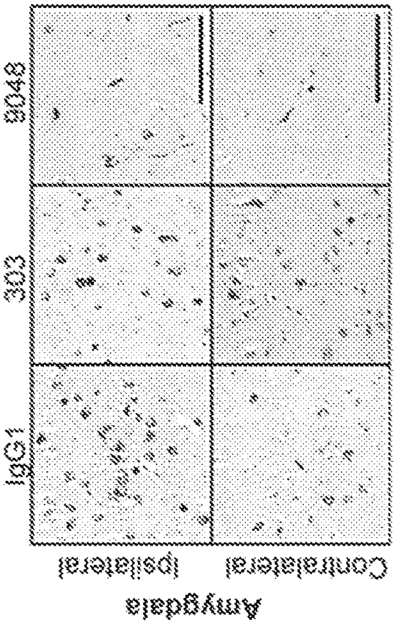
Figure 9E:
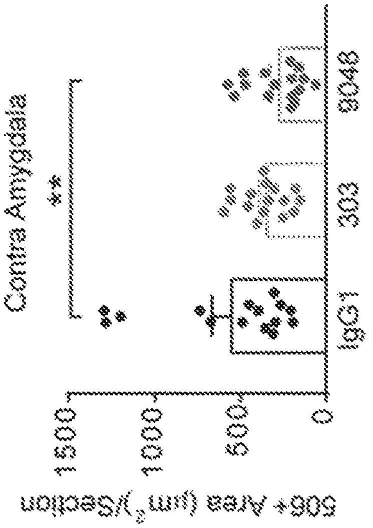
Figure 9F:
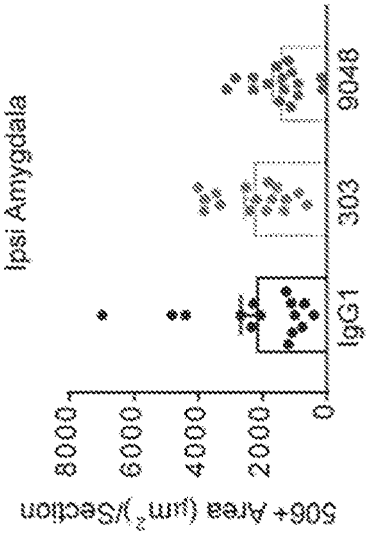

FIGS. 9A-9F illustrate that Syn9048 reduces α-Synuclein pathology in the SN and Amygdala. FIG. 9A: Mice injected with α-Synuclein PFFs accumulate substantial α-Synuclein pathology in the ipsilateral SN, as recognized by the conformation-selective antibody Syn506. Rare pathology is also observed in the contralateral SN at this time point. Scale bars=100 μm. FIG. 9B: Syn506+ area/section was quantified throughout the contralateral SN, and was substantially, albeit not significantly, reduced (One-way ANOVA with Dunnett's multiple comparison test: IgG1 vs. Syn303 p=0.0827; IgG1 vs. Syn9048 p=0.0847). N=14-16/group. FIG. 9C: α-Synuclein pathology was also reduced with immunotherapy treatment in the ipsilateral SN (One-way ANOVA with Dunnett's multiple comparison test: IgG1 vs. Syn303 p=0.0937; IgG1 vs. Syn9048 p=0.0444). N=14-16/group. FIG. 9D: Mice injected with α-Synuclein PFFs accumulate substantial α-Synuclein pathology in the ipsilateral and contralateral amygdala, as recognized by the conformation-selective antibody Syn506. Scale bars=100 μm. FIG. 9E: Syn506+ area/section was quantified throughout the contralateral amygdala, and was substantially reduced (One-way ANOVA with Dunnett's multiple comparison test: IgG1 vs. Syn303 p=0.0521; IgG1 vs. Syn9048 p=0.0069). N=14-16/group. FIG. 9F: α-Synuclein pathology was not reduced to the same extent in the ipsilateral amygdala (One-way ANOVA with Dunnett's multiple comparison test: IgG1 vs. Syn303 p=0.8694; IgG1 vs. Syn9048 p=0.2464). N=14-16/group. All points represent individual mice and error bars represent standard error.

Figure 10:
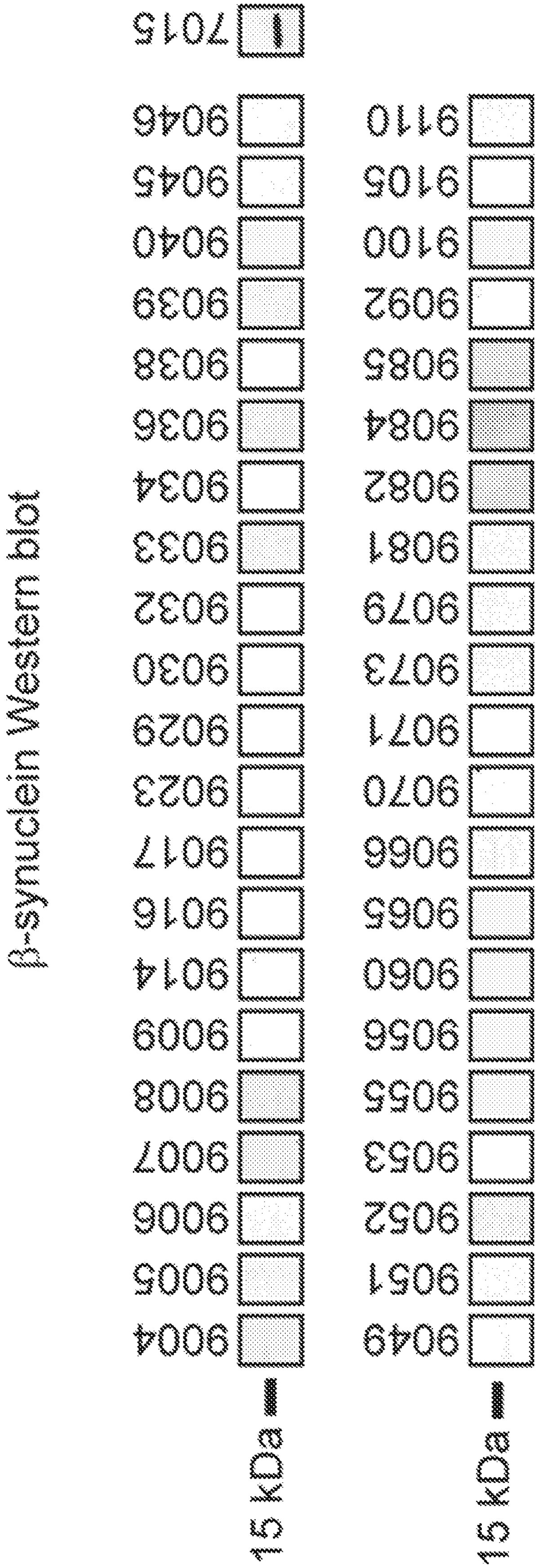

FIG. 10 illustrates non-limiting recognition of β-Synuclein. Most antibodies did not recognize β-Synuclein by Western blot. Syn9030 and Syn9066 had slight reactivity with β-Synuclein, indicating some cross-reactivity of these antibodies. Syn7015 is used as a positive control since this antibody cross-reacts with β-Synuclein.

Figure 11A:
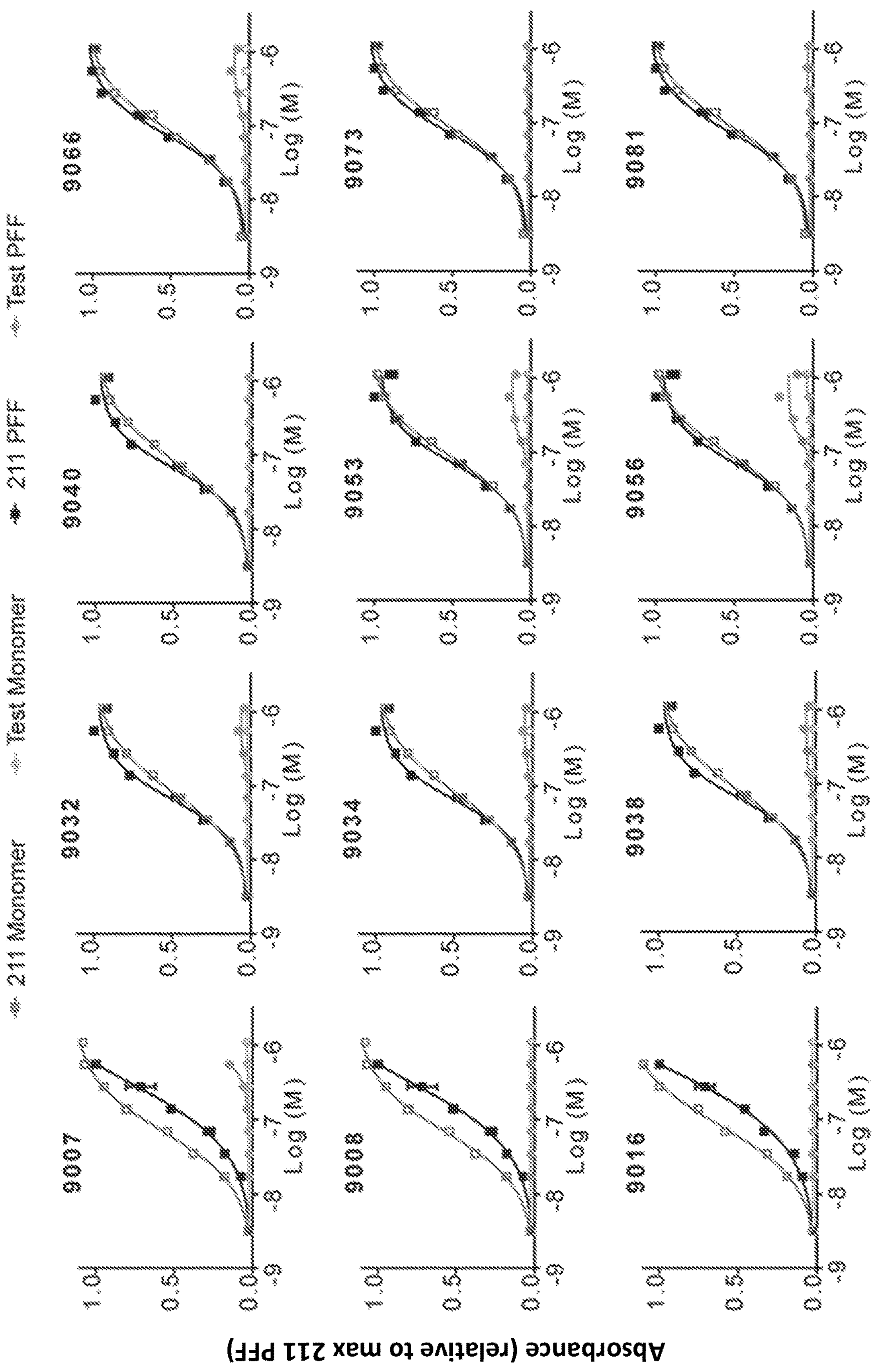
Figure 11B:
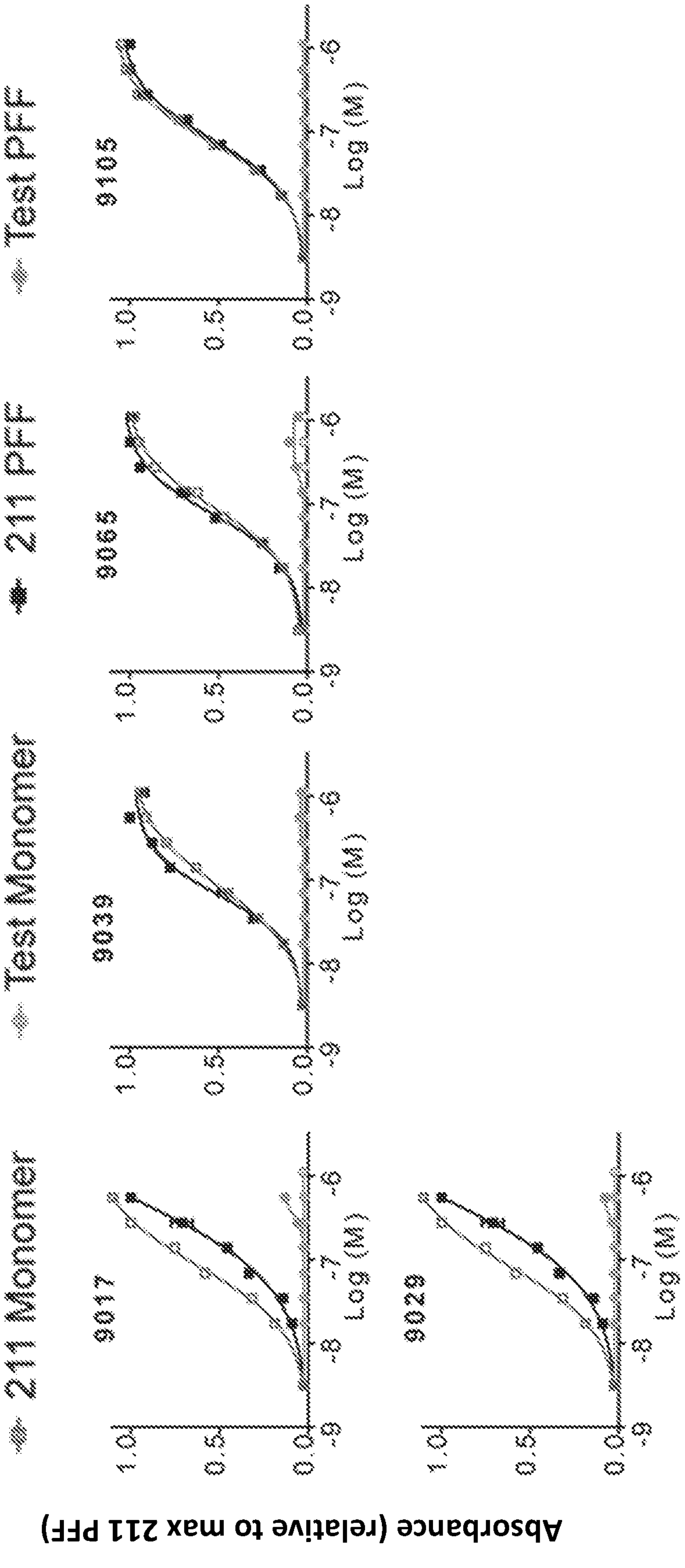

FIGS. 11A-11B illustrate a non-limiting sandwich ELISA that identifies non-binding antibodies. Antibodies were assessed for a preference for misfolded α-Synuclein by performing parallel sandwich ELISAs with either α-Synuclein monomer or α-Synuclein PFFs as the antigen. Syn211 was also used on each plate as a non-selective control antibody. This figure displays antibodies which were non-binding in this assay. Plots represent the means from 3 technical replicates, and error bars represent standard error.

Figure 12A:
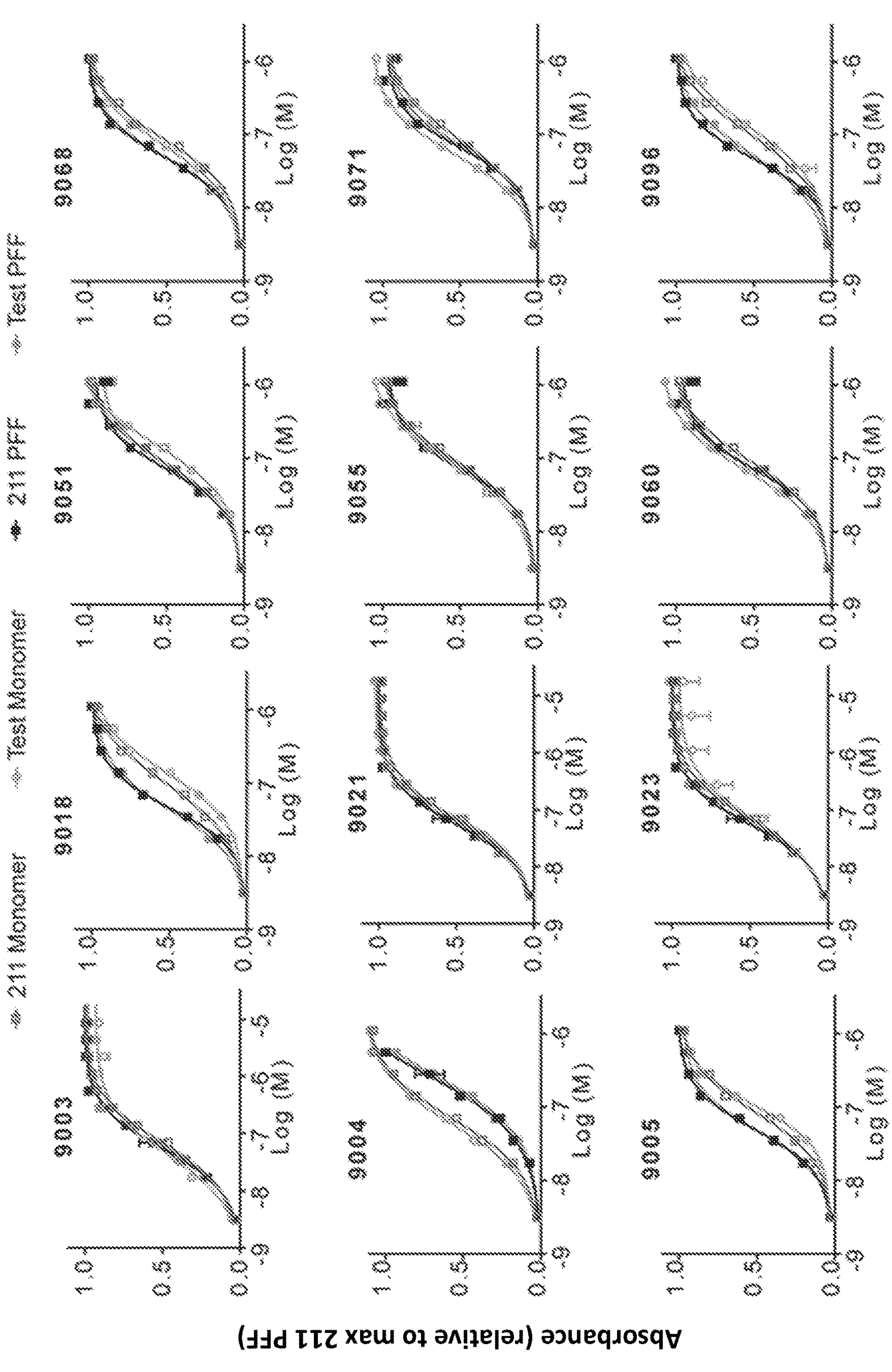
Figure 12B:
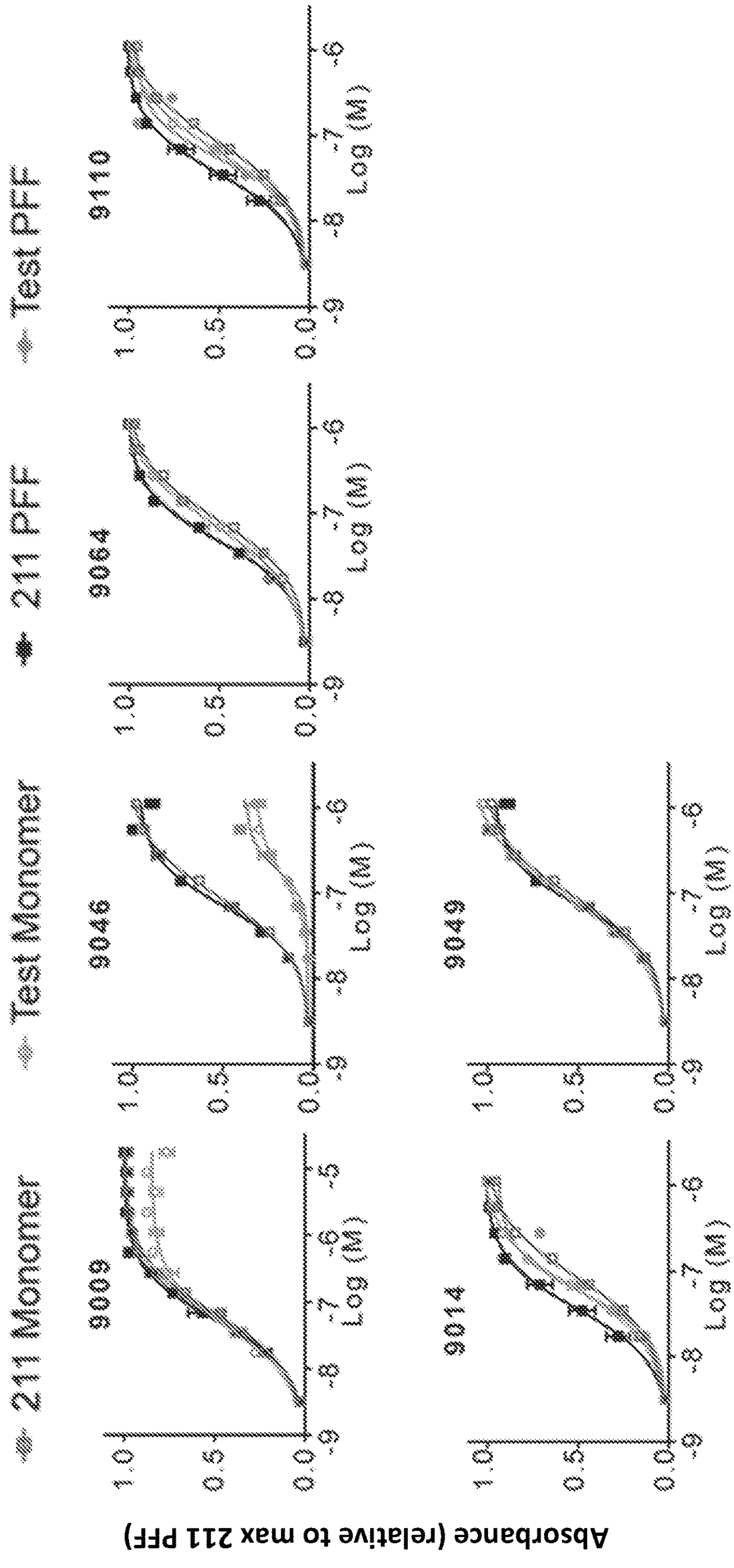

FIGS. 12A-12B illustrate a non-limiting sandwich ELISA that identifies non-selective antibodies. Antibodies were assessed for a preference for misfolded α-Synuclein by performing parallel sandwich ELISAs with either α-Synuclein monomer or α-Synuclein PFFs as the antigen. Syn211 was also used on each plate as a non-selective control antibody. This figure displays antibodies which were non-selective in this assay. Plots represent the means from 3 technical replicates, and error bars represent standard error.

Figure 13A:
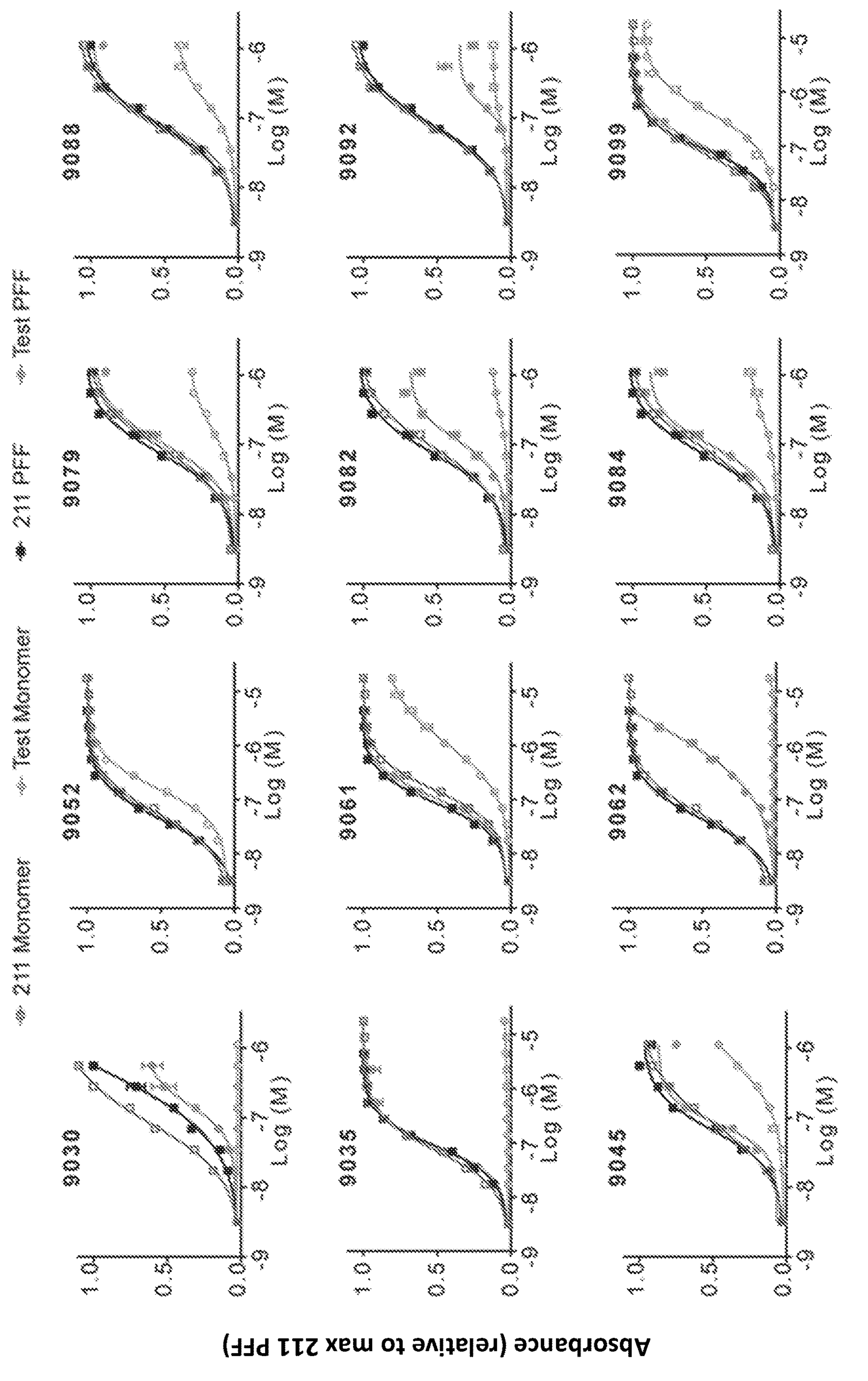
Figure 13B:
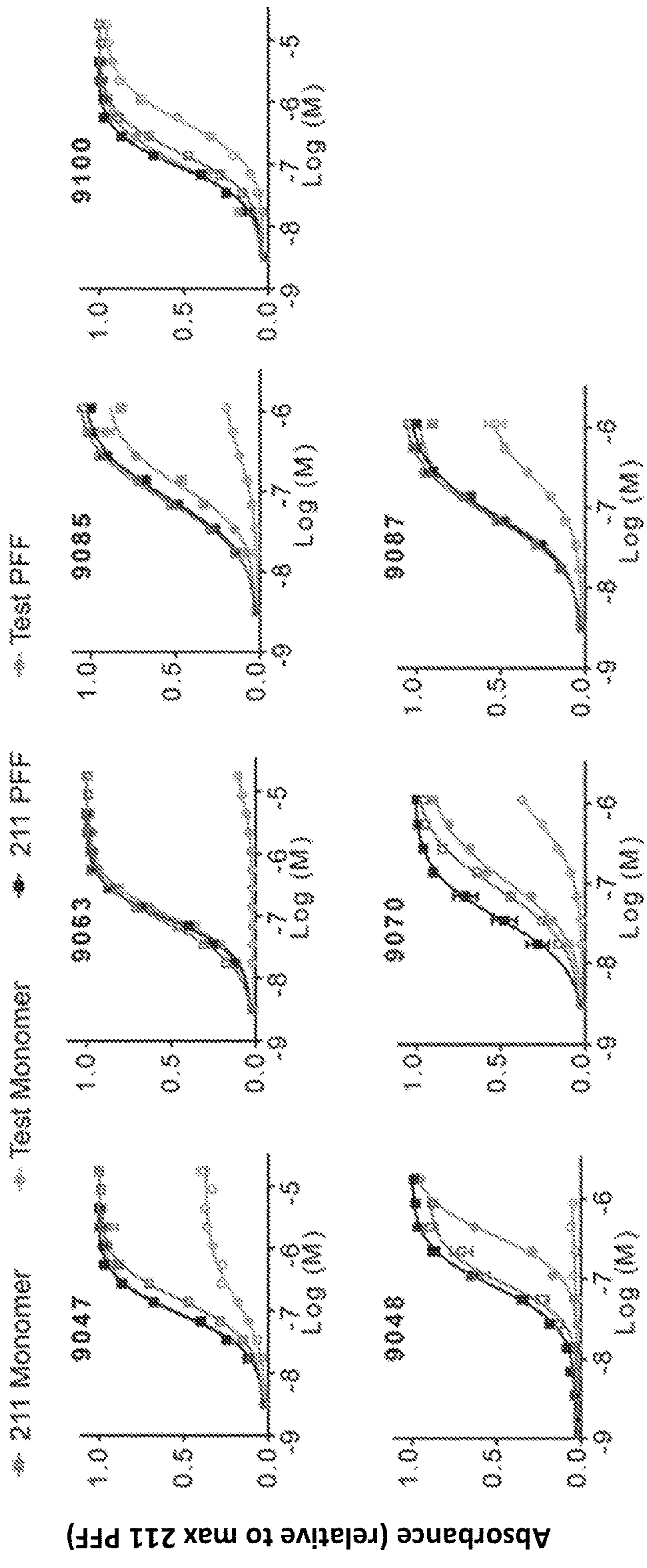

FIGS. 13A-13B illustrate a non-limiting sandwich ELISA that identifies α-Synuclein PFF-selective antibodies. Antibodies were assessed for a preference for misfolded α-Synuclein by performing parallel sandwich ELISAs with either α-Synuclein monomer or α-Synuclein PFFs as the antigen. Syn211 was also used on each plate as a non-selective control antibody. This figure displays antibodies which showed a preference for α-Synuclein PFFs in this assay. Plots represent the means from 3 technical replicates, and error bars represent standard error.

Figure 14:
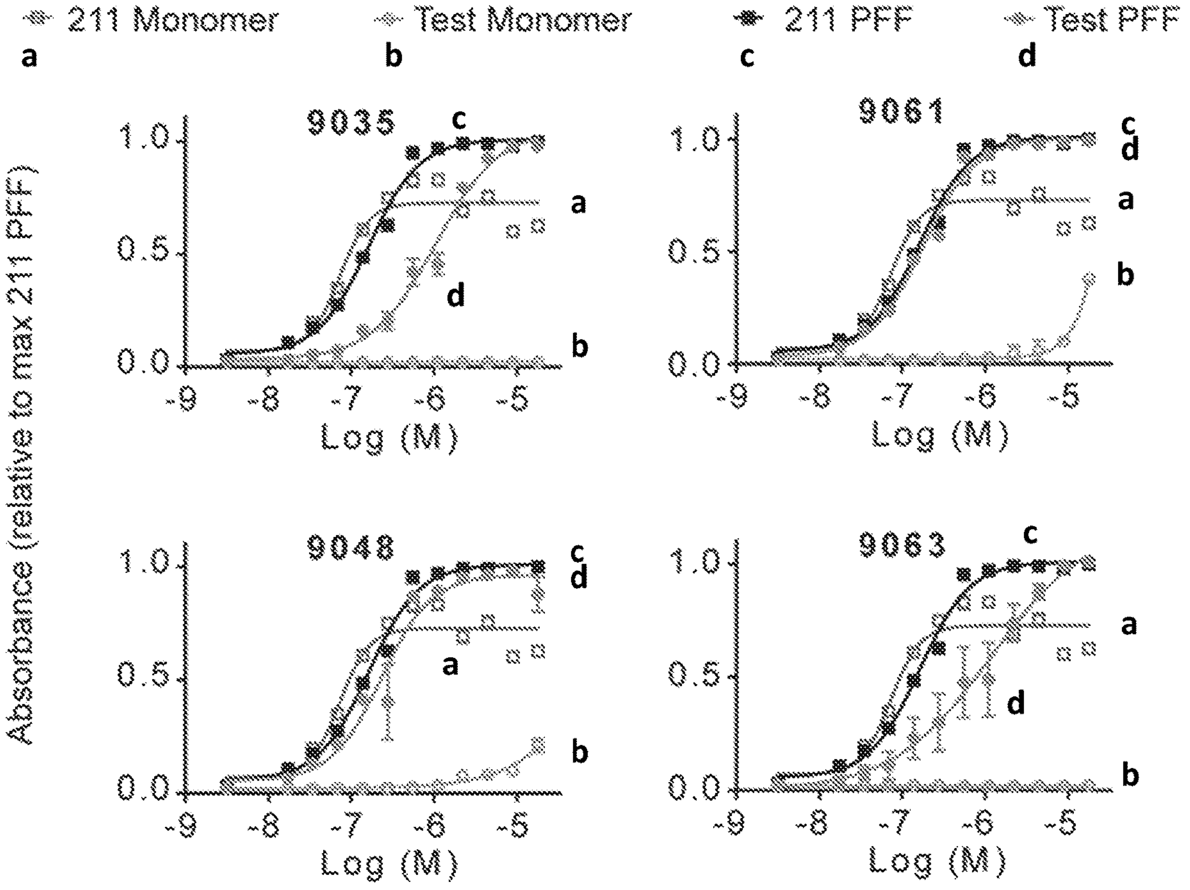

FIG. 14 illustrates a non-limiting second sandwich ELISA that confirms α-Synuclein PFF-selective antibodies. Antibodies were assessed for a preference for misfolded α-Synuclein by performing second set of parallel sandwich ELISAs with either α-Synuclein monomer or α-Synuclein PFFs as the antigen and the polyclonal α-Synuclein antibody SNL4. Plots represent the means from 3 technical replicates, and error bars represent standard error.

Figure 15:
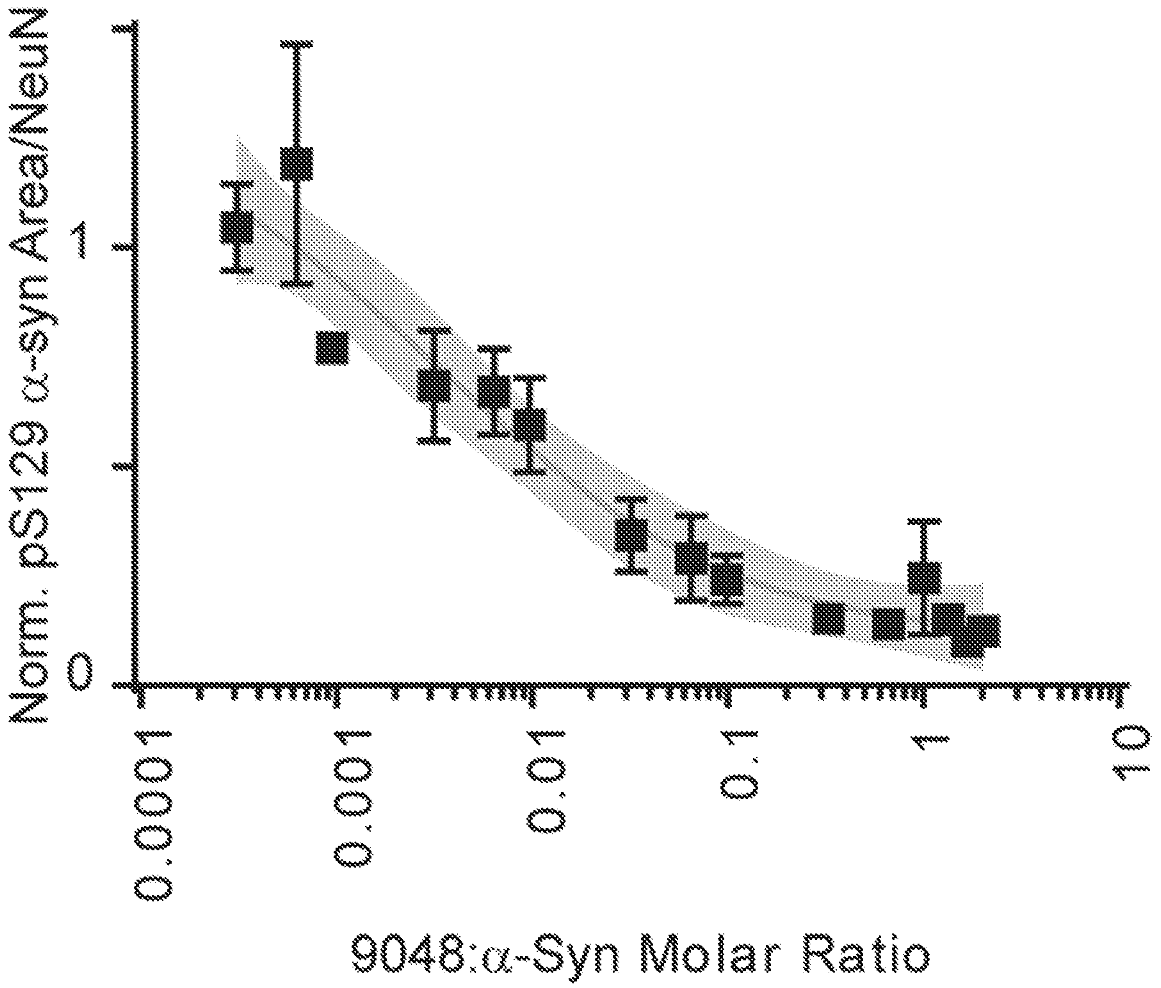

FIG. 15 illustrates that Syn9048 prevents α-Synuclein pathology induced by mouse α-Synuclein PFFs. Syn9048 was assayed for its ability to prevent α-Synuclein pathology induced by mouse α-Synuclein in neurons. Primary hippocampal neurons were cultured as previously described and treated with mouse α-Synuclein PFFs concurrently with increasing concentrations of Syn9048. Quantification of pS129 α-Synuclein area/neuron number normalized to IgG treatment is shown. Increasing molar ratios of Syn9048 reduced pS129 α-Synuclein pathology in a dose-dependent manner and is fit by a sigmoidal dose curve with an $IC_{50}$ of 0.004 ($R^2$=0.8026). N=3/condition. Error bars represent standard error and the shaded area represents the 95% confidence interval of the sigmoidal fit.

DETAILED DESCRIPTION OF THE DISCLOSURE

Definitions

Unless defined otherwise, all technical and scientific terms used herein have the same meaning as commonly understood by one of ordinary skill in the art to which the disclosure pertains. Although any methods and materials similar or equivalent to those described herein can be used in the practice for testing of the present disclosure, illustrative materials and methods are described herein. In describing and claiming the present disclosure, the following terminology will be used. It is also to be understood that the terminology used herein is for the purpose of describing particular embodiments only, and is not intended to be limiting.

As used herein, each of the following terms has the meaning associated with it in this section.

Unless defined otherwise, all technical and scientific terms used herein generally have the same meaning as commonly understood by one of ordinary skill in the art to which this disclosure belongs. Generally, the nomenclature used herein and the laboratory procedures in cell culture, molecular genetics, analytical chemistry, immunology, and nucleic acid chemistry and hybridization are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

As used herein, the term "α-Synuclein" or "α-Syn" or "α-syn" refers to a protein that is expressed mainly in brain tissues and is primarily located at the presynpatic terminal of neurons. In certain embodiments, the disclosure contemplates human α-Syn, which has the sequence SEQ ID NO:245:

```
        10         20         30         40
MDVFMKGLSK AKEGVVAAAE KTKQGVAEAA GKTKEGVLYV

        50         60         70         80
GSKTKEGVVH GVATVAEKTK EQVTNVGGAV VTGVTAVAQK

        90        100        110        120
TVEGAGSIAA ATGFVKKDQL GKNEEGAPQE GILEDMPVDP

       130        140
DNEAYEMPSE EGYQDYEPEA
```

As used herein, the term "α-Syn" refers to total α-Syn, α-Syn monomers, α-Syn fibrils, and/or α-Syn oligomers. As used herein, α-Syn oligomer refers to any multimeric assembly of α-Syn comprising two or more α-Syn monomers.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "affinity" for a molecule towards another refers to the degree (or tightness) of binding between the two molecules. A higher affinity means tighter binding between the two molecules. Affinity can be quantified in terms of dissociation constant (or $K_d$), where a $K_d$ value that is lower in magnitude (closer to zero) indicates a higher affinity.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half-life without adversely affecting activity of the peptide. Additionally, a disulfide linkage may be present or absent in the peptides.

The term "antibody," as used herein, refers to an immunoglobulin molecule able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present disclosure may exist in a variety of forms including, for example, polyclonal antibodies, monoclonal antibodies, intracellular antibodies ("intrabodies"), Fv, Fab and $F(ab)_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). As used herein, a "neutralizing antibody" is an immunoglobulin molecule that binds to and blocks the biological activity of the antigen.

The term “antigen” or “Ag” as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an “antigen” as that term is used herein. Furthermore, one skilled in the art will understand that an antigen need not be encoded solely by a full length nucleotide sequence of a gene. It is readily apparent that the present disclosure includes, but is not limited to, the use of partial nucleotide sequences of more than one gene and that these nucleotide sequences are arranged in various combinations to elicit the desired immune response. Moreover, a skilled artisan will understand that an antigen need not be encoded by a “gene” at all. It is readily apparent that an antigen can be generated or synthesized, or can be derived from a biological sample. Such a biological sample can include, but is not limited to a tissue sample, a tumor sample, a cell or a biological fluid.

A “coding region” of a gene consists of the nucleotide residues of the coding strand of the gene and the nucleotides of the non-coding strand of the gene that are homologous with or complementary to, respectively, the coding region of an mRNA molecule produced by transcription of the gene.

A “coding region” of an mRNA molecule also consists of the nucleotide residues of the mRNA molecule that are matched with an anti-codon region of a transfer RNA molecule during translation of the mRNA molecule or that encode a stop codon. The coding region may thus include nucleotide residues corresponding to amino acid residues not present in the mature protein encoded by the mRNA molecule (e.g., amino acid residues in a protein export signal sequence).

“Complementary” as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds (“base pairing”) with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term “delivery vehicle” is used herein as a generic reference to any delivery vehicle capable of delivering a compound to a subject, including, but not limited to, dermal delivery vehicles and transdermal delivery vehicles.

The term “DNA” as used herein is defined as deoxyribonucleic acid.

“Effective amount” or “therapeutically effective amount” are used interchangeably herein, and refer to an amount of a compound, formulation, material, or composition, as described herein, effective to achieve a particular biological result. Such results may include, but are not limited to, treatment of a disease or condition as determined by any means suitable in the art.

“Encoding” refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term “fragment,” as applied to a protein or peptide, refers to a subsequence of a larger protein or peptide. A “fragment” of a protein or peptide can be at least about 20 amino acids in length; for example at least about 50 amino acids in length; at least about 100 amino acids in length, at least about 200 amino acids in length, at least about 300 amino acids in length, and at least about 400 amino acids in length (and any integer value in between). As used herein, an antibody fragment refers to active fragments thereof, i.e., fragments having the same characteristics that are used for the definition of an antibody according to the disclosure, in certain embodiments high affinity for α-Syn fibrils (composed of misfolded α-Syn) and low or high binding affinity to α-Syn monomers. For convenience when the term antibody is used, fragments thereof exhibiting the same characteristic are also being considered.

As used herein, the term “fragment,” as applied to a nucleic acid, refers to a subsequence of a larger nucleic acid. A “fragment” of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the “coding strand”; sequences on the DNA strand which are located 5' to a reference point on the DNA are referred to as “upstream sequences”; sequences on the DNA strand which are 3' to a reference point on the DNA are referred to as “downstream sequences.”

An “individual”, “patient” or “subject”, as that term is used herein, includes a member of any animal species including, but are not limited to, birds, humans and other primates, and other mammals including commercially relevant mammals such as cattle, pigs, horses, sheep, cats, and dogs. Preferably, the subject is a human.

"Instructional material," as that term is used herein, includes a publication, a recording, a diagram, or any other medium of expression which can be used to communicate the usefulness of the composition and/or compound of the disclosure in a kit. The instructional material of the kit may, for example, be affixed to a container that contains the compound and/or composition of the disclosure or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

As used herein, the term "pharmaceutical composition" refers to a mixture of at least one compound of the disclosure with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "protein", "peptide" and "polypeptide" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types. "Proteins" include, for example, biologically active fragments, substantially homologous proteins, oligopeptides, homodimers, heterodimers, variants of proteins, modified proteins, derivatives, analogs, and fusion proteins, among others. The proteins include natural proteins, recombinant proteins, synthetic proteins, or a combination thereof.

The term "recombinant DNA" as used herein is defined as DNA produced by joining pieces of DNA from different sources.

The term "recombinant polypeptide" as used herein is defined as a polypeptide produced by using recombinant DNA methods.

The term "RNA" as used herein is defined as ribonucleic acid.

The term "therapeutic" as used herein means a treatment and/or prophylaxis.

The term to "treat," as used herein, means reducing the frequency with which symptoms are experienced by a subject or administering an agent or compound to reduce the frequency and/or severity with which symptoms are experienced. As used herein, "alleviate" is used interchangeably with the term "treat."

As used herein, "treating a disease, disorder or condition" means reducing the frequency or severity with which a symptom of the disease, disorder or condition is experienced by a subject. Treating a disease, disorder or condition may or may not include complete eradication or elimination of the symptom.

The following abbreviations are used herein: BBB, blood-brain barrier; CDR, complementary-determining region; DLB, dementia with Lewy bodies; FL, full length; LB, Lewy body; LN, Lewy neurite; MSA, multiple system atrophy; NAC, non-amyloid component; PD, Parkinson's disease; PDD, Parkinson's disease dementia; PFF, pre-formed fibril; VH, heavy chain variable region; VL, light chain variable region.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

This disclosure is generally directed to certain monoclonal (mouse) antibodies, or fragments thereof, that recognize certain pathogenic forms of α-Syn, a protein that is misfolded in Parkinson's disease (PD) and related neurodegenerative disorders known as synucleinopathies. PD and dementia with Lewy bodies (DLB) are progressive neurodegenerative diseases for which there is no disease-modifying treatment. PD and DLB are characterized by aggregation of the synaptic protein α-Synuclein, and there is compelling evidence to suggest that progression of these diseases is associated with the transcellular spread of pathogenic α-Synuclein through the brains of afflicted individuals. Therapies targeting extracellular, pathogenic α-Synuclein may therefore hold promise for slowing or halting disease progression.

At the onset of this investigation, it was unclear what the preferred properties are for a therapeutic α-Synuclein antibody. For example, targeting all α-Synuclein species with a pan-α-Synuclein antibody can have deleterious effects in the central nervous system or in the blood, where α-Synuclein is abundant in red blood cells. Moreover, the binding of a pan-α-Synuclein antibody to non-pathogenic forms of the protein would reduce the antibody available for binding to misfolded species.

Previous research has identified several antibodies that are effective in animal models of PD at reducing α-Synuclein aggregates. These antibodies had differing selectivity profiles (α-Synuclein oligomers, C-terminal truncated α-Synuclein, or fibrillar α-Synuclein) and it is currently unclear whether antibodies directed against certain epitopes will be more efficacious than others. As it is generally acknowledged that only ~0.1% of administered antibody passes the BBB, there are likely to be benefits to utilizing α-Synuclein antibodies that preferentially bind to pathogenic species and not the α-Synuclein monomer that is present in the brain. This would increase the effective concentration of antibody that could target the α-Synuclein that promotes disease progression, without loss of antibody in non-productive binding to monomers.

In a non-limiting aspect, the present studies were directed to identifying an antibody with high selectivity for pathogenic, misfolded α-Synuclein. After first immunizing mice with misfolded α-Synuclein and creating a library of B-cell hybridomas, antibodies produced by clonal hybridoma cultures were passed through a series of screening assays to select for antibodies that show high selectivity for misfolded α-Synuclein and are able to inhibit the formation of LB-like structures in a primary neuron model of α-synucleinopathy. An illustrative candidate antibody, Syn9048, was tested for efficacy in a wildtype mouse model of pathological α-Synuclein transmission. Chronic 6-month administration of Syn9048 was well-tolerated by mice, and Syn9048 was able to preserve striatal dopamine levels and reduce α-Synuclein pathology, especially in areas where α-Synuclein inclusions likely resulted from transcellular spread of pathogenic α-Synuclein. In all measures, Syn9048 showed improved efficacy over a previously validated α-Synuclein antibody (Tran, et al., 2014, Cell Reports 7:2054-2065), indicating that Syn9048 has desirable properties for treating, ameliorating, and/or preventing the diseases contemplated herein. This study highlights the therapeutic potential of α-Synuclein immunotherapy for the treatment of PD and DLB, and provides a framework for screening of α-Synuclein antibodies to identify those with desirable properties.

In certain embodiments, the antibodies of the disclosure are highly selective towards pathogenic forms of α-Synuclein and can be administered as therapeutic agents targeting those pathogenic protein forms. In certain embodiments, the antibodies of the disclosure recognize a conformational epitope comprising amino acids 110-120 and/or 120-130 in combination with another region of α-Syn.

In certain embodiments, the antibodies of the disclosure show preferential binding towards the pathological form of α-Syn (i.e., fibrils and/or oligomers) compared to the native (i.e., monomeric) form. In other embodiments, the antibodies of the disclosure reduce formation of pathological α-Syn inclusions/fibrils that normally form in cultured neurons that are exposed to recombinant α-Syn fibrils. In yet other embodiments, the antibodies of the disclosure detect pathological α-Syn fibrils. In yet other embodiments, the antibodies of the disclosure are used as therapeutics for decreasing the development/spread of pathological α-Syn fibrils and/or oligomers in synucleinopathies. In yet other embodiments, the antibodies of the disclosure do not cross-react with Tau and/or beta-amyloid protein.

In certain embodiments, the antibodies of the disclosure bind to α-Syn fibrils and/or oligomers with a dissociation constant $K_d$ equal to or less than about $10^{-6}$ M, about $10^{-7}$ M, about $10^{-8}$M, about $10^{-9}$M, about $10^{-10}$ M, or about $10^{-11}$ M. In other embodiments, the antibodies of the disclosure bind to α-Syn monomers with an affinity that at least about 10 times, 30 times, 100 times, 300 times, or 1000 times lower than the affinity of the antibodies for α-Syn fibrils. In yet other embodiments, the antibodies of the disclosure bind to α-Syn monomers with a dissociation constant $K_d$ equal to or higher than about $10^{-10}$ M, about $10^{-9}$ M, about $10^{-8}$ M, about $10^{-7}$M, about $10^{-6}$ M, about $10^{-5}$ M, about $10^{-4}$ M, or about $10^{-3}$M. In yet other embodiments, the antibodies of the disclosure bind with nearly equal affinity to α-Syn fibrils and monomers. In yet other embodiments, the antibodies of the disclosure bind with nearly equal affinity to α-Syn fibrils, oligomers and monomers, with a dissociation constant $K_d$ equal to or less than about $10^{-7}$ M, about $10^{-8}$ M, about $10^{-9}$ M, about $10^{-10}$ M, or about $10^{-11}$ M. Binding affinities of the antibodies can be determined by using a variety of methods recognized in the art, including methods described elsewhere herein, such as but not limited to isothermal calorimetry, surface plasmon resonance, immunoassays such as ELISA or RIAs, and the like.

Compositions Comprising Antibodies

In one aspect, the disclosure comprises isolated monoclonal antibodies that selectively bind α-Syn in the fibrillar and/or oligomeric conformation, and/or bind both soluble, oligomeric, and fibrillar α-Syn with high affinity. In certain embodiments, the antibody comprises a heavy chain. In other embodiments, the heavy chain comprises three complementary-determining regions (CDR), namely CDR1, CDR2, and CDR3. In yet other embodiments, the light chain comprises three complementary-determining regions (CDR), namely CDR1, CDR2, and CDR3.

In certain embodiments, the monoclonal antibody (named 9003 herein) comprises light and heavy variable chains having the sequences shown below:

```
Heavy chain: DNA sequence (414 bp)
Signal sequence-FR1-CDR1-FR2-CDR2-FR3-CDR3-FR4
SEQ ID NO: 1 - SEQ ID NO: 2 - SEQ ID NO: 3 - SEQ ID NO: 4 - SEQ ID NO: 5 -
SEQ ID NO: 6 - SEQ ID NO: 7 - SEQ ID NO: 8
ATGCTGTTGGGGCTGAAGTGGGTTTTCTTTGTTGTTTTTATCAAGGTGTGCATTGTGAGGTGCAGC

TTGTTGAGTCTGGTGGAGGATTGGTGCAACCTAAAGGGTCATTGAAACTCTCATGTGCAGCCTCTGG

ATTCACCTTCAATACCTACGCCATGCACTGGGTCCGCCAGGCTCCAGGAAAGGGTTTGGAATGGGTT

GCTCGCATAAGAAGTGAAAGTAATAATTTTGCAACATATTATGCCGATTCAGTGAAAGACAGTTTCA

CCATCTCCAGAGATGATTCACAAAGCATGCTCTATCTGCAAATGAACAACTTGAAAACTGAGGACAC

AGCCGTATATTACTGTGTGAGAGGGGGGTTATCTCCCTTTGACTACTGGGGCCAAGGCACCACTCTC

ACAGTCTCCTCA

Heavy chain: Amino acid sequence (138 aa)
Signal peptide-FR1-CDR1-FR2-CDR2-FR3-CDR3-FR4
SEQ ID NO: 9 - SEQ ID NO: 10 - SEQ ID NO: 11 - SEQ ID NO: 12 - SEQ ID NO: 13
- SEQ ID NO: 14 - SEQ ID NO: 15 - SEQ ID NO: 16
MLLGLKWVFFVVFYQGVHCEVQLVESGGGLVQPKGSLKLSCAASGFTFNTYAMHWVRQAPGKGLEWV

ARIRSESNNFATYYADSVKDSFTISRDDSQSMLYLQMNNLKTEDTAVYYCVRGGLSPFDYWGQGTTL

TVSS

Light chain: DNA sequence (384 bp)
Signal sequence-FR1-CDR1-FR2-CDR2-FR3-CDR3-FR4
SEQ ID NO: 17 - SEQ ID NO: 18 - SEQ ID NO: 19 - SEQ ID NO: 20 - SEQ ID NO: 21
- SEQ ID NO: 22 - SEQ ID NO: 23 - SEQ ID NO: 24
ATGGATTTTCAAGTGCAGATTTTCAGCTTCCTGCTAATCAGTGCCTCAGTCATAATATCCAGAGGAC

AAATTGTTCTCACCCAGTCTCCAGCAATCATGTCTGCATCTCCAGGGGAGAAGGTCACCATGACCTG

CAGTGCCAGCTCAAGTGTAAGTTACATGCACTGGTACCAACAGAAGTCAGGCACCTCCCCCAAAAGA

TGGATTTATGACACTTCCAAACTGGCTTCTGGAGTCCCTGCTCGCTTCAGTGGCAGTGGGTCTGGGA

CCTCTTACTCTCTCACAATCAACAGCATGGAGGCTGAAGATGCTGCCACTTATTACTGCCAGCAGTG

GAGTAGAAATCCACCCACGTTCGGAGGGGGGACCAAGCTGGAAATAAAA

Light chain: Amino acid sequence (128 aa)
Signal peptide-FR1-CDR1-FR2-CDR2-FR3-CDR3-FR4
SEQ ID NO: 25 - SEQ ID NO: 26 - SEQ ID NO: 27 - SEQ ID NO: 28 - SEQ ID NO: 29
- SEQ ID NO: 30 - SEQ ID NO: 31 - SEQ ID NO: 32
MDFQVQIFSFLLISASVIISRGQIVLTQSPAIMSASPGEKVTMTCSASSSVSYMHWYQQKSGTSPKR

WIYDTSKLASGVPARFSGSGSGTSYSLTINSMEAEDAATYYCQQWSRNPPTFGGGTKLEIK
```

In certain embodiments, the monoclonal antibody (named 9004 herein) comprises light and heavy variable chains having the sequences shown below:

Heavy chain: DNA sequence (426 bp)
Signal sequence-FR1-CDR1-FR2-CDR2-FR3-CDR3-FR4
SEQ ID NO 33 - SEQ ID NO: 34 - SEQ ID NO: 3 - SEQ ID NO: 4 - SEQ ID NO: 35 - SEQ ID NO: 36 - SEQ ID NO: 7 - SEQ ID NO: 37
ATGACATTGAACGTGCTGTTGGGGCTGAAGTGGGTTTTCTTTGTTGTTTTTTATCAAGGTGTGCATT

GTGAGGTGCACCTTGTTGAGTCTGGTGGAGGATTGGTGCAGCCTAAAGGGTCATTGAAACTCTCATG

TGCAGCCTCTGGATTCACCTTCAATACCTACGCCATGCACTGGGTCCGCCAGGCTCCAGGAAAGGGT

TTGGAATGGGTTGCTCGCATAAGAAGTAAAAGTAATAATTATGCAACATATTATGCCGATTCAGTGA

AAGACAGGTTCACCATCTCCAGAGATGATTCACAAAGCATGCTCTATCTGCAAATGAACAACTTGAA

AACTGAGGACACAGCCATGTATTACTGTGTGAGAGGGGGGTTATCTCCCTTTGACTACTGGGGCCAA

GGCACCACACTCACAGTCTCCTCA

Heavy chain: Amino acid sequence (142 aa)
Signal peptide-FR1-CDR1-FR2-CDR2-FR3-CDR3-FR4
SEQ ID NO: 38 - SEQ ID NO: 39 - SEQ ID NO: 11 - SEQ ID NO: 12 - SEQ ID NO: 40 - SEQ ID NO: 41 - SEQ ID NO: 15 - SEQ ID NO: 16
MTLNVLLGLKWVFFVVFYQGVHCEVHLVESGGGLVQPKGSLKLSCAASGFTFNTYAMHWVRQAPGKG

LEWVARIRSKSNNYATYYADSVKDRFTISRDDSQSMLYLQMNNLKTEDTAMYYCVRGGLSPFDYWGQ

GTTLTVSS

Light chain: DNA sequence (384 bp)
Signal sequence-FR1-CDR1-FR2-CDR2-FR3-CDR3-FR4
SEQ ID NO: 17 - SEQ ID NO: 18 - SEQ ID NO: 19 - SEQ ID NO: 42 - SEQ ID NO: 43 - SEQ ID NO: 22 - SEQ ID NO: 44 - SEQ ID NO: 45
ATGGATTTTCAAGTGCAGATTTTCAGCTTCCTGCTAATCAGTGCCTCAGTCATAATATCCAGAGGAC

AAATTGTTCTCACCCAGTCTCCAGCAATCATGTCTGCATCTCCAGGGGAGAAGGTCACCATGACCTG

CAGTGCCAGCTCAAGTGTAACTTACATGCACTGGTACCAGCAGAAGTCAGGCACCTCCCCCAAAAGA

TGGATTTATGACACATCCAAACTGGCTTCTGGAGTCCCTGCTCGCTTCAGTGGCAGTGGGTCTGGGA

CCTCTTACTCTCTCACAATCAGCAGCATGGAGGCTGAAGATGCTGCCACTTATTACTGCCAGCAGTG

GAGTAGTAACCCACCCACGTTCGGAGGGGGGACCAAGCTGGAAATAAGA

Light chain: Amino acid sequence (128 aa)
Signal peptide-FR1-CDR1-FR2-CDR2-FR3-CDR3-FR4
SEQ ID NO: 25 - SEQ ID NO: 26 - SEQ ID NO: 46 - SEQ ID NO: 28 - SEQ ID NO: 29 - SEQ ID NO: 30 - SEQ ID NO: 31 - SEQ ID NO: 47
MDFQVQIFSFLLISASVIISRGQIVLTQSPAIMSASPGEKVTMTCSASSSVTYMHWYQQKSGTSPKR

WIYDTSKLASGVPARFSGSGSGTSYSLTISSMEAEDAATYYCQQWSSNPPTFGGGTKLEIR

In certain embodiments, the monoclonal antibody (named 9005 herein) comprises light and heavy variable chains having the sequences shown below:

Heavy chain: DNA sequence (414 bp)
Signal sequence-FR1-CDR1-FR2-CDR2-FR3-CDR3-FR4
SEQ ID NO: 48 - SEQ ID NO: 49 - SEQ ID NO: 50 - SEQ ID NO: 51 - SEQ ID NO: 52 - SEQ ID NO: 53 - SEQ ID NO: 54 - SEQ ID NO: 55
ATGAACTTCGGGCTCAGCTTGATTTTCCTTGTCCTTGTTTTAAAAGGTGTCCAGTGTGAAGTGATGC

TGGTGGAGTCTGGGGGAGGCTTAGTGAAGTCTGGAGGGTCCCTAAAACTCTCCTGTGCAGCCTCTGG

ATTCACTTTCAGTAGCTATGCCATGTCTTGGGTTCGCCAGACTCCGGAGAAGAGGCTGGAATGGGTC

GCAACTATTAGTACTGGTGGTGGTTACACCTACTATCCAGACAGTGTGAAGGGGCGATTCACCATCT

CCAGAGACAATGCCAAGAACACCCTGTACCTGCAAATGAGCAGTCTGAGGTCTGAGGACACGGCCAT

GTATTATTGTGTAAGAAGGGGGACGGCTAGAGGGTACTTCGATGTCTGGGGCGCAGGGACCACGGTC

ACCGTCTCCTCA

-continued

Heavy chain: Amino acid sequence (138 aa)
Signal peptide-FR1-CDR1-FR2-CDR2-FR3-CDR3-FR4
SEQ ID NO: 56 - SEQ ID NO: 57 - SEQ ID NO: 58 - SEQ ID NO: 59 - SEQ ID NO: 60 - SEQ ID NO: 61 - SEQ ID NO: 62 - SEQ ID NO: 63

MNFGLSLIFLVLVLKGVQCEVMLVESGGGLVKSGGSLKLSCAASGFTFSSYAMSWVRQTPEKRLEWV

ATISTGGGYTYYPDSVKGRFTISRDNAKNTLYLQMSSLRSEDTAMYYCVRRGTARGYFDVWGAGTTV

TVSS

Light chain: DNA sequence (384 bp)
Signal sequence-FR1-CDR1-FR2-CDR2-FR3-CDR3-FR4
SEQ ID NO: 64 - SEQ ID NO: 18 - SEQ ID NO: 19 - SEQ ID NO: 65 - SEQ ID NO: 66 - SEQ ID NO: 67 - SEQ ID NO: 68 - SEQ ID NO: 24

ATGGATTTTCAAGTGCAGATTTTCAGCTTCCTGCTAATCAGTGCCTCAGTCATACTGTCCAGAGGAC

AAATTGTTCTCACCCAGTCTCCAGCAATCATGTCTGCATCTCCAGGGGAGAAGGTCACCATGACCTG

CAGTGCCAGCTCAAGTGTAAGTTACATGTACTGGTACCAGCAGAAGCCAGAATCCTCCCCCAGACTC

CTGATTTATGACACATCCAACCTGGCTTCTGGAGTCCCTGTTCGCTTCAGTGGCAGTGGGTCTGGGA

CCTCTTATTTTCTCACAATCAGCCGAATGGAGGCTGAAGATGCTGCCACTTATTACTGCCAGCAGTG

GAAGACTTACCCACCCACGTTCGGAGGGGGGACCAAGCTGGAAATAAAA

Light chain: Amino acid sequence (128 aa)
Signal peptide-FR1-CDR1-FR2-CDR2-FR3-CDR3-FR4
SEQ ID NO: 69 - SEQ ID NO: 26 - SEQ ID NO: 70 - SEQ ID NO: 71 - SEQ ID NO: 72 - SEQ ID NO: 73 - SEQ ID NO: 85 - SEQ ID NO: 32

MDFQVQIFSFLLISASVILSRGQIVLTQSPAIMSASPGEKVTMTCSASSSVSYMYWYQQKPESSPRL

LIYDTSNLASGVPVRFSGSGSGTSYFLTISRMEAEDAATYYCQQWKTYPPTFGGGTKLEIK

In certain embodiments, the monoclonal antibody (named 9009 herein) comprises light and heavy variable chains having the sequences shown below:

Heavy chain: DNA sequence (414 bp)
Signal sequence-FR1-CDR1-FR2-CDR2-FR3-CDR3-FR4
SEQ ID NO: 1 - SEQ ID NO: 2 - SEQ ID NO: 3 - SEQ ID NO: 4 - SEQ ID NO: 5 - SEQ ID NO: 6 - SEQ ID NO: 7 - SEQ ID NO: 8

ATGCTGTTGGGGCTGAAGTGGGTTTTCTTTGTTGTTTTTTATCAAGGTGTGCATTGTGAGGTGCAGC

TTGTTGAGTCTGGTGGAGGATTGGTGCAACCTAAAGGGTCATTGAAACTCTCATGTGCAGCCTCTGG

ATTCACCTTCAATACCTACGCCATGCACTGGGTCCGCCAGGCTCCAGGAAAGGGTTTGGAATGGGTT

GCTCGCATAAGAAGTGAAAGTAATAATTTTGCAACATATTATGCCGATTCAGTGAAAGACAGTTTCA

CCATCTCCAGAGATGATTCACAAAGCATGCTCTATCTGCAAATGAACAACTTGAAAACTGAGGACAC

AGCCGTATATTACTGTGTGAGAGGGGGGTTATCTCCCTTTGACTACTGGGGCCAAGGCACCACTCTC

ACAGTCTCCTCA

Heavy chain: Amino acid sequence (138 aa)
Signal peptide-FR1-CDR1-FR2-CDR2-FR3-CDR3-FR4
SEQ ID NO: 9 - SEQ ID NO: 10 - SEQ ID NO: 11 - SEQ ID NO: 12 - SEQ ID NO: 13 - SEQ ID NO: 14 - SEQ ID NO: 15 - SEQ ID NO: 16

MLLGLKWVFFVVFYQGVHCEVQLVESGGGLVQPKGSLKLSCAASGFTFNTYAMHWVRQAPGKGLEWV

ARIRSESNNFATYYADSVKDSFTISRDDSQSMLYLQMNNLKTEDTAVYYCVRGGLSPFDYWGQGTTL

TVSS

Light chain: DNA sequence (384 bp)
Signal sequence-FR1-CDR1-FR2-CDR2-FR3-CDR3-FR4
SEQ ID NO: 17 - SEQ ID NO: 18 - SEQ ID NO: 19 - SEQ ID NO: 20 - SEQ ID NO: 21 - SEQ ID NO: 22 - SEQ ID NO: 23 - SEQ ID NO: 24

ATGGATTTTCAAGTGCAGATTTTCAGCTTCCTGCTAATCAGTGCCTCAGTCATAATATCCAGAGGAC

AAATTGTTCTCACCCAGTCTCCAGCAATCATGTCTGCATCTCCAGGGGAGAAGGTCACCATGACCTG

CAGTGCCAGCTCAAGTGTAAGTTACATGCACTGGTACCAACAGAAGTCAGGCACCTCCCCCAAAAGA

TGGATTTATGACACTTCCAAACTGGCTTCTGGAGTCCCTGCTCGCTTCAGTGGCAGTGGGTCTGGGA

-continued

CCTCTTACTCTCTCACAATCAACAGCATGGAGGCTGAAGATGCTGCCACTTATTACTGCCAGCAGTG

GAGTAGAAATCCACCCACGTTCGGAGGGGGGACCAAGCTGGAAATAAAA

Light chain: Amino acid sequence (128 aa)
Signal peptide-FR1-CDR1-FR2-CDR2-FR3-CDR3-FR4
SEQ ID NO: 25 - SEQ ID NO: 26 - SEQ ID NO: 27 - SEQ ID NO: 28 - SEQ ID NO: 29 - SEQ ID NO: 30 - SEQ ID NO: 31 - SEQ ID NO: 32
MDFQVQIFSFLLISASVIISRGQIVLTQSPAIMSASPGEKVTMTCSASSSVSYMHWYQQKSGTSPKR

WIYDTSKLASGVPARFSGSGSGTSYSLTINSMEAEDAATYYCQQWSRNPPTFGGGTKLEIK

In certain embodiments, the monoclonal antibody (named 9014 herein) comprises light and heavy variable chains having the sequences shown below:

Heavy chain: DNA sequence (414 bp)
Signal sequence-FR1-CDR1-FR2-CDR2-FR3-CDR3-FR4
SEQ ID NO: 1 - SEQ ID NO: 2 - SEQ ID NO: 3 - SEQ ID NO: 4 - SEQ ID NO: 5 - SEQ ID NO: 6 - SEQ ID NO: 7 - SEQ ID NO: 8
ATGCTGTTGGGGCTGAAGTGGGTTTTCTTTGTTGTTTTTTATCAAGGTGTGCATTGTGAGGTGCAGC

TTGTTGAGTCTGGTGGAGGATTGGTGCAACCTAAAGGGTCATTGAAACTCTCATGTGCAGCCTCTGG

ATTCACCTTCAATACCTACGCCATGCACTGGGTCCGCCAGGCTCCAGGAAAGGGTTTGGAATGGGTT

GCTCGCATAAGAAGTGAAAGTAATAATTTTGCAACATATTATGCCGATTCAGTGAAAGACAGTTTCA

CCATCTCCAGAGATGATTCACAAAGCATGCTCTATCTGCAAATGAACAACTTGAAAACTGAGGACAC

AGCCGTATATTACTGTGTGAGAGGGGGGTTATCTCCCTTTGACTACTGGGGCCAAGGCACCACTCTC

ACAGTCTCCTCA

Heavy chain: Amino acid sequence (138 aa)
Signal peptide-FR1-CDR1-FR2-CDR2-FR3-CDR3-FR4
SEQ ID NO: 9 - SEQ ID NO: 10 - SEQ ID NO: 11 - SEQ ID NO: 12 - SEQ ID NO: 13 - SEQ ID NO: 14 - SEQ ID NO: 15 - SEQ ID NO: 16
MLLGLKWVFFVVFYQGVHCEVQLVESGGGLVQPKGSLKLSCAASGFTFNTYAMHWVRQAPGKGLEWV

ARIRSESNNFATYYADSVKDSFTISRDDSQSMLYLQMNNLKTEDTAVYYCVRGGLSPFDYWGQGTTL

TVSS

Light chain: DNA sequence (384 bp)
Signal sequence-FR1-CDR1-FR2-CDR2-FR3-CDR3-FR4
SEQ ID NO: 17 - SEQ ID NO: 18 - SEQ ID NO: 19 - SEQ ID NO: 20 - SEQ ID NO: 21 - SEQ ID NO: 22 - SEQ ID NO: 23 - SEQ ID NO: 24
ATGGATTTTCAAGTGCAGATTTTCAGCTTCCTGCTAATCAGTGCCTCAGTCATAATATCCAGAGGAC

AAATTGTTCTCACCCAGTCTCCAGCAATCATGTCTGCATCTCCAGGGGAGAAGGTCACCATGACCTG

CAGTGCCAGCTCAAGTGTAAGTTACATGCACTGGTACCAACAGAAGTCAGGCACCTCCCCCAAAAGA

TGGATTTATGACACTTCCAAACTGGCTTCTGGAGTCCCTGCTCGCTTCAGTGGCAGTGGGTCTGGGA

CCTCTTACTCTCTCACAATCAACAGCATGGAGGCTGAAGATGCTGCCACTTATTACTGCCAGCAGTG

GAGTAGAAATCCACCCACGTTCGGAGGGGGGACCAAGCTGGAAATAAAA

-continued

Light chain: Amino acid sequence (128 aa)
Signal peptide-FR1-CDR1-FR2-CDR2-FR3-CDR3-FR4
SEQ ID NO: 25 - SEQ ID NO: 26 - SEQ ID NO: 27 - SEQ ID NO: 28 - SEQ ID NO: 29 - SEQ ID NO: 30 - SEQ ID NO: 31 - SEQ ID NO: 32
MDFQVQIFSFLLISASVIISRGQIVLTQSPAIMSASPGEKVTMTCSASSSVSYMHWYQQKSGTSPKR

WIYDTSKLASGVPARFSGSGSGTSYSLTINSMEAEDAATYYCQQWSRNPPTFGGGTKLEIK

In certain embodiments, the monoclonal antibody (named 9018 herein) comprises light and heavy variable chains having the sequences shown below:

Heavy chain: DNA sequence (414 bp)
Signal sequence-FR1-CDR1-FR2-CDR2-FR3-CDR3-FR4
SEQ ID NO: 48 - SEQ ID NO: 74 - SEQ ID NO: 50 - SEQ ID NO: 51 - SEQ ID NO: 75 - SEQ ID NO: 76 - SEQ ID NO: 77 - SEQ ID NO: 78
ATGAACTTCGGGCTCAGCTTGATTTTCCTTGTCCTTGTTTTAAAAGGTGTCCAGTGTGAAGTGATGC

TGGTGGAGTCTGGGGGAGGCTTAGTGAAGCCTGGAGGGTCCCTGAAACTCTCCTGTGCAGCCTCTGG

ATTCACTTTCAGTAGCTATGCCATGTCTTGGGTTCGCCAGACTCCGGAGAAGAGGCTGGAATGGGTC

GCAACCATTAGTACTGGTGGTGGTTACACCTACTATCCAGACAGTGTGAAGGGGCGATTCACCGTCT

CCAGAGACAATGCCAAGAACACCCTGTACCTGCAAATGAGCAGTCTGAGGTCTGAGGACACGGCCAT

GTATTACTGTGCAAGAAGGGGGACGTCTAGAGGGTACTTCGATGTCTGGGGCGCAGGGACTACGGTC

ACCGTCTCCTCA

Heavy chain: Amino acid sequence (138 aa)
Signal peptide-FR1-CDR1-FR2-CDR2-FR3-CDR3-FR4
SEQ ID NO: 56 - SEQ ID NO: 79 - SEQ ID NO: 58 - SEQ ID NO: 59 - SEQ ID NO: 60 - SEQ ID NO: 80 - SEQ ID NO: 81 - SEQ ID NO: 63
MNFGLSLIFLVLVLKGVQCEVMLVESGGGLVKPGGSLKLSCAASGFTFSSYAMSWVRQTPEKRLEWV

ATISTGGGYTYYPDSVKGRFTVSRDNAKNTLYLQMSSLRSEDTAMYYCARRGTSRGYFDVWGAGTTV

TVSS

Light chain: DNA sequence (384 bp)
Signal sequence-FR1-CDR1-FR2-CDR2-FR3-CDR3-FR4
SEQ ID NO: 64 - SEQ ID NO: 82 - SEQ ID NO: 19 - SEQ ID NO: 65 - SEQ ID NO: 66 - SEQ ID NO: 67 - SEQ ID NO: 68 - SEQ ID NO: 83
ATGGATTTTCAAGTGCAGATTTTCAGCTTCCTGCTAATCAGTGCCTCAGTCATACTGTCCAGAGGAC

AAATTATTCTCACCCAGTCTCCAGCAATCATGTCTGCATCTCCAGGGGAGAAGGTCACCATGACCTG

CAGTGCCAGCTCAAGTGTAAGTTACATGTACTGGTACCAGCAGAAGCCAGAATCCTCCCCCAGACTC

CTGATTTATGACACATCCAACCTGGCTTCTGGAGTCCCTGTTCGCTTCAGTGGCAGTGGGTCTGGGA

CCTCTTATTTTCTCACAATCAGCCGAATGGAGGCTGAAGATGCTGCCACTTATTACTGCCAGCAGTG

GAAGACTTACCCACCCACGTTCGGAGGGGGGACCAGGCTGGAAATAAAA

Light chain: Amino acid sequence (128 aa)
Signal peptide-FR1-CDR1-FR2-CDR2-FR3-CDR3-FR4
SEQ ID NO: 69 - SEQ ID NO: 84 - SEQ ID NO: 70 - SEQ ID NO: 71 - SEQ ID NO: 72 - SEQ ID NO: 73 - SEQ ID NO: 85 - SEQ ID NO: 86
MDFQVQIFSFLLISASVILSRGQIILTQSPAIMSASPGEKVTMTCSASSSVSYMYWYQQKPESSPRL

LIYDTSNLASGVPVRFSGSGSGTSYFLTISRMEAEDAATYYCQQWKTYPPTFGGGTRLEIK

In certain embodiments, the monoclonal antibody (named 9021 herein) comprises light and heavy variable chains having the sequences shown below:

Heavy chain: DNA sequence (414 bp)
Signal sequence-FR1-CDR1-FR2-CDR2-FR3-CDR3-FR4
SEQ ID NO: 48 - SEQ ID NO: 87 - SEQ ID NO: 88 - SEQ ID NO: 51 - SEQ ID NO: 89 - SEQ ID NO: 90 - SEQ ID NO: 54 - SEQ ID NO: 55
ATGAACTTCGGGCTCAGCTTGATTTTCCTTGTCCTTGTTTTAAAAGGTGTCCAGTGTGAAGTGATGA

TGGTGGAGTCTGGGGGAGGCTTAGTGAAGCCTGGAGGGTCCCTGAAACTCTCCTGTGCAGCCTCTGG

-continued

ATTCACTTTCAGTAACTATGCCATGTCTTGGGTTCGCCAGACTCCGGAGAAGAGGCTGGAATGGGTC

GCAACGATTAGTACTGGTGGTGGTTACACCTACTATCCAGACAGTATGAAGGGGCGATTCACCATCT

CCAGAGACAATGCCAAGAACACCCTGTACCTGCAAATGAGCAGTCTGAGGTCTGAGGACACGGCCAT

GTATTACTGTGCAAGAAGGGGGACGGCTAGAGGGTACTTCGATGTCTGGGGCGCAGGGACCACGGTC

ACCGTCTCCTCA

Heavy chain: Amino acid sequence (138 aa)
Signal peptide-FR1-CDR1-FR2-CDR2-FR3-CDR3-FR4
SEQ ID NO: 56 - SEQ ID NO: 91 - SEQ ID NO: 92 - SEQ ID NO: 59 - SEQ ID NO: 93 - SEQ ID NO: 94 - SEQ ID NO: 62 - SEQ ID NO: 63
MNFGLSLIFLVLVLKGVQCEVMMVESGGGLVKPGGSLKLSCAASGFTFSNYAMSWVRQTPEKRLEWV

ATISTGGGYTYYPDSMKGRFTISRDNAKNTLYLQMSSLRSEDTAMYYCARRGTARGYFDVWGAGTTV

TVSS

Light chain: DNA sequence (384 bp)
Signal sequence-FR1-CDR1-FR2-CDR2-FR3-CDR3-FR4
SEQ ID NO: 64 - SEQ ID NO: 18 - SEQ ID NO: 19 - SEQ ID NO: 65 - SEQ ID NO: 66 - SEQ ID NO: 95 - SEQ ID NO: 96 - SEQ ID NO: 24
ATGGATTTTCAAGTGCAGATTTTCAGCTTCCTGCTAATCAGTGCCTCAGTCATACTGTCCAGAGGAC

AAATTGTTCTCACCCAGTCTCCAGCAATCATGTCTGCATCTCCAGGGGAGAAGGTCACCATGACCTG

CAGTGCCAGCTCAAGTGTAAGTTACATGTACTGGTACCAGCAGAAGCCAGAATCCTCCCCCAGACTC

CTGATTTATGACACATCCAACCTGGCTTCTGGAGTCCCTGTTCGCTTCAGTGGCAGTGGGTCTGGGA

CCTCTTATTTTCTCACAATCAGCCGAATGGAGGCTGAAGATGCTGCCACTTATTATTGCCAACAGTG

GAAGACTTACCCACCCACGTTCGGAGGGGGGACCAAGCTGGAAATAAAA

Light chain: Amino acid sequence (128 aa)
Signal peptide-FR1-CDR1-FR2-CDR2-FR3-CDR3-FR4
SEQ ID NO: 69 - SEQ ID NO: 26 - SEQ ID NO: 70 - SEQ ID NO: 71 - SEQ ID NO: 72 - SEQ ID NO: 73 - SEQ ID NO: 85 - SEQ ID NO: 32
MDFQVQIFSFLLISASVILSRGQIVLTQSPAIMSASPGEKVTMTCSASSSVSYMYWYQQKPESSPRL

LIYDTSNLASGVPVRFSGSGSGTSYFLTISRMEAEDAATYYCQQWKTYPPTFGGGTKLEIK

In certain embodiments, the monoclonal antibody (named 9023 herein) comprises light and heavy variable chains having the sequences shown below:

Individual Positive Clones with Correct VH and VL Insert Sizes were Sequenced. One Kind of VH DNA Sequence and Two Kinds of VL DNA Sequences were Obtained in the Trial.

Heavy chain: DNA sequence (414 bp)

Signal sequence-FR1-CDR1-FR2-CDR2-FR3-CDR3-FR4

SEQ ID NO: 48 - SEQ ID NO: 74 - SEQ ID NO: 97 - SEQ ID NO: 98 - SEQ ID NO: 99 - SEQ ID NO: 100 - SEQ ID NO: 54 - SEQ ID NO: 55

ATGAACTTCGGGCTCAGCTTGATTTTCCTTGTCCTTGTTTTAAAAGGTGTCCAGTGTGAAGTGATGC

TGGTGGAGTCTGGGGGAGGCTTAGTGAAGCCTGGAGGGTCCCTGAAACTCTCCTGTGCAGCCTCTGG

ATTCACTTTCAGTCGCTATGCCATGTCTTGGGTTCGACAGACTCCGGAGAAGAGGCTGGAGTGGGTC

GCAACCACTAGTATTGGTGGTGGTTACACCTACTATCTTGACAGTGTGAAGGGGCGATTCACCATCT

CCAGAGACAATGTCGAGAATACCCTATACCTGCAAATGACCAGTCTGAGGTCTGAGGACACGGCCAT

GTATTTCTGTACAAGAAGGGGGACGGCTAGAGGGTACTTCGATGTCTGGGGCGCAGGGACCACGGTC

ACCGTCTCCTCA

-continued

Heavy chain: Amino acid sequence (138 aa)
Signal peptide-FR1-CDR1-FR2-CDR2-FR3-CDR3-FR4
SEQ ID NO: 56 - SEQ ID NO: 79 - SEQ ID NO: 101 - SEQ ID NO: 59 - SEQ ID NO: 102 - SEQ ID NO: 103 - SEQ ID NO: 62 - SEQ ID NO: 63

MNFGLSLIFLVLVLKGVQCEVMLVESGGGLVKPGGSLKLSCAASGFTFSRYAMSWVRQTPEKRLEWV

ATTSIGGGYTYYLDSVKGRFTISRDNVENTLYLQMTSLRSEDTAMYFCTRRGTARGYFDVWGAGTTV

TVSS

Light chain 1: DNA sequence (381 bp)
Signal sequence-FR1-CDR1-FR2-CDR2-FR3-CDR3-FR4
SEQ ID NO: 104 - SEQ ID NO: 105 - SEQ ID NO: 106 - SEQ ID NO: 107 - SEQ ID NO: 108 - SEQ ID NO: 109 - SEQ ID NO: 110 - SEQ ID NO: 111

ATGGAGACACATTCTCAGGTCTTTGTATACATGTTGCTGTGGTTGTCTGGTGTTGAAGGAGACATTG

TGATGACCCAGTCTCACAAATTCATGTCCACATCAGTAGGAGACAGGGTCAGCATCACCTGCAAGGC

CAGTCAGGATGTGGGTACTGCTGTAGCCTGGTATCAACAGAAACCAGGGCAATCTCCTAAACTACTG

ATTTACTGGGCATCCACCCGGCACACTGGAGTCCCTGATCGCTTCACAGGCAGTGGATCTGGGACAG

ATTTCACTCTCACCATTAGCAATGTGCAGTCTGAAGACTTGGCAGATTATTTCTGTCAGCAATATAG

CAGCTATCCTCTCACGTTCGGTGCTGGGACCAAGCTGGAGCTGAAA

Light chain 1: Amino acid sequence (127 aa)
Signal peptide-FR1-CDR1-FR2-CDR2-FR3-CDR3-FR4
SEQ ID NO: 112 - SEQ ID NO: 113 - SEQ ID NO: 114 - SEQ ID NO: 115 - SEQ ID NO: 116 - SEQ ID NO: 117 - SEQ ID NO: 118 - SEQ ID NO: 119

METHSQVFVYMLLWLSGVEGDIVMTQSHKFMSTSVGDRVSITCKASQDVGTAVAWYQQKPGQSPKLL

IYWASTRHTGVPDRFTGSGSGTDFTLTISNVQSEDLADYFCQQYSSYPLTFGAGTKLELK

Light chain 2: DNA sequence (384 bp)
Signal sequence-FR1-CDR1-FR2-CDR2-FR3-CDR3-FR4
SEQ ID NO: 64 - SEQ ID NO: 120 - SEQ ID NO: 121 - SEQ ID NO: 122 - SEQ ID NO: 66 - SEQ ID NO: 123 - SEQ ID NO: 68 - SEQ ID NO: 124

ATGGATTTTCAAGTGCAGATTTTCAGCTTCCTGCTAATCAGTGCCTCAGTCATACTGTCCAGAGGAC

AAATTGTTCTCACCCAGTCTCCAGCAATCATGTCTGCATCTCCAGGGGACAAGGTCACCATGACCTG

CAGTGCCACCTCAAGTGTAAGTTACATGTACTGGTACCAGCAGAAGCCAGGATCCTCCCCCAGACTC

CTGATTTATGACACATCCAACCTGGCTTCTGGAGTCCCTGTTCGCTTCAGTGGCAGTGGGTCTGGGA

CCTCTTACTCTCTCACAATCAGCCGAATGGAGCCTGAAGATGCTGCCTCTTATTACTGCCAGCAGTG

GAAGAGTTACCCACCCACGTTCGGCTCGGGGACAAAGTTGGAAATAAAA

Light chain 2: Amino acid sequence (128 aa)
Signal peptide-FR1-CDR1-FR2-CDR2-FR3-CDR3-FR4
SEQ ID NO: 69 - SEQ ID NO: 125 - SEQ ID NO: 126 - SEQ ID NO: 127 - SEQ ID NO: 72 - SEQ ID NO: 128 - SEQ ID NO: 129 - SEQ ID NO: 130

MDFQVQIFSFLLISASVILSRGQIVLTQSPAIMSASPGDKVTMTCSATSSVSYMYWYQQKPGSSPRL

LIYDTSNLASGVPVRFSGSGSGTSYSLTISRMEPEDAASYYCQQWKSYPPTFGSGTKLEIK

In certain embodiments, the monoclonal antibody (named 9060 herein) comprises light and heavy variable chains having the sequences shown below:

Heavy chain: DNA sequence (426 bp)
Signal sequence-FR1-CDR1-FR2-CDR2-FR3-CDR3-FR4
SEQ ID NO: 33 - SEQ ID NO: 131 - SEQ ID NO: 3 - SEQ ID NO: 4 - SEQ ID NO: 132 - SEQ ID NO: 133 - SEQ ID NO: 7 - SEQ ID NO: 37

ATGACATTGAACGTGCTGTTGGGGCTGAAGTGGGTTTTCTTTGTTGTTTTTTATCAAGGTGTGCATT

GTGAGGTACACCTTGTTGAGTCTGGTGGAGGATTGGTGCAGCCTAAAGGGTCATTGAAACTCTCATG

TGCAGCCTCTGGATTCACCTTCAATACCTACGCCATGCACTGGGTCCGCCAGGCTCCAGGAAAGGGT

TTGGAATGGGTTGCTCGCATAAGAAATAAAAGTAATAATTATGCAACATATTATGCCGATTCAGTGA

-continued

AAGACAGGTTCACCATCTCCAGAGATGATTCACAAAGCATGCTCTTTCTGCAAATGGACAACTTGAA

AACTGAGGACACAGCCATATATTACTGTGTGAGAGGGGGGTTATCTCCCTTTGACTACTGGGGCCAA

GGCACCACACTCACAGTCTCCTCA

Heavy chain: Amino acid sequence (142 aa)
Signal peptide-FR1-CDR1-FR2-CDR2-FR3-CDR3-FR4
SEQ ID NO: 38 - SEQ ID NO: 39 - SEQ ID NO: 11 - SEQ ID NO: 12 - SEQ ID NO: 134 - SEQ ID NO: 135 - SEQ ID NO: 15 - SEQ ID NO: 16

MTLNVLLGLKWVFFVVFYQGVHCEVHLVESGGGLVQPKGSLKLSCAASGFTFNTYAMHWVRQAPGKG

LEWVARIRNKSNNYATYYADSVKDRFTISRDDSQSMLFLQMDNLKTEDTAIYYCVRGGLSPFDYWGQ

GTTLTVSS

Light chain: DNA sequence (384 bp)
Signal sequence-FR1-CDR1-FR2-CDR2-FR3-CDR3-FR4
SEQ ID NO: 17 - SEQ ID NO: 18 - SEQ ID NO: 19 - SEQ ID NO: 42 - SEQ ID NO: 43 - SEQ ID NO: 22 - SEQ ID NO: 44 - SEQ ID NO: 45

ATGGATTTTCAAGTGCAGATTTTCAGCTTCCTGCTAATCAGTGCCTCAGTCATAATATCCAGAGGAC

AAATTGTTCTCACCCAGTCTCCAGCAATCATGTCTGCATCTCCAGGGGAGAAGGTCACCATGACCTG

CAGTGCCAGCTCAAGTGTAACTTACATGCACTGGTACCAGCAGAAGTCAGGCACCTCCCCCAAAAGA

TGGATTTATGACACATCCAAACTGGCTTCTGGAGTCCCTGCTCGCTTCAGTGGCAGTGGGTCTGGGA

CCTCTTACTCTCTCACAATCAGCAGCATGGAGGCTGAAGATGCTGCCACTTATTACTGCCAGCAGTG

GAGTAGTAACCCACCCACGTTCGGAGGGGGGACCAAGCTGGAAATAAGA

Light chain: Amino acid sequence (128 aa)
Signal peptide-FR1-CDR1-FR2-CDR2-FR3-CDR3-FR4
SEQ ID NO: 25 - SEQ ID NO: 26 - SEQ ID NO: 46 - SEQ ID NO: 28 - SEQ ID NO: 29 - SEQ ID NO: 30 - SEQ ID NO: 31 - SEQ ID NO: 47

MDFQVQIFSFLLISASVIISRGQIVLTQSPAIMSASPGEKVTMTCSASSSVTYMHWYQQKSGTSPKR

WIYDTSKLASGVPARFSGSGSGTSYSLTISSMEAEDAATYYCQQWSSNPPTFGGGTKLEIR

In certain embodiments, the monoclonal antibody (named 9064 herein) comprises light and heavy variable chains having the sequences shown below:

Heavy chain: DNA sequence (426 bp)
Signal sequence-FR1-CDR1-FR2-CDR2-FR3-CDR3-FR4
SEQ ID NO: 33 - SEQ ID NO: 131 - SEQ ID NO: 3 - SEQ ID NO: 4 - SEQ ID NO: 132 - SEQ ID NO: 133 - SEQ ID NO: 7 - SEQ ID NO: 37

ATGACATTGAACGTGCTGTTGGGGCTGAAGTGGGTTTTCTTTGTTGTTTTTATCAAGGTGTGCATT

GTGAGGTACACCTTGTTGAGTCTGGTGGAGGATTGGTGCAGCCTAAAGGGTCATTGAAACTCTCATG

TGCAGCCTCTGGATTCACCTTCAATACCTACGCCATGCACTGGGTCCGCCAGGCTCCAGGAAAGGGT

TTGGAATGGGTTGCTCGCATAAGAAATAAAAGTAATAATTATGCAACATATTATGCCGATTCAGTGA

AAGACAGGTTCACCATCTCCAGAGATGATTCACAAAGCATGCTCTTTCTGCAAATGGACAACTTGAA

AACTGAGGACACAGCCATATATTACTGTGTGAGAGGGGGGTTATCTCCCTTTGACTACTGGGGCCAA

GGCACCACACTCACAGTCTCCTCA

Heavy chain: Amino acid sequence (142 aa)
Signal peptide-FR1-CDR1-FR2-CDR2-FR3-CDR3-FR4
SEQ ID NO: 38 - SEQ ID NO: 39 - SEQ ID NO: 11 - SEQ ID NO: 12 - SEQ ID NO: 134 - SEQ ID NO: 135 - SEQ ID NO: 15 - SEQ ID NO: 16

MTLNVLLGLKWVFFVVFYQGVHCEVHLVESGGGLVQPKGSLKLSCAASGFTFNTYAMHWVRQAPGKG

LEWVARIRNKSNNYATYYADSVKDRFTISRDDSQSMLFLQMDNLKTEDTAIYYCVRGGLSPFDYWGQ

GTTLTVSS

-continued

Light chain: DNA sequence (384 bp)
Signal sequence-FR1-CDR1-FR2-CDR2-FR3-CDR3-FR4
SEQ ID NO: 17 - SEQ ID NO: 18 - SEQ ID NO: 19 - SEQ ID NO: 42 - SEQ ID NO: 43 - SEQ ID NO: 22 - SEQ ID NO: 44 - SEQ ID NO: 45

ATGGATTTTCAAGTGCAGATTTTCAGCTTCCTGCTAATCAGTGCCTCAGTCATAATATCCAGAGGAC

AAATTGTTCTCACCCAGTCTCCAGCAATCATGTCTGCATCTCCAGGGGAGAAGGTCACCATGACCTG

CAGTGCCAGCTCAAGTGTAACTTACATGCACTGGTACCAGCAGAAGTCAGGCACCTCCCCCAAAAGA

TGGATTTATGACACATCCAAACTGGCTTCTGGAGTCCCTGCTCGCTTCAGTGGCAGTGGGTCTGGGA

CCTCTTACTCTCTCACAATCAGCAGCATGGAGGCTGAAGATGCTGCCACTTATTACTGCCAGCAGTG

GAGTAGTAACCCACCCACGTTCGGAGGGGGGACCAAGCTGGAAATAAGA

Light chain: Amino acid sequence (128 aa)
Signal peptide-FR1-CDR1-FR2-CDR2-FR3-CDR3-FR4
SEQ ID NO: 25 - SEQ ID NO: 26 - SEQ ID NO: 46 - SEQ ID NO: 28 - SEQ ID NO: 29 - SEQ ID NO: 30 - SEQ ID NO: 31 - SEQ ID NO: 47

MDFQVQIFSFLLISASVIISRGQIVLTQSPAIMSASPGEKVTMTCSASSSVTYMHWYQQKSGTSPKR

WIYDTSKLASGVPARFSGSGSGTSYSLTISSMEAEDAATYYCQQWSSNPPTFGGGTKLEIR

In certain embodiments, the monoclonal antibody (named 9071 herein) comprises light and heavy variable chains having the sequences shown below:

Heavy chain: DNA sequence (426 bp)
Signal sequence-FR1-CDR1-FR2-CDR2-FR3-CDR3-FR4
SEQ ID NO: 33 - SEQ ID NO: 131 - SEQ ID NO: 3 - SEQ ID NO: 4 - SEQ ID NO: 132 - SEQ ID NO: 133 - SEQ ID NO: 7 - SEQ ID NO: 37

ATGACATTGAACGTGCTGTTGGGGCTGAAGTGGGTTTTCTTTGTTGTTTTTTATCAAGGTGTGCATT

GTGAGGTACACCTTGTTGAGTCTGGTGGAGGATTGGTGCAGCCTAAAGGGTCATTGAAACTCTCATG

TGCAGCCTCTGGATTCACCTTCAATACCTACGCCATGCACTGGGTCCGCCAGGCTCCAGGAAAGGGT

TTGGAATGGGTTGCTCGCATAAGAAATAAAAGTAATAATTATGCAACATATTATGCCGATTCAGTGA

AAGACAGGTTCACCATCTCCAGAGATGATTCACAAAGCATGCTCTTTCTGCAAATGGACAACTTGAA

AACTGAGGACACAGCCATATATTACTGTGTGAGAGGGGGGTTATCTCCCTTTGACTACTGGGGCCAA

GGCACCACACTCACAGTCTCCTCA

Heavy chain: Amino acid sequence (142 aa)
Signal peptide-FR1-CDR1-FR2-CDR2-FR3-CDR3-FR4
SEQ ID NO: 38 - SEQ ID NO: 39 - SEQ ID NO: 11 - SEQ ID NO: 12 - SEQ ID NO: 134 - SEQ ID NO: 135 - SEQ ID NO: 15 - SEQ ID NO: 16

MTLNVLLGLKWVFFVVFYQGVHCEVHLVESGGGLVQPKGSLKLSCAASGFTFNTYAMHWVRQAPGKG

LEWVARIRNKSNNYATYYADSVKDRFTISRDDSQSMLFLQMDNLKTEDTAIYYCVRGGLSPFDYWGQ

GTTLTVSS

Light chain: DNA sequence (384 bp)
Signal sequence-FR1-CDR1-FR2-CDR2-FR3-CDR3-FR4
SEQ ID NO: 17 - SEQ ID NO: 18 - SEQ ID NO: 19 - SEQ ID NO: 42 - SEQ ID NO: 43 - SEQ ID NO: 22 - SEQ ID NO: 44 - SEQ ID NO: 45

ATGGATTTTCAAGTGCAGATTTTCAGCTTCCTGCTAATCAGTGCCTCAGTCATAATATCCAGAGGAC

AAATTGTTCTCACCCAGTCTCCAGCAATCATGTCTGCATCTCCAGGGGAGAAGGTCACCATGACCTG

CAGTGCCAGCTCAAGTGTAACTTACATGCACTGGTACCAGCAGAAGTCAGGCACCTCCCCCAAAAGA

TGGATTTATGACACATCCAAACTGGCTTCTGGAGTCCCTGCTCGCTTCAGTGGCAGTGGGTCTGGGA

CCTCTTACTCTCTCACAATCAGCAGCATGGAGGCTGAAGATGCTGCCACTTATTACTGCCAGCAGTG

GAGTAGTAACCCACCCACGTTCGGAGGGGGGACCAAGCTGGAAATAAGA

-continued

Light chain: Amino acid sequence (128 aa)
Signal peptide-FR1-CDR1-FR2-CDR2-FR3-CDR3-FR4
SEQ ID NO: 25 - SEQ ID NO: 26 - SEQ ID NO: 46 - SEQ ID NO: 28 - SEQ ID NO: 29 - SEQ ID NO: 30 - SEQ ID NO: 31 - SEQ ID NO: 47
MDFQVQIFSFLLISASVIISRGQIVLTQSPAIMSASPGEKVTMTCSASSSVTYMHWYQQKSGTSPKR

WIYDTSKLASGVPARFSGSGSGTSYSLTISSMEAEDAATYYCQQWSSNPPTFGGGTKLEIR

In certain embodiments, the monoclonal antibody (named 9096 herein) comprises light and heavy variable chains having the sequences shown below:

Heavy chain: DNA sequence (414 bp)
Signal sequence-FR1-CDR1-FR2-CDR2-FR3-CDR3-FR4
SEQ ID NO: 136 - SEQ ID NO: 137 - SEQ ID NO: 138 - SEQ ID NO: 51 - SEQ ID NO: 139 - SEQ ID NO: 140 - SEQ ID NO: 141 - SEQ ID NO: 8
ATGAACTTTGTGCTCAGCTTGATTTTCCTTGCCCTCATTTTAAAAGGTGTCCAGTGTGAAGTGCAGC

TGGTGGAGTCTGGGGGAGGCTTAGTGAAGCCTGGAGGGTCCCTGAAACTCTCCTGTGCAGCCTCTGG

ATTCACTTTCAGTGGGTATGCCATGTCTTGGGTTCGCCAGACTCCGGAGAAGAGGCTGGAGTGGGTC

GCAACCATTAGTAATGGTGGTAGTTACACCTACTATCCAGACAGTGTGAAGGGTCGATTCACCATCT

CCAGAGACAATGCCAAGAAGACCCTGTACCTGCAAATGAGCAGTCTGAGGTCTGAGGACACGGCCAT

GTATTACTGTACAAGACGGGCTGCTACGAGGGGATACTTTGACTACTGGGGCCAAGGCACCACTCTC

ACAGTCTCCTCA

Heavy chain: Amino acid sequence (138 aa)
Signal peptide-FR1-CDR1-FR2-CDR2-FR3-CDR3-FR4
SEQ ID NO: 142 - SEQ ID NO: 143 - SEQ ID NO: 144 - SEQ ID NO: 59 - SEQ ID NO: 145 - SEQ ID NO: 146 - SEQ ID NO: 147 - SEQ ID NO: 16
MNFVLSLIFLALILKGVQCEVQLVESGGGLVKPGGSLKLSCAASGFTFSGYAMSWVRQTPEKRLEWV

ATISNGGSYTYYPDSVKGRFTISRDNAKKTLYLQMSSLRSEDTAMYYCTRRAATRGYFDYWGQGTTL

TVSS

Light chain: DNA sequence (384 bp)
Signal sequence-FR1-CDR1-FR2-CDR2-FR3-CDR3-FR4
SEQ ID NO: 64 - SEQ ID NO: 18 - SEQ ID NO: 19 - SEQ ID NO: 122 - SEQ ID NO: 148 - SEQ ID NO: 149 - SEQ ID NO: 150 - SEQ ID NO: 111
ATGGATTTTCAAGTGCAGATTTTCAGCTTCCTGCTAATCAGTGCCTCAGTCATACTGTCCAGAGGAC

AAATTGTTCTCACCCAGTCTCCAGCAATCATGTCTGCATCTCCAGGGGAGAAGGTCACCATGACCTG

CAGTGCCAGCTCAAGTGTAAGTTACATGTACTGGTACCAGCAGAAGCCAGGATCCTCCCCCAGACTC

CTGATTTATGACACATCCAAGCTGGCTTCTGGCGTCCCTGTTCGCTTCAGTGGCAGTGGGTCTGGGA

CCTCTTACTCTCTCACAATCAGCCGAATGGAGGCTGAAGATGCTGCCACTTATTACTGCCAGCAGTG

GAGAAGTTACCCACCCACGTTCGGTGCTGGGACCAAGCTGGAGCTGAAA

Light chain: Amino acid sequence (128 aa)
Signal peptide-FR1-CDR1-FR2-CDR2-FR3-CDR3-FR4
SEQ ID NO: 69 - SEQ ID NO: 26 - SEQ ID NO: 70 - SEQ ID NO: 127 - SEQ ID NO: 29 - SEQ ID NO: 151 - SEQ ID NO: 152 - SEQ ID NO: 119
MDFQVQIFSFLLISASVILSRGQIVLTQSPAIMSASPGEKVTMTCSASSSVSYMYWYQQKPGSSPRL

LIYDTSKLASGVPVRFSGSGSGTSYSLTISRMEAEDAATYYCQQWRSYPPTFGAGTKLELK

In certain embodiments, the monoclonal antibody (named 9110 herein) comprises light and heavy variable chains having the sequences shown below:

Heavy chain: DNA sequence (426 bp)
Signal sequence-FR1-CDR1-FR2-CDR2-FR3-CDR3-FR4
SEQ ID NO: 33 - SEQ ID NO: 131 - SEQ ID NO: 3 - SEQ ID NO: 4 - SEQ ID NO: 132 - SEQ ID NO: 133 - SEQ ID NO: 7 - SEQ ID NO: 37
ATGACATTGAACGTGCTGCTGTTGGGGCTGAAGTGGGTTTTCTTTGTTGTTTTTTATCAAGGTGTGCATT

GTGAGGTACACCTTGTTGAGTCTGGTGGAGGATTGGTGCAGCCTAAAGGGTCATTGAAACTCTCATG

-continued

TGCAGCCTCTGGATTCACCTTCAATACCTACGCCATGCACTGGGTCCGCCAGGCTCCAGGAAAGGGT

TTGGAATGGGTTGCTCGCATAAGAAATAAAAGTAATAATTATGCAACATATTATGCCGATTCAGTGA

AAGACAGGTTCACCATCTCCAGAGATGATTCACAAAGCATGCTCTTTCTGCAAATGGACAACTTGAA

AACTGAGGACACAGCCATATATTACTGTGTGAGAGGGGGGTTATCTCCCTTTGACTACTGGGGCCAA

GGCACCACACTCACAGTCTCCTCA

Heavy chain: Amino acid sequence (142 aa)
Signal peptide-FR1-CDR1-FR2-CDR2-FR3-CDR3-FR4
SEQ ID NO: 38 - SEQ ID NO: 39 - SEQ ID NO: 11 - SEQ ID NO: 12 - SEQ ID NO: 134 - SEQ ID NO: 135 - SEQ ID NO: 15 - SEQ ID NO: 16

MTLNVLLGLKWVFFVVFYQGVHCEVHLVESGGGLVQPKGSLKLSCAASGFTFNTYAMHWVRQAPGKG

LEWVARIRNKSNNYATYYADSVKDRFTISRDDSQSMLFLQMDNLKTEDTAIYYCVRGGLSPFDYWGQ

GTTLTVSS

Light chain: DNA sequence (384 bp)
Signal sequence-FR1-CDR1-FR2-CDR2-FR3-CDR3-FR4
SEQ ID NO: 17 - SEQ ID NO: 18 - SEQ ID NO: 19 - SEQ ID NO: 42 - SEQ ID NO: 43 - SEQ ID NO: 22 - SEQ ID NO: 44 - SEQ ID NO: 45

ATGGATTTTCAAGTGCAGATTTTCAGCTTCCTGCTAATCAGTGCCTCAGTCATAATATCCAGAGGAC

AAATTGTTCTCACCCAGTCTCCAGCAATCATGTCTGCATCTCCAGGGGAGAAGGTCACCATGACCTG

CAGTGCCAGCTCAAGTGTAACTTACATGCACTGGTACCAGCAGAAGTCAGGCACCTCCCCCAAAAGA

TGGATTTATGACACATCCAAACTGGCTTCTGGAGTCCCTGCTCGCTTCAGTGGCAGTGGGTCTGGGA

CCTCTTACTCTCTCACAATCAGCAGCATGGAGGCTGAAGATGCTGCCACTTATTACTGCCAGCAGTG

GAGTAGTAACCCACCCACGTTCGGAGGGGGGACCAAGCTGGAAATAAGA

Light chain: Amino acid sequence (128 aa)
Signal peptide-FR1-CDR1-FR2-CDR2-FR3-CDR3-FR4
SEQ ID NO: 25 - SEQ ID NO: 26 - SEQ ID NO: 46 - SEQ ID NO: 28 - SEQ ID NO: 29 - SEQ ID NO: 30 - SEQ ID NO: 31 - SEQ ID NO: 47

MDFQVQIFSFLLISASVIISRGQIVLTQSPAIMSASPGEKVTMTCSASSSVTYMHWYQQKSGTSPKR

WIYDTSKLASGVPARFSGSGSGTSYSLTISSMEAEDAATYYCQQWSSNPPTFGGGTKLEIR

In certain embodiments, the monoclonal antibody (named 9035 herein) comprises light and heavy variable chains having the sequences shown below:

Heavy chain: DNA sequence (414 bp)
Signal sequence-FR1-CDR1-FR2-CDR2-FR3-CDR3-FR4
SEQ ID NO: 136 - SEQ ID NO: 153 - SEQ ID NO: 50 - SEQ ID NO: 154 - SEQ ID NO: 155 - SEQ ID NO: 156 - SEQ ID NO: 157 - SEQ ID NO: 158

ATGAACTTTGTGCTCAGCTTGATTTTCCTTGCCCTCATTTTAAAAGGTGTCCAGTGTGAAGTGCAGC

TGGTGGAGTCTGGGGGAGGCTTAGTGAAGCCTGGAGGGTCCCTGAAACTCTCCTGTGGAGCCTCTGG

ATTCACTTTCAGTAGCTTTGCCATGTCTTGGGTTCGCCAGACTCCGGAAAAGAGGCTGGAGTGGGTC

GCAACCATTAGTAATGGTGGCAGTTACACCTACTATCCAGACAGTGTGCAGGGTCGATTCACCATCT

CCAGAGACAATGCCAAGAACACCCTGTACCTGCGCATGAGCAGTCTGCGGTCTGAGGACACGGCCAT

GTATTACTGTGCAAGACGGAGTAGTACGAGGGGCTTCTTTGACTACTGGGGCCACGGCACCACTCTC

ACAGTCTCCTCA

Heavy chain: Amino acid sequence (138 aa)
Signal peptide-FR1-CDR1-FR2-CDR2-FR3-CDR3-FR4
SEQ ID NO: 142 - SEQ ID NO: 159 - SEQ ID NO: 160 - SEQ ID NO: 59 - SEQ ID NO: 161 - SEQ ID NO: 162 - SEQ ID NO: 163 - SEQ ID NO: 164

MNFVLSLIFLALILKGVQCEVQLVESGGGLVKPGGSLKLSCGASGFTFSSFAMSWVRQTPEKRLEWV

ATISNGGSYTYYPDSVQGRFTISRDNAKNTLYLRMSSLRSEDTAMYYCARRSSTRGFFDYWGHGTTL

TVSS

-continued

Light chain: DNA sequence (384 bp)
Signal sequence-FR1-CDR1-FR2-CDR2-FR3-CDR3-FR4
SEQ ID NO: 165 - SEQ ID NO: 166 - SEQ ID NO: 167 - SEQ ID NO: 122 - SEQ ID NO: 168 - SEQ ID NO: 169 - SEQ ID NO: 170 - SEQ ID NO: 111

ATGGATTTTCAAGTGCAGATTTTCAGCTTCCTGCTAATCAGTGCCTCAGTCATACTGTCCCGAGGAC

AAATTTTTCTCACCCAGTCTCCAGCAATCATGTCTGCATCTCCAGGGGAGAAGGTCACCATGACCTG

CAGTGCCAGCTCAAGTGTTAGTTACATGTACTGGTACCAGCAGAAGCCAGGATCCTCCCCCAGACTC

CTGATTTATGACTCATCCAAGCTGGCTTCTGGAGTCCCTGTTCAGTTCAGCGGCAGTGGGTCTGGGA

CCTCTTACTCTCTCACAATCAGCCGAATGGAGGCTGAAGATGCTGCCACTTATTACTGCCAGCAGTG

GAGGAGTTACCCACCCACGTTCGGTGCTGGGACCAAGCTGGAGCTGAAA

Light chain: Amino acid sequence (128 aa)
Signal peptide-FR1-CDR1-FR2-CDR2-FR3-CDR3-FR4
SEQ ID NO: 69 - SEQ ID NO: 171 - SEQ ID NO: 70 - SEQ ID NO: 127 - SEQ ID NO: 29 - SEQ ID NO: 172 - SEQ ID NO: 152 - SEQ ID NO: 119

MDFQVQIFSFLLISASVILSRGQIFLTQSPAIMSASPGEKVTMTCSASSSVSYMYWYQQKPGSSPRL

LIYDSSKLASGVPVQFSGSGSGTSYSLTISRMEAEDAATYYCQQWRSYPPTFGAGTKLELK

In certain embodiments, the monoclonal antibody (named 9047 herein) comprises light and heavy variable chains having the sequences shown below:

Heavy chain: DNA sequence (414 bp)
Signal sequence-FR1-CDR1-FR2-CDR2-FR3-CDR3-FR4
SEQ ID NO: 173 - SEQ ID NO: 153 - SEQ ID NO: 50 - SEQ ID NO: 154 - SEQ ID NO: 139 - SEQ ID NO: 174 - SEQ ID NO: 175 - SEQ ID NO: 176

ATGAACTTTGTGCTCAGTTTGATTTTCCTTGCCCTCATTTTAAAAGGTGTCCAGTGTGAAGTGCAGC

TGGTGGAGTCTGGGGGAGGCTTAGTGAAGCCTGGAGGGTCCCTGAAACTCTCCTGTGGAGCCTCTGG

ATTCACTTTCAGTAGCTTTGCCATGTCTTGGGTTCGCCAGACTCCGGAAAAGAGGCTGGAGTGGGTC

GCAACCATTAGTAATGGTGGTAGTTACACCTACTATCCAGACAGTGTGAAGGGTCGATTCACCATCT

CCAGAGACAATGCCAAGAACACCCTGTACCTGCGCATGAGCAGTCTGCGGTCTGAGGACACGGCCCT

GTATTACTGTACAAGACGGAGTTCTACGAGGGGCTTCTTTGACTACTGGGGCCCCGGCACCACTCTC

ACAGTCTCCTCA

Heavy chain: Amino acid sequence (138 aa)
Signal peptide-FR1-CDR1-FR2-CDR2-FR3-CDR3-FR4
SEQ ID NO: 142 - SEQ ID NO: 159 - SEQ ID NO: 160 - SEQ ID NO: 59 - SEQ ID NO: 145 - SEQ ID NO: 177 - SEQ ID NO: 163 - SEQ ID NO: 178

MNFVLSLIFLALILKGVQCEVQLVESGGGLVKPGGSLKLSCGASGFTFSSFAMSWVRQTPEKRLEWV

ATISNGGSYTYYPDSVKGRFTISRDNAKNTLYLRMSSLRSEDTALYYCTRRSSTRGFFDYWGPGTTL

TVSS

Light chain: DNA sequence (384 bp)
Signal sequence-FR1-CDR1-FR2-CDR2-FR3-CDR3-FR4
SEQ ID NO: 179 - SEQ ID NO: 166 - SEQ ID NO: 180 - SEQ ID NO: 181 - SEQ ID NO: 168 - SEQ ID NO: 182 - SEQ ID NO: 68 - SEQ ID NO: 183

ATGGATTTTCAAGTGCAGATTTTCAGCTTCCTGCTAATCAGTGCCTCAGTCTTACTGTCCCGAGGAC

AAATTTTTCTCACCCAGTCTCCAGCAATCATGTCTGCATCTCCAGGGGAGAAGGTCACCATGACCTG

CAGTGCCAGCTCAAGTGTTACTTACATGTACTGGTACCAGCAGAATCCAGGATCCTCCCCCAGACTC

CTGATTTATGACTCATCCAAGCTGGCTTCTGGAGTCCCTGTTCGGTTCAGCGGCAGTGGGTCTGGGA

CCTCTTACTCTCTCACAATCAGCCGAATGGAGGCTGAAGATGCTACCACTTATTACTGCCAGCAGTG

GAAGAGTTACCCACCCACGTTCGGTACTGGGACCAAGCTGGACCTGAAA

-continued

Light chain: Amino acid sequence (128 aa)

Signal peptide-FR1-CDR1-FR2-CDR2-FR3-CDR3-FR4

SEQ ID NO: 184 - SEQ ID NO: 171 - SEQ ID NO: 185 - SEQ ID NO: 186 - SEQ ID NO: 29 - SEQ ID NO: 187 - SEQ ID NO: 129 - SEQ ID NO: 188

MDFQVQIFSFLLISASVLLSRGQIFLTQSPAIMSASPGEKVTMTCSASSSVTYMYWYQQNPGSSPRL

LIYDSSKLASGVPVRFSGSGSGTSYSLTISRMEAEDATTYYCQQWKSYPPTFGTGTKLDLK

In certain embodiments, the monoclonal antibody (named 9052 herein) comprises light and heavy variable chains having the sequences shown below:

Heavy chain: DNA sequence (414 bp)

Signal sequence-FR1-CDR1-FR2-CDR2-FR3-CDR3-FR4

SEQ ID NO: 136 - SEQ ID NO: 189 - SEQ ID NO: 50 - SEQ ID NO: 154 - SEQ ID NO: 139 - SEQ ID NO: 190 - SEQ ID NO: 191 - SEQ ID NO: 8

ATGAACTTTGTGCTCAGCTTGATTTTCCTTGCCCTCATTTTAAAAGGTGTCCAGTGTGAAGTGCAGC

TGGTGGAGTCTGGGGGAGTCTTAGTGAAGCCTGGAGGGTCCCTGAAACTCTCCTGTGCAGCCTCTGG

ATTCACTTTCAGTAGCTTTGCCATGTCTTGGGTTCGCCAGACTCCGGAAAAGAGGCTGGAGTGGGTC

GCAACCATTAGTAATGGTGGTAGTTACACCTACTATCCAGACAGTGTGAAGGGTCGATTCACCATCT

CCAGAGACAATGCCAAGAACACCCTGTACCTGCGAATGAGCAGTCTGCGGTCTGAGGACACGGCCAT

GTATTACTGTGTAAGACGGGCTACTACGAGGGGCTACTTTGACTACTGGGGCCAAGGCACCACTCTC

ACAGTCTCCTCA

Heavy chain: Amino acid sequence (138 aa)

Signal peptide-FR1-CDR1-FR2-CDR2-FR3-CDR3-FR4

SEQ ID NO: 142 - SEQ ID NO: 192 - SEQ ID NO: 160 - SEQ ID NO: 59 - SEQ ID NO: 145 - SEQ ID NO: 193 - SEQ ID NO: 194 - SEQ ID NO: 16

MNFVLSLIFLALILKGVQCEVQLVESGGVLVKPGGSLKLSCAASGFTFSSFAMSWVRQTPEKRLEWV

ATISNGGSYTYYPDSVKGRFTISRDNAKNTLYLRMSSLRSEDTAMYYCVRRATTRGYFDYWGQGTTL

TVSS

Light chain: DNA sequence (384 bp)

Signal sequence-FR1-CDR1-FR2-CDR2-FR3-CDR3-FR4

SEQ ID NO: 165 - SEQ ID NO: 166 - SEQ ID NO: 167 - SEQ ID NO: 122 - SEQ ID NO: 168 - SEQ ID NO: 169 - SEQ ID NO: 195 - SEQ ID NO: 111

ATGGATTTTCAAGTGCAGATTTTCAGCTTCCTGCTAATCAGTGCCTCAGTCATACTGTCCCGAGGAC

AAATTTTTCTCACCCAGTCTCCAGCAATCATGTCTGCATCTCCAGGGGAGAAGGTCACCATGACCTG

CAGTGCCAGCTCAAGTGTTAGTTACATGTACTGGTACCAGCAGAAGCCAGGATCTTCCCCCAGACTC

CTGATTTATGACTCATCCAAGCTGGCTTCTGGAGTCCCTGTTCAGTTCAGCGGCAGTGGGTCTGGGA

CCTCTTACTCTCTCACAATCAGCCGAATGGAGGCTGAAGATGCTGCCACTTATTACTGCCAGCAGTG

GAGGAGTTATCCACCCACGTTCGGTGCTGGGACCAAGCTGGAGCTGAAA

-continued

Light chain: Amino acid sequence (128 aa)
Signal peptide-FR1-CDR1-FR2-CDR2-FR3-CDR3-FR4
SEQ ID NO: 69 - SEQ ID NO: 171 - SEQ ID NO: 70 - SEQ ID NO: 127 - SEQ ID NO: 29 - SEQ ID NO: 172 - SEQ ID NO: 152 - SEQ ID NO: 119
MDFQVQIFSFLLISASVILSRGQIFLTQSPAIMSASPGEKVTMTCSASSSVSYMYWYQQKPGSSPRL

LIYDSSKLASGVPVQFSGSGSGTSYSLTISRMEAEDAATYYCQQWRSYPPTFGAGTKLELK

In certain embodiments, the monoclonal antibody (named 9061 herein) comprises light and heavy variable chains having the sequences shown below:

Individual Positive Clones with Correct VH and VL Insert Sizes were Sequenced. One Kind of VH DNA Sequence and Two Kinds of VL DNA Sequences were Obtained in the Trial.

Heavy chain: DNA sequence (414 bp)
Signal sequence-FR1-CDR1-FR2-CDR2-FR3-CDR3-FR4
SEQ ID NO: 136 - SEQ ID NO: 196 - SEQ ID NO: 50 - SEQ ID NO: 51 - SEQ ID NO: 197 - SEQ ID NO: 90 - SEQ ID NO: 198 - SEQ ID NO: 8
ATGAACTTTGTGCTCAGCTTGATTTTCCTTGCCCTCATTTTAAAAGGTGTCCAGTGTGAAGTGCAGC

TGGTGGAGTCTGGGAGAGGCTTAGTGAAGCCTGGCGGGTCCCTGAAACTCTCCTGTGCAGCCTCTGG

ATTCACTTTCAGTAGCTATGCCATGTCTTGGGTTCGCCAGACTCCGGAGAAGAGGCTGGAGTGGGTC

GCAACCATTAGTACTGGTGGTAGTTACACCTACTATCCAGACAGTGTGAAGGGTCGATTCACCATCT

CCAGAGACAATGCCAAGAACACCCTGTACCTGCAAATGAGCAGTCTGAGGTCTGAGGACACGGCCAT

GTATTACTGTGCAAGACGGGGTACTACGAGGGGATACTTTGACTACTGGGGCCAAGGCACCACTCTC

ACAGTCTCCTCA

Heavy chain: Amino acid sequence (138 aa)
Signal peptide-FR1-CDR1-FR2-CDR2-FR3-CDR3-FR4
SEQ ID NO: 142 - SEQ ID NO: 199 - SEQ ID NO: 58 - SEQ ID NO: 59 - SEQ ID NO: 200 - SEQ ID NO: 94 - SEQ ID NO: 201 - SEQ ID NO: 16
MNFVLSLIFLALILKGVQCEVQLVESGRGLVKPGGSLKLSCAASGFTFSSYAMSWVRQTPEKRLEWV

ATISTGGSYTYYPDSVKGRFTISRDNAKNTLYLQMSSLRSEDTAMYYCARRGTTRGYFDYWGQGTTL

TVSS

Light chain 1: DNA sequence (384 bp)
Signal sequence-FR1-CDR1-FR2-CDR2-FR3-CDR3-FR4
SEQ ID NO: 64 - SEQ ID NO: 18 - SEQ ID NO: 19 - SEQ ID NO: 122 - SEQ ID NO: 66 - SEQ ID NO: 202 - SEQ ID NO: 203 - SEQ ID NO: 111
ATGGATTTTCAAGTGCAGATTTTCAGCTTCCTGCTAATCAGTGCCTCAGTCATACTGTCCAGAGGAC

AAATTGTTCTCACCCAGTCTCCAGCAATCATGTCTGCATCTCCAGGGGAGAAGGTCACCATGACCTG

CAGTGCCAGCTCAAGTGTAAGTTACATGTACTGGTACCAGCAGAAGCCAGGATCCTCCCCCAGACTC

CTGATTTATGACACATCCAACCTGGCTTCTGGAGTCCCTGTTCGCTTCAGTGGCAGTGGGTCTGGGA

CCTCTTACTCTCTCACAATCAGCCGAATGGAGGCTGAAGATGCTGCCACTTATTCCTGCCAGCAGTG

GAGTAGTTACCCACCCACGTTCGGTGCTGGGACCAAGCTGGAGCTGAAA

Light chain 1: Amino acid sequence (128 aa)
Signal peptide-FR1-CDR1-FR2-CDR2-FR3-CDR3-FR4
SEQ ID NO: 69 - SEQ ID NO: 26 - SEQ ID NO: 70 - SEQ ID NO: 127 - SEQ ID NO: 72 - SEQ ID NO: 204 - SEQ ID NO: 205 - SEQ ID NO: 119
MDFQVQIFSFLLISASVILSRGQIVLTQSPAIMSASPGEKVTMTCSASSSVSYMYWYQQKPGSSPRL

LIYDTSNLASGVPVRFSGSGSGTSYSLTISRMEAEDAATYSCQQWSSYPPTFGAGTKLELK

Light chain 2: DNA sequence (381 bp)
Signal sequence-FR1-CDR1-FR2-CDR2-FR3-CDR3-FR4
SEQ ID NO: 206 - SEQ ID NO: 105 - SEQ ID NO: 207 - SEQ ID NO: 208 - SEQ ID NO: 209 - SEQ ID NO: 210 - SEQ ID NO: 211 - SEQ ID NO: 24
ATGGAGTCACAGATTCAGGTCTTTGTATTCGTGTTTCTCTGGTTGTCTGGTGTTGACGGAGACATTG

TGATGACCCAGTCTCACAAATTCATGTCCACATCAGTAGGAGACAGGGTCAGCATCACCTGCAAGGC

CAGTCAGGATGTGAGTACTGCTGTAGCCTGGTATCAACAGAAACCAGGACAATCTCCTAAACTACTG

-continued

ATTTACTCGGCATCCTACCGGTACACTGGAGTCCCTGATCGCTTCACTGGCAGTGGATCTGGGACGG

ATTTCACTTTCACCATCAGCAGTGTGCAGGCTGAAGACCTGGCAGTTTATTACTGTCAGCAACATTA

TAGTACTCCGTACACGTTCGGAGGGGGGACCAAGCTGGAAATAAAA

Light chain 2: Amino acid sequence (127 aa)
Signal peptide-FR1-CDR1-FR2-CDR2-FR3-CDR3-FR4
SEQ ID NO: 212 - SEQ ID NO: 113 - SEQ ID NO: 213 - SEQ ID NO: 115 - SEQ ID NO: 214 - SEQ ID NO: 215 - SEQ ID NO: 216 - SEQ ID NO: 32
MESQIQVFVFVFLWLSGVDGDIVMTQSHKFMSTSVGDRVSITCKASQDVSTAVAWYQQKPGQSPKLL

IYSASYRYTGVPDRFTGSGSGTDFTFTISSVQAEDLAVYYCQQHYSTPYTFGGGTKLEIK

In certain embodiments, the monoclonal antibody (named 9092 herein) comprises light and heavy variable chains having the sequences shown below:

Heavy chain: DNA sequence (405 bp)
Signal sequence-FR1-CDR1-FR2-CDR2-FR3-CDR3-FR4
SEQ ID NO: 217 - SEQ ID NO: 218 - SEQ ID NO: 219 - SEQ ID NO: 220 - SEQ ID NO: 221 - SEQ ID NO: 222 - SEQ ID NO: 223 - SEQ ID NO: 8
ATGGGATGGAGCCGGATCTTTCTCTTCCTCCTGTCAATAATTGCAGGTGTCCATTGCCAGGTCCAGC

TGCAGCAGTCTGGACCTGAGCTGGTGAAGCCTGGGGCTTCAGTGCGGATATCCTGCAAGGCTTCTGG

CTACACCTTCACAACCTTCTATTTACACTGGGTGAAGCAGAGGCCTGGACAGGGACTTGAGTGGATT

GGATGGATTTATCCTGTAAATGTTAAAATTAAGTACAGTGAGAGGTTCAAGGGCAAGGCCACACTGA

CTGCAGACAAATCCTCCAGCACAGCCTACATGCAGCTCGGCAGCCTGACCTCTGAGGACTCTGCGGT

CTATTTCTGTGTAAGAGGGGGGAGGGGACTTGACTACTGGGGCCAAGGCACCACTCTCACAGTCTCC

TCA

Heavy chain: Amino acid sequence (135 aa)
Signal peptide-FR1-CDR1-FR2-CDR2-FR3-CDR3-FR4
SEQ ID NO: 224 - SEQ ID NO: 225 - SEQ ID NO: 226 - SEQ ID NO: 227 - SEQ ID NO: 228 - SEQ ID NO: 229 - SEQ ID NO: 230 - SEQ ID NO: 16
MGWSRIFLFLLSIIAGVHCQVQLQQSGPELVKPGASVRISCKASGYTFTTFYLHWVKQRPGQGLEWI

GWIYPVNVKIKYSERFKGKATLTADKSSSTAYMQLGSLTSEDSAVYFCVRGGRGLDYWGQGTTLTVS

S

Light chain: DNA sequence (396 bp)
Signal sequence-FR1-CDR1-FR2-CDR2-FR3-CDR3-FR4
SEQ ID NO: 231 - SEQ ID NO: 232 - SEQ ID NO: 233 - SEQ ID NO: 234 - SEQ ID NO: 235 - SEQ ID NO: 236 - SEQ ID NO: 237 - SEQ ID NO: 124
ATGGAATCACAGACTCAGGTCTTCCTCTCCCTGCTGCTCTGGGTATCTGGTACCTGTGGGAACATTA

TGATGACACAGTCGCCATCATCTCTGGCTGTGTCTGCAGGAGAAAAGGTCACTATGAGCTGTAAGTC

CAGTCAAAGTGTTTTATACAGTTCAAATCAGAAGAACTACTTGGCCTGGTACCAGCAGAAACCAGGG

CAGTCTCCTAAAATGCTGATCTACTGGGCATCCTTTAGGGAATCTGGTGTCCCTGATCGCTTCACAG

GCAGTGGATCTGGGACAGATTTTACTCTTACCATCAGCAGTGTACAAGCTGAAGACCTGGCAGTTTA

TTACTGTCATCAATACCTCTCCTTATTCACGTTCGGCTCGGGGACAAAGTTGGAAATAAAA

-continued

Light chain: Amino acid sequence (132 aa)
Signal peptide-FR1-CDR1-FR2-CDR2-FR3-CDR3-FR4
SEQ ID NO: 238 - SEQ ID NO: 239 - SEQ ID NO: 240 - SEQ ID NO: 241 - SEQ ID NO: 242 - SEQ ID NO: 243 - SEQ ID NO: 244 - SEQ ID NO: 130
MESQTQVFLSLLLWVSGTCGNIMMTQSPSSLAVSAGEKVTMSCKSSQSVLYSSNQKNYLAWYQQKPG

QSPKMLIYWASFRESGVPDRFTGSGSGTDFTLTISSVQAEDLAVYYCHQYLSLFTFGSGTKLEIK

In certain embodiments, the monoclonal antibody (named 9099 herein) comprises light and heavy variable chains having the sequences shown below:

Heavy chain: DNA sequence (414 bp)
Signal sequence-FR1-CDR1-FR2-CDR2-FR3-CDR3-FR4
SEQ ID NO: 136 - SEQ ID NO: 189 - SEQ ID NO: 50 - SEQ ID NO: 154 - SEQ ID NO: 139 - SEQ ID NO: 190 - SEQ ID NO: 191 - SEQ ID NO: 8
ATGAACTTTGTGCTCAGCTTGATTTTCCTTGCCCTCATTTTAAAAGGTGTCCAGTGTGAAGTGCAGC

TGGTGGAGTCTGGGGGAGTCTTAGTGAAGCCTGGAGGGTCCCTGAAACTCTCCTGTGCAGCCTCTGG

ATTCACTTTCAGTAGCTTTGCCATGTCTTGGGTTCGCCAGACTCCGGAAAAGAGGCTGGAGTGGGTC

GCAACCATTAGTAATGGTGGTAGTTACACCTACTATCCAGACAGTGTGAAGGGTCGATTCACCATCT

CCAGAGACAATGCCAAGAACACCCTGTACCTGCGAATGAGCAGTCTGCGGTCTGAGGACACGGCCAT

GTATTACTGTGTAAGACGGGCTACTACGAGGGGCTACTTTGACTACTGGGGCCAAGGCACCACTCTC

ACAGTCTCCTCA

Heavy chain: Amino acid sequence (138 aa)
Signal peptide-FR1-CDR1-FR2-CDR2-FR3-CDR3-FR4
SEQ ID NO: 142 - SEQ ID NO: 192 - SEQ ID NO: 160 - SEQ ID NO: 59 - SEQ ID NO: 145 - SEQ ID NO: 193 - SEQ ID NO: 194 - SEQ ID NO: 16
MNFVLSLIFLALILKGVQCEVQLVESGGVLVKPGGSLKLSCAASGFTFSSFAMSWVRQTPEKRLEWV

ATISNGGSYTYYPDSVKGRFTISRDNAKNTLYLRMSSLRSEDTAMYYCVRRATTRGYFDYWGQGTTL

TVSS

Light chain: DNA sequence (384 bp)
Signal sequence-FR1-CDR1-FR2-CDR2-FR3-CDR3-FR4
SEQ ID NO: 165 - SEQ ID NO: 166 - SEQ ID NO: 167 - SEQ ID NO: 122 - SEQ ID NO: 168 - SEQ ID NO: 169 - SEQ ID NO: 195 - SEQ ID NO: 111
ATGGATTTTCAAGTGCAGATTTTCAGCTTCCTGCTAATCAGTGCCTCAGTCATACTGTCCCGAGGAC

AAATTTTTCTCACCCAGTCTCCAGCAATCATGTCTGCATCTCCAGGGGAGAAGGTCACCATGACCTG

CAGTGCCAGCTCAAGTGTTAGTTACATGTACTGGTACCAGCAGAAGCCAGGATCTTCCCCCAGACTC

CTGATTTATGACTCATCCAAGCTGGCTTCTGGAGTCCCTGTTCAGTTCAGCGGCAGTGGGTCTGGGA

CCTCTTACTCTCTCACAATCAGCCGAATGGAGGCTGAAGATGCTGCCACTTATTACTGCCAGCAGTG

GAGGAGTTATCCACCCACGTTCGGTGCTGGGACCAAGCTGGAGCTGAAA

Light chain: Amino acid sequence (128 aa)
Signal peptide-FR1-CDR1-FR2-CDR2-FR3-CDR3-FR4
SEQ ID NO: 69 - SEQ ID NO: 171 - SEQ ID NO: 70 - SEQ ID NO: 127 - SEQ ID NO: 29 - SEQ ID NO: 172 - SEQ ID NO: 152 - SEQ ID NO: 119
MDFQVQIFSFLLISASVILSRGQIFLTQSPAIMSASPGEKVTMTCSASSSVSYMYWYQQKPGSSPRL

LIYDSSKLASGVPVQFSGSGSGTSYSLTISRMEAEDAATYYCQQWRSYPPTFGAGTKLELK

In certain embodiments, the monoclonal antibody (named 9100 herein) comprises light and heavy variable chains having the sequences shown below:

Heavy chain: DNA sequence (414 bp)
Signal sequence-FR1-CDR1-FR2-CDR2-FR3-CDR3-FR4
SEQ ID NO: 136 - SEQ ID NO: 189 - SEQ ID NO: 50 - SEQ ID NO: 154 - SEQ ID NO: 139 - SEQ ID NO: 190 - SEQ ID NO: 191 - SEQ ID NO: 8
ATGAACTTTGTGCTCAGCTTGATTTTCCTTGCCCTCATTTTAAAAGGTGTCCAGTGTGAAGTGCAGC

TGGTGGAGTCTGGGGGAGTCTTAGTGAAGCCTGGAGGGTCCCTGAAACTCTCCTGTGCAGCCTCTGG

-continued

ATTCACTTTCAGTAGCTTTGCCATGTCTTGGGTTCGCCAGACTCCGGAAAAGAGGCTGGAGTGGGTC

GCAACCATTAGTAATGGTGGTAGTTACACCTACTATCCAGACAGTGTGAAGGGTCGATTCACCATCT

CCAGAGACAATGCCAAGAACACCCTGTACCTGCGAATGAGCAGTCTGCGGTCTGAGGACACGGCCAT

GTATTACTGTGTAAGACGGGCTACTACGAGGGGCTACTTTGACTACTGGGGCCAAGGCACCACTCTC

ACAGTCTCCTCA

Heavy chain: Amino acid sequence (138 aa)
Signal peptide-FR1-CDR1-FR2-CDR2-FR3-CDR3-FR4
SEQ ID NO: 142 - SEQ ID NO: 192 - SEQ ID NO: 160 - SEQ ID NO: 59 - SEQ ID NO: 145 - SEQ ID NO: 193 - SEQ ID NO: 194 - SEQ ID NO: 16
MNFVLSLIFLALILKGVQCEVQLVESGGVLVKPGGSLKLSCAASGFTFSSFAMSWVRQTPEKRLEWV

ATISNGGSYTYYPDSVKGRFTISRDNAKNTLYLRMSSLRSEDTAMYYCVRRATTRGYFDYWGQGTTL

TVSS

Light chain: DNA sequence (384 bp)
Signal sequence-FR1-CDR1-FR2-CDR2-FR3-CDR3-FR4
SEQ ID NO: 165 - SEQ ID NO: 166 - SEQ ID NO: 167 - SEQ ID NO: 122 - SEQ ID NO: 168 - SEQ ID NO: 169 - SEQ ID NO: 195 - SEQ ID NO: 111
ATGGATTTTCAAGTGCAGATTTTCAGCTTCCTGCTAATCAGTGCCTCAGTCATACTGTCCCGAGGAC

AAATTTTTCTCACCCAGTCTCCAGCAATCATGTCTGCATCTCCAGGGGAGAAGGTCACCATGACCTG

CAGTGCCAGCTCAAGTGTTAGTTACATGTACTGGTACCAGCAGAAGCCAGGATCTTCCCCCAGACTC

CTGATTTATGACTCATCCAAGCTGGCTTCTGGAGTCCCTGTTCAGTTCAGCGGCAGTGGGTCTGGGA

CCTCTTACTCTCTCACAATCAGCCGAATGGAGGCTGAAGATGCTGCCACTTATTACTGCCAGCAGTG

GAGGAGTTATCCACCCACGTTCGGTGCTGGGACCAAGCTGGAGCTGAAA

Light chain: Amino acid sequence (128 aa)
Signal peptide-FR1-CDR1-FR2-CDR2-FR3-CDR3-FR4
SEQ ID NO: 69 - SEQ ID NO: 171 - SEQ ID NO: 70 - SEQ ID NO: 127 - SEQ ID NO: 29 - SEQ ID NO: 172 - SEQ ID NO: 152 - SEQ ID NO: 119
MDFQVQIFSFLLISASVILSRGQIFLTQSPAIMSASPGEKVTMTCSASSSVSYMYWYQQKPGSSPRL

LIYDSSKLASGVPVQFSGSGSGTSYSLTISRMEAEDAATYYCQQWRSYPPTFGAGTKLELK

In certain embodiments, the isolated monoclonal antibody comprises a light chain variable region (VL) and a heavy chain variable region (VH). In certain embodiments, the VL comprises a CDR1 region comprising the amino acid sequence of SEQ ID NO:27, 46, 70, 114, 126, 185, 213, or 240. In certain embodiments, the VL comprises a CDR2 region comprising the amino acid sequence of SEQ ID NO:29, 72, 116, 214, or 242. In certain embodiments, the VL comprises a CDR3 region comprising the amino acid sequence of SEQ ID NO:31, 85, 118, 129, 152, 205, 216, or 244. In certain embodiments, the VH comprises a CDR1 region comprising the amino acid sequence of SEQ ID NO:11, 58, 92, 101, 144, 160, or 226. In certain embodiments, the VH comprises a CDR2 region comprising the amino acid sequence of SEQ ID NO:13, 40, 60, 93, 102, 134, 145, 161, 200, or 228. In certain embodiments, the VH comprises a CDR3 region comprising the amino acid sequence of SEQ ID NO:15, 62, 81, 147, 163, 194, 201, or 230.

In certain embodiments, the VL comprises a CDR1 region comprising the amino acid sequence of SEQ ID NO:27, 46, 70, 114, or 126.

In certain embodiments, the VL comprises a CDR2 region comprising the amino acid sequence of SEQ ID NO:29, 72, or 116.

In certain embodiments, the VL comprises a CDR3 region comprising the amino acid sequence of SEQ ID NO:31, 85, 118, 129, or 152.

In certain embodiments, the VL comprises a CDR1 region comprising the amino acid sequence of SEQ ID NO:70, 185, 213, or 240.

In certain embodiments, the VL comprises a CDR2 region comprising the amino acid sequence of SEQ ID NO:29, 72, 214, or 242.

In certain embodiments, the VL comprises a CDR3 region comprising the amino acid sequence of SEQ ID NO:152, 129, 205, 216, or 244.

In certain embodiments, the VL comprises: a CDR1 region comprising the amino acid sequence of SEQ ID NO:27; a CDR2 region comprising the amino acid sequence of SEQ ID NO:29; and a CDR3 region comprising the amino acid sequence of SEQ ID NO:31.

In certain embodiments, the VL comprises: a CDR1 region comprising the amino acid sequence of SEQ ID NO:46; a CDR2 region comprising the amino acid sequence of SEQ ID NO:29; and a CDR3 region comprising the amino acid sequence of SEQ ID NO:31.

In certain embodiments, the VL comprises: a CDR1 region comprising the amino acid sequence of SEQ ID NO:70; a CDR2 region comprising the amino acid sequence of SEQ ID NO:29; and a CDR3 region comprising the amino acid sequence of SEQ ID NO:152.

In certain embodiments, the VL comprises: a CDR1 region comprising the amino acid sequence of SEQ ID NO:70; a CDR2 region comprising the amino acid sequence of SEQ ID NO:72; and a CDR3 region comprising the amino acid sequence of SEQ ID NO:85.

In certain embodiments, the VL comprises: a CDR1 region comprising the amino acid sequence of SEQ ID NO:70; a CDR2 region comprising the amino acid sequence of SEQ ID NO:72; and a CDR3 region comprising the amino acid sequence of SEQ ID NO:205.

In certain embodiments, the VL comprises: a CDR1 region comprising the amino acid sequence of SEQ ID NO:114; a CDR2 region comprising the amino acid sequence of SEQ ID NO:116; and a CDR3 region comprising the amino acid sequence of SEQ ID NO:118.

In certain embodiments, the VL comprises: a CDR1 region comprising the amino acid sequence of SEQ ID NO:126; a CDR2 region comprising the amino acid sequence of SEQ ID NO:72; and a CDR3 region comprising the amino acid sequence of SEQ ID NO:129.

In certain embodiments, the VL comprises: a CDR1 region comprising the amino acid sequence of SEQ ID NO:185; a CDR2 region comprising the amino acid sequence of SEQ ID NO:29; and a CDR3 region comprising the amino acid sequence of SEQ ID NO:129.

In certain embodiments, the VL comprises: a CDR1 region comprising the amino acid sequence of SEQ ID NO:213; a CDR2 region comprising the amino acid sequence of SEQ ID NO:214; and a CDR3 region comprising the amino acid sequence of SEQ ID NO:216.

In certain embodiments, the VL comprises: a CDR1 region comprising the amino acid sequence of SEQ ID NO:240; a CDR2 region comprising the amino acid sequence of SEQ ID NO:242; and a CDR3 region comprising the amino acid sequence of SEQ ID NO:244.

In certain embodiments, the VH comprises a CDR1 region comprising the amino acid sequence of SEQ ID NO:11, 58, 92, 101, or 144.

In certain embodiments, the VH comprises a CDR2 region comprising the amino acid sequence of SEQ ID NO:13, 40, 60, 93, 102, 134, or 145.

In certain embodiments, the VH comprises a CDR3 region comprising the amino acid sequence of SEQ ID NO:15, 62, 81, or 147.

In certain embodiments, the VH comprises a CDR1 region comprising the amino acid sequence of SEQ ID NO:160, 58, or 226.

In certain embodiments, the VH comprises a CDR2 region comprising the amino acid sequence of SEQ ID NO:161, 145, 200, or 228.

In certain embodiments, the VH comprises a CDR3 region comprising the amino acid sequence of SEQ ID NO:163, 194, 201, or 230.

In certain embodiments, the VH comprises: a CDR1 region comprising the amino acid sequence of SEQ ID NO:11; a CDR2 region comprising the amino acid sequence of SEQ ID NO:13; and a CDR3 region comprising the amino acid sequence of SEQ ID NO:15;

In certain embodiments, the VH comprises: a CDR1 region comprising the amino acid sequence of SEQ ID NO:11; a CDR2 region comprising the amino acid sequence of SEQ ID NO:40; and a CDR3 region comprising the amino acid sequence of SEQ ID NO:15.

In certain embodiments, the VH comprises: a CDR1 region comprising the amino acid sequence of SEQ ID NO:11; a CDR2 region comprising the amino acid sequence of SEQ ID NO:134; and a CDR3 region comprising the amino acid sequence of SEQ ID NO:15.

In certain embodiments, the VH comprises: a CDR1 region comprising the amino acid sequence of SEQ ID NO:58; a CDR2 region comprising the amino acid sequence of SEQ ID NO:60; and a CDR3 region comprising the amino acid sequence of SEQ ID NO:62.

In certain embodiments, the VH comprises: a CDR1 region comprising the amino acid sequence of SEQ ID NO:58; a CDR2 region comprising the amino acid sequence of SEQ ID NO:60; and a CDR3 region comprising the amino acid sequence of SEQ ID NO:81.

In certain embodiments, the VH comprises: a CDR1 region comprising the amino acid sequence of SEQ ID NO:58; a CDR2 region comprising the amino acid sequence of SEQ ID NO:200; and a CDR3 region comprising the amino acid sequence of SEQ ID NO:201.

In certain embodiments, the VH comprises: a CDR1 region comprising the amino acid sequence of SEQ ID NO:92; a CDR2 region comprising the amino acid sequence of SEQ ID NO:93; and a CDR3 region comprising the amino acid sequence of SEQ ID NO:62.

In certain embodiments, the VH comprises: a CDR1 region comprising the amino acid sequence of SEQ ID NO:101; a CDR2 region comprising the amino acid sequence of SEQ ID NO:102; and a CDR3 region comprising the amino acid sequence of SEQ ID NO:62.

In certain embodiments, the VH comprises: a CDR1 region comprising the amino acid sequence of SEQ ID NO:144; a CDR2 region comprising the amino acid sequence of SEQ ID NO:145; and a CDR3 region comprising the amino acid sequence of SEQ ID NO:147.

In certain embodiments, the VH comprises: a CDR1 region comprising the amino acid sequence of SEQ ID NO:160; a CDR2 region comprising the amino acid sequence of SEQ ID NO:145; and a CDR3 region comprising the amino acid sequence of SEQ ID NO:163.

In certain embodiments, the VH comprises a CDR1 region comprising the amino acid sequence of SEQ ID NO:160; a CDR2 region comprising the amino acid sequence of SEQ ID NO:145; and a CDR3 region comprising the amino acid sequence of SEQ ID NO:194.

In certain embodiments, the VH comprises: a CDR1 region comprising the amino acid sequence of SEQ ID NO:160; a CDR2 region comprising the amino acid sequence of SEQ ID NO:161; and a CDR3 region comprising the amino acid sequence of SEQ ID NO:163.

In certain embodiments, the VH comprises: a CDR1 region comprising the amino acid sequence of SEQ ID NO:226; a CDR2 region comprising the amino acid sequence of SEQ ID NO:228; and a CDR3 region comprising the amino acid sequence of SEQ ID NO:230.

In certain embodiments, the VL comprises the amino acid sequence of SEQ ID NO:27-SEQ ID NO:28-SEQ ID NO:29-SEQ ID NO:30-SEQ ID NO:31, SEQ ID NO:46-SEQ ID NO:28-SEQ ID NO:29-SEQ ID NO:30-SEQ ID NO:31, SEQ ID NO:70-SEQ ID NO:71-SEQ ID NO:72-SEQ ID NO:73-SEQ ID NO:85, SEQ ID NO:70-SEQ ID NO:127-SEQ ID NO:29-SEQ ID NO:151-SEQ ID NO:152, SEQ ID NO:70-SEQ ID NO:127-SEQ ID NO:29-SEQ ID NO:172-SEQ ID NO: 152, SEQ ID NO:70-SEQ ID NO:127-SEQ ID NO:72-SEQ ID NO:204-SEQ ID NO:205, SEQ ID NO:114-SEQ ID NO:115-SEQ ID NO:116-SEQ ID NO:117-SEQ ID NO: 118, SEQ ID NO:126-SEQ ID NO:127-SEQ ID NO:72-SEQ ID NO:128-SEQ ID NO:129, SEQ ID NO:185-SEQ ID NO:186-SEQ ID NO:29-SEQ ID NO:187-SEQ ID NO: 129, SEQ ID NO:213-SEQ ID NO:115-SEQ ID NO:214-SEQ ID NO:215-SEQ ID NO: 216, or SEQ ID NO:240-SEQ ID NO:241-SEQ ID NO:242-SEQ ID NO:243-SEQ ID NO: 244.

In certain embodiments, the VH comprises the amino acid sequence of SEQ ID NO:11-SEQ ID NO:12-SEQ ID NO:13-SEQ ID NO:14-SEQ ID NO:15, SEQ ID NO:11-SEQ ID NO:12-SEQ ID NO:40-SEQ ID NO:41-SEQ ID NO: 15, SEQ ID NO:11-SEQ ID NO:12-SEQ ID NO:134-SEQ ID NO:135-SEQ ID NO: 15, SEQ ID NO:58-SEQ ID NO:59-SEQ ID NO:60-SEQ ID NO:61-SEQ ID NO:62, SEQ ID NO:58-SEQ ID NO:59-SEQ ID NO:60-SEQ ID NO:80-SEQ ID NO:81, SEQ ID NO:58-SEQ ID NO:59-SEQ ID NO:200-SEQ ID NO:94-SEQ ID NO:201, SEQ ID NO:92-SEQ ID NO:59-SEQ ID NO:93-SEQ ID NO:94-SEQ ID NO:62, SEQ ID NO:101-SEQ ID NO:59-SEQ ID NO:102-SEQ ID NO:103-SEQ ID NO:62, SEQ ID NO:144-SEQ ID NO:59-SEQ ID NO:145-SEQ ID NO:146-SEQ ID NO: 147, SEQ ID NO:160-SEQ ID NO:59-SEQ ID NO:145-SEQ ID NO:177-SEQ ID NO: 163, SEQ ID NO:160-SEQ ID NO:59-SEQ ID NO:145-SEQ ID NO:193-SEQ ID NO: 194, SEQ ID NO:160-SEQ ID NO:59-SEQ ID NO:161-SEQ ID NO:162-SEQ ID NO:163, or SEQ ID NO:226-SEQ ID NO:227-SEQ ID NO:228-SEQ ID NO:229-SEQ ID NO:230.

In certain embodiments, the VL comprises the amino acid sequence of: SEQ ID NO:27-SEQ ID NO:28-SEQ ID NO:29-SEQ ID NO:30-SEQ ID NO:31, SEQ ID NO:46-SEQ ID NO:28-SEQ ID NO:29-SEQ ID NO:30-SEQ ID NO:31, SEQ ID NO:70-SEQ ID NO:71-SEQ ID NO:72-SEQ ID NO:73-SEQ ID NO:85, SEQ ID NO:70-SEQ ID NO:127-SEQ ID NO:29-SEQ ID NO:151-SEQ ID NO:152. SEQ ID NO:114-SEQ ID NO:115-SEQ ID NO:116-SEQ ID NO:117-SEQ ID NO: 118, or SEQ ID NO:126-SEQ ID NO:127-SEQ ID NO:72-SEQ ID NO:128-SEQ ID NO: 129.

In certain embodiments, the VH comprises the amino acid sequence of: SEQ ID NO:11-SEQ ID NO:12-SEQ ID NO:13-SEQ ID NO:14-SEQ ID NO:15, SEQ ID NO:11-SEQ ID NO:12-SEQ ID NO:40-SEQ ID NO:41-SEQ ID NO:15, SEQ ID NO:11-SEQ ID NO:12-SEQ ID NO:134-SEQ ID NO:135-SEQ ID NO:15, SEQ ID NO:58-SEQ ID NO:59-SEQ ID NO:60-SEQ ID NO:61-SEQ ID NO:62, SEQ ID NO:58-SEQ ID NO:59-SEQ ID NO:60-SEQ ID NO:80-SEQ ID NO:81, SEQ ID NO:92-SEQ ID NO:59-SEQ ID NO:93-SEQ ID NO:94-SEQ ID NO:62, SEQ ID NO:101-SEQ ID NO:59-SEQ ID NO:102-SEQ ID NO:103-SEQ ID NO:62, or SEQ ID NO:144-SEQ ID NO:59-SEQ ID NO:145-SEQ ID NO:146-SEQ ID NO:147.

In certain embodiments, the VL comprises the amino acid sequence of: SEQ ID NO:70-SEQ ID NO:127-SEQ ID NO:29-SEQ ID NO:172-SEQ ID NO:152, SEQ ID NO:70-SEQ ID NO:127-SEQ ID NO:72-SEQ ID NO:204-SEQ ID NO:205, SEQ ID NO:185-SEQ ID NO:186-SEQ ID NO:29-SEQ ID NO:187-SEQ ID NO:129, SEQ ID NO:213-SEQ ID NO:115-SEQ ID NO:214-SEQ ID NO:215-SEQ ID NO:216, or SEQ ID NO:240-SEQ ID NO:241-SEQ ID NO:242-SEQ ID NO:243-SEQ ID NO:244.

In certain embodiments, the VH comprises the amino acid sequence of: SEQ ID NO:58-SEQ ID NO:59-SEQ ID NO:200-SEQ ID NO:94-SEQ ID NO:201, SEQ ID NO:160-SEQ ID NO:59-SEQ ID NO:145-SEQ ID NO:177-SEQ ID NO:163, SEQ ID NO:160-SEQ ID NO:59-SEQ ID NO:145-SEQ ID NO:193-SEQ ID NO:194, SEQ ID NO:160-SEQ ID NO:59-SEQ ID NO:161-SEQ ID NO:162-SEQ ID NO:163, or SEQ ID NO:226-SEQ ID NO:227-SEQ ID NO:228-SEQ ID NO:229-SEQ ID NO:230.

In certain embodiments, the monoclonal antibody is humanized.

In certain embodiments, the monoclonal antibody is labeled.

In certain embodiments, the antibody of the disclosure is capable of crossing the blood-brain barrier (BBB). In certain embodiments, the antibody of the disclosure is bispecific, being IgG-like or non-IgG-like. The antibody can bind to alpha-synuclein, as described elsewhere herein and using any of the CDR sequences recited herein, and can also bind to a BBB target receptor that allows for transport of the antibody through the BBB (in a non-limiting example, through receptor-mediated transcytosis). A non-limiting example of such BBB target receptor is transferrin receptor, which activates a molecular channel that normally imports iron into the brain. Anti-human transferrin receptor antibodies contemplated within the invention include those recited in US20160369001, which is incorporated herein in its entirety by reference. Other non-limiting examples of such BBB target receptors are low-density lipoprotein (LDL) receptor and insulin receptor. In certain embodiments, the antibodies of the disclosure comprise a single-chain anti-BBB target receptor antibody. In certain embodiments, the antibodies of the disclosure have an Fc fragment engineered to be capable of binding to a BBB target receptor. Approaches contemplated in the present disclosure are described in Pulgar, Front. Neurosci., January 2019, Vol. 12, Article 2019, and Kariolis, et al., Science Translational Medicine 12(545), eaay 1359, which are incorporated herein in their entireties by reference.

The disclosure further provides isolated polynucleotides (including RNA and/or DNA) encoding the antibodies or antigen binding fragments thereof, for example a nucleic acid encoding for one or more CDRs, or a variable heavy chain or variable light chain region of the α-Syn antibodies of the disclosure. Nucleic acid includes DNA and RNA.

In certain embodiments, the disclosure provides an isolated polynucleotide comprising the nucleic acid sequence of SEQ ID NOs:3, 5, 7, 19, 21, 23, 35, 43, 44, 50, 52, 54, 66, 68, 75, 77, 88, 89, 96, 97, 99, 106, 108, 110, 121, 132, 138, 139, 141, 148, 150, 155, 157, 167, 168, 170, 175, 180, 191, 195, 197, 198, 203, 207, 209, 211, 219, 221, 223, 233, 235, and 237.

In certain embodiments, the disclosure provides an isolated polynucleotide comprising at least one nucleic acid sequence selected from the group consisting of SEQ ID NOs:3, 5, 7, 35, 50, 52, 54, 75, 77, 88, 89, 97, 99, 132, 138, 139, 141, 155, 157, 175, 191, 197, 198, 219, 221, and 223.

In certain embodiments, the disclosure provides an isolated polynucleotide comprising at least one nucleic acid sequence selected from the group consisting of SEQ ID NOs:19, 21, 23, 43, 44, 66, 68, 96, 106, 108, 110, 121, 148, 150, 167, 168, 170, 180, 195, 203, 207, 209, 211, 233, 235, and 237.

In certain embodiments, the antibody has a VL encoded by a nucleic acid sequence group comprising a nucleic acid sequence set selected from the group consisting of: SEQ ID NOs:19, 21, 23; SEQ ID NOs:19, 43, 44; SEQ ID NOs:19, 66, 68; SEQ ID NOs:19, 66, 96; SEQ ID NOs:19, 66, 203; SEQ ID NOs:19, 148, 150; SEQ ID NOs:106, 108, 110; SEQ ID NOs:121, 66, 68; SEQ ID NOs:167, 168, 170; SEQ ID NOs:167, 168, 195; SEQ ID NOs:180, 168, 68; SEQ ID NOs:213, 214, 216; and SEQ ID NOs:233, 235, 237.

In certain embodiments, the antibody has a VH encoded by a nucleic acid sequence group comprising a nucleic acid sequence set selected from the group consisting of: SEQ ID NOs:3, 5, 7; SEQ ID NOs:3, 35, 7; SEQ ID NOs:3, 132, 7; SEQ ID NOs:50, 52, 54; SEQ ID NOs:50, 75, 77; SEQ ID NOs:50, 139, 175; SEQ ID NOs:50, 139, 191; SEQ ID NOs:50, 155, 157; SEQ ID NOs:50, 197, 198; SEQ ID NOs:88, 89, 54; SEQ ID NOs:97, 99, 54; SEQ ID NOs:138, 139, 141; and SEQ ID NOs:219, 221, 223.

In certain embodiments, the disclosure provides an autonomously replicating or an integrative mammalian cell vector comprising a recombinant nucleic acid of the disclosure. In other embodiments, the disclosure provides a vector comprising a recombinant nucleic acid of the disclosure. In yet other embodiments, the recombinant nucleic acid of the disclosure encodes an antibody comprising a light chain variable region (VL) and a heavy chain variable region (VH). In certain embodiments, the VL comprises a CDR1 region comprising the amino acid sequence of SEQ ID NO:27, 46, 70, 114, 126, 185, 213, or 240. In certain embodiments, the VL comprises a CDR2 region comprising the amino acid sequence of SEQ ID NO:29, 72, 116, 214, or 242. In certain embodiments, the VL comprises a CDR3 region comprising the amino acid sequence of SEQ ID NO:31, 85, 118, 129, 152, 205, 216, or 244. In certain embodiments, the VH comprises a CDR1 region comprising the amino acid sequence of SEQ ID NO:11, 58, 92, 101, 144, 160, or 226. In certain embodiments, the VH comprises a CDR2 region comprising the amino acid sequence of SEQ ID NO:13, 40, 60, 93, 102, 134, 145, 161, 200, or 228. In certain embodiments, the VH comprises a CDR3 region comprising the amino acid sequence of SEQ ID NO:15, 62, 81, 62, 147, 163, 194, 201, or 230. In yet other embodiments, the vector comprises a plasmid or virus. In yet other embodiments, the vector comprises a mammalian cell expression vector. The expression vector can comprise nucleic acid sequences that direct and/or control expression of the inserted polynucleotide. Such nucleic acid sequences can include regulatory sequence, including promoter sequences, terminator sequences, polyadenylation sequences, and enhancer sequences. Systems for cloning and expression of a polypeptide in a variety of cells are well known in the art.

The disclosure further provides a host cell comprising the expression vector of the disclosure. In certain embodiments, the host cell is isolated. In other embodiments, the host cell is a non-human cell. In yet other embodiments, the host cell is mammalian.

The antibody of the disclosure can be a mammalian antibody, such as primate, human, rodent, rabbit, ovine, porcine or equine antibody. The antibody can be any class or isotype antibody, for example IgM or IgG. In certain embodiments, the antibody is IgG.

The disclosure further provides a kit comprising an antibody of the disclosure. The antibody may be an intact immunoglobulin molecule or fragment thereof such as Fab, F(ab)2 or Fv fragment. The antibody can be labelled as described elsewhere herein. The kit can be for use in a method of determining whether a subject has a neurodegenerative disease, and/or for treating, ameliorating, and/or preventing a subject afflicted or thought to be afflicted with a neurodegenerative disease. The kit can further any other reagent or instrument that is required to implement a method of the disclosure, such as a buffer, an applicator, and the like.

The following table illustrates the relationship between the SEQ ID NOs: used in the priority document (U.S. Provisional Patent Application No. 62/937,636) and the SEQ ID NOs: used in the present disclosure -continued

| SEQ ID NO: present disclosure | SEQ ID NO(s): priority document |
|---|---|
| 1 | 1, 97, 129 |
| 2 | 2, 98, 130 |
| 3 | 3, 35, 99, 131, 275, 307, 339, 403 |
| 4 | 4, 36, 100, 132, 276, 308, 340, 404 |
| 5 | 5, 101, 133 |
| 6 | 6, 102, 134 |
| 7 | 7, 39, 103, 135, 279, 311, 343, 407 |
| 8 | 8, 104, 136, 376, 504, 536, 584, 616, 648 |
| 9 | 9, 105, 137 |
| 10 | 10, 106, 138 |
| 11 | 11, 43, 107, 139, 283, 315, 347, 411 |
| 12 | 12, 44, 108, 140, 284, 316, 348, 412 |
| 13 | 13, 109, 141 |
| 14 | 14, 110, 142 |
| 15 | 15, 47, 111, 143, 287, 319, 351, 415 |
| 16 | 16, 48, 112, 144, 288, 320, 352, 384, 416, 512, 544, 592, 624, 656 |
| 17 | 17, 49, 113, 145, 289, 321, 353, 417 |
| 18 | 18, 50, 82, 114, 146, 210, 290, 322, 354, 386, 418, 546 |
| 19 | 19, 51, 83, 115, 147, 179, 211, 291, 323, 355, 387, 419, 547 |
| 20 | 20, 116, 148 |
| 21 | 21, 117, 149 |
| 22 | 22, 54, 118, 150, 294, 326, 358, 422 |
| 23 | 23, 119, 151 |
| 24 | 24, 88, 120, 152, 216, 568 |
| 25 | 25, 57, 121, 153, 297, 329, 361, 425 |
| 26 | 26, 58, 90, 122, 154, 218, 298, 330, 362, 394, 426, 554 |
| 27 | 27, 123, 155 |
| 28 | 28, 60, 124, 156, 300, 322, 364, 428 |
| 29 | 29, 61, 125, 157, 301, 333, 365, 397, 429, 461, 493, 525, 637, 669 |
| 30 | 30, 62, 126, 158, 302, 334, 366, 430 |
| 31 | 31, 63, 127, 159, 303, 335, 367, 431 |
| 32 | 32, 96, 128, 160, 224, 576 |
| 33 | 33, 273, 305, 337, 401 |
| 34 | 34 |
| 35 | 37 |
| 36 | 38 |
| 37 | 40, 280, 312, 344, 408 |
| 38 | 41, 281, 313, 345, 409 |
| 39 | 42, 282, 314, 346, 410 |
| 40 | 45 |
| 41 | 46 |
| 42 | 52, 292, 324, 356, 420 |
| 43 | 53, 293, 325, 357, 421 |
| 44 | 55, 295, 327, 359, 423 |
| 45 | 56, 296, 328, 360, 424 |
| 46 | 59, 299, 331, 363, 427 |
| 47 | 64, 304, 336, 368, 432 |
| 48 | 65, 161, 193, 225 |
| 49 | 66 |
| 50 | 67, 163, 435, 467, 499, 531, 611, 643 |
| 51 | 68, 164, 196, 372, 532 |
| 52 | 69 |
| 53 | 70 |
| 54 | 71, 199, 231 |
| 55 | 72, 200, 232 |
| 56 | 73, 169, 201, 233 |
| 57 | 74 |
| 58 | 75, 171, 539 |
| 59 | 76, 172, 204, 236, 380, 444, 476, 508, 540, 620, 652 |
| 60 | 77, 173 |
| 61 | 78 |
| 62 | 79, 207, 239 |
| 63 | 80, 176, 208, 240 |
| 64 | 81, 177, 209, 257, 385, 545 |
| 65 | 84, 180, 212 |
| 66 | 85, 181, 213, 261, 549 |
| 67 | 86, 182 |
| 68 | 87, 183, 263, 487 |
| 69 | 89, 185, 217, 265, 393, 457, 521, 553, 633, 665 |
| 70 | 91, 187, 219, 395, 459, 523, 555, 635, 667 |
| 71 | 92, 188, 220 |
| 72 | 93, 189, 221, 269, 557 |
| 73 | 94, 190, 222 |
| 74 | 162, 226 |
| 75 | 165 |
| 76 | 166 |
| 77 | 167 |
| 78 | 168 |
| 79 | 170, 234 |

-continued

| SEQ ID NO: present disclosure | SEQ ID NO(s): priority document |
|---|---|
| 80 | 174 |
| 81 | 175 |
| 82 | 178 |
| 83 | 184 |
| 84 | 186 |
| 85 | 95, 191, 223 |
| 86 | 192 |
| 87 | 194 |
| 88 | 195 |
| 89 | 197 |
| 90 | 198, 534 |
| 91 | 202 |
| 92 | 203 |
| 93 | 205 |
| 94 | 206, 542 |
| 95 | 214 |
| 96 | 215 |
| 97 | 227 |
| 98 | 228 |
| 99 | 229 |
| 100 | 230 |
| 101 | 235 |
| 102 | 237 |
| 103 | 238 |
| 104 | 241 |
| 105 | 242, 562 |
| 106 | 243 |
| 107 | 244 |
| 108 | 245 |
| 109 | 246 |
| 110 | 247 |
| 111 | 248, 392, 456, 520, 552, 632, 664 |
| 112 | 249 |
| 113 | 250, 570 |
| 114 | 251 |
| 115 | 252, 572 |
| 116 | 253 |
| 117 | 254 |
| 118 | 255 |
| 119 | 256, 400, 464, 528, 560, 640, 672 |
| 120 | 258 |
| 121 | 259 |
| 122 | 260, 388, 452, 516, 548, 628, 660 |
| 123 | 262 |
| 124 | 264, 600 |
| 125 | 266 |
| 126 | 267 |
| 127 | 268, 396, 460, 524, 556, 636, 668 |
| 128 | 270 |
| 129 | 271, 495 |
| 130 | 272, 608 |
| 131 | 274, 306, 338, 402 |
| 132 | 277, 309, 341, 405 |
| 133 | 278, 310, 342, 406 |
| 134 | 285, 317, 349, 413 |
| 135 | 286, 318, 350, 414 |
| 136 | 369, 433, 497, 529, 609, 641 |
| 137 | 370 |
| 138 | 371 |
| 139 | 373, 469, 501, 613, 645 |
| 140 | 374 |
| 141 | 375 |
| 142 | 377, 441, 473, 505, 537, 617, 649 |
| 143 | 378 |
| 144 | 379 |
| 145 | 381, 477, 509, 621, 653 |
| 146 | 382 |
| 147 | 383 |
| 148 | 389 |
| 149 | 390 |
| 150 | 391 |
| 151 | 398 |
| 152 | 399, 463, 527, 639, 671 |
| 153 | 434, 466 |

-continued

| SEQ ID NO: present disclosure | SEQ ID NO(s): priority document |
|---|---|
| 154 | 436, 468, 500, 612, 644 |
| 155 | 437 |
| 156 | 438 |
| 157 | 439 |
| 158 | 440 |
| 159 | 442, 474 |
| 160 | 443, 475, 507, 619, 651 |
| 161 | 445 |
| 162 | 446 |
| 163 | 447, 479 |
| 164 | 448 |
| 165 | 449, 513, 625, 657 |
| 166 | 450, 482, 514, 626, 658 |
| 167 | 451, 515, 627, 659 |
| 168 | 453, 485, 517, 629, 661 |
| 169 | 454, 518, 630, 662 |
| 170 | 455 |
| 171 | 458, 490, 522, 634, 666 |
| 172 | 462, 526, 638, 670 |
| 173 | 465 |
| 174 | 470 |
| 175 | 471 |
| 176 | 472 |
| 177 | 478 |
| 178 | 480 |
| 179 | 481 |
| 180 | 483 |
| 181 | 484 |
| 182 | 486 |
| 183 | 488 |
| 184 | 489 |
| 185 | 491 |
| 186 | 492 |
| 187 | 494 |
| 188 | 496 |
| 189 | 498, 610, 642 |
| 190 | 502, 614, 646 |
| 191 | 503, 615, 647 |
| 192 | 506, 618, 650 |
| 193 | 510, 622, 654 |
| 194 | 511, 623, 655 |
| 195 | 519, 631, 663 |
| 196 | 530 |
| 197 | 533 |
| 198 | 535 |
| 199 | 538 |
| 200 | 541 |
| 201 | 543 |
| 202 | 550 |
| 203 | 551 |
| 204 | 558 |
| 205 | 559 |
| 206 | 561 |
| 207 | 563 |
| 208 | 564 |
| 209 | 565 |
| 210 | 566 |
| 211 | 567 |
| 212 | 569 |
| 213 | 571 |
| 214 | 573 |
| 215 | 574 |
| 216 | 575 |
| 217 | 577 |
| 218 | 578 |
| 219 | 579 |
| 220 | 580 |
| 221 | 581 |
| 222 | 582 |
| 223 | 583 |
| 224 | 585 |
| 225 | 586 |
| 226 | 587 |
| 227 | 588 |

-continued

| SEQ ID NO: present disclosure | SEQ ID NO(s): priority document |
|---|---|
| 228 | 589 |
| 229 | 590 |
| 230 | 591 |
| 231 | 593 |
| 232 | 594 |
| 233 | 595 |
| 234 | 596 |
| 235 | 597 |
| 236 | 598 |
| 237 | 599 |
| 238 | 601 |
| 239 | 602 |
| 240 | 603 |
| 241 | 604 |
| 242 | 605 |
| 243 | 606 |
| 244 | 607 |
| 245 | 673 |

The non-limiting generation of these antibodies is illustrated in the Examples and Figures provided herein. In certain embodiments, the disclosure comprises pharmaceutical compositions comprising each of these antibodies in combination with one or more pharmaceutically acceptable excipients. In some embodiments the pharmaceutical composition is formulated for parenteral delivery. In other embodiments, the antibodies are humanized.

Method of Treating, Ameliorating, and/or Preventing a Synucleopathic Disease

In one aspect, the disclosure provides a method of treating, ameliorating, and/or preventing a synucleopathic disease comprising administering a therapeutically effective amount of an isolated monoclonal antibody of the disclosure to a patient. In another aspect, the disclosure provides an isolated monoclonal antibody of the disclosure for use as a medicament for treating, ameliorating, and/or preventing a synucleopathic disease. In yet another aspect, the disclosure provides use of an isolated monoclonal antibody of the disclosure in the manufacture of a medicament for the treatment, amelioration, and/or prevention of a synucleopathic disease. In yet another aspect, the disclosure provides an isolated monoclonal antibody of the disclosure for use in a method for treating, ameliorating, and/or preventing a synucleopathic disease.

In certain embodiments, the antibody is humanized. In other embodiments, the antibody is administered as a pharmaceutical composition.

The monoclonal antibodies described above may be used to treat, ameliorate, and/or prevent a synucleopathic disease by reducing α-Syn pathology in neurons induced by α-Syn fibrils and/or oligomers. In certain embodiments, the neurodegenerative disorders associated with α-Syn include but are not limited to Parkinson's disease, dementia (such as Parkinson's disease with dementia and/or dementia with Lewy bodies), Alzheimer's disease, Down's syndrome, multiple-system atrophy, prion diseases, and other α-Syn related neurodegenerative disorders. The antibody can be administered systemically or directly to the site where α-Syn fibrils, e.g. a Lewy body, are observed or thought to be present. In a non-limiting example, the antibody can be administered by injection into a blood vessel supplying the brain or into the brain itself. The subject can be a mammal, such as a human or a non-human mammal.

Methods of Detecting a Synucleopathic Disease

In yet another aspect, the disclosure provides methods of detecting synucleopathic disease in a patient. In other embodiments, the antibodies of the disclosure can be used as diagnostic tools for neurodegenerative disorders associated with α-Syn, including but not limited to Parkinson's disease, dementia (such as Parkinson's disease with dementia and/or dementia with Lewy bodies), Alzheimer's disease, Down's syndrome, multiple-system atrophy, prion diseases, and other α-Syn related neurodegenerative disorders. In certain embodiments, the methods are performed in vitro. In certain embodiments, the methods are performed ex vivo.

In certain embodiments, the method of detecting a synucleopathic disease in a subject comprises the steps of administering a labeled, isolated monoclonal antibody of the disclosure to the subject, and detecting the presence of absence of a complex between any α-Syn fibrils and/or oligomers in the subject and the antibody. If the complex is present, that indicates that α-Syn fibrils and/or oligomers exist in the subject. In certain embodiments, if α-Syn fibrils and/or oligomers are present in the subject, the subject has a neurodegenerative disease. In other embodiments, if α-Syn fibrils or oligomers are not present in the subject, the subject does not have a neurodegenerative disease. In yet other embodiments, if the subject has a neurodegenerative disease, the individual is counseled to undergo therapy and/or pharmacological treatment for the neurodegenerative disease. In yet other embodiments, if the subject has a neurodegenerative disease, the individual is provided therapy and/or pharmacological treatment for the neurodegenerative disease.

In certain embodiments, the method further comprises comparing the level of antibody/α-Syn fibrils and/or oligomer complexes formed in the subject with the level of antibody/α-Syn fibrils and/or oligomer complexes formed in a reference subject. The reference subject can be a subject known not to have α-Syn fibrils and/or oligomers, a subject known to have detectable α-Syn fibrils and/or oligomers, and/or a subject known to have a certain level of α-Syn fibrils and/or oligomers. The reference subject can further be the same subject being treated or evaluated, but corresponding to an earlier α-Syn fibrils and/or oligomers detection experiment, as a way to evaluate disease progression and/or treatment efficacy in the subject.

In yet another aspect, the disclosure provides methods of detecting α-Syn fibrils in a sample. In certain embodiments, the antibodies of the disclosure can be used as diagnostic tools for detecting the presence of α-Syn fibrils, oligomers or other misfolded α-Syn species in a sample.

In certain embodiments, the method of detecting α-Syn fibrils, oligomers, or other misfolded α-Syn species in a sample (for example, from a subject) comprises the steps of contacting the sample with a labeled, isolated monoclonal antibody of the disclosure, and detecting the presence or absence of a complex between any α-Syn fibrils, oligomers, or other misfolded α-Syn species in the sample and the antibody. If the complex is detected, that indicates the presence of α-Syn fibrils, oligomers, or other misfolded α-Syn species in the sample. The sample can be, in non-limiting examples, cerebrospinal fluid (CSF), blood, urine, saliva, or tissues from brain, gut, colon, skin, or salivary gland. In certain embodiments, the sample is a CSF sample and/or a brain tissue sample. In other embodiments, the sample is used as is after being removed from the subject. In other embodiments, the sample is pre-treated being used within the present methods.

In certain embodiments, the method further comprises comparing the level of antibody-α-Syn fibrils/oligomers or other antibody-misfolded α-Syn complexes formed in the sample with the level of antibody-α-Syn fibrils/oligomers or other antibody-misfolded α-Syn complexes formed in a reference sample. The reference sample can be from a subject known not to have α-Syn fibrils/oligomers or other misfolded α-Syn species, a subject known to have detectable α-Syn fibrils/oligomers or other misfolded α-Syn species, and/or a subject known to have a certain level of α-Syn fibrils/oligomers or other misfolded α-Syn species. The reference sample can further be from the same subject being treated or evaluated, but corresponding to an earlier α-Syn fibrils/oligomers or other misfolded α-Syn species detection, as a way to evaluate disease progression and/or treatment efficacy in the subject.

In certain embodiments, the level of α-Syn fibrils/oligomers or other misfolded α-Syn species detected in a subject or in a sample from a subject correlates with severity or progression of a neurodegenerative disease in the subject. In other embodiments, the methods of the disclosure can be used to monitor severity or progression of a neurodegenerative disease in the subject. In yet other embodiments, the methods of the disclosure can be used to monitor effectiveness of a therapy and/or pharmacological intervention in a subject afflicted or believed to be afflicted with a neurodegenerative disease.

In certain embodiments, the sample comprises or is an in vitro sample. In certain embodiments, the sample comprises or is an ex vivo sample.

Methods for detecting formation of a complex between the antibody and α-Syn fibrils/oligomers or other misfolded α-Syn species comprise, but are not limited to, radioimmunoassay, enzyme-linked immunosorbant assay (ELISA), sandwich immunoassay, fluorescent immunoassay, precipitation reaction, gel immunodiffusion assay, agglutination assay, protein A immunoassay, immunoelectrophoresis assay, electrophoresis, western blotting, or any other technique known in the art.

In certain embodiments, the antibodies of the disclosure can be combined with a label and used to detect over α-Syn levels in a patient or in a sample. In other embodiments, the antibodies of the disclosure can be combined with a label and used to detect α-Syn fibrils/oligomers or other misfolded α-Syn species in a patient or in a sample. Methods of labeling antibodies are known in the art and a variety of approaches may be employed. In certain embodiments the label is a radiolabel, such as but not limited to $F^{18}$, $I^{123}$, $In^{111}$, $I^{131}$, $C^{14}$, $H^{3}$, $Tc^{99m}$, $P^{32}$, $I^{125}$, $Ga^{68}$ and the like. In other embodiments, the label is a fluorescent label, such as but not limited to fluorescein, rhodamine and the like. In yet other embodiments, the label is a contrast agent, such as but not limited to gadolinium (Gd), dysprosium and iron, magnetic agents, and the like. Other labels include nuclear magnetic resonance active labels, positron emitting isotopes detectable by a PET scanner, chemiluminescent and enzymatic markers. Non-limiting imaging techniques include electron microscopy, confocal microscopy, light microscopy, positron emission tomography (PET), gamma-scintigraphy, magnetic resonance imaging (MM), functional magnetic resonance imaging (FMRI), magnetoencephalography (MEG), and single photon emission computerized tomography (SPECT). In yet other embodiments, the label is on a secondary antibody that binds a primary antibody comprising the above described sequences.

Administration/Dosage/Formulations

Administration of the compounds and/or compositions of the present disclosure to a patient, preferably a mammal, more preferably a human, may be carried out using known procedures, at dosages and for periods of time effective to perform a therapeutic and/or imaging method contemplated in the disclosure. An effective amount of the compound necessary for adequate therapeutic treatment and/or imaging signal may vary according to factors such as the state of a disease or disorder in the patient; the age, sex, and weight of the patient; and/or the equipment used to detect the compound of the disclosure. One of ordinary skill in the art would be able to study the relevant factors and make the determination regarding the effective amount of the therapeutic and/or imaging compound without undue experimentation.

Actual dosage levels of the active ingredients in the pharmaceutical compositions of this disclosure may be varied so as to obtain an amount of the active ingredient that is effective to achieve successful therapy and/or imaging for a particular patient, composition, and mode of administration, without being toxic to the patient.

In certain embodiments, the compositions of the disclosure are formulated using one or more pharmaceutically acceptable excipients or carriers. In certain embodiments, the pharmaceutical compositions of the disclosure comprise an effective amount of a compound of the disclosure and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like.

Routes of administration of any of the compositions of the disclosure include oral, nasal, rectal, intravaginal, parenteral, buccal, sublingual or topical. The compounds for use in the disclosure may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this disclosure include dosage forms as described in U.S. Pat. Nos. 6,340,475; 6,488,962; 6,451,808; 5,972,389; 5,582,837; and 5,007,790. Additional dosage forms of this disclosure also include dosage forms as described in U.S. Patent Applications Nos. 2003/0147952; 2003/0104062; 2003/0104053; 2003/0044466; 2003/0039688; and 2002/0051820. Additional dosage forms of this disclosure also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

EXPERIMENTAL EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, practice the claimed methods of the present disclosure. The following working examples therefore, specifically point out the preferred embodiments of the present disclosure, and are not to be construed as limiting in any way the remainder of the disclosure.

Animals

Mice used for antibody generation were Balb/c; mice used for primary neuron culture were CD-1 (Charles River, Cat #CRL:22, RRID:IMSR_CRL:22), and mice used for in vivo studies were B6C3F1 (Charles River, Cat #CRL:31, RRID: IMSR_CRL:31).

Primary Hippocampal Neuron Cultures

Primary hippocampal neuron cultures were prepared as previously described (Henderson, et al., 2017, J Neurosci.; Henderson, et al., 2018, Acta Neuropathologica Comm. 6:45) from embryonic day (E) 16-18 CD1 embryos. Dissociated hippocampal neurons were plated at 17,500 cells/well (96-well plate) in neuron media (Neurobasal medium (ThermoFisher 21103049) supplemented with B27 (ThermoFisher 17504044), 2 mM GlutaMax (ThermoFisher 35050061), and 100 U/mL penicillin/streptomycin (ThermoFisher 15140122).

α-Synuclein PFFs

Purification of recombinant α-Synuclein and generation of α-Synuclein PFFs was conducted as described elsewhere (Luk, et al., 2009, Proc Natl Acad Sci USA 106:20051-20056; Volpicelli-Daley, et al., 2014, Nature Protocols 9:2135-2146). The pRK172 plasmid containing the gene of interest was transformed into BL21 (DE3) RIL-competent *E. coli* (Agilent Technologies Cat #230245). A single colony from this transformation was expanded in Terrific Broth (12 g/L of Bacto-tryptone, 24 g/L of yeast extract 4% (vol/vol) glycerol, 17 mM $KH_2PO_4$ and 72 mM $K_2HPO_4$) with ampicillin. Bacterial pellets from the growth were sonicated and sample was boiled to precipitate undesired proteins. The supernatant was dialyzed with 10 mM Tris, pH 7.6, 50 mM NaCl, 1 mM EDTA overnight. Protein was filtered with a 0.22 μm filter and concentrated using Amicon Ultra-15 centrifugal filter units (Millipore Sigma Cat #UFC901008). Protein was then loaded onto a Superdex 200 column and 1 mL fractions were collected. Fractions were run on SDS-PAGE and stained with Coomassie blue to select fractions that were highly enriched in α-Synuclein. These fractions were combined and dialyzed in 10 mM Tris, pH 7.6, 50 mM NaCl, 1 mM EDTA overnight. Dialyzed fractions were applied to the MonoQ column (GE Health, HiTrap Q HP 645932) and run using a linear gradient from 25 mM NaCl to 1 M NaCl. Collected fractions were run on SDS-PAGE and stained with Coomassie blue. Fractions that were highly enriched in α-Synuclein were collected and dialyzed into DPBS. Protein was filtered through a 0.22 μm filter and concentrated to 5 mg/mL with Amicon Ultra-15 centrifugal filter units (Millipore Sigma Cat #UFC901008). Monomer was aliquoted and frozen at −80° C. For preparation of α-Synuclein PFFs, α-Synuclein monomer was shaken at 1,000 rpm for 7 days. Conversion to PFFs was validated by sedimentation at 100,000×g for 60 minutes and by Thioflavin T fluorescence.

α-Synuclein PFF Treatments

Primary Neurons

For treatment of neurons, mouse α-Synuclein PFFs, which were generated at a concentration of 5 mg/mL, were vortexed and diluted with Dulbecco's phosphate-buffered saline (DPBS, Corning Cat #21-031-CV) to 100 μg/mL. They were then sonicated on high for 10 cycles of 30 seconds on, 30 seconds off (Diagenode Biorupter UCD-300 bath sonicator). α-Synuclein PFFs were then diluted in neuron media to 5 μg/mL and added to neuron cultures at the noted concentrations.

Mice

Mouse α-Synuclein PFFs, which were generated at a concentration of 5 mg/mL were vortexed and diluted with DPBS to 2 mg/mL. They were then sonicated on high for 10 cycles of 30 seconds on, 30 seconds off (Diagenode Biorupter UCD-300 bath sonicator). Mice were injected when 3 months old. Mice were injected unilaterally by insertion of a single needle into the right forebrain (coordinates: +0.2 mm relative to Bregma, +2.0 mm from midline) targeting the dorsal striatum (2.6 mm beneath the dura) with 5 μg α-Synuclein PFFs (2.5 μL). Injections were performed using a 10 μL syringe (Hamilton, Nev.) at a rate of 0.4 μL/minute. After 6 months, mice were perfused transcardially with PBS, brains were removed and underwent overnight fixation in 70% ethanol in 150 mM NaCl, pH 7.4.

Antibody Production

Murine monoclonal antibodies were raised as described previously (Gibbons, et al., 2018, Neuropathol Exp Neurol 77:216-228) against sonicated, human α-Synuclein PFFs emulsified with complete Freund's adjuvant (0.05 mg α-Synuclein/mouse) followed by 2 subsequent boosts of 0.025 mg α-Synuclein emulsified with incomplete Freund's adjuvant 3 and 6 weeks following the initial injections. Nine weeks after initial antigen injection, mice received an intravenous boost of 0.025 mg/mouse. Four days after intravenous injection, spleens were dissociated into single cell suspensions and fused with SP2 cells by 1-minute treatment with a mixture of 50% polyethylene glycol and 5% DMSO. Hybridoma cells were selected for 7 days in medium containing 5.7 μM azaserine-10; 100 μM hypoxanthine (Sigma Cat #A9666) and cultured in Kennett's HY (90% DMEM, 10% NCTC135, 4.15 g/L glucose, 3.55 g/L $NaHCO_3$), supplemented with 20% fetal bovine serum (FBS; Atlanta Biological Cat #E0118), 100 U/mL penicillin/100 μg/mL streptomycin (Gibco Cat #15140-122); 2 mM L-glutamine (Corning Cat #25-005-C1) and OPI media supplement (1 mM oxoloacetate, 0.45 mM pyruvate, 0.2 U/mL insulin; Sigma Cat #05003). Monoclonal populations were isolated by limiting dilution to 0.3 cells/well in 96-well plates. Antibodies were further characterized as described below. Hybridomas with selectivity for pathological misfolded α-syn were expanded and subcloned at least twice.

Epitope Mapping

Recombinant α-Synuclein constructs were produced in *E. coli* as previously established (Volpicelli-Daley, et al., 2014, Nature Protocols 9:2135-2146). Total protein concentration in each sample was determined by a bicinchoninic acid colorimetric assay (Fisher Cat #23223 and 23224), using bovine serum albumin as a standard (Thermo Fisher Cat #23210). Protein was resolved on 5-20% gradient polyacrylamide gels using equal protein loading (250 ng α-Synuclein/well). Proteins were transferred to 0.2 μm nitrocellulose membranes and detected with primary antibodies (1:1000). Primary antibodies were detected using IRDye 800 (LI-COR 925-32210) or IRDye 680 (LI-COR 925-68071) secondary antibodies, scanned on a LI-COR Odyssey Imaging System and analyzed using Image Studio software.

Primary Neuron Immunotherapy Assay

Neurons were treated using a modified version of the procedure previously described (Tran, et al., 2014, Cell Reports 7:2054-2065). Neurons were fed every three days after plating until 10 DIV. At that point, 125 μL of media was removed from each well, and sterile α-Synuclein antibodies were added in 20 μL of fresh neuron media at incubated at 37° C. for 30 minutes. 125 μg of freshly sonicated PFFs were added in an additional 20 μL of neuron media. Neurons were fed at 1 and 4 DPT and fixed and stained at 7-days post transduction as described previously (Tran, et al., 2014, Cell Reports 7:2054-2065). Data are reported as the normalized pS129 α-Synuclein area divided by NeuN count. For initial clone selection, antibodies were included at a 1:1 molar ratio to α-Synuclein PFFs. For more detailed characterization of high priority clones, antibodies were included at molar ratios ranging from 2:1 to 0.0003:1 (antibody:PFFs).

Immunocytochemistry

Primary neuron or cell line cultures were fixed with 4% paraformaldehyde, 4% sucrose in phosphate-buffered saline and washed five times in PBS. Immunostaining of neuronal cultures was carried out as described previously (Henderson, et al., 2018, Acta Neuropathologica Comm. 6:45). Cells were permeabilized in 3% BSA+0.3% TX-100 in PBS for 15 minutes at room temperature. After a PBS wash, cells were blocked for 50 minutes with 3% BSA in PBS prior to incubation with primary antibodies for 2 hours at room temperature. Primary antibodies used were targeting pS129 α-Synuclein (81A, CNDR, 1:5,000) and NeuN (Millipore Cat #MAB377, 1:1,500). Cells were washed 5× with PBS and incubated with secondary antibodies for 1 hour at room temperature. After 5× wash with PBS, cells were incubated in DAPI (ThermoFisher Cat #D21490, 1:10,000) in PBS. 96-well plates were imaged on In Cell Analyzer 2200 (GE Healthcare) and analyzed in the accompanying software. A standard intensity-based threshold was applied to the pS129 α-Synuclein channel equally across plates and positive area was quantified. For NeuN quantification, an object-based analysis was applied to identify objects of specified size and intensity. All quantification was optimized and applied equally across all conditions.

Sandwich ELISA

A 384-well Maxisorp clear plate (Thermo Fisher Scientific, Cat #12565347) was coated with 30 μL per well (50 ng) of antibody in Takeda coating buffer, then plate was spun at 1000×g for 1 minute and incubated overnight at 4° C. The plate was washed 4 times with PBST (PBS with 0.05% Tween) and blocked using Block Ace blocking solution (95 μL per well) (AbD Serotec) overnight at 4° C. Serial double dilutions of human wild-type α-Synuclein fibrils and monomer were made in Buffer C (0.02 M sodium phosphate buffer, 2 mM EDTA, 0.4 M NaCl, 1% BSA, 0.005% thimerisol) starting at 256 μg/mL of monomer and 25.6 μg/mL of fibrils. Fibrils were then sonicated on high for 10 cycles of 30 seconds on, 30 seconds off (Diagenode Biorupter UCD-300 bath sonicator) prior to dilutions. Dilutions were added to each well (30 μL per well) and incubated overnight at 4° C. The plate was washed 4 times with PBST. 30 μL of MJF-R1 (1:3,000, Abcam Cat #ab138501) in Buffer C was added to each well and the plate was incubated for 4 hours at 37° C. After washing with PBST 4 times, 1:10 k diluted goat-anti-rabbit IgG-HRP conjugate (Cell Signaling Technology) was added to the plate and the plate was incubated for 1 hour at 37° C. Following washing with PBST 4 times the plate was developed for 10-15 minutes using 30 μL per well of room temperature 1-Step Ultra TMB-ELISA Substrate Solution (Thermo Fisher Scientific, Cat #34029) and the reaction was quenched using 10% phosphoric acid (30 μL per well). Plates were read on 384-450 nm on the SpectraMax M5 plate reader (Molecular Devices).

Antibody Purification (Small Preparation)

Small amounts of antibodies for in vitro experiments were purified using the DynaBead magnetic system (Invitrogen, Cat #10003D) using 1 mL of Protein A and 1 mL of Protein G beads per 50 mL of supernatant. The beads were first washed 3 times with PBS, with 10 minutes of wash time on a rotator. The supernatant was added and incubated with the beads for 4 hours at room temperature or overnight at 4° C. The supernatant was removed and the beads were washed 3 times with PBS. Elution buffer (100 mM glycine, pH 2.8) was added to beads for 30 seconds and immediately neutralized with 1.5 M Tris-base. Buffer solution was removed and put into 50 kD filter Eppendorf tubes and a buffer exchange was completed 3 times spinning according to the manufacturer's protocol. Antibodies were stored at 1 mg/mL.

Antibody Purification (Large Preparation)

For large preparations of hybridoma supernatant, antibodies were purified using a HiTrap Mab Select SuRe column (GE Healthcare Life Sciences, Cat #11003494) on an AKTA Pure FPLC system (GE Healthcare Life Sciences). Supernatant was sterile filtered with a 0.2 μm filter and loaded on the column. After washing, antibodies were eluted with 100 mM glycine, 150 mM NaCl, pH 3.0. Eluate was immediately neutralized with 1 M Tris-base, pH 9.0. The UV trace was used to select and pool fractions containing antibody. Antibody was concentrated using Amicon Ultra-15 50 K centrifugal filter units (Millipore Sigma, Cat #UFC905024) and dialyzed into phosphate-buffered saline, pH 7.2. Antibodies were then sterile filtered with a 0.2 μm filter, protein concentration in each sample was determined by a bicinchoninic acid colorimetric assay (Fisher Cat #23223 and 23224), using bovine serum albumin as a standard (Thermo Fisher Cat #23210). Samples were run on a 15% SDS-PAGE gel and coomassie stained to ensure presence of heavy and light changes and protein purity. After purification from hybridoma supernatant, antibodies were frozen in 1 mL aliquots and stored at −20° C.

In Vivo Antibody Administration

Immediately prior to use, antibodies were thawed and kept on ice until administration. Mice were weighed and antibodies were administered intraperitoneally to a final concentration of 30 mg/kg body weight. Injection side was alternated between injections, and mice were monitored for adverse events related to injection.

Striatal Dopamine/DOPAC Detection

Following transcardial perfusion, a 1 mm coronal section was removed from the rostral brain between approximately Bregma and Bregma+1 mm. The dorsal striatum was manually dissected from both the right (ipsilateral) and left (contralateral) side of the brain and flash frozen on dry ice for liquid chromatography-mass spectrometry (LC-MS) analysis of dopamine (DA) and dihydroxyphenylacetic acid (DOPAC). Frozen tissue was suspended in 10 μL Milli-Q water/mg tissue and sonicated at power level 1.5 using 15-20 short pulses (QSONICA MICROSON™ XL-2000) until solution was homogenous. Lysate was briefly spun down and 30 μL was transferred to a new tube containing 30 μL 0.4 M perchloric acid. Remaining lysate was suspended in 2× RIPA buffer with protease inhibitors for assay of protein levels. Perchlorate sample were spun at 3000×g and 4° C. for 15 minutes. Two volumes of 0.4 M sodium acetate was added to supernatant and spin filtered through a 0.65 μm filter. DA and DOPAC were subsequently quantitated using a Waters Acquity UPLC-TQD LC-MS system. Ten microliters of each sample were injected onto a Waters Acquity HSS T3, C18, 1.8 μm, 2.1×100 mm column at 35° C. and 0.4 mL/min. Mobile phase B was held at 0% B for 1 minute post injection and gradient separated from 0 to 25% B between 2 and 3 minutes followed by wash and equilibration steps (A: 0.1% (v/v) formic acid in water; B: acetonitrile with 0.1% (v/v) formic acid). Compounds were detected using multiple reaction monitoring of their specific collision-induced ion transitions (Dopamine, ES+ 154>137; 3,4-Dihydrophenylacetic acid, ES− 167>123). Peak areas were quantitated using Waters QuaLynx software against standard curves analyzed concurrently (Dopamine Hydrochloride (DA), Sigma Cat #H8502-5G; 3,4-Dihydrophenylacetic acid (DOPAC), Sigma Cat #850217-1G) and normalized to total protein level.

Immunohistochemistry

After perfusion and fixation, brains were embedded in paraffin blocks, cut into 6 μm sections, and mounted on glass slides. Slides were then stained using standard immunohistochemistry as described elsewhere herein. Slides were deparaffinized with 2 sequential 5-minute washes in xylenes, followed by 1-minute washes in a descending series of ethanols: 100%, 100%, 95%, 80%, 70%. Slides were then incubated in deionized water for one minute prior to antigen retrieval as noted. After antigen retrieval, slides were incubated in 5% hydrogen peroxide in methanol to quench endogenous peroxidase activity. Slides were washed for 10 minutes in running tap water, 5 minutes in 0.1 M Tris, then blocked in 0.1 M Tris/2% fetal bovine serum (FBS). Slides were incubated in primary antibodies overnight. The following primary antibodies were used. For misfolded α-Synuclein, Syn506 was used at 0.4 ug/mL final concentration with microwave antigen retrieval (95° C. for 15 minutes with citric acid based antigen unmasking solution (Vector H-3300). To stain midbrain dopaminergic neurons, Tyrosine hydroxylase (TH-16; Sigma-Aldrich T2928, RRID: AB_477569) was used at 1:5,000 with formic acid antigen retrieval.

Primary antibody was rinsed off with 0.1 M Tris for 5 minutes, then incubated with goat anti-rabbit (Vector BA1000, RRID:AB_2313606) or horse anti-mouse (Vector BA2000, RRID:AB_2313581) biotinylated IgG in 0.1 M Tris/2% FBS 1:1000 for 1 hour. Biotinylated antibody was rinsed off with 0.1 M Tris for 5 minutes, then incubated with avidin-biotin solution (Vector PK-6100, RRID: AB_2336819) for 1 hour. Slides were then rinsed for 5 minutes with 0.1 M Tris, then developed with ImmPACT DAB peroxidase substrate (Vector SK-4105, RRID: AB_2336520) and counterstained briefly with Harris Hematoxylin (Fisher 67-650-01). Slides were washed in running tap water for 5 minutes, dehydrated in ascending ethanol for 1 minute each: 70%, 80%, 95%, 100%, 100%, then washed twice in xylenes for 5 minutes and coversliped in Cytoseal Mounting Media (Fisher 23-244-256). Digitized slides were then used for quantitative pathology.

Quantitative Histology

To assay for antibody binding to Lewy body α-Synuclein, undiluted hybridoma supernatant or supernatant diluted 1:3 in PBS was directly added to sections of human amygdala tissue with abundant Lewy bodies. Tissue was processed and developed in DAB reagent in parallel. A similar 1 $mm^2$ section from each piece of tissue was then used to assay the ability of the antibody to preferentially bind Lewy bodies. Staining intensity was manually thresholded to only highlight Lewy bodies blind to antibody treatment and analyzed for mean optical density. Mean optical density for the whole section was then assayed using a standardized cutoff. The mean optical density of Lewy body staining divided by the mean optical density of the piece of tissue was calculated and is reported at the Lewy body discrimination index.

For mice, all section selection, annotation and quantification was done blinded to treatment group. All quantitation was performed in HALO quantitative pathology software (Indica Labs). Every $10^{th}$ slide through the midbrain was stained with tyrosine hydroxylase (TH). TH-stained sections were used to annotate the SN, and cell counting was performed manually in a blinded manner for all sections. The sum of all sections was multiplied by 10 to estimate the total count that would be obtained by counting every section. The SN annotations drawn onto the TH-stained sections were then transferred to sequential sections that had been stained for misfolded α-Synuclein (Syn506). Amygdala regions were also annotated on every $10^{th}$ section through the length of the amygdala. A single analysis algorithm was then applied equally to all stained sections to quantify the percentage of area occupied by Syn506 staining. Specifically, the analysis included all DAB signal that was above a 0.157 optical density threshold, which was empirically determined to not include any background signal. This signal was then normalized to the total tissue area. A minimal tissue optical density of 0.02 was used to exclude any areas where tissue was split.

Antibody Sequencing

Total RNA was isolated from the hybridoma cells following the technical manual of TRIZOL® Reagent. Total RNA was then reverse-transcribed into cDNA using either isotype-specific anti-sense primers or universal primers following the technical manual of PRIMESCRIPT™ 1 st Strand cDNA Synthesis Kit. Antibody fragments of heavy chain and light chain were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. The consensus sequence was provided elsewhere herein.

Statistical Analysis

All statistical analyses were done in GraphPad Prism 7. The analysis used for each data set is described in the figure legends. The number of samples (n) is noted in each figure legend. For primary neuron experiments, the n represents the number of independent wells assayed. For in vivo experiments, n represents the number of mice.

Example 1

There is concern that pan-α-Synuclein antibodies may have liabilities as a therapeutic approach for PD. For example, there are conflicting data on whether reducing overall α-Synuclein levels in the brain would be deleterious to neuronal function. The abundance of α-Synuclein in red blood cells also raises the possibility that a pan-α-Synuclein antibody could cause on-target side effects in the blood, as antibody concentrations in the blood are approximately 1000-fold higher than in the brain. In addition, serum α-Synuclein could act as a sink for a pan-α-Synuclein antibodies, thereby reducing engagement with the intended target in the brain.

Thus, the present study related in part to the identification of e antibodies that are highly selective for pathogenic, misfolded α-Synuclein. In order to develop these antibodies, mice were first immunized with misfolded α-Synuclein pre-formed fibrils (PFFs) formed from recombinant human α-Synuclein (FIG. 1A). Mice developed an immune response to the α-Synuclein PFF immunogen, and antibody-producing B cells were harvested and fused to myeloma cells to generate antibody-producing hybridoma cells (FIG. 1B). Monoclonal hybridomas were isolated by limiting dilution, and antibody-containing supernatant from these clones was tested in several assays to determine which hybridoma clones were producing antibodies with preferred properties (FIG. 1C). Candidate antibodies were further subcloned to ensure monoclonality (FIG. 1D), with antibody properties confirmed through a screen to ensure retention of properties (FIG. 1E). Upon inspection of the results from the different screening assays, a non-limiting candidate antibody was selected for efficacy testing in an in vivo model of PD (FIG. 1F), where it was compared to a previously characterized immunotherapy antibody.

Figure 2A:
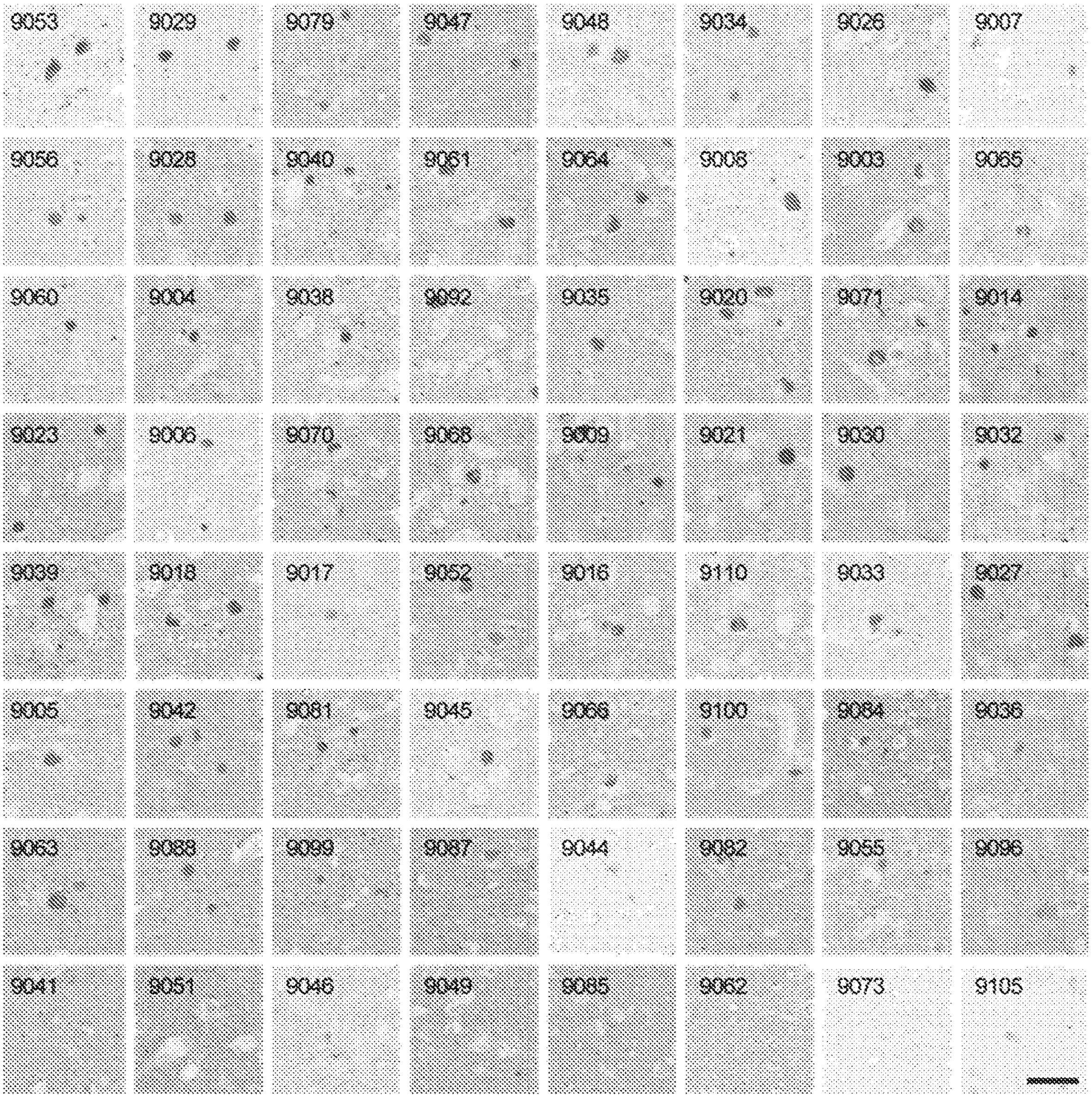
FIGS. 2A-2B illustrate non-limiting immunohistochemistry results that reveal antibodies that preferentially bind LBs.
Figure 2B:
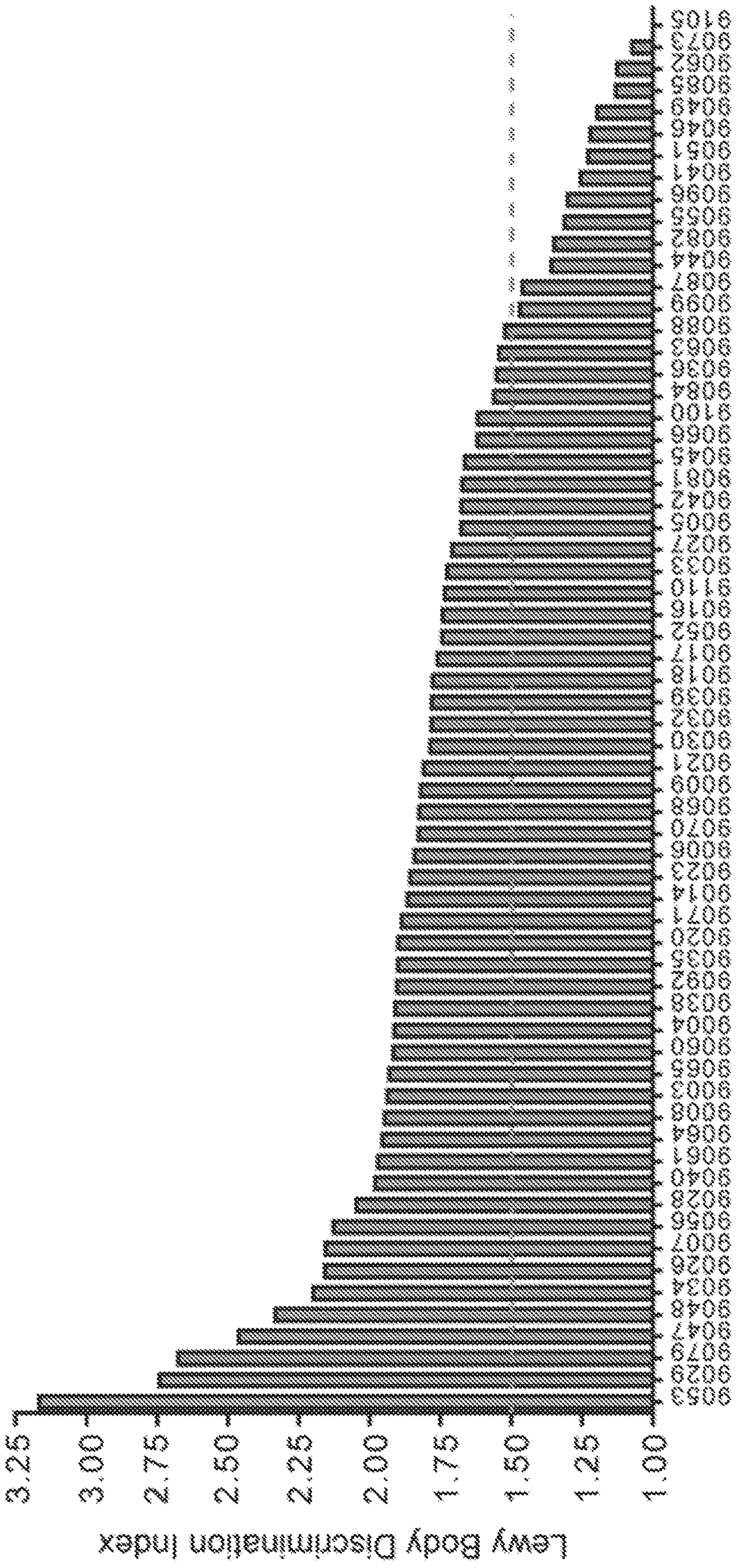

Example 2: Immunohistochemistry Reveals Antibodies that Preferentially Bind LBs In a non-limiting aspect, certain antibodies of interest have a high binding preference for misfolded LB α-Synuclein over monomeric α-Synuclein. In order to rapidly screen for antibody selectivity to pathological α-Synuclein, amygdala sections from PD patients with abundant LB pathology were immunostained. Hybridoma supernatants were used undiluted or at a 1:3 dilution on screening slides processed in parallel to allow direct comparison of immunostaining. Most antibodies tested showed a preference for binding to LB α-Synuclein over normal synaptic α-Synuclein in the neuropil (FIG. 2A). A LB discrimination index (optical density of LB/optical density of all tissue) was developed to better compare the relative binding of antibodies to LB over the neuropil pool (FIG. 2B). A value of 1 indicates no discrimination of LBs over normal synaptic neuropil staining. While most of the antibodies had a preference for LBs, a cutoff of 1.5 was established to remove antibodies that showed relatively non-selective staining of LBs from further consideration.

Figure 3A:
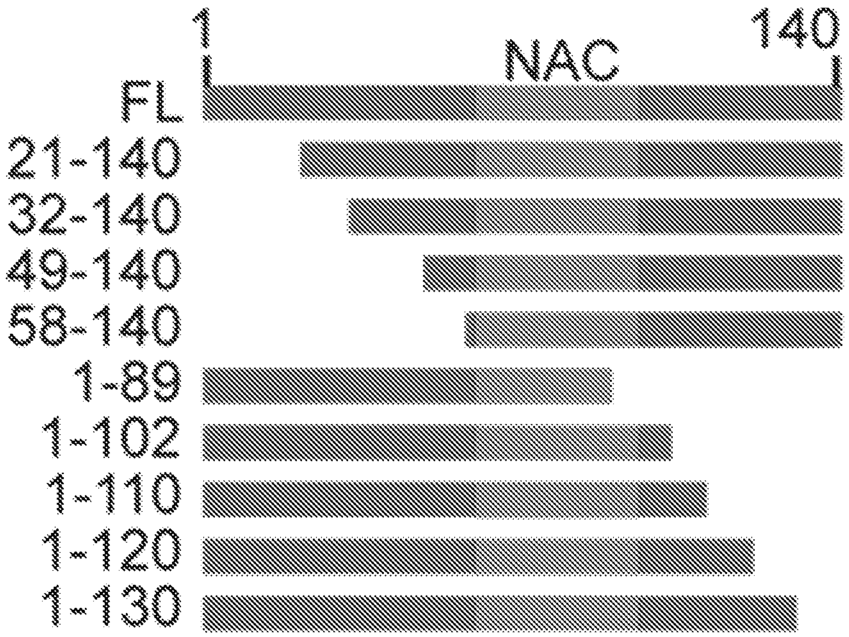
FIGS. 3A-3C illustrate non-limiting epitope mapping that ensures that certain antibodies recognize human and mouse α-Synuclein.
Figure 3B:
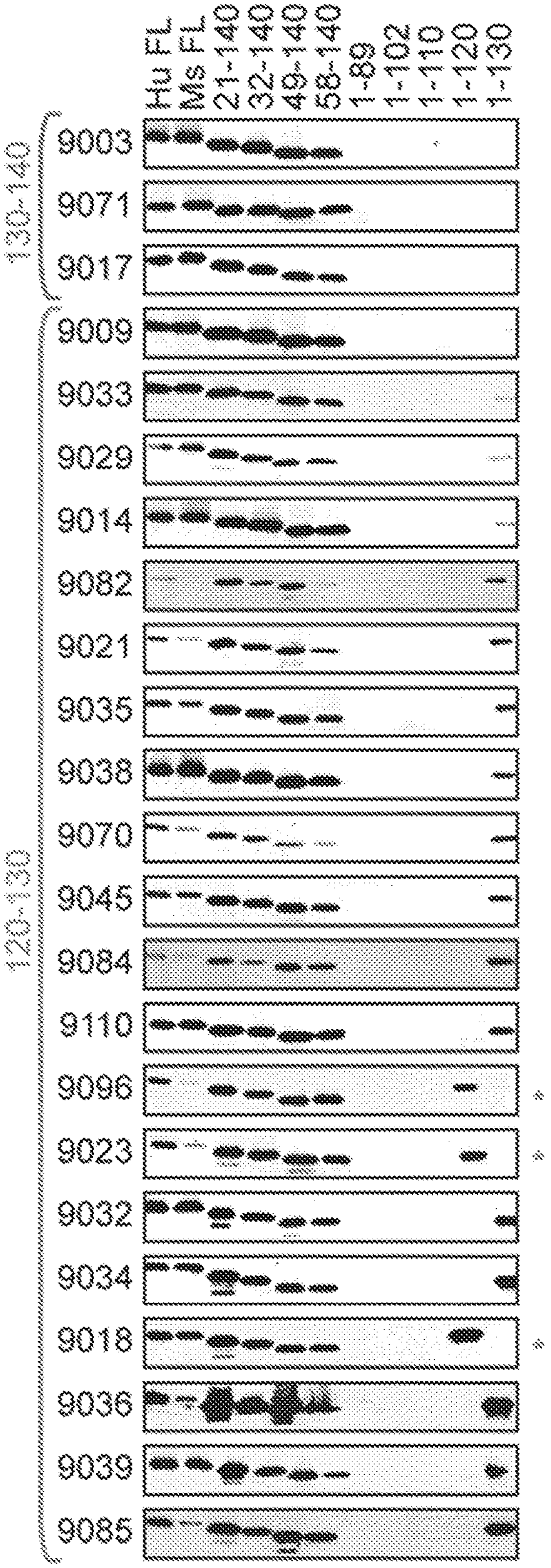
Figure 3C:
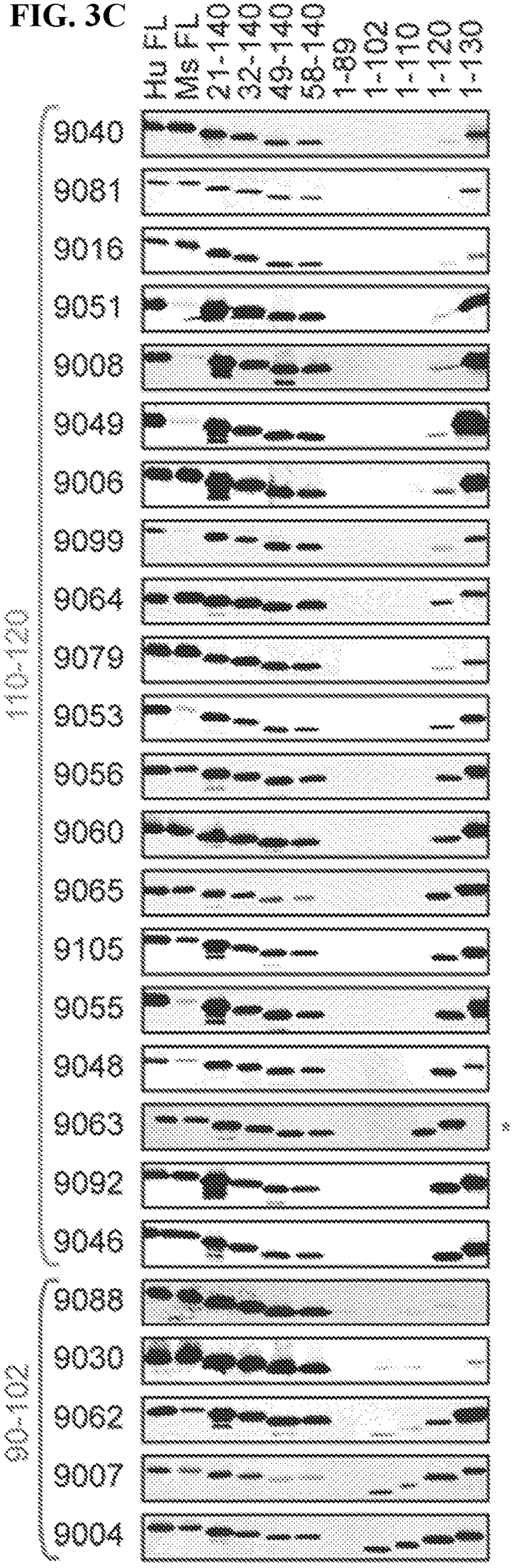

Example 3: Epitope Mapping Ensures that Preferred Antibodies Recognize Human and Mouse α-Synuclein While selected immunotherapy antibodies can in principle be used in humans, the present study in certain non-limiting embodiments identified antibodies that can recognize both mouse and human α-Synuclein to allow further characterization in mouse primary neuron and wild-type mouse models of PD. Antibodies were assayed by Western blot to determine whether they bound to human and mouse α-Synuclein (FIGS. 3A-3C). Multiple truncated forms of human α-Synuclein (FIG. 3A) were also analyzed in parallel to determine the epitope within α-Synuclein that was recognized by each antibody. All antibodies recognized some portion of the immunogenic C-terminus of α-Synuclein, with a large proportion recognizing far C-terminal amino acids (120-140; FIG. 3B). Another large group of antibodies recognized a slightly more internal epitope (110-120), and only a few antibodies recognized a region closer to the aggregation-prone NAC (non-Aβ component of Alzheimer's disease amyloid domain (residue 61-95) of α-Synuclein (FIG. 3C). The majority of antibodies recognized mouse as well as human α-Synuclein, although there were examples of antibodies in each epitope class that showed preferential binding to human α-Synuclein. Only two antibodies showed evidence of cross-reactivity with β-Synuclein (FIG. 10).

Example 4: Sandwich ELISA Identifies Antibodies with a Preference for Misfolded α-Synuclein Antibodies that showed selectivity for LBs in human tissue by immunohistochemistry and recognized both human and mouse α-Synuclein underwent a further testing of selectivity by assessing their ability to bind to monomeric human α-Synuclein and α-Synuclein PFFs in a sandwich ELISA format. This assay retains the conformation of α-Synuclein by allowing binding of α-Synuclein that is in solution to immobilized antibody, and allows a broad range of affinity detection. Antibodies of interest were coated on an ELISA plate and either α-Synuclein monomer or PFF were incubated with the antibodies at increasing α-Synuclein concentrations to determine relative affinity of the antibodies for each form of α-Synuclein. The previously characterized Syn211 antibody (Giasson, et al., 2000, J. Neurosci. Res. 59:528-533) was also coated on each plate as a non-selective antibody control. Bound α-Synuclein was detected with a monoclonal antibody (MJF-R1, Abcam, Cat #138501) and a goat-anti-rabbit IgG-HRP conjugate.

Figures 4A, 4B, 4C:
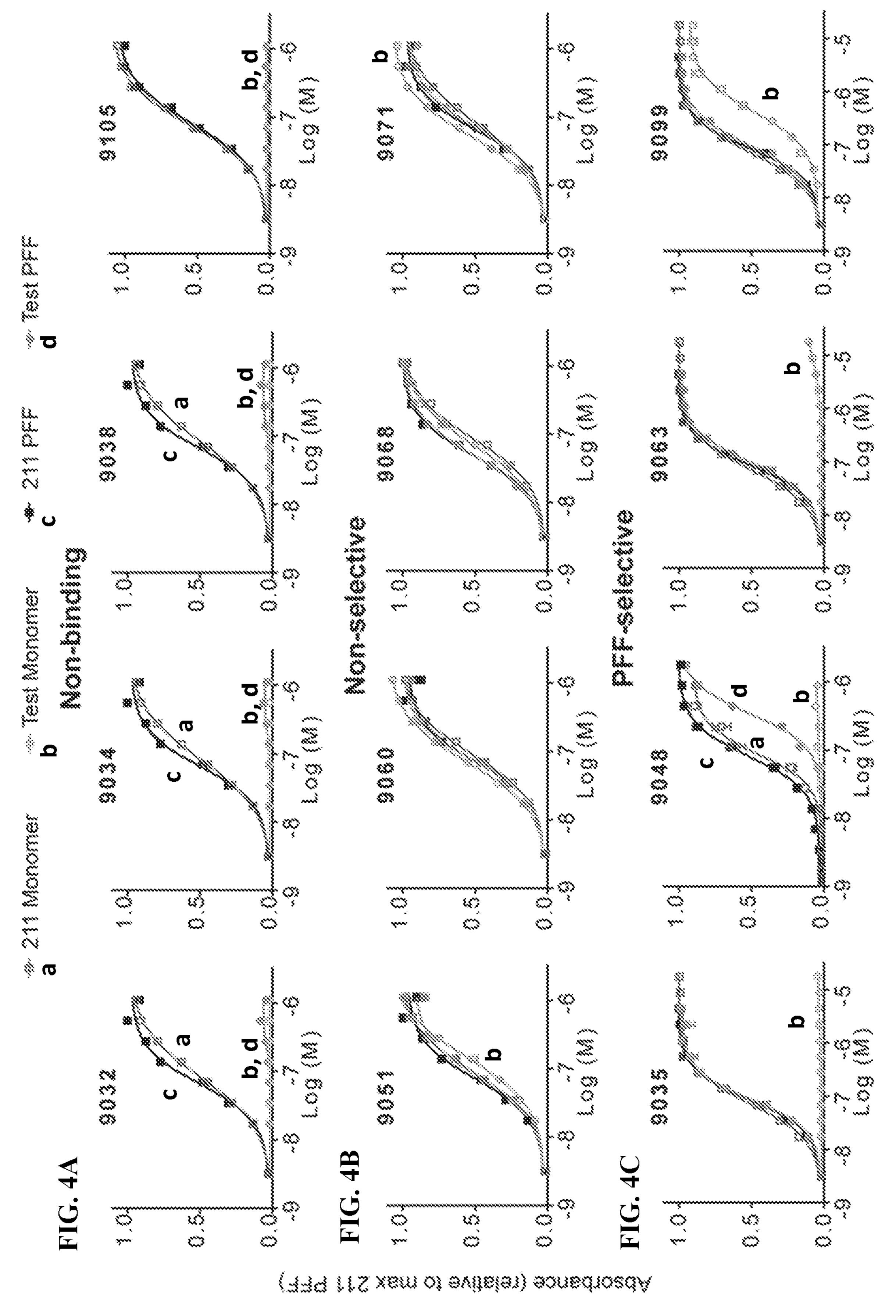
FIGS. 4A-4C illustrate a non-limiting sandwich ELISA that identifies antibodies with a preference for misfolded α-Synuclein. Antibodies were assessed for a preference for misfolded α-Synuclein by performing parallel sandwich ELISAs with either human α-Synuclein monomer or α-Synuclein PFFs as the antigen. Syn211 was also used on each plate as a non-selective control antibody. Using this method, three classes of antibodies were distinguished—(FIG. 4A) antibodies that did not bind in this assay and thus did not have a signal for either monomer or PFF.

Capture antibodies could be categorized almost evenly into three categories: 17 non-binding (FIGS. 4A & 11), 18 non-selective (FIGS. 4B & 12), 19 PFF-selective (FIGS. 4C & 13). Without wishing to be limited by any theory, since nearly all of the non-binding antibodies bound to LB pathology and detected α-Synuclein by immunoblotting, the lack of activity in the sandwich ELISA can suggest that immobilization on ELISA plate wells affected their ability to capture α-Synuclein.

By fitting the absorbance values with a sigmoid dose curve, $EC_{50}$ values were calculated for each antibody. PFF preference values were then calculated for each antibody using the following equation, with Syn211 as a non-selective control:

$$PFF \text{ Preference} = \frac{Test\ AbPFFEC_{50}}{Test\ Ab\ Monomer\ EC_{50}} \Big/ \frac{211PFFEC_{50}}{211\ Monomer\ EC_{50}}$$

Values are summarized in Table 1. To confirm that the apparent conformation selectivity was not due to shared epitopes between the capture and the detection antibody that would reduce detection of α-Synuclein monomers, four of the most selective antibodies were evaluated by sandwich ELISA using an alternate, polyclonal detection antibody, SNL4 (FIG. 14). This assay confirmed the conformation selectivity of the α-Synuclein antibodies.

Figure 5A:
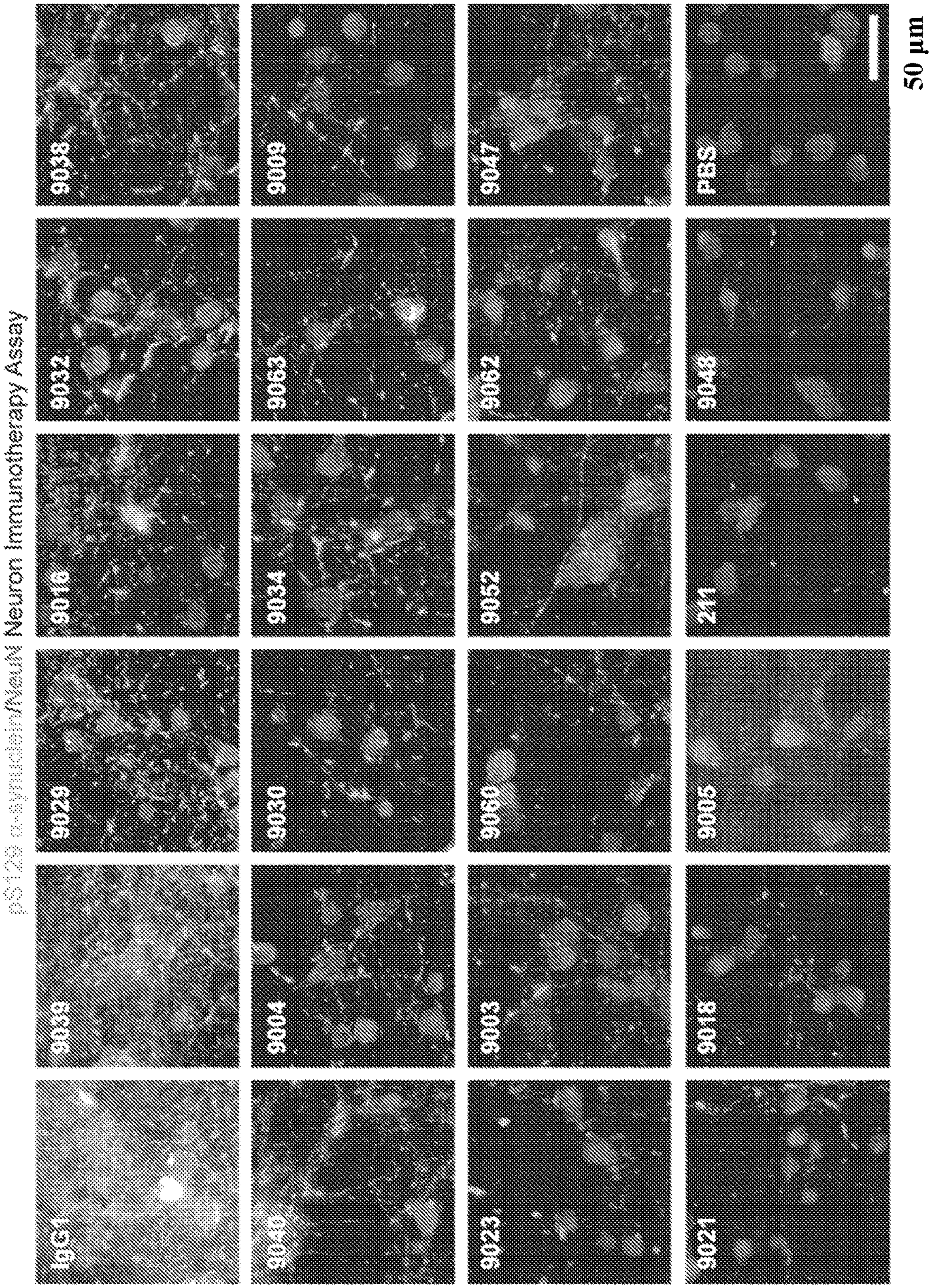
FIGS. 5A-5B illustrate a non-limiting neuron immunotherapy assay that reveals differential potency of α-Synuclein antibodies to prevent LB-like pathology.
Figure 5B:
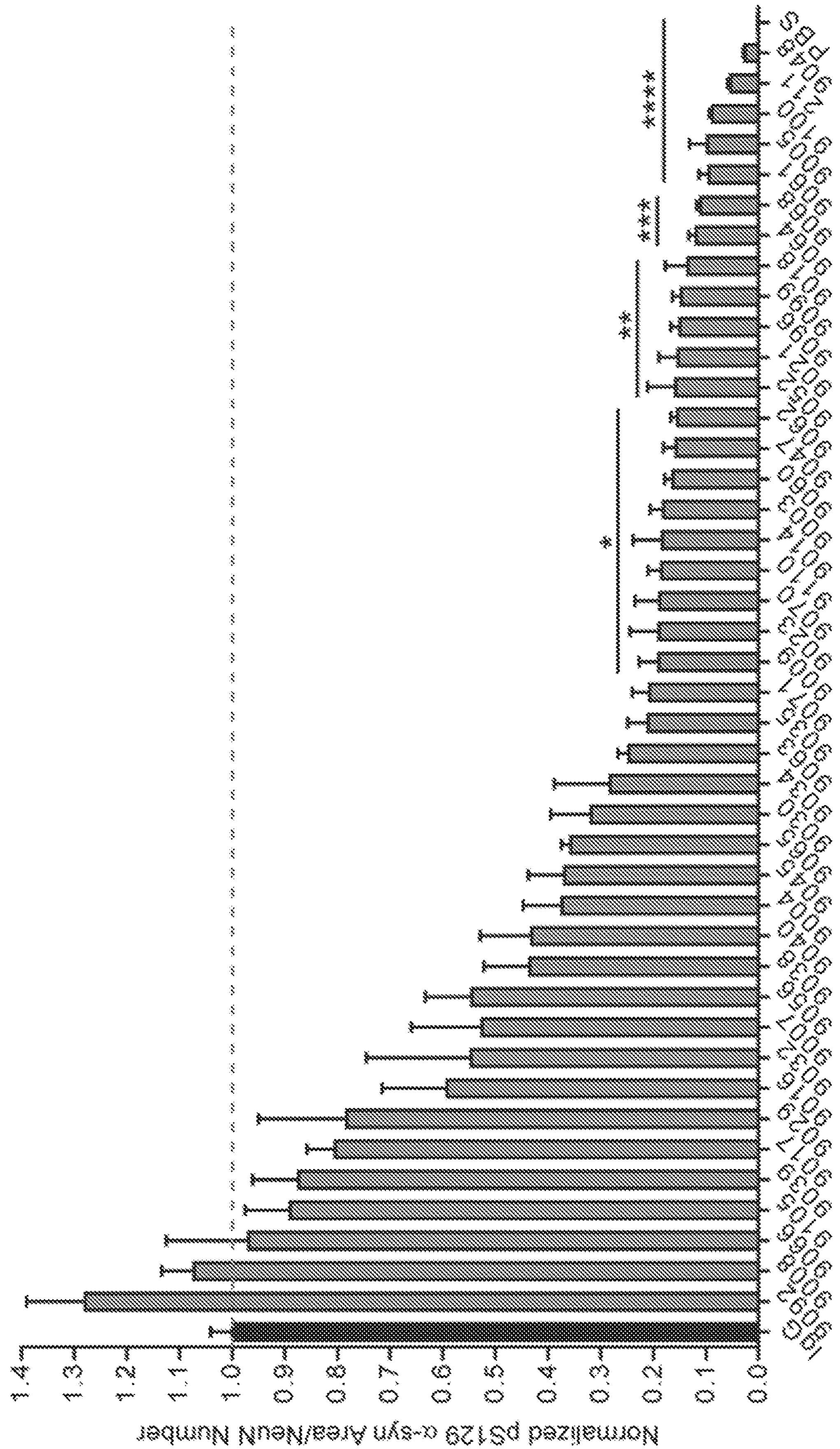

Example 5: Primary Neuron Immunotherapy Assay Reveals Differential Potency of α-Synuclein Antibodies to Prevent LB-Like Pathology While the intrinsic properties of antibodies are important, the ability of antibodies to prevent the induction of α-Synuclein pathology, a property which is critical for therapeutic success, was investigated. To accomplish this, a neuron immunotherapy assay was developed to allow co-treatment of antibodies with α-Synuclein PFFs in a high-content format. After 10 days in culture, neurons were treated with purified antibodies of interest. Thirty minutes later, neurons were treated with human α-Synuclein PFFs, which seed the recruitment of endogenous mouse α-Synuclein into LB- and LN-like inclusions. Neurons were fixed 7 days later and assayed for pathological pS129 α-Synuclein and neuron number (NeuN; FIG. 5A). Antibodies showed a wide range of efficacy in this assay with 22 of the 41 antibodies causing over 75 percent reduction in pathology (FIG. 5B). The highest performing antibody, Syn9048, reduced pathology by a remarkable 97 percent.

Figure 6A:
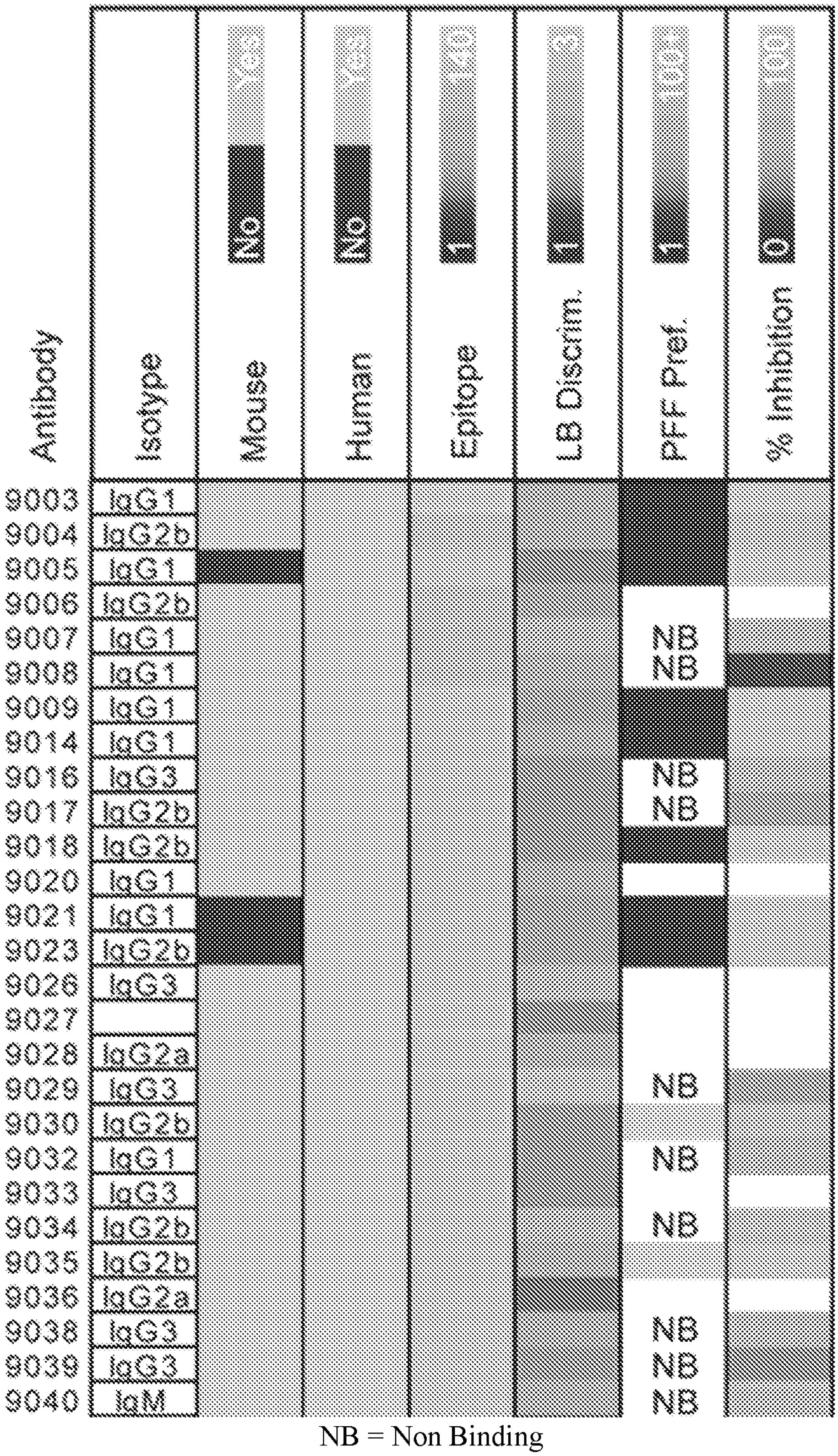
FIGS. 6A-6B comprise a summary of antibody characteristics, shown as a heat map with the scale bars shown at the top of each column. Antibodies are mostly from IgG subclasses. Most antibodies recognize mouse α-Synuclein, and all antibodies recognize human α-Synuclein. The LB discrimination index, derived from immunohistochemistry reflects the ability of antibodies to bind selectively to LB α-Synuclein. The α-Synuclein PFF preference is derived from sandwich ELISA results and spanned over 100-fold differences to allow for selection of antibodies that have a preference for misfolded α-Synuclein (NB=non-binding).
Figure 6B:
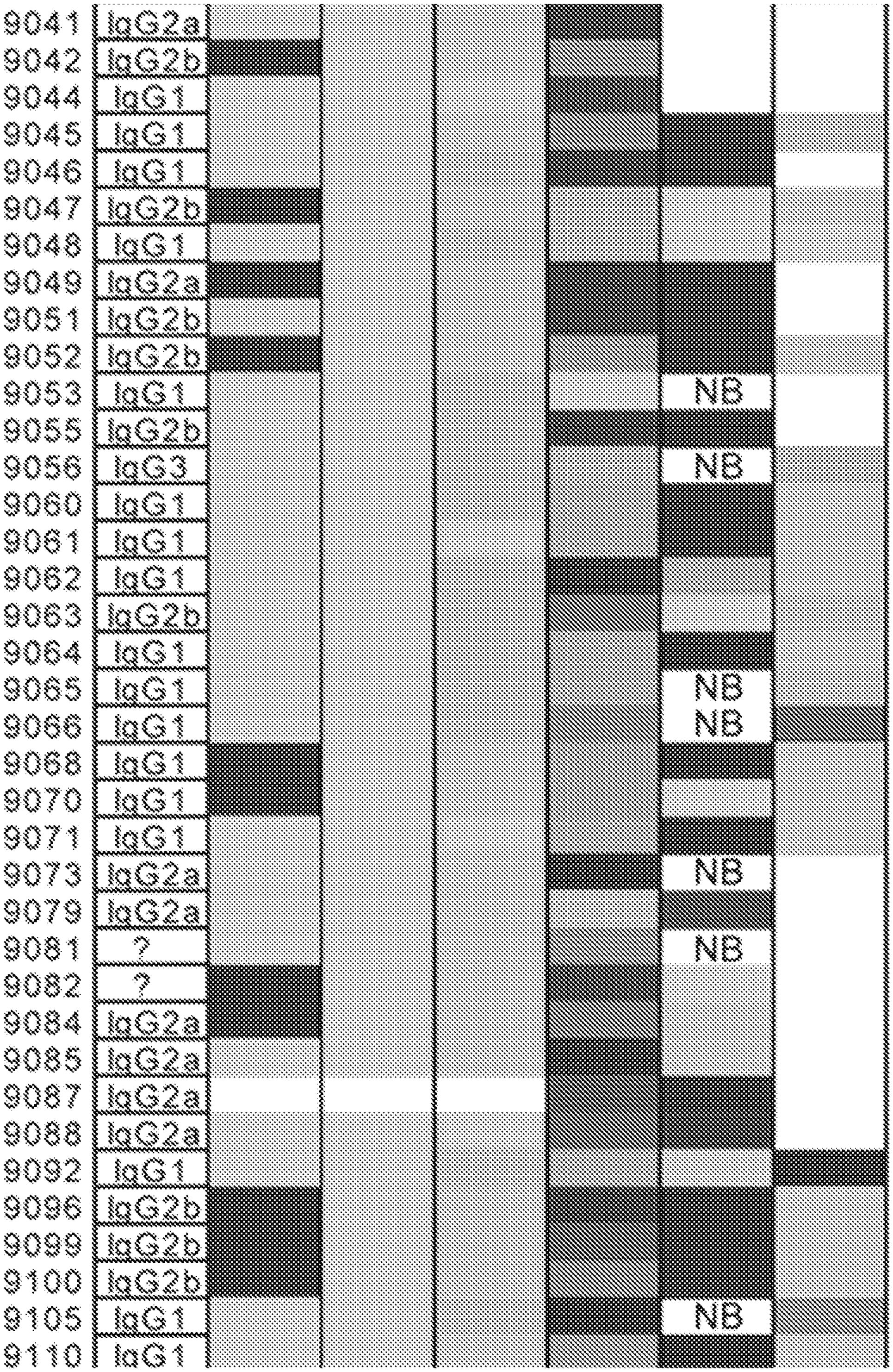

The thorough characterization of α-Synuclein antibodies in multiple assays allowed one to compare antibodies quantitatively and select favored antibodies for subcloning and further screening (FIGS. 6A-6B). In certain embodiments, certain antibodies of interest recognize both mouse and human α-Synuclein, bind LBs preferentially in human tissue, show greater affinity for misfolded α-Synuclein than monomeric α-Synuclein, and reduce PFF-seeded α-Synuclein pathology in primary neurons. Based on these criteria, two antibodies (Syn9063 and Syn9048) were selected for subcloning, large-scale production and in vivo testing.

Example 6: Subclones Retain Properties of Parent Clones

One of the key features of the selected antibodies was their preference for misfolded α-Synuclein. Therefore, supernatants from clones derived during additional subcloning of Syn9063 and Syn9048 hybridomas were analyzed in the sandwich ELISA platform to identify clones producing the desired antibodies. All but one of the Syn9063 subclones showed a similar preference for α-Synuclein PFFs as the parental clone (FIG. 7A). However, upon clonal expansion, Syn9063 subclones had very low antibody yields, precluding their use in vivo, where greater antibody amounts are needed. All Syn9048 clones showed high selectivity for α-Synuclein PFFs (FIG. 7B) and clone #3 was used for further studies due to high yields of antibody obtained from roller cultures.

To gain a further understanding of the concentration of antibody necessary to effectively inhibit α-Synuclein pathology induction, purified Syn9048 was diluted over several log concentrations and assessed in the human α-Synuclein PFF-seeded primary hippocampal neuron assay as described above. Syn9048 reduced neuronal α-Synuclein pathology in a dose-dependent manner, with a molar antibody:α-Synuclein ratio $IC_{50}$ of 0.006 (1:166) (FIGS. 7C-7D). Syn9048 showed almost complete inhibition of α-Synuclein pathology at a molar ratio of 0.03 or higher, suggesting that only one antibody per 33 α-Synuclein monomer units is sufficient to fully inhibit α-Synuclein seeding in neurons. Syn9048 was also capable of reducing α-Synuclein pathology induced by mouse α-Synuclein PFFs with a similar $IC_{50}$ (FIG. 15), suggesting that it would be suitable for testing in a non-transgenic mouse model of PD.

Example 7: In Vivo Immunotherapy is Well-Tolerated and Improves Dopaminergic Tone Several α-Synuclein antibodies have been tested in animal models for their abilities to prevent PD-like pathology. However, in the absence of prodromal disease biomarkers, patients with neurodegenerative disorders are unlikely to be given immunotherapy treatments prior to the symptomatic stages of disease when brain pathology is already established.

Therefore, the efficacy of Syn9048 in reducing pathology and rescuing neuronal function after the initiation of pathology was tested. A previously established model of α-Synuclein pathology induction and transmission (Luk, et al., 2012, Science 338:949-953) was employed in which non-transgenic mice were injected with 5 μg α-Synuclein PFFs in the dorsal striatum at 2-3 months of age. Mice were allowed 1 week for the BBB to recover and for pathogenic α-Synuclein to be taken up by neurons and induce pathology prior to treatment with antibody. The mice then received Syn9048 or isotype control antibody treatment (30 mg/kg intraperitoneally) weekly thereafter for 6 months (FIG. 8A, 16 mice/group). An additional group of mice was treated with a comparator antibody, Syn303, which has previously been validated for in vivo immunotherapy models (Tran, et al., 2014, Cell Reports 7:2054-2065). The one-week delay in antibody dosing after intrastriatal PFF injection was intended to minimize inhibition of initial PFF-seeding in neurons. In certain embodiments, sites of secondary α-Synuclein pathology formation that result from pathology transmission are most affected by antibody treatment. Mice in all three groups gained weight steadily over the course of the study, suggesting that the passive immunotherapy was well-tolerated (FIG. 8B).

Dopaminergic neuron loss in the substantia nigra (SN) is a primary feature of PD and is recapitulated in the PFF injection mouse model (Henderson, et al., 2019, Nature Neuroscience 22:1248-1257; Luk, et al., 2012, Science 338:949-953) (FIG. 8C). IgG1-treated mice have dramatic tyrosine hydroxylase (TH)-positive neuron loss ipsilateral to the injection site, and this neuron loss was not abrogated by either Syn303 or Syn9048 treatment (FIGS. 8D-8E). The dopaminergic neuron loss is consistent with these cells having direct connections to the injection site, such that antibody treatment one week after PFF injections would not be expected to block the initiation of pathology in these neurons. Dopaminergic tone is also reduced in the dorsal striatum in response to PFF injection (FIG. 8F). Somewhat surprisingly Syn9048, but not Syn303, was able to rescue the loss of striatal dopamine and DOPAC (FIGS. 8F-8G). Thus, while neurons are still lost, the function of remaining neurons may be improved by Syn9048 treatment, possibly due to reductions in α-Synuclein pathology.

Example 8: Syn9048 Reduces α-Synuclein Pathology in the SN and Amygdala

To better understand how α-Synuclein pathology is changed in mice following passive immunotherapy, quantitative pathology for misfolded α-Synuclein (Syn506) in the SN (FIGS. 9A-9C) and amygdala (FIGS. 9D-9F) were performed. Syn303 and Syn9048 reduced mean pathology in the SN contralateral (FIG. 9B) and ipsilateral (FIG. 9C) to the injection site, although only the reduction by Syn9048 in the ipsilateral SN was statistically significant. A reduction in pathology was also more apparent in the contralateral amygdala (FIG. 9E) than in the ipsilateral amygdala (FIG. 9F), and was more substantial in Syn9048-treated animals than those treated with Syn303. Only the reduction by Syn9048 in the contralateral amygdala was statistically significant. The reduction in ipsilateral SN pathology by Syn9048, though modest may explain the improvement in striatal dopamine and DOPAC levels. Moreover, the greater effect of antibody treatment on contralateral α-Synuclein pathology suggests that efficacy is greater at sites where extracellular α-Synuclein spread is responsible for pathology induction.

TABLE 1

| Summary Measurements | | | | | | | |
|---|---|---|---|---|---|---|---|
| | | Scales | | | | | |
| | | 0-1 | 0-1 | 1-140 | 1-3 Immuno-histochemistry | 1-100+ Sandwich ELISA | 0-100 Primary Neuron |
| | | Epitope Mapping | | | | | |
| Antibody | Isotype | Mouse | Human | N-C Term | LB Discrimination Index | PFF Preference | Assay % Inhibition |
| IgG | | | | 0 | | | 0 |
| 303 | | | | | 2.102558371 | | N/A |
| 211 | IgG1 | | | | | | 94.70322144 |
| 9003 | IgG1 | 1 | 1 | 135 | 1.938167721 | 0.564509868 | 81.95231038 |
| 9004 | IgG2b | 1 | 1 | 100 | 1.912677821 | 1.024512426 | 62.66002839 |
| 9005 | IgG1 | 0 | 1 | 125 | 1.676619269 | 1.311373334 | 90.34220519 |
| 9006 | IgG2b | 1 | 1 | 115 | 1.841105957 | | |
| 9007 | IgG1 | 1 | 1 | 100 | 2.154276464 | NB | 47.4859399 |
| 9008 | IgG1 | 1 | 1 | 115 | 1.946097798 | NB | −7.183775226 |
| 9009 | IgG1 | 1 | 1 | 135 | 1.818983421 | 0.506566936 | 81.04917198 |
| 9014 | IgG1 | 1 | 1 | 135 | 1.86561235 | 0.477593579 | 81.69756389 |
| 9016 | IgG3 | 1 | 1 | 130 | 1.743174628 | NB | 40.79944101 |
| 9017 | IgG2b | 1 | 1 | 135 | 1.759921505 | NB | 19.57409354 |
| 9018 | IgG2b | 1 | 1 | 125 | 1.776573737 | 1.452890884 | 86.53008752 |
| 9020 | IgG1 | 1 | 1 | 125 | 1.898486476 | | |
| 9021 | IgG1 | 0 | 1 | 125 | 1.808068314 | 1.001556366 | 84.72158171 |

TABLE 1-continued

| Summary Measurements | | | | | | | | |
|---|---|---|---|---|---|---|---|---|
| | | Scales | | | | | | |
| | | 0-1 | 0-1 | 1-140 | 1-3 Immuno-histochemistry | 1-100+ Sandwich ELISA | 0-100 Primary Neuron | |
| | | Epitope Mapping | | | | | | |
| Antibody | Isotype | Mouse | Human | N-C Term | LB Discrimination Index | PFF Preference | Assay % Inhibition |
| 9023 | IgG2b | 0 | 1 | 125 | 1.856789996 | 0.940892812 | 81.07943667 |
| 9026 | IgG3 | 1 | 1 | 125 | 2.157036996 | | |
| 9027 | | 1 | 1 | 135 | 1.708640239 | | |
| 9028 | IgG2a | 1 | 1 | 125 | 2.047618133 | | |
| 9029 | IgG3 | 1 | 1 | 135 | 2.741320163 | NB | 21.71340697 |
| 9030 | IgG2b | 1 | 1 | 135 | 1.785518122 | 26107.88231 | 68.20868143 |
| 9032 | IgG1 | 1 | 1 | 125 | 1.781066922 | NB | 45.39663155 |
| 9033 | IgG3 | 1 | 1 | 135 | 1.726626766 | | |
| 9034 | IgG2b | 1 | 1 | 125 | 2.198618942 | NB | 71.78442502 |
| 9035 | IgG2b | 1 | 1 | 125 | 1.898684741 | 211141309.8 | 79.02376904 |
| 9036 | IgG2a | 1 | 1 | 125 | 1.551813481 | | |
| 9038 | IgG3 | 1 | 1 | 125 | 1.909677926 | NB | 56.53976144 |
| 9039 | IgG3 | 1 | 1 | 125 | 1.780138819 | NB | 12.60705807 |
| 9040 | IgM | 1 | 1 | 125 | 1.980942765 | NB | 56.90384649 |
| 9041 | IgG2a | 1 | 1 | 125 | 1.254635299 | | |
| 9042 | IgG2b | 0 | 1 | 125 | 1.674599081 | | |
| 9044 | IgG1 | 1 | 1 | 135 | 1.358186693 | | |
| 9045 | IgG1 | 1 | 1 | 125 | 1.663796381 | 7.028489682 | 63.14110706 |
| 9046 | IgG1 | 1 | 1 | 115 | 1.220027967 | 1.42064567 | |
| 9047 | IgG2b | 0 | 1 | 125 | 2.463145491 | 132.8572232 | 84.29704757 |
| 9048 | IgG1 | 1 | 1 | 115 | 2.333155775 | 33985.20584 | 97.45615883 |
| 9049 | IgG2a | 0 | 1 | 125 | 1.195783782 | 0.944993509 | |
| 9051 | IgG2b | 1 | 1 | 125 | 1.228198919 | 1.572975632 | |
| 9052 | IgG2b | 0 | 1 | 125 | 1.743967584 | 1.467339585 | 84.25345282 |
| 9053 | IgG1 | 1 | 1 | 115 | 3.167283996 | NB | |
| 9055 | IgG2b | 1 | 1 | 115 | 1.311656877 | 0.848250847 | |
| 9056 | IgG3 | 1 | 1 | 115 | 2.128130086 | NB | 45.59045848 |
| 9060 | IgG1 | 1 | 1 | 115 | 1.915573361 | 0.730181055 | 83.7616799 |
| 9061 | IgG1 | 1 | 1 | 135 | 1.970313305 | 5.787799999 | 90.60524361 |
| 9062 | IgG1 | 1 | 1 | 100 | 1.127006752 | 42.40523017 | 84.57517842 |
| 9063 | IgG2b | 1 | 1 | 115 | 1.544143866 | 4594.600085 | 75.33211375 |
| 9064 | IgG1 | 1 | 1 | 115 | 1.954834344 | 0.855337888 | 88.1481552 |
| 9065 | IgG1 | 1 | 1 | 115 | 1.929979845 | NB | 64.37415014 |
| 9066 | IgG1 | 1 | 1 | 115 | 1.618110863 | NB | 3.140358677 |
| 9068 | IgG1 | 0 | 1 | 125 | 1.823538424 | 0.833142391 | 88.96617336 |
| 9070 | IgG1 | 0 | 1 | 125 | 1.826058109 | 3791.888899 | 81.1856481 |
| 9071 | IgG1 | 1 | 1 | 135 | 1.887937014 | 0.605223949 | 79.30176246 |
| 9073 | IgG2a | 1 | 1 | 125 | 1.072869389 | NB | |
| 9079 | IgG2a | 1 | 1 | 125 | 2.67447041 | 19.7887918 | |
| 9081 | ? | 1 | 1 | 125 | 1.672674272 | NB | |
| 9082 | ? | 0 | 1 | 125 | 1.348355081 | 218.4626674 | |
| 9084 | IgG2a | 0 | 1 | 125 | 1.56116963 | 93.96101824 | |
| 9085 | IgG2a | 1 | 1 | 125 | 1.13018571 | 93.509089 | |
| 9087 | IgG2a | | | | 1.459685102 | 7.766246483 | |
| 9088 | IgG2a | 1 | 1 | 135 | 1.521301357 | 15.62079665 | |
| 9092 | IgG1 | 1 | 1 | 115 | 1.904081455 | 93.78920095 | −27.92898402 |
| 9096 | IgG2b | 0 | 1 | 125 | 1.300607955 | 1.014395132 | 85.07831285 |
| 9099 | IgG2b | 0 | 1 | 125 | 1.470001262 | 5.262694093 | 85.28493567 |
| 9100 | IgG2b | 0 | 1 | 125 | 1.617548864 | 2.725095996 | 91.25504631 |
| 9105 | IgG1 | 1 | 1 | 115 | 1 | NB | 11.04988152 |
| 9110 | IgG1 | 1 | 1 | 125 | 1.73455107 | 0.533106113 | 81.55654221 |

NB = non-binding

Enumerated Embodiments

The following exemplary embodiments are provided, the numbering of which is not to be construed as designating levels of importance:

Embodiment 1 provides an isolated monoclonal antibody comprising a light chain variable region (VL) and a heavy chain variable region (VH), wherein the VL comprises:

- a CDR1 region comprising the amino acid sequence of SEQ ID NO:27, 46, 70, 114, 126, 185, 213, or 240;
- a CDR2 region comprising the amino acid sequence of SEQ ID NO:29, 72, 116, 214, or 242; and
- a CDR3 region comprising the amino acid sequence of SEQ ID NO:31, 85, 118, 129, 152, 205, 216, or 244;

and wherein the VH comprises:

- a CDR1 region comprising the amino acid sequence of SEQ ID NO:11, 58, 92, 101, 144, 160, or 226;
- a CDR2 region comprising the amino acid sequence of SEQ ID NO:13, 40, 60, 93, 102, 134, 145, 161, 200, or 228; and
- a CDR3 region comprising the amino acid sequence of SEQ ID NO:15, 62, 81, 147, 163, 194, 201, or 230.

Embodiment 2 provides the monoclonal antibody of Embodiment 1, wherein the VL comprises:
- a CDR1 region comprising the amino acid sequence of SEQ ID NO:27, 46, 70, 114, or 126;
- a CDR2 region comprising the amino acid sequence of SEQ ID NO:29, 72, or 116; and
- a CDR3 region comprising the amino acid sequence of SEQ ID NO:31, 85, 118, 129, or 152;

and wherein the VH comprises:
- a CDR1 region comprising the amino acid sequence of SEQ ID NO:11, 58, 92, 101, or 144;
- a CDR2 region comprising the amino acid sequence of SEQ ID NO:13, 40, 60, 93, 102, 134, or 145; and
- a CDR3 region comprising the amino acid sequence of SEQ ID NO:15, 62, 81, or 147.

Embodiment 3 provides the monoclonal antibody of Embodiment 1, wherein the VL comprises:
- a CDR1 region comprising the amino acid sequence of SEQ ID NO:70, 185, 213, or 240;
- a CDR2 region comprising the amino acid sequence of SEQ ID NO:29, 72, 214, or 242; and
- a CDR3 region comprising the amino acid sequence of SEQ ID NO:152, 129, 205, 216, or 244;

and wherein the VH comprises:
- a CDR1 region comprising the amino acid sequence of SEQ ID NO:160, 58, or 226;
- a CDR2 region comprising the amino acid sequence of SEQ ID NO:161, 145, 200, or 228; and
- a CDR3 region comprising the amino acid sequence of SEQ ID NO:163, 194, 201, or 230.

Embodiment 4 provides the monoclonal antibody of any one of Embodiments 1-3, wherein at least one applies:

(a) the VL comprises:
- a CDR1 region comprising the amino acid sequence of SEQ ID NO:27;
- a CDR2 region comprising the amino acid sequence of SEQ ID NO:29; and
- a CDR3 region comprising the amino acid sequence of SEQ ID NO:31;

and the VH comprises:
- a CDR1 region comprising the amino acid sequence of SEQ ID NO:11;
- a CDR2 region comprising the amino acid sequence of SEQ ID NO:13; and
- a CDR3 region comprising the amino acid sequence of SEQ ID NO:15;

(b) the VL comprises:
- a CDR1 region comprising the amino acid sequence of SEQ ID NO:46;
- a CDR2 region comprising the amino acid sequence of SEQ ID NO:29; and
- a CDR3 region comprising the amino acid sequence of SEQ ID NO:31;

and the VH comprises:
- a CDR1 region comprising the amino acid sequence of SEQ ID NO:11;
- a CDR2 region comprising the amino acid sequence of SEQ ID NO:40; and
- a CDR3 region comprising the amino acid sequence of SEQ ID NO:15;

(c) the VL comprises:
- a CDR1 region comprising the amino acid sequence of SEQ ID NO:70;
- a CDR2 region comprising the amino acid sequence of SEQ ID NO:72; and
- a CDR3 region comprising the amino acid sequence of SEQ ID NO:85;

and the VH comprises:
- a CDR1 region comprising the amino acid sequence of SEQ ID NO:58;
- a CDR2 region comprising the amino acid sequence of SEQ ID NO:60; and
- a CDR3 region comprising the amino acid sequence of SEQ ID NO:62;

(d) the VL comprises:
- a CDR1 region comprising the amino acid sequence of SEQ ID NO:70;
- a CDR2 region comprising the amino acid sequence of SEQ ID NO:72; and
- a CDR3 region comprising the amino acid sequence of SEQ ID NO:85;

and the VH comprises:
- a CDR1 region comprising the amino acid sequence of SEQ ID NO:58;
- a CDR2 region comprising the amino acid sequence of SEQ ID NO:60; and
- a CDR3 region comprising the amino acid sequence of SEQ ID NO:81;

(e) the VL comprises:
- a CDR1 region comprising the amino acid sequence of SEQ ID NO:70;
- a CDR2 region comprising the amino acid sequence of SEQ ID NO:72; and
- a CDR3 region comprising the amino acid sequence of SEQ ID NO:85;

and the VH comprises:
- a CDR1 region comprising the amino acid sequence of SEQ ID NO:92;
- a CDR2 region comprising the amino acid sequence of SEQ ID NO:93; and
- a CDR3 region comprising the amino acid sequence of SEQ ID NO:62;

(f) the VL comprises:
- a CDR1 region comprising the amino acid sequence of SEQ ID NO:114;
- a CDR2 region comprising the amino acid sequence of SEQ ID NO:116; and
- a CDR3 region comprising the amino acid sequence of SEQ ID NO:118;

and the VH comprises:
- a CDR1 region comprising the amino acid sequence of SEQ ID NO:101;
- a CDR2 region comprising the amino acid sequence of SEQ ID NO:102; and
- a CDR3 region comprising the amino acid sequence of SEQ ID NO:62;

(g) the VL comprises:
- a CDR1 region comprising the amino acid sequence of SEQ ID NO:126;
- a CDR2 region comprising the amino acid sequence of SEQ ID NO:72; and
- a CDR3 region comprising the amino acid sequence of SEQ ID NO:129;

and the VH comprises:
- a CDR1 region comprising the amino acid sequence of SEQ ID NO:101;
- a CDR2 region comprising the amino acid sequence of SEQ ID NO:102; and
- a CDR3 region comprising the amino acid sequence of SEQ ID NO:62;

(h) the VL comprises:

a CDR1 region comprising the amino acid sequence of SEQ ID NO:46;

a CDR2 region comprising the amino acid sequence of SEQ ID NO:29; and a CDR3 region comprising the amino acid sequence of SEQ ID NO:31;

and the VH comprises:

a CDR1 region comprising the amino acid sequence of SEQ ID NO:11;

a CDR2 region comprising the amino acid sequence of SEQ ID NO:134; and a CDR3 region comprising the amino acid sequence of SEQ ID NO:15;

(i) the VL comprises:

a CDR1 region comprising the amino acid sequence of SEQ ID NO:70;

a CDR2 region comprising the amino acid sequence of SEQ ID NO:29; and a CDR3 region comprising the amino acid sequence of SEQ ID NO:152;

and the VH comprises:

a CDR1 region comprising the amino acid sequence of SEQ ID NO:144;

a CDR2 region comprising the amino acid sequence of SEQ ID NO:145; and a CDR3 region comprising the amino acid sequence of SEQ ID NO:147;

(j) the VL comprises:

a CDR1 region comprising the amino acid sequence of SEQ ID NO:70;

a CDR2 region comprising the amino acid sequence of SEQ ID NO:29; and a CDR3 region comprising the amino acid sequence of SEQ ID NO:152;

and the VH comprises:

a CDR1 region comprising the amino acid sequence of SEQ ID NO:160;

a CDR2 region comprising the amino acid sequence of SEQ ID NO:161; and a CDR3 region comprising the amino acid sequence of SEQ ID NO:163;

(k) the VL comprises:

a CDR1 region comprising the amino acid sequence of SEQ ID NO:185;

a CDR2 region comprising the amino acid sequence of SEQ ID NO:29; and a CDR3 region comprising the amino acid sequence of SEQ ID NO:129;

and the VH comprises:

a CDR1 region comprising the amino acid sequence of SEQ ID NO:160;

a CDR2 region comprising the amino acid sequence of SEQ ID NO:145; and a CDR3 region comprising the amino acid sequence of SEQ ID NO:163;

(l) the VL comprises:

a CDR1 region comprising the amino acid sequence of SEQ ID NO:70;

a CDR2 region comprising the amino acid sequence of SEQ ID NO:29; and a CDR3 region comprising the amino acid sequence of SEQ ID NO:152;

and the VH comprises:

a CDR1 region comprising the amino acid sequence of SEQ ID NO:160;

a CDR2 region comprising the amino acid sequence of SEQ ID NO:145; and a CDR3 region comprising the amino acid sequence of SEQ ID NO:194;

(m) the VL comprises:

a CDR1 region comprising the amino acid sequence of SEQ ID NO:70;

a CDR2 region comprising the amino acid sequence of SEQ ID NO:72; and a CDR3 region comprising the amino acid sequence of SEQ ID NO:205;

and the VH comprises:

a CDR1 region comprising the amino acid sequence of SEQ ID NO:58;

a CDR2 region comprising the amino acid sequence of SEQ ID NO:200; and a CDR3 region comprising the amino acid sequence of SEQ ID NO:201;

(n) the VL comprises:

a CDR1 region comprising the amino acid sequence of SEQ ID NO:213;

a CDR2 region comprising the amino acid sequence of SEQ ID NO:214; and a CDR3 region comprising the amino acid sequence of SEQ ID NO:216;

and the VH comprises:

a CDR1 region comprising the amino acid sequence of SEQ ID NO:58;

a CDR2 region comprising the amino acid sequence of SEQ ID NO:200; and a CDR3 region comprising the amino acid sequence of SEQ ID NO:201;

(o) the VL comprises:

a CDR1 region comprising the amino acid sequence of SEQ ID NO:240;

a CDR2 region comprising the amino acid sequence of SEQ ID NO:242; and a CDR3 region comprising the amino acid sequence of SEQ ID NO:244;

and the VH comprises:

a CDR1 region comprising the amino acid sequence of SEQ ID NO:226;

a CDR2 region comprising the amino acid sequence of SEQ ID NO:228; and a CDR3 region comprising the amino acid sequence of SEQ ID NO:230.

Embodiment 5 provides the monoclonal antibody of any one of Embodiments 1-4, wherein the VL comprises the amino acid sequence of

SEQ ID NO:27-SEQ ID NO:28-SEQ ID NO:29-SEQ ID NO:30-SEQ ID NO:31,

SEQ ID NO:46-SEQ ID NO:28-SEQ ID NO:29-SEQ ID NO:30-SEQ ID NO:31,

SEQ ID NO:70-SEQ ID NO:71-SEQ ID NO:72-SEQ ID NO:73-SEQ ID NO:85,

SEQ ID NO:70-SEQ ID NO:127-SEQ ID NO:29-SEQ ID NO:151-SEQ ID NO:152,

SEQ ID NO:70-SEQ ID NO:127-SEQ ID NO:29-SEQ ID NO:172-SEQ ID NO:152,

SEQ ID NO:70-SEQ ID NO:127-SEQ ID NO:72-SEQ ID NO:204-SEQ ID NO:205,

SEQ ID NO:114-SEQ ID NO:115-SEQ ID NO:116-SEQ ID NO:117-SEQ ID NO:118,

SEQ ID NO:126-SEQ ID NO:127-SEQ ID NO:72-SEQ ID NO:128-SEQ ID NO:129,

SEQ ID NO:185-SEQ ID NO:186-SEQ ID NO:29-SEQ ID NO:187-SEQ ID NO:129,

SEQ ID NO:213-SEQ ID NO:115-SEQ ID NO:214-SEQ ID NO:215-SEQ ID NO:216, or

SEQ ID NO:240-SEQ ID NO:241-SEQ ID NO:242-SEQ ID NO:243-SEQ ID NO:244, and wherein the VH comprises the amino acid sequence of

SEQ ID NO:11-SEQ ID NO:12-SEQ ID NO:13-SEQ ID NO:14-SEQ ID NO:15,

SEQ ID NO:11-SEQ ID NO:12-SEQ ID NO:40-SEQ ID NO:41-SEQ ID NO:15,

SEQ ID NO:11-SEQ ID NO:12-SEQ ID NO:134-SEQ ID NO:135-SEQ ID NO:15,

SEQ ID NO:58-SEQ ID NO:59-SEQ ID NO:60-SEQ ID NO:61-SEQ ID NO:62,

SEQ ID NO:58-SEQ ID NO:59-SEQ ID NO:60-SEQ ID NO:80-SEQ ID NO:81,

SEQ ID NO:58-SEQ ID NO:59-SEQ ID NO:200-SEQ ID NO:94-SEQ ID NO:201,

SEQ ID NO:92-SEQ ID NO:59-SEQ ID NO:93-SEQ ID NO:94-SEQ ID NO:62,

SEQ ID NO:101-SEQ ID NO:59-SEQ ID NO:102-SEQ ID NO:103-SEQ ID NO:62,

SEQ ID NO:144-SEQ ID NO:59-SEQ ID NO:145-SEQ ID NO:146-SEQ ID NO:147,

SEQ ID NO:160-SEQ ID NO:59-SEQ ID NO:145-SEQ ID NO:177-SEQ ID NO:163,

SEQ ID NO:160-SEQ ID NO:59-SEQ ID NO:145-SEQ ID NO:193-SEQ ID NO:194,

SEQ ID NO:160-SEQ ID NO:59-SEQ ID NO:161-SEQ ID NO:162-SEQ ID NO:163, or

SEQ ID NO:226-SEQ ID NO:227-SEQ ID NO:228-SEQ ID NO:229-SEQ ID NO:230.

Embodiment 6 provides the monoclonal antibody of any one of Embodiments 1-5, wherein the VL comprises the amino acid sequence of:

SEQ ID NO:27-SEQ ID NO:28-SEQ ID NO:29-SEQ ID NO:30-SEQ ID NO:31,

SEQ ID NO:46-SEQ ID NO:28-SEQ ID NO:29-SEQ ID NO:30-SEQ ID NO:31,

SEQ ID NO:70-SEQ ID NO:71-SEQ ID NO:72-SEQ ID NO:73-SEQ ID NO:85,

SEQ ID NO:70-SEQ ID NO:127-SEQ ID NO:29-SEQ ID NO:151-SEQ ID NO:152,

SEQ ID NO:114-SEQ ID NO:115-SEQ ID NO:116-SEQ ID NO:117-SEQ ID NO:118, or

SEQ ID NO:126-SEQ ID NO:127-SEQ ID NO:72-SEQ ID NO:128-SEQ ID NO:129;

and wherein the VH comprises the amino acid sequence of:

SEQ ID NO:11-SEQ ID NO:12-SEQ ID NO:13-SEQ ID NO:14-SEQ ID NO:15,

SEQ ID NO:11-SEQ ID NO:12-SEQ ID NO:40-SEQ ID NO:41-SEQ ID NO:15,

SEQ ID NO:11-SEQ ID NO:12-SEQ ID NO:134-SEQ ID NO:135-SEQ ID NO:15,

SEQ ID NO:58-SEQ ID NO:59-SEQ ID NO:60-SEQ ID NO:61-SEQ ID NO:62,

SEQ ID NO:58-SEQ ID NO:59-SEQ ID NO:60-SEQ ID NO:80-SEQ ID NO:81,

SEQ ID NO:92-SEQ ID NO:59-SEQ ID NO:93-SEQ ID NO:94-SEQ ID NO:62,

SEQ ID NO:101-SEQ ID NO:59-SEQ ID NO:102-SEQ ID NO:103-SEQ ID NO:62, or

SEQ ID NO:144-SEQ ID NO:59-SEQ ID NO:145-SEQ ID NO:146-SEQ ID NO:147.

Embodiment 7 provides the monoclonal antibody of any one of Embodiments 1-5, wherein the VL comprises the amino acid sequence of:

SEQ ID NO:70-SEQ ID NO:127-SEQ ID NO:29-SEQ ID NO:172-SEQ ID NO:152,

SEQ ID NO:70-SEQ ID NO:127-SEQ ID NO:72-SEQ ID NO:204-SEQ ID NO:205,

SEQ ID NO:185-SEQ ID NO:186-SEQ ID NO:29-SEQ ID NO:187-SEQ ID NO:129,

SEQ ID NO:213-SEQ ID NO:115-SEQ ID NO:214-SEQ ID NO:215-SEQ ID NO:216, or

SEQ ID NO:240-SEQ ID NO:241-SEQ ID NO:242-SEQ ID NO:243-SEQ ID NO:244.

and wherein the VH comprises the amino acid sequence of:

SEQ ID NO:58-SEQ ID NO:59-SEQ ID NO:200-SEQ ID NO:94-SEQ ID NO:201,

SEQ ID NO:160-SEQ ID NO:59-SEQ ID NO:145-SEQ ID NO:177-SEQ ID NO:163,

SEQ ID NO:160-SEQ ID NO:59-SEQ ID NO:145-SEQ ID NO:193-SEQ ID NO:194,

SEQ ID NO:160-SEQ ID NO:59-SEQ ID NO:161-SEQ ID NO:162-SEQ ID NO:163, or

SEQ ID NO:226-SEQ ID NO:227-SEQ ID NO:228-SEQ ID NO:229-SEQ ID NO:230.

Embodiment 8 provides the monoclonal antibody of any one of Embodiments 1-7, which is humanized.

Embodiment 9 provides the monoclonal antibody of any one of Embodiments 1-8, which is labeled.

Embodiment 10 provides a pharmaceutical composition comprising the monoclonal antibody of any one of Embodiments 1-9 and at least one pharmaceutical excipient.

Embodiment 11 provides an isolated polynucleotide comprising at least one of the nucleic acid sequences of SEQ ID NOs:3, 5, 7, 19, 21, 23, 35, 43, 44, 50, 52, 54, 66, 68, 75, 77, 88, 89, 96, 97, 99, 106, 108, 110, 121, 132, 138, 139, 141, 148, 150, 155, 157, 167, 168, 170, 175, 180, 191, 195, 197, 198, 203, 207, 209, 211, 219, 221, 223, 233, 235, and 237.

Embodiment 12 provides the isolated polynucleotide of Embodiment 11, comprising:

at least one nucleic acid sequence selected from the group consisting of SEQ ID NOs:3, 5, 7, 35, 50, 52, 54, 75, 77, 88, 89, 97, 99, 132, 138, 139, 141, 155, 157, 175, 191, 197, 198, 219, 221, and 223; and at least one nucleic acid sequence selected from the group consisting of SEQ ID NOs:19, 21, 23, 43, 44, 66, 68, 96, 106, 108, 110, 121, 148, 150, 167, 168, 170, 180, 195, 203, 207, 209, 211, 233, 235, and 237.

Embodiment 13 provides the isolated polynucleotide of any of Embodiments 11-12, comprising:

at least one nucleic acid sequence group selected from the group consisting of:

SEQ ID NOs:3, 5, 7; SEQ ID NOs:3, 35, 7; SEQ ID NOs:3, 132, 7; SEQ ID NOs:50, 52, 54; SEQ ID NOs:50, 75, 77; SEQ ID NOs:50, 139, 175; SEQ ID NOs:50, 139, 191; SEQ ID NOs:50, 155, 157; SEQ ID NOs:50, 197, 198; SEQ ID NOs:88, 89, 54; SEQ ID NOs:97, 99, 54; SEQ ID NOs:138, 139, 141; and SEQ ID NOs:219, 221, 223; and at least one nucleic acid sequence group selected from the group consisting of:

SEQ ID NOs:19, 21, 23; SEQ ID NOs:19, 43, 44; SEQ ID NOs:19, 66, 68; SEQ ID NOs:19, 66, 96; SEQ ID NOs:19, 66, 203; SEQ ID NOs:19, 148, 150; SEQ ID NOs:106, 108, 110; SEQ ID NOs:121, 66, 68; SEQ ID NOs:167, 168, 170; SEQ ID NOs:167, 168, 195; SEQ ID NOs:180, 168, 68; SEQ ID NOs:213, 214, 216; and SEQ ID NOs:233, 235, 237.

Embodiment 14 provides a method of treating, ameliorating, and/or preventing a synucleopathic disease in a subject in need thereof, the method comprising administering to the subject a therapeutically effective amount of at least one isolated monoclonal antibody of any one of Embodiments 1-9.

Embodiment 15 provides the method of Embodiment 14, wherein the synucleopathic disease is at least one from the group consisting of Parkinson's disease, Parkinson's disease with dementia, dementia with Lewy bodies, Alzheimer's disease, Down's syndrome, multiple-system atrophy, prion diseases, and other α-Syn related neurodegenerative disorders.

Embodiment 16 provides the method of any one of Embodiments 14-15, wherein the antibody is provided to the subject as a pharmaceutical composition.

Embodiment 17 provides the method of any one of Embodiments 14-16, wherein the antibody is administered parenterally to the subject.

Embodiment 18 provides a method of detecting a synucleopathic disease in a subject, the method comprising administering to the subject at least one labeled isolated monoclonal antibody of any one of Embodiments 1-9, and detecting presence or absence of a complex of the labeled isolated monoclonal antibody with any α-Syn fibrils, oligomers, and/or other misfolded α-Syn species present in the subject, wherein, if the complex is detected, the subject has a synucleopathic disease.

Embodiment 19 provides a method of detecting total α-Syn, α-Syn fibrils and/or α-Syn oligomeric species in a sample, the method comprising contacting the sample with at least one labeled isolated monoclonal antibody of any one of Embodiments 1-9, and detecting presence or absence of a complex of the labeled isolated monoclonal antibody with total α-Syn, α-Syn monomer, α-Syn fibrils, and/or α-Syn oligomeric species present in the sample, wherein, if the complex is detected, total α-Syn, α-Syn monomers, α-Syn fibrils and/or α-Syn oligomeric species are present in the sample.

Embodiment 20 provides the method of Embodiment 19, wherein the sample comprises an in vitro and/or ex vivo sample.

Embodiment 21 provides an autonomously replicating or an integrative mammalian cell vector comprising a recombinant nucleic acid encoding an antibody comprising a light chain variable region (VL) and a heavy chain variable region (VH), wherein the VL comprises:
- a CDR1 region comprising the amino acid sequence of SEQ ID NO:27, 46, 70, 114, 126, 185, 213, or 240;
- a CDR2 region comprising the amino acid sequence of SEQ ID NO:29, 72, 116, 214, or 242; and
- a CDR3 region comprising the amino acid sequence of SEQ ID NO:31, 85, 118, 129, 152, 205, 216, or 244;

and wherein the VH comprises:
- a CDR1 region comprising the amino acid sequence of SEQ ID NO:11, 58, 92, 101, 144, 160, or 226;
- a CDR2 region comprising the amino acid sequence of SEQ ID NO:13, 40, 60, 93, 102, 134, 145, 161, 200, or 228; and
- a CDR3 region comprising the amino acid sequence of SEQ ID NO:15, 62, 81, 147, 163, 194, 201, or 230.

Embodiment 22 provides the cell vector of Embodiment 21, which comprises a plasmid or a virus.

Embodiment 23 provides the cell vector of any one of Embodiments 21-22, which comprises a mammalian cell expression vector.

Embodiment 24 provides the cell vector of any one of Embodiments 21-23, further comprising at least one nucleic acid sequence that directs and/or controls expression of the antibody.

Embodiment 25 provides an isolated host cell comprising at least one vector of any one of Embodiments 21-24.

Embodiment 26 provides the host cell of Embodiment 25, which is a non-human cell.

Embodiment 27 provides the cell vector of any one of Embodiments 25-26, which is mammalian.

The disclosures of each and every patent, patent application, and publication cited herein are hereby incorporated herein by reference in their entirety.

While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. An isolated monoclonal antibody comprising a light chain variable region (VL) and a heavy chain variable region (VH), wherein the VL comprises:

a CDR1 region comprising the amino acid sequence of SEQ ID NO:70;

a CDR2 region comprising the amino acid sequence of SEQ ID NO:72; and a CDR3 region comprising the amino acid sequence of SEQ ID NO:85; and the VH comprises:

a CDR1 region comprising the amino acid sequence of SEQ ID NO:58;

a CDR2 region comprising the amino acid sequence of SEQ ID NO:60; and a CDR3 region comprising the amino acid sequence of SEQ ID NO:81.

2. The monoclonal antibody of claim 1, wherein at least one of the following applies:

(a) the monoclonal antibody is humanized; or (b) the monoclonal antibody is labeled.

3. A pharmaceutical composition comprising the monoclonal antibody of claim 1 and at least one pharmaceutical excipient.

4. A method of treating or ameliorating a synucleopathic disease in a subject in need thereof, the method comprising administering to the subject a therapeutically effective amount of an isolated monoclonal antibody comprising a light chain variable region (VL) and a heavy chain variable region (VH), wherein the VL comprises:

a CDR1 region comprising the amino acid sequence of SEQ ID NO:70;

a CDR2 region comprising the amino acid sequence of SEQ ID NO:72; and a CDR3 region comprising the amino acid sequence of SEQ ID NO:85; and the VH comprises:

a CDR1 region comprising the amino acid sequence of SEQ ID NO:58;

a CDR2 region comprising the amino acid sequence of SEQ ID NO:60; and a CDR3 region comprising the amino acid sequence of SEQ ID NO:81.

5. The method of claim 4, wherein at least one of the following applies:

(a) the synucleopathic disease is at least one from the group consisting of Parkinson's disease, Parkinson's disease with dementia, dementia with Lewy bodies, Alzheimer's disease, Down's syndrome, multiple-system atrophy, and prion diseases, (b) the antibody is provided to the subject as a pharmaceutical composition, or (c) the antibody is administered parenterally to the subject.

* * * * *